(12) United States Patent
Frost et al.

(10) Patent No.: US 11,939,320 B2
(45) Date of Patent: Mar. 26, 2024

(54) MODULATORS OF THE INTEGRATED STRESS PATHWAY

(71) Applicants: Calico Life Sciences LLC, South San Francisco, CA (US); AbbVie Inc., North Chicago, IL (US)

(72) Inventors: Jennifer M. Frost, Gurnee, IL (US); Lei Shi, Vernon Hills, IL (US); Yunsong Tong, Libertyville, IL (US); Michael J. Dart, Highland Park, IL (US); Kathleen J. Murauski, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 16/761,365

(22) PCT Filed: Nov. 2, 2018

(86) PCT No.: PCT/US2018/058972
§ 371 (c)(1),
(2) Date: May 4, 2020

(87) PCT Pub. No.: WO2019/090088
PCT Pub. Date: May 9, 2019

(65) Prior Publication Data
US 2021/0171508 A1 Jun. 10, 2021

Related U.S. Application Data

(60) Provisional application No. 62/643,075, filed on Mar. 14, 2018, provisional application No. 62/580,755, filed on Nov. 2, 2017.

(51) Int. Cl.
| | |
|---|---|
| C07D 405/12 | (2006.01) |
| A61K 45/06 | (2006.01) |
| C07D 205/04 | (2006.01) |
| C07D 207/08 | (2006.01) |
| C07D 213/40 | (2006.01) |
| C07D 213/75 | (2006.01) |
| C07D 235/14 | (2006.01) |
| C07D 263/32 | (2006.01) |
| C07D 309/14 | (2006.01) |
| C07D 413/14 | (2006.01) |
| C07D 487/04 | (2006.01) |

(52) U.S. Cl.
CPC ............ C07D 405/12 (2013.01); A61K 45/06 (2013.01); C07D 205/04 (2013.01); C07D 207/08 (2013.01); C07D 213/40 (2013.01); C07D 213/75 (2013.01); C07D 235/14 (2013.01); C07D 263/32 (2013.01); C07D 309/14 (2013.01); C07D 413/14 (2013.01); C07D 487/04 (2013.01)

(58) Field of Classification Search
CPC ..... C07D 263/32; C07D 309/14; A61K 45/06
See application file for complete search history.

(56) References Cited

U.S. PATENT DOCUMENTS

| | | | |
|---|---|---|---|
| 3,264,351 | A | 8/1966 | Humber |
| 3,347,919 | A | 10/1967 | Elmore |
| 3,967,629 | A | 7/1976 | Chappell et al. |
| 4,861,760 | A | 8/1989 | Mazuel et al. |
| 4,911,920 | A | 3/1990 | Jani et al. |
| 5,047,406 | A | 9/1991 | Caprathe et al. |
| 5,403,841 | A | 4/1995 | Lang et al. |
| 5,506,257 | A | 4/1996 | MacLeod et al. |
| 5,686,454 | A | 11/1997 | Bock et al. |
| 5,852,192 | A | 12/1998 | Himmelsbach et al. |
| 7,560,569 | B2 | 7/2009 | Fukuda et al. |
| 7,994,211 | B2 | 8/2011 | Ray et al. |
| 8,569,283 | B2 | 10/2013 | Molteni et al. |
| 10,836,725 | B2 | 11/2020 | Pliushchev et al. |
| 10,864,196 | B2 | 12/2020 | Pliushchev et al. |
| 10,913,727 | B2 | 2/2021 | Pliushchev et al. |
| 11,149,043 | B2 | 10/2021 | Dart et al. |
| 2004/0133011 | A1 | 7/2004 | Waddell et al. |
| 2004/0186140 | A1 | 9/2004 | Cherney et al. |
| 2005/0085667 | A1 | 4/2005 | Wood et al. |
| 2006/0149070 | A1 | 7/2006 | Rohde et al. |
| 2007/0185079 | A1 | 8/2007 | Evertsson et al. |
| 2007/0265320 | A1 | 11/2007 | Fukuda et al. |
| 2010/0144852 | A1 | 6/2010 | Finch et al. |
| 2011/0046093 | A1 | 2/2011 | Hollick et al. |
| 2011/0294801 | A1 | 12/2011 | Yu et al. |
| 2014/0323748 | A1 | 10/2014 | Dosa et al. |
| 2015/0045368 | A1 | 2/2015 | Bregman et al. |
| 2015/0057289 | A1 | 2/2015 | Li et al. |
| 2015/0362847 | A1 | 12/2015 | Tanaka et al. |

(Continued)

FOREIGN PATENT DOCUMENTS

| | | |
|---|---|---|
| CN | 103369961 A | 10/2013 |
| CN | 106349130 A | 1/2017 |

(Continued)

OTHER PUBLICATIONS

Dey, J Bio Chem, vol. 287(26), 21936-21949, 2012. (Year: 2012).*
Wong, eLIFE, 20198e42940, 1-31, 2019. (Year: 2019).*
Delbrel, Int J ol Sci, VOI 20, 1299, 1-17, 2019. (Year: 2019).*
André et al., (S)-Aboc: A Rigid Bicyclic β-Amino Acid as Turn Inducer, Org Lett, 14(4):960-963 (2012).
Berkessel et al., Chemically Induced Cardiomyogenesis of Mouse Embryonic Stem Cells, ChemBiochem, 11(2):208-217 (2010).
Busacca et al., Stereoselective synthesis of (1R,2S,3R)-camphordiamine, J Org Chem, 65(15):4753-4755 (2000).
Co-Pending U.S. Appl. No. 16/761,369, filed May 4, 2020.
Co-Pending U.S. Appl. No. 16/761,388, filed May 4, 2020.
Co-Pending U.S. Appl. No. 16/863,737, filed Apr. 30, 2020.
Co-Pending U.S. Appl. No. 17/103,003, filed Nov. 24, 2020.

(Continued)

*Primary Examiner* — D Margaret M Seaman
(74) *Attorney, Agent, or Firm* — Goodwin Procter LLP

(57) ABSTRACT

Provided herein are compounds, compositions, and methods useful for modulating the integrated stress response (ISR) and for treating related diseases; disorders and conditions.

20 Claims, No Drawings

(56) References Cited

U.S. PATENT DOCUMENTS

| | | | |
|---|---|---|---|
| 2016/0096800 A1* | 4/2016 | Walter | C07C 235/20 514/616 |
| 2016/0318856 A1 | 11/2016 | Aktas et al. | |
| 2019/0144440 A1 | 5/2019 | Sidrauski et al. | |
| 2019/0177310 A1 | 6/2019 | Bernales et al. | |
| 2020/0345727 A1 | 11/2020 | Martin et al. | |
| 2020/0347033 A1 | 11/2020 | Martin et al. | |
| 2020/0347043 A1* | 11/2020 | Martin | A61K 31/397 |
| 2020/0361881 A1 | 11/2020 | Martin et al. | |
| 2020/0361941 A1 | 11/2020 | Martin et al. | |
| 2021/0113532 A1 | 4/2021 | Sidrauski et al. | |
| 2021/0169892 A1 | 6/2021 | Martin et al. | |
| 2021/0205277 A1 | 7/2021 | Martin et al. | |
| 2021/0230195 A1 | 7/2021 | Martin et al. | |
| 2021/0269399 A1 | 9/2021 | Sidrauski et al. | |
| 2021/0363136 A1 | 11/2021 | Martin et al. | |
| 2021/0393599 A1 | 12/2021 | Martin et al. | |
| 2022/0106281 A1 | 4/2022 | Sidrauski et al. | |
| 2022/0251123 A1 | 8/2022 | Martin et al. | |
| 2022/0363678 A1 | 11/2022 | Sidrauski et al. | |
| 2023/0144871 A1 | 5/2023 | Martin et al. | |

FOREIGN PATENT DOCUMENTS

| | | |
|---|---|---|
| EA | 22325 B1 | 4/2013 |
| EP | 0431580 A2 | 6/1991 |
| EP | 1571146 A1 | 9/2005 |
| GB | 1026506 A | 4/1966 |
| JP | H02215779 A | 8/1990 |
| JP | H03251568 A | 11/1991 |
| JP | H0592921 A | 4/1993 |
| JP | H09500133 A | 1/1997 |
| JP | 2009190971 A | 8/2009 |
| JP | 2015508826 A | 3/2015 |
| JP | 2015199722 A | 11/2015 |
| JP | 2017538713 A | 12/2017 |
| JP | 2020522553 A | 7/2020 |
| SU | 587856 A3 | 1/1978 |
| WO | WO-1995002587 A1 | 1/1995 |
| WO | WO-1996005194 A1 | 2/1996 |
| WO | WO-2003066577 A1 | 8/2003 |
| WO | WO-2004050024 A2 | 6/2004 |
| WO | WO-2005066132 A1 | 7/2005 |
| WO | WO-2005077900 A1 | 8/2005 |
| WO | WO-2007005214 A1 | 1/2007 |
| WO | WO-2007142253 A1 | 12/2007 |
| WO | WO-2008075196 A1 | 6/2008 |
| WO | WO-2009040556 A1 | 4/2009 |
| WO | WO-2010011570 A1 | 1/2010 |
| WO | WO-2010028116 A1 | 3/2010 |
| WO | WO-2010112946 A1 | 10/2010 |
| WO | WO-2010115491 A2 | 10/2010 |
| WO | WO-2011087758 A1 | 7/2011 |
| WO | WO-2011119663 A1 | 9/2011 |
| WO | WO-2011159854 A1 | 12/2011 |
| WO | WO-2012088365 A1 | 6/2012 |
| WO | WO-2013130890 A1 | 9/2013 |
| WO | WO-2013134079 A1 | 9/2013 |
| WO | WO-2013161980 A1 | 10/2013 |
| WO | WO-2013186159 A1 | 12/2013 |
| WO | WO-2014144952 A2 | 9/2014 |
| WO | WO-2015038778 A1 | 3/2015 |
| WO | WO-2015154039 A2 | 10/2015 |
| WO | WO-2016058544 A1 | 4/2016 |
| WO | WO-2016106237 A1 | 6/2016 |
| WO | WO-2016177658 A1 | 11/2016 |
| WO | WO-2017035408 A1 | 3/2017 |
| WO | WO-2017040606 A1 | 3/2017 |
| WO | WO-2017046738 A1 | 3/2017 |
| WO | WO-2017049173 A1 | 3/2017 |
| WO | WO-2017193030 A1 | 11/2017 |
| WO | WO-2017193034 A1 | 11/2017 |
| WO | WO-2017193041 A1 | 11/2017 |
| WO | WO-2017193063 A1 | 11/2017 |
| WO | WO-2017212425 A1 | 12/2017 |
| WO | WO-2017223275 A1 | 12/2017 |
| WO | WO-2018119395 A1 | 6/2018 |
| WO | WO-2018225093 A1 | 12/2018 |
| WO | WO-2019027054 A1 | 2/2019 |
| WO | WO-2019032743 A1 | 2/2019 |
| WO | WO-2019046779 A1 | 3/2019 |
| WO | WO-2019090069 A1 | 5/2019 |
| WO | WO-2019090074 A1 | 5/2019 |
| WO | WO-2019090076 A1 | 5/2019 |
| WO | WO-2019090078 A1 | 5/2019 |
| WO | WO-2019090081 A1 | 5/2019 |
| WO | WO-2019090082 A1 | 5/2019 |
| WO | WO-2019090085 A1 | 5/2019 |
| WO | WO-2019090088 A1 | 5/2019 |
| WO | WO-2019090090 A1 | 5/2019 |
| WO | WO-2019183589 A1 | 9/2019 |
| WO | WO-2020012339 A1 | 1/2020 |
| WO | WO-2020077217 A1 | 4/2020 |
| WO | WO-2020221816 A1 | 11/2020 |
| WO | WO-2020223536 A1 | 11/2020 |
| WO | WO-2020223538 A1 | 11/2020 |
| WO | WO-2022094244 A1 | 5/2022 |

OTHER PUBLICATIONS

Co-Pending U.S. Appl. No. 17/108,416, filed Dec. 1, 2020.
Co-Pending U.S. Appl. No. 17/446,807, filed Sep. 2, 2021.
Database PubChem Compound [Online] Dec. 1, 2012, retrieved from NCBI, Database accession No. 69612403.
Database PubChem Compound [Online] Dec. 5, 2007, retrieved from NCBI, Database accession No. 20755106.
Database PubChem Compound [Online] Dec. 11, 2015, retrieved from NCBI, Database accession No. 98260962.
Database PubChem Compound [Online] Dec. 18, 2015, retrieved from NCBI, Database accession No. 101566942.
Database PubChem Compound [Online] Feb. 23, 2016, retrieved from NCBI, Database accession No. 118417886.
Database PubChem Compound [Online] Jul. 10, 2005, retrieved from NCBI, Database accession No. 1300563.
Database PubChem Compound [Online] Mar. 23, 2015, retrieved from NCBI, Database accession No. 91663862.
Database PubChem Compound [Online] May 3, 2011, retrieved from NCBI, Database accession No. 51064332.
Database PubChem Compound [Online] Nov. 13, 2007, retrieved from NCBI, Database accession No. 17565335.
Database PubChem Compound [Online] Nov. 15, 2010, retrieved from NCBI, Database accession No. 46939935.
Database PubChem Compound [Online] Nov. 15, 2010, retrieved from NCBI, Database accession No. 46939936.
Database PubChem Compound [Online] Nov. 30, 2012, retrieved from NCBI, Database accession No. 66910924.
Database PubChem Compound [Online] Nov. 30, 2012, retrieved from NCBI, Database accession No. 66910946.
Database PubChem Compound [Online] Nov. 30, 2012, retrieved from NCBI, Database accession No. 66910949.
Database PubChem Compound [Online] Nov. 30, 2012, retrieved from NCBI, Database accession No. 68048074.
Database Registry, Chemical Abstracts Services, CAS Registry No. 136524-58-8 (Entered STN: Oct. 4, 1991).
Database Registry, Chemical Abstracts Services, CAS Registry No. 136524-59-9 (Entered STN: Oct. 4, 1991).
Database Registry, Chemical Abstracts Services, CAS Registry No. 136524-60-2 (Entered STN: Oct. 4, 1991).
Database Registry, Chemical Abstracts Services, CAS Registry No. 136524-61-3 (Entered STN: Oct. 4, 1991).
Database Registry, Chemical Abstracts Services, CAS Registry No. 136524-62-4 (Entered STN: Oct. 4, 1991).
Database Registry, Chemical Abstracts Services, CAS Registry No. 136524-68-0 (Entered STN: Oct. 4, 1991).
Database Registry, Chemical Abstracts Services, CAS Registry No. 136524-95-3 (Entered STN: Oct. 4, 1991).
Database Registry, Chemical Abstracts Services, CAS Registry No. 1566649-44-2 (Entered STN: Nov. 3, 2014).

(56) References Cited

OTHER PUBLICATIONS

Database Registry, Chemical Abstracts Services, CAS Registry No. 350024-42-9 (Entered STN: Feb. 8, 2001).
Database Registry, Chemical Abstracts Services, CAS Registry No. 69994-07-6 (Entered STN: Nov. 16, 1984).
Database Registry, Chemical Abstracts Services, CAS Registry No. 710983-35-0 (Entered STN: Jul. 16, 2004).
Database Registry, Chemical Abstracts Services, CAS Registry No. 899259-90-6 (Entered STN: Jul. 8, 2006).
Database Registry, Chemical Abstracts Services, CAS Registry No. 899259-94-0 (Entered STN: Jul. 8, 2006).
Dornow et al., Reduktionen mit LiAlH4, XII. Über Eine Weitere Hydrierende Spaltung von C-C-Bindungen, Chemische Berichte 90(10):2124-2137 (1957).
Flachner et al., Rapid in silico selection of an MCHR1 antagonists' focused library from multi-million compounds' repositories: Biological evaluation, Med. Chem. Res. 23:1234-1247 (2014).
Fogli and Boespflug-Tanguy, The large spectrum of eIF2B-related diseases, Biochem Soc Trans, 34(Pt. 1): 22-29 (2006).
Font et al., Structural characteristics of novel symmetrical diaryl derivatives with nitrogenated functions, requirements for cytotoxic activity, Bioorg Med Chem, 14(6):1942-1948 (2006).
International Search Report and Written Opinion dated Aug. 14, 2020 in Application No. PCT/US2020/030819 (14 pages).
International Search Report and Written Opinion dated Aug. 24, 2020 for Application No. PCT/US2020/030817 (13 pages).
International Search Report and Written Opinion dated Feb. 11, 2019 for Application No. PCT/US2018/058955 (14 pages).
International Search Report and Written Opinion dated Feb. 11, 2019 for Application No. PCT/US2018/058969 (12 pages).
International Search Report and Written Opinion dated Feb. 14, 2019 for Application No. PCT/US2018/058960 (12 pages).
International Search Report and Written Opinion dated Feb. 19, 2019 for Application No. PCT/US2018/058963 (14 pages).
International Search Report and Written Opinion dated Feb. 5, 2019 for Application No. PCT/US2018/058957 (15 pages).
International Search Report and Written Opinion dated Jan. 2, 2020 for Application No. PCT/US2019/055850 (7 pages).
International Search Report and Written Opinion dated Jan. 28, 2019 for Application No. PCT/US2018/058972 (13 pages).
International Search Report and Written Opinion dated Jan. 29, 2019 for Application No. PCT/US2018/058965 (12 pages).
International Search Report and Written Opinion dated Jan. 29, 2019 for Application No. PCT/US2018/058974 (16 pages).
International Search Report and Written Opinion dated Jan. 30, 2019 for Application No. PCT/US2018/058949 (14 pages).
International Search Report and Written Opinion dated Jul. 3, 2017 for Application No. PCT/US2017/031393 (13 pages).
International Search Report and Written Opinion dated Jul. 10, 2017 for Application No. PCT/US2017/031352 (12 pages).
International Search Report and Written Opinion dated Jun. 26, 2017 for Application No. PCT/US2017/031360 (16 pages).
International Search Report and Written Opinion dated Jun. 26, 2017 for Application No. PCT/US2017/031367 (13 pages).
Montaudo, et al., Effect of Strong acids on the circular dichroism of asymmetric aromatic polyamides, Plymer Letter, 10:433-436 (1972).
Moteki et al., Supporting information for: Design of structurally rigid trans-diamine-based Tf-amide organocatalysts with a dihydroanthracene framework for asymmetric conjugate additions of heterosubstituted aldehydes to vinyl sulfones, J Am Chern Soc 132(48):17074-17076 (2010).
Patel et al., Discovery of adamantine ethers as inhibitors of 11beta-HSD-1: Synthesis and biological evaluation, Bioorg Med Chem Lett 17(3):750-755 (2007).
Shimono, R., et al., Preparation of nitrogen-containing condensed heterocyclic compounds as positive allosteric modulators of GABAB receptor, Accession No. 2017:661225, Document No. 166:490715 (2017), Retrieved from ,https://www.stn.org/stn/#/. on May 8, 2021.
Smith et al., Norbornyl dipeptide analogues: Mimics of both a transition state and a Torsionally distorted ground state, Bioorg Chem 23(4):397-414 (1995).
Tydlitát et al., Camphor-annelated imidazolines with various N1 and C2 pendants as tunable ligands for nitroaldol reactions, Tetrahedron: Asymmetry 23(13):1010-1018 (2012).
U.S. Appl. No. 16/098,675, Modulators of the Integrated Stress Pathway, filed Nov. 2, 2018, Abandoned.
U.S. Appl. No. 17/103,003, Modulators of the Integrated Stress Pathway, filed Nov. 24, 2020, Pending.
U.S. Appl. No. 17/038,179, Modulators of the Integrated Stress Pathway, filed Sep. 30, 2020, Issued as U.S. Pat. No. 10,836,725 on Nov. 17, 2020.
U.S. Appl. No. 16/098,946, Modulators of the Integrated Stress Pathway, filed Nov. 5, 2018, Pending.
U.S. Appl. No. 16/098,679, Modulators of the Integrated Stress Pathway, filed Nov. 2, 2018, Issued as U.S. Pat. No. 10,913,727 on Feb. 9, 2021.
U.S. Appl. No. 17/108,416, Modulators of the Integrated Stress Pathway, filed Dec. 1, 2020, Pending.
U.S. Appl. No. 16/885,766, Modulators of the Integrated Stress Pathway, filed May 28, 2020, Issued as U.S. Pat. No. 10,864,196 on Dec. 15, 2020.
U.S. Appl. No. 16/098,950, Modulators of the Integrated Stress Pathway, filed Nov. 5, 2018, Pending.
U.S. Appl. No. 16/761,386, Modulators of the Integrated Stress Pathway, filed May 4, 2020, Pending.
U.S. Appl. No. 16/761,388, Modulators of the Integrated Stress Pathway, filed May 4, 2020, Pending.
U.S. Appl. No. 16/761,390, Modulators of the Integrated Stress Pathway, filed May 4, 2020, Pending.
U.S. Appl. No. 16/761,392, Modulators of the Integrated Stress Pathway, filed May 4, 2020, Pending.
U.S. Appl. No. 16/761,394, Modulators of the Integrated Stress Pathway, filed May 4, 2020, Pending.
U.S. Appl. No. 16/761,349, Modulators of the Integrated Stress Pathway, filed May 4, 2020, Pending.
U.S. Appl. No. 16/761,354, Modulators of the Integrated Stress Pathway, filed May 4, 2020, Pending.
U.S. Appl. No. 16/761,369, Modulators of the Integrated Stress Pathway, filed May 4, 2020, Pending.
U.S. Appl. No. 17/227,071, Prodrug Modulators of the Integrated stress Pathway, filed Apr. 9, 2021, Allowed.
U.S. Appl. No. 17/446,807, Prodrug Modulators of the Integrated stress Pathway, filed Sep. 2, 2021, Pending.
U.S. Appl. No. 16/863,737, Modulators of the Integrated Stress Pathway, filed Apr. 30, 2020, Pending.
U.S. Appl. No. 16/863,747, Modulators of the Integrated Stress Pathway, filed Apr. 30, 2020, Pending.
Ciapetti, P., et al., Chapter 15—Molecular variations based on isosteric replacements In Wermuth, C.G. (Ed.) The practice of medicinal chemistry, Elsevier, p. 290-342 (2008).
Database Registry, Chemical Abstracts Services, CAS Registry No. 1349152-90-4 (Entered STN: Dec. 5, 2011).
Database Registry, Chemical Abstracts Services, CAS Registry No. 1349810-01-0 (Entered STN: Dec. 6, 2011).
Database Registry, Chemical Abstracts Services, CAS Registry No. 1349832-07-0 (Entered STN: Dec. 6, 2011).
Database Registry, Chemical Abstracts Services, CAS Registry No. 2349401-20-1 (Entered STN: Jul. 1, 2019).
Hu, J., et al., ER stress inhibitor attenuates hearing loss and hair cell death in Cdh23$^{erl/erl}$ mutant mice, Cell Death Dis, 7(11): e2485 (2016).
Bregman, H., et al., Discovery of novel, induced-pocket binding oxazolidinones as potent, selective, and orally bioavailable tankyrase inhibitors, J Med Chem, 56(11): 4320-4342 (2013).
Leopoldo, M., et al., Synthesis and binding profile of constrained analogues of N-[4-(4-arylpiperazin-1-yl)butyl]-3-methoxybenzamides, a class of potent dopamine D3 receptor ligands, Journal of Pharmacy and Pharmacology, 58(2): 209-218 (2006).

(56) References Cited

OTHER PUBLICATIONS

Matsuo, J., et al., A practical synthesis of enantiopure N-carbobenzyloxy-N'-phthaloyl-cis-1,2-cyclohexanediamine by asymmetric reductive amination and the Curtius rearrangement, Tetrahedron: Asymmetry, 18(16): 1906-1910 (2007).

Sar, A., et al., Synthesis of Hydroxy- and Polyhydroxy-Substituted 1,3-Diaminocyclohexanes, Synthesis, 6: 921-928 (2011).

Cancer, retrieved from <http://www.nlm.nih.gov/medlineplus/cancer.html> on Jul. 6, 2007.

Golub, T.R., et al., Molecular classification of cancer: class discovery and class prediction by gene expression monitoring, Science, 286(5439): 531-537 (1999).

International Search Report and Written Opinion dated Mar. 25, 2022 for Application No. PCT/US2021/057300 (19 pages).

Lala, P.K., et al., Role of nitric oxide in tumor progression: lessons from experimental tumors, Cancer Metastasis Rev, 17(1): 91-106 (1998).

Moteki et al., Design of structurally rigid trans-diamine-based Tf-amide organocatalysts with a dihydroanthracene framework for asymmetric conjugate additions of heterosubstituted aldehydes to vinyl sulfones, J Am Chem Soc 132(48): 17074-17076, Supporting Information, pp. S1-S62 (2010).

U.S. Appl. No. 17/103,003, Modulators of the Integrated Stress Pathway, filed Nov. 5, 2018.

U.S. Appl. No. 16/761,386, Modulators of the Integrated Stress Pathway, filed May 4, 2020.

U.S. Appl. No. 18/324,901, Modulators of the Integrated Stress Pathway, filed May 28, 2023.

U.S. Appl. No. 16/761,388, Modulators of the Integrated Stress Pathway, filed May 4, 2020.

U.S. Appl. No. 18/330,171, Modulators of the Integrated Stress Pathway, filed Jun. 6, 2023.

U.S. Appl. No. 16/761,390, Modulators of the Integrated Stress Pathway, filed May 4, 2020.

U.S. Appl. No. 18/330,185, Modulators of the Integrated Stress Pathway, filed Jun. 6, 2023.

U.S. Appl. No. 17/446,807, Modulators of the Integrated Stress Pathway, filed Sep. 2, 2021.

U.S. Appl. No. 18/251,079, Modulators of the Integrated Stress Pathway, filed Apr. 28, 2023.

Database Registry, Chemical Abstracts Services, CAS Registry No. 1149383-79-8 (Entered STN: May 26, 2009).

Database Registry, Chemical Abstracts Services, CAS Registry No. 2202513-40-2 (Entered STN: Mar. 30, 2018).

\* cited by examiner

MODULATORS OF THE INTEGRATED STRESS PATHWAY

CROSS-REFERENCE TO RELATED APPLICATIONS

This application is a national stage filing under 35 U.S.C. § 371 of PCT/US2018/058972, filed Nov. 2, 2018, which claims the benefit of, and priority to, U.S. Provisional Application No. 62/580,755, filed Nov. 2, 2017 and U.S. Provisional Application No. 62/643,075, filed Mar. 14, 2018, the disclosures of each of which are incorporated herein by reference in their entireties.

BACKGROUND

In metazoa, diverse stress signals converge at a single phosphorylation event at serine 51 of a common effector, the translation initiation factor eIF2α. This step is carried out by four eIF2α kinases in mammalian cells: PERK, which responds to an accumulation of unfolded proteins in the endoplasmic reticulum (ER), GCN2 to amino acid starvation and UV light, PKR to viral infection and metabolic stress, and HRI to heme deficiency. This collection of signaling pathways has been termed the "integrated stress response" (ISR), as they converge on the same molecular event. eIF2α phosphorylation results in an attenuation of translation with consequences that allow cells to cope with the varied stresses (Wek, R. C. et al, Biochem Soc Trans (2006) 34(Pt 1):7-11). eIF2 (which is comprised of three subunits, α, β and γ) binds GTP and the initiator Met-tRNA to form the ternary complex (eIF2-GTP-Met-tRNA$_i$), which, in turn, associates with the 40S ribosomal subunit scanning the 5'UTR of mRNAs to select the initiating AUG codon. Upon phosphorylation of its α-subunit, eIF2 becomes a competitive inhibitor of its GTP-exchange factor (GEF), eIF2B (Hinnebusch, A. G. and Lorsch, J. R. Cold Spring Harbor Perspect Biol (2012) 4(10)). The tight and nonproductive binding of phosphorylated eIF2 to eIF2B prevents loading of the eIF2 complex with GTP, thus blocking ternary complex formation and reducing translation initiation (Krishnamoorthy, T. et al, Mol Cell Biol (2001) 21(15):5018-5030). Because eIF2B is less abundant than eIF2, phosphorylation of only a small fraction of the total eIF2 has a dramatic impact on eIF2B activity in cells.

eIF2B is a complex molecular machine, composed of five different subunits, eIF2B1 through eIF2B5. eIF2B5 catalyzes the GDP/GTP exchange reaction and, together with a partially homologous subunit eIF2B3, constitutes the "catalytic core" (Williams, D. D. et al, J Biol Chem (2001) 276:24697-24703). The three remaining subunits (eIF2B1, eIF2B2, and eIF2B4) are also highly homologous to one another and form a "regulatory sub-complex" that provides binding sites for eIF2B's substrate eIF2 (Dev, K. et al, Mol Cell Biol (2010) 30:5218-5233). The exchange of GDP with GTP in eIF2 is catalyzed by its dedicated guanine nucleotide exchange factor (GEF) eIF2B. eIF2B exists as a decamer (B1$_2$B2$_2$ B3$_2$ B4$_2$ B5$_2$) or dimer of two pentamers in cells (Gordiyenko, Y. et al, Nat Commun (2014) 5:3902; Wortham, N.C. et al, FASEB J(2014) 28:2225-2237). Molecules such as ISRIB interact with and stabilize the eIF2B dimer conformation, thereby enhancing intrinsic GEF activity and making cells less sensitive to the cellular effects of phosphorylation of eIF2α (Sidrauski, C. et al, eLife (2015) e07314; Sekine, Y. et al, Science (2015) 348:1027-1030). As such, small molecule therapeutics that can modulate eIF2B activity may have the potential to attenuate the PERK branch of the UPR and the overall ISR, and therefore may be used in the prevention and/or treatment of various diseases, such as a neurodegenerative disease, a leukodystrophy, cancer, an inflammatory disease, a musculoskeletal disease, or a metabolic disease.

SUMMARY OF THE INVENTION

The present disclosure is directed, at least in part, to compounds, compositions, and methods for the modulation of eIF2B (e.g., activation of eIF2B) and the attenuation of the ISR signaling pathway. In some embodiments, disclosed herein is an eIF2B modulator (e.g., an eIF2B activator) comprising a compound of Formula (I) or a pharmaceutically acceptable salt, solvate, hydrate, tautomer, N-oxide, or stereoisomer thereof. In other embodiments, disclosed herein are methods of using a compound of Formula (I) or a pharmaceutically acceptable salt, solvate, hydrate, tautomer, N-oxide, or stereoisomer thereof for the treatment of a disease or disorder, e.g., a neurodegenerative disease, a leukodystrophy, cancer, an inflammatory disease, a musculoskeletal disease, a metabolic disease, or a disease or disorder associated with impaired function of eIF2B or components in the ISR pathway (e.g., eIF2 pathway).

For example, disclosed herein is a compound of Formula (I):

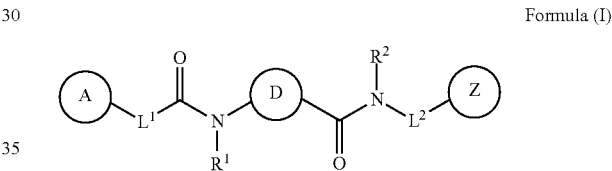

Formula (I)

or a pharmaceutically acceptable salt, solvate, hydrate, tautomer, N-oxide, or stereoisomer thereof, wherein:

D is cyclohexyl, cyclobutyl, or tetrahydropyranyl, each optionally substituted with 1-4 $R^X$.

$L^1$ is a bond, $C_1$-$C_6$ alkylene, 2-7 membered heteroalkylene, —$NR^{N1}$—, or —O—, wherein $C_1$-$C_6$ alkylene or 2-7 membered heteroalkylene is optionally substituted with 1-5 $R^{L1}$;

$R^1$ is hydrogen, hydroxy-$C_1$-$C_6$ alkyl, or $C_1$-$C_6$ alkyl;

$L^2$ is a bond, $C_1$-$C_6$ alkylene, or 2-7 membered heteroalkylene, wherein $C_1$-$C_6$ alkylene or 2-7 membered heteroalkylene is optionally substituted with 1-5 $R^{L2}$;

$R^2$ is hydrogen, hydroxy-$C_1$-$C_6$ alkyl, or $C_1$-$C_6$ alkyl; or $L^2$ and $R^2$, together with the nitrogen to which they are attached, form a 4-9 membered monocyclic, bridged bicyclic, fused bicyclic or spirocyclic heterocyclyl; wherein the 4-9 membered monocyclic, bridged bicyclic, fused bicyclic or spirocyclic heterocyclyl is optionally substituted on one or more available carbons with 1-5 $R^W$; and wherein if the 4-9 membered monocyclic, bridged bicyclic, fused bicyclic or spirocyclic heterocyclyl contains a substitutable nitrogen moiety, the substitutable nitrogen may be optionally substituted with $R^{N2}$;

A and Z are each independently phenyl or 5-6-membered heteroaryl, wherein each phenyl or 5-6-membered heteroaryl is optionally substituted on one or more available carbons with 1-5 $R^Y$; and wherein if the 5-6-membered heteroaryl contains a substitutable nitrogen moiety, the substitutable nitrogen may be optionally substituted with $R^{N3}$; or one $R^Y$, $R^2$ and $L^2$, together with the nitrogen to which $R^2$ and $L^2$ are attached, form a 4-9 membered monocyclic heterocycle, wherein Z is fused to the formed 4-9 membered monocyclic heterocycle, wherein the available carbon atoms of Z are optionally substituted with 1-4 $R^Y$; and wherein if Z contains a substitutable nitrogen moiety, the substitutable nitrogen may be optionally substituted with $R^{N3}$;

each $R^{L1}$ is independently selected from the group consisting of $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, $NR^BC(O)R^D$, —$C(O)NR^BR^C$, —$C(O)R^D$, —$C(O)OH$, —$C(O)OR^D$, —$SR^E$, —$S(O)R^D$, and —$S(O)_2R^D$; or 2 geminal $R^{L2}$ groups together with the carbon to which they are attached form a cyclopropyl moiety;

each $R^{L2}$ is independently selected from the group consisting of hydrogen, $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$N^BC(O)R^D$, —$C(O)NR^BR^C$, —$C(O)R^D$, —$C(O)OH$, —$C(O)OR^D$, —$SR^E$, —$S(O)R^D$ and —$S(O)_2R^D$;

$R^{N1}$ is selected from the group consisting of hydrogen, $C_1$-$C_6$ alkyl, hydroxy-$C_2$-$C_6$ alkyl, halo-$C_2$-$C_6$ alkyl, amino-$C_2$-$C_6$ alkyl, cyano-$C_2$-$C_6$ alkyl, —$C(O)NR^BR^C$, —$C(O)R^D$, —$C(O)OR^D$, and —$S(O)_2R^D$;

$R^{N2}$ is selected from the group consisting of hydrogen, $C_1$-$C_6$ alkyl, hydroxy-$C_2$-$C_6$ alkyl, halo-$C_2$-$C_6$ alkyl, amino-$C_2$-$C_6$ alkyl, cyano-$C_2$-$C_6$ alkyl, —$C(O)NR^BR^C$, —$C(O)R^D$, —$C(O)OR^D$ and —$S(O)_2R^D$;

$R^{N3}$ is selected from the group consisting of hydrogen, $C_1$-$C_6$ alkyl, hydroxy-$C_2$-$C_6$ alkyl, halo-$C_2$-$C_6$ alkyl, amino-$C_2$-$C_6$ alkyl, cyano-$C_2$-$C_6$ alkyl, —$C(O)NR^BR^C$, —$C(O)R^D$, —$C(O)OR^D$ and —$S(O)_2R^D$;

each $R^W$ is independently selected from the group consisting of hydrogen, $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$N^BC(O)R^D$, —$C(O)NR^BR^C$, —$C(O)R^D$, —$C(O)OH$, —$C(O)OR^D$, —$SR^E$, —$S(O)R^D$ and —$S(O)_2R^D$;

each $R^X$ is independently selected from the group consisting of hydrogen, $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$N^BC(O)R^D$, —$C(O)NR^BR^C$, —$C(O)R^D$, —$C(O)OH$, —$C(O)OR^D$, —$SR^E$, —$S(O)R^D$ and —$S(O)_2R^D$;

each $R^X$ is independently selected from the group consisting of hydrogen, $C_1$-$C_6$ alkyl, hydroxy-$C_1$-$C_6$ alkyl, halo-$C_1$-$C_6$ alkyl, halo-$C_1$-$C_6$ alkoxy, amino-$C_1$-$C_6$ alkyl, cyano-$C_1$-$C_6$ alkyl, —$O$—$C_1$-$C_6$ cycloalkyl, halo, cyano, —$OR^A$, —$NR^BR^C$, —$N^BC(O)R^D$, —$C(O)NR^BR^C$, —$C(O)R^D$, —$C(O)OH$, —$C(O)OR^D$, —$S(R^F)_m$, —$S(O)R^D$, —$S(O)_2R^D$, and $G^1$; or 2 $R^Y$ groups or one $R^Y$ and one $R^{N3}$ on adjacent atoms, together with the atoms to which they are attached, form a 3-7 membered fused cycloalkyl, 3-7-membered fused heterocyclyl, fused aryl, or 5-6 membered fused heteroaryl, each of which is optionally substituted with 1-5 $R^X$;

each $G^1$ is independently 3-7-membered cycloalkyl, 3-7-membered heterocyclyl, aryl, or 5-6-membered heteroaryl, wherein each 3-7-membered cycloalkyl, 3-7-membered heterocyclyl, aryl, or 5-6-membered heteroaryl is optionally substituted with 1-3 $R^Z$;

each $R^Z$ is independently selected from the group consisting of $C_1$-$C_6$ alkyl, hydroxy-$C_1$-$C_6$ alkyl, halo-$C_1$-$C_6$ alkyl, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, and —$S(O)_2R^D$;

$R^A$ is, at each occurrence, independently hydrogen, $C_1$-$C_6$ alkyl, halo-$C_1$-$C_6$ alkyl, —$C(O)NR^BR^C$, —$C(O)R^D$, or —$C(O)OR^D$;

each of $R^B$ and $R^C$ is independently hydrogen or $C_1$-$C_6$ alkyl; or $R^B$ and $R^C$ together with the atom to which they are attached form a 3-7-membered heterocyclyl optionally substituted with 1-3 $R^Z$;

each $R^D$ is independently $C_1$-$C_6$ alkyl or halo-$C_1$-$C_6$ alkyl;

each $R^E$ is independently hydrogen, $C_1$-$C_6$ alkyl, or halo-$C_1$-$C_6$ alkyl;

each $R^F$ is independently hydrogen, $C_1$-$C_6$ alkyl, or halo; and m is 1 when $R^F$ is hydrogen or $C_1$-$C_6$ alkyl, 3 when $R^F$ is $C_1$-$C_6$ alkyl, or 5 when $R^F$ is halo.

In some embodiments, D is

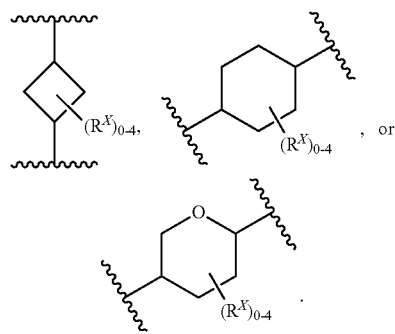

In some embodiments, each $R^X$ is independently selected from the group consisting of oxo, —OH, —$C(O)OH$, —$C(O)OR^D$, halo, and hydroxy-$C_1$-$C_6$ alkyl.

In some embodiments, $L^1$ is a bond, 2-7 membered heteroalkylene, —$N^{N1}$—, or —O—, wherein 2-7 membered heteroalkylene is optionally substituted with 1-5 $R^L$.

In some embodiments, $L^1$ is a bond, 2-7 membered heteroalkylene, —$N^{N1}$—, or —O—, wherein 2-7 membered heteroalkylene is substituted with 0 $R^L$.

In some embodiments, $L^1$ is selected from a bond, —$CH_2O$—*, —$CH_2CH_2O$—*, —$CH_2OCH_2$—*, —$NCH_3$—, —NH—, or —O—, wherein "—*" indicates the attachment point to A.

In some embodiments, $R^1$ is hydrogen, $CH_3$, or $CH_2CH_2OH$.

In some embodiments, each of A and Z is independently phenyl or 5-6-membered heteroaryl; wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$.

In some embodiments, each of A and Z is independently phenyl, pyridyl, pyrimidinyl, pyrazinyl, oxazolyl, isoxazolyl, indolyl, imidazolyl, pyrrolyl, triazolyl or pyrazolyl, each of which is optionally substituted with 1-5 $R^Y$ groups.

In some embodiments, each of A and Z is selected from the group consisting of:

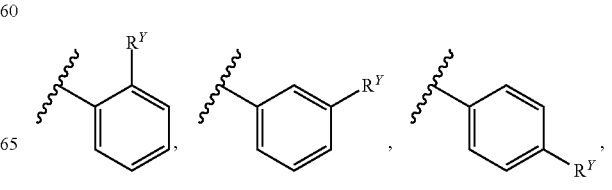

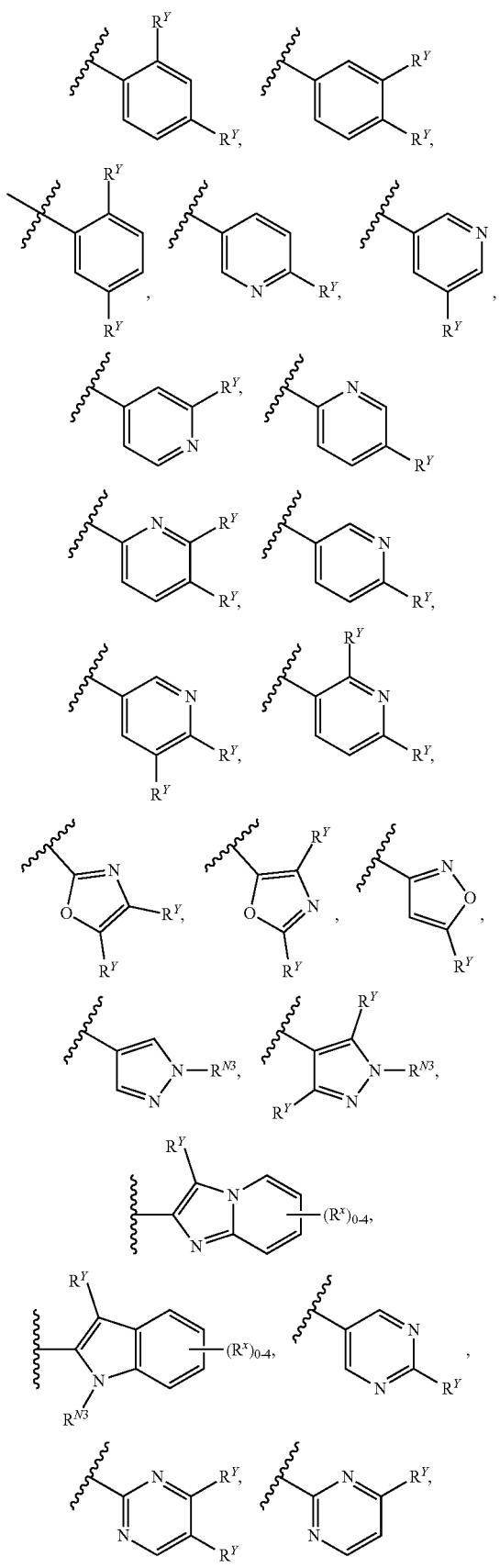
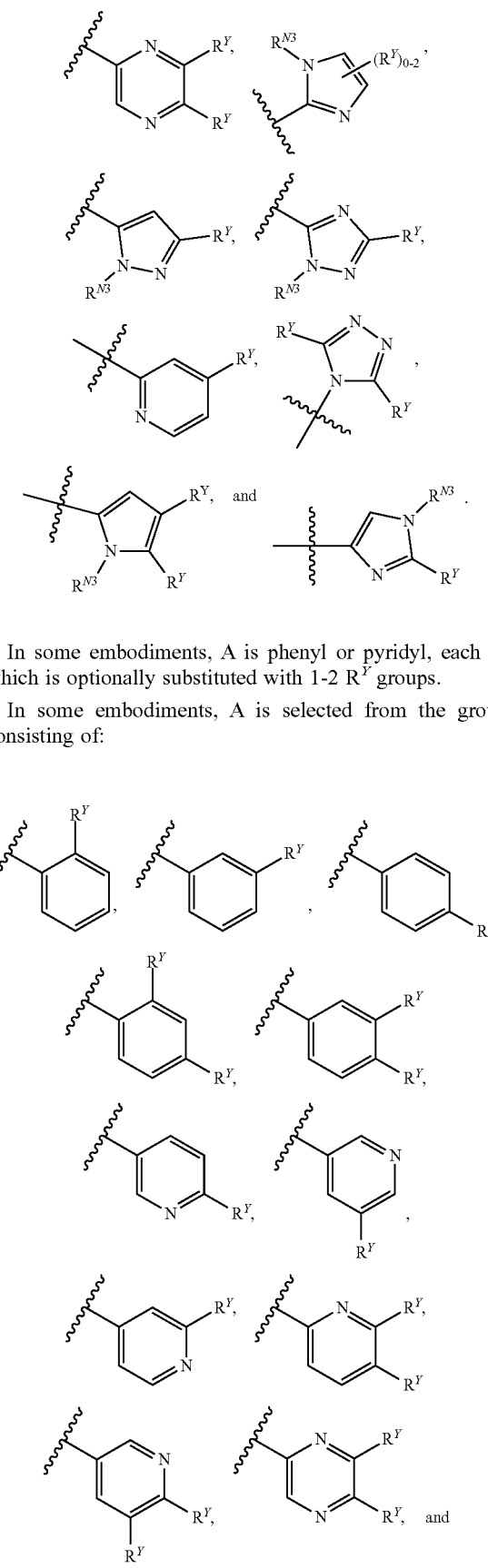
In some embodiments, A is phenyl or pyridyl, each of which is optionally substituted with 1-2 $R^Y$ groups.
In some embodiments, A is selected from the group consisting of:

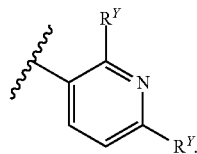

In some embodiments, Z is phenyl, pyridyl, pyrimidinyl, oxazolyl, isoxazolyl, indolyl, imidazolyl, pyrrolyl, triazolyl, pyrazinyl or pyrazolyl, each of which is optionally substituted with 1-3 $R^Y$ groups.

In some embodiments, Z is selected from the group consisting of:

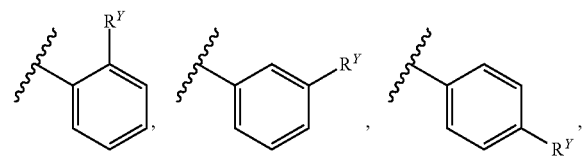

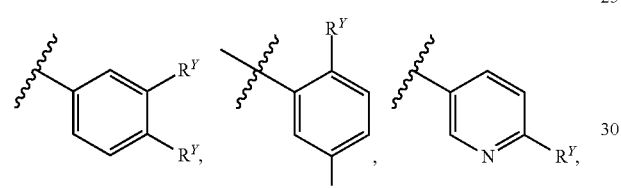

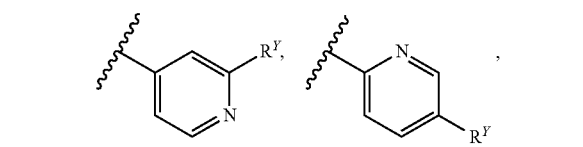

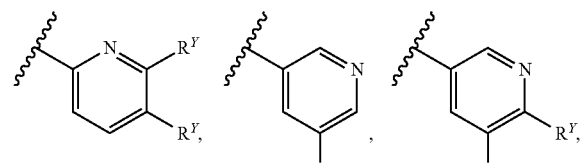

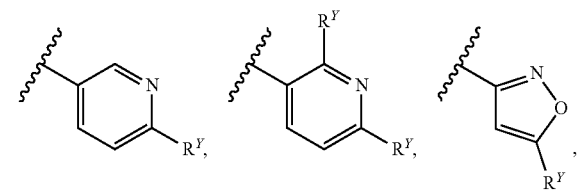

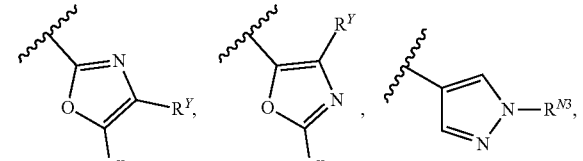

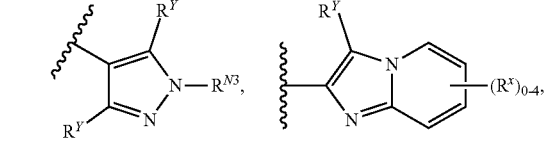

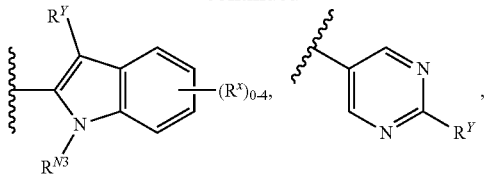

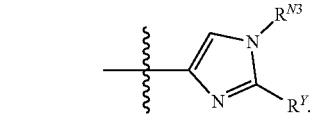

, and

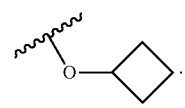

wherein $R^{N3}$ is hydrogen or $CH_3$.

In some embodiments, each $R^Y$ is independently selected from the group consisting of hydrogen, chloro, fluoro, $CHF_2$, $CF_3$, $CH_3$, $CH_2CH_3$, $CH(CH_3)_2$, $OCH_3$, $OCHF_2$, $OCF_3$, $OCH_2CF_3$, $OCH(CH_3)_2$, CN, $C(O)NH_2$, $CH_2OH$ and In some embodiments, $L^2$ is a bond, $C_1$-$C_6$ alkylene or 2-7 membered heteroalkylene, wherein $C_1$-$C_6$ alkylene or 2-7 membered heteroalkylene is optionally substituted by 1-5 $R^{1L}$.

In some embodiments, $L^2$ is a bond, $C_1$-$C_6$ alkylene or 2-7 membered heteroalkylene, wherein $C_1$-$C_6$ alkylene or 2-7 membered heteroalkylene is substituted by 0 $R^L$.

In some embodiments, $L^2$ is selected from a bond, —$CH_2$—*, —$CH_2CH_2$—*, or —$CH_2CH_2O$—* wherein "—*" indicates the attachment point to Z.

In some embodiments, $R^2$ is hydrogen or $CH_3$.

In some embodiments, $L^2$ and $R^2$, together with the nitrogen to which they are attached, form a 4-7 membered monocyclic or 7-9 membered spirocyclic heterocyclyl, each of which is optionally substituted with 1-5 $R^W$.

In some embodiments, the compound is represented by Formula (II):

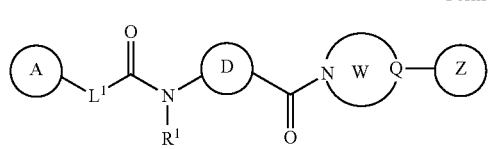

Formula (II)

wherein:
W is a 4-7 membered monocyclic or 7-9 membered spirocyclic heterocyclyl, wherein the 4-7 membered monocyclic or 7-9 membered spirocyclic heterocyclyl is optionally substituted with 1-4 $R^W$;
Q is nitrogen or $C(R^Q)$; and
$R^Q$ is selected from the group consisting of hydrogen, hydroxyl, and $C_1$-$C_6$ alkyl.

In some embodiments, Q is nitrogen.

In some embodiments, W is a piperazine, piperazinone, or 2,6-diazaspiro[3.3]heptane moiety, each of which is optionally substituted with 1-4 $R^W$ groups, and each $R^W$ is independently selected from the group consisting of $C_1$-$C_6$ alkyl, halo-$C_1$-$C_6$ alkyl, halo, oxo, cyano, and —$OR^A$.

In some embodiments, W is selected from the group consisting of:

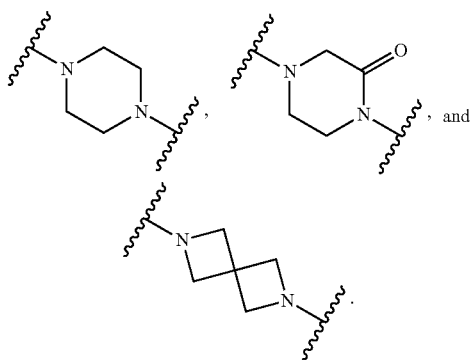

, and

In some embodiments, Q is CH.

In some embodiments, W is an azetidine, pyrrolidine, piperidine, or 2-azaspiro[3.3]heptane moiety, each of which is optionally substituted with 1-4 $R^W$ groups, and each $R^W$ is independently $C_1$-$C_6$ alkyl, halo-$C_1$-$C_6$ alkyl, halo, oxo, cyano, or —$OR^A$.

In some embodiments, W is selected from the group consisting of:

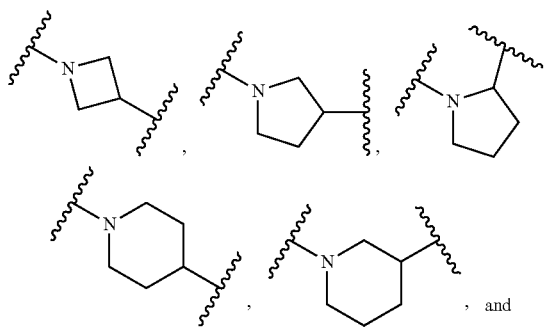

, and

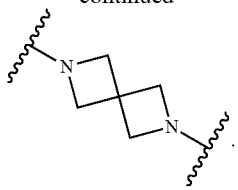

.

In some embodiments, one $R^Y$, $R^2$ and $L^2$, together with the nitrogen to which $R^2$ and $L^2$ are attached, form a 4-9 membered monocyclic heterocycle, wherein Z is fused to the formed 4-9 membered monocyclic heterocycle, wherein the available carbon atoms of Z are optionally substituted with 1-4 $R^Y$; and wherein if Z contains a substitutable nitrogen moiety, the substitutable nitrogen may be optionally substituted with $R^{N3}$.

In some embodiments, the compound of Formula (I) is a compound of Formula (I-a):

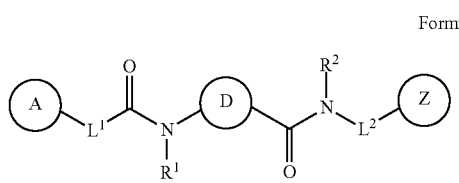

Formula (I-a)

or a pharmaceutically acceptable salt, solvate, hydrate, tautomer, N-oxide, or stereoisomer thereof, wherein:
D is cyclohexyl, cyclobutyl, or tetrahydropyranyl each optionally substituted with 1-4 $R^X$ groups;
$L^1$ is selected from the group consisting of a bond, $CH_2O$—*, $CH_2OCH_2$—*, —$NCH_3$—, —NH—, and —O—, wherein "—*" indicates the attachment point to A;
$R^1$ is selected from the group consisting of hydrogen and $CH_3$;
$L^2$ is selected from the group consisting of a bond and $CH_2$—*, wherein "—*" indicates the attachment point to Z;
$R^2$ is selected from the group consisting of hydrogen and $CH_3$; or
$L^2$ and $R^2$, together with the nitrogen to which they are attached, form an azetidine, pyrrolidine, piperidine, 2-azaspiro[3.3]heptane, piperazine, piperazinone, or 2,6-diazaspiro[3.3]heptane moiety, each of which is optionally substituted with 1-4 $R^W$ groups; or
one $R^Y$, $R^2$ and $L^2$, together with the nitrogen to which $R^2$ and $L^2$ are attached, form a 4-9 membered monocyclic heterocycle, wherein Z is fused to the formed 4-9 membered monocyclic heterocycle, wherein the available carbon atoms of Z are optionally substituted with 1-4 $R^Y$; and wherein if Z contains a substitutable nitrogen moiety, the substitutable nitrogen may be optionally substituted with $R^{N3}$;
A is phenyl or pyridyl, each of which is optionally substituted with 1-5 $R^Y$ groups;
Z is phenyl, pyridyl, oxazolyl, isoxazolyl, imidazolyl, pyrimidinyl, or pyrazolyl, each of which is optionally substituted on one or more available carbons with 1-5 $R^Y$ groups; and wherein pyrazolyl may be optionally substituted on an available nitrogen with hydrogen or $CH_3$;
each $R^W$ is independently fluoro, chloro, oxo, OH, $OCH_3$, $CF_3$, $CH_3$, $CH_2CH_3$, or $CH(CH_3)_2$;
each $R^X$ is independently fluoro, oxo, OH, $OCH_3$, $C(O)OH$, or $C(O)OCH_3$;

each $R^Y$ is independently chloro, fluoro, $CHF_2$, $CF_3$, $CH_3$, $CH_2CH_3$, $CH(CH_3)_2$, $OCH_3$, $OCHF_2$, $OCF_3$, $OCH_2CF_3$, $OCH(CH_3)_2$, or CN; or 2 $R^Y$ groups on adjacent atoms, together with the atoms to which they are attached form a furanyl, pyrrolyl, pyridyl, phenyl, or dioxolanyl ring, each of which is optionally substituted with 1-2 $R^X$.

In some embodiments, the compound of Formula (I) is a compound of Formula (I-b) or Formula (I-b'):

Formula (I-b)

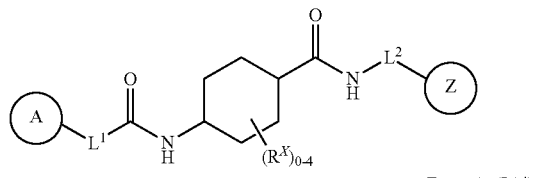

Formula (I-b')

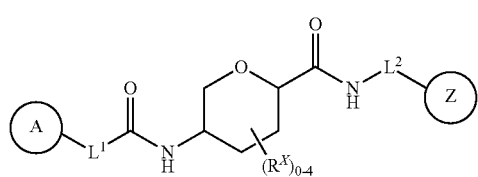

or a pharmaceutically acceptable salt, solvate, hydrate, tautomer, N-oxide, or stereoisomer thereof.

In some embodiments, the compound of Formula (I) is a compound of Formula (I-c) or Formula (I-c'):

Formula (I-c)

Formula (I-c')

or a pharmaceutically acceptable salt, solvate, hydrate, tautomer, N-oxide, or stereoisomer thereof.

In some embodiments, the compound of Formula (I) is a compound of Formula (I-d) or Formula (I-d'):

Formula (I-d)

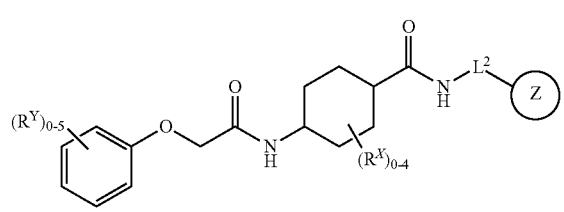

Formula (I-d")

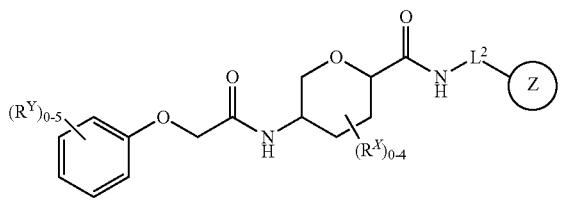

or a pharmaceutically acceptable salt, solvate, hydrate, tautomer, N-oxide, or stereoisomer thereof.

In some embodiments, the compound of Formula (I) is a compound of Formula (I-e-1), Formula (I-e-1'), Formula (I-e-2), Formula (I-e-2'), Formula (I-e-3), Formula (I-e-3'), Formula (I-e-4), Formula (I-e-4'), Formula (I-e-5), Formula (I-e-5'), Formula (I-e-6), Formula (I-e-6'), Formula (I-e-7), Formula (I-e-7'), Formula (I-e-8), Formula (I-e-8'), Formula (I-e-9) or Formula (I-e-9'):

Formula (I-e-1)

Formula (I-e-1')

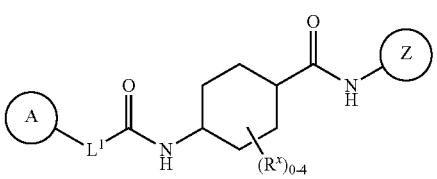

Formula (I-e-2)

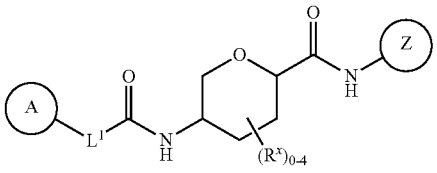

Formula (I-e-2')

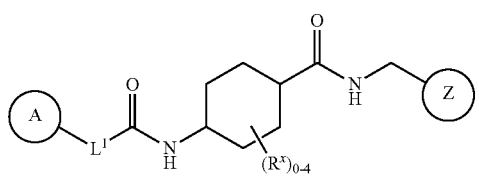

Formula (I-e-3)

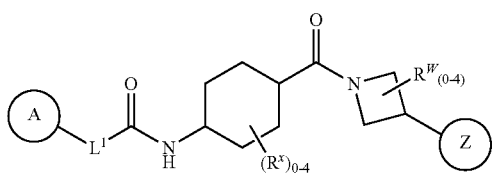

Formula (I-e-3′)
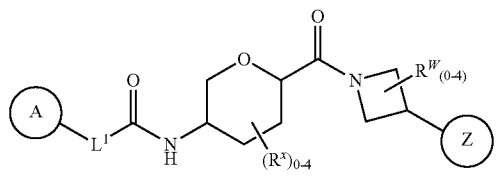

Formula (I-e-4)
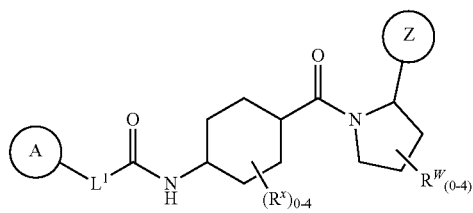

Formula (I-e-4′)
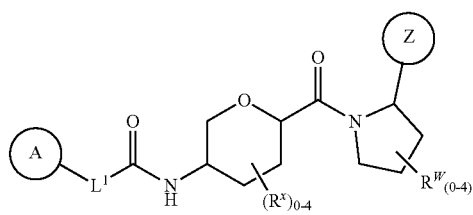

Formula (I-e-5)
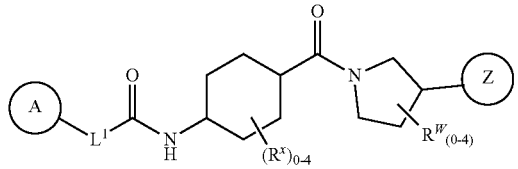

Formula (I-e-5′)
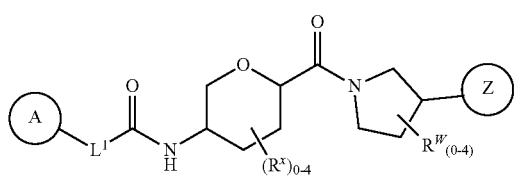

Formula (I-e-6)
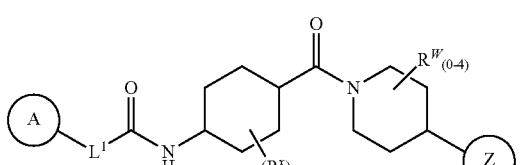

Formula (I-e-6′)
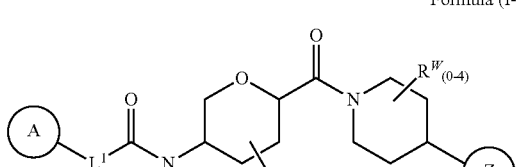

Formula (I-e-7)
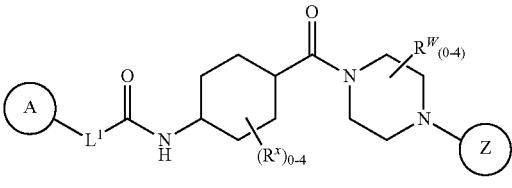

Formula (I-e-7′)
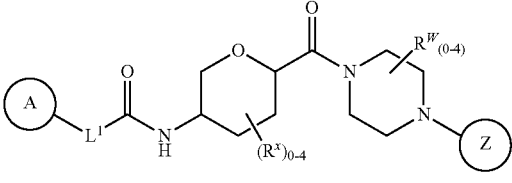

Formula (I-e-8)
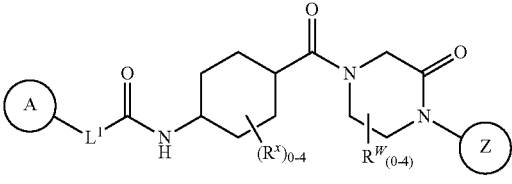

Formula (I-e-8′)
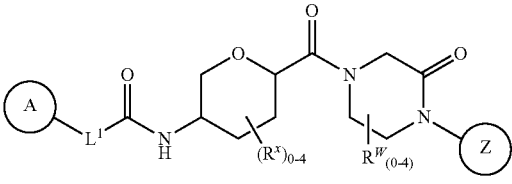

Formula (I-e-9)
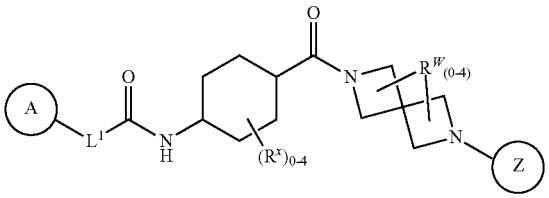

Formula (I-e-9′)
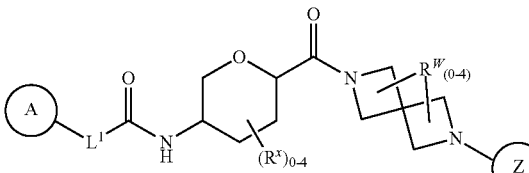

or a pharmaceutically acceptable salt, solvate, hydrate, tautomer, N-oxide, or stereoisomer thereof.

In some embodiments, the compound is selected from any compound set forth in Table 1 or a pharmaceutically acceptable salt, solvate, hydrate, tautomer, N-oxide, or stereoisomer thereof.

Also disclosed herein is a compound represented by Formula (III):

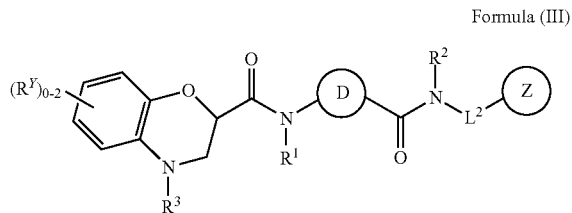

Formula (III)

or a pharmaceutically acceptable salt, solvate, hydrate, tautomer, N-oxide, or stereoisomer thereof, wherein:

D is cyclohexyl, cyclobutyl, or tetrahydropyranyl, each optionally substituted with 1-2 $R^X$ groups;

$R^1$ is selected from the group consisting of hydrogen and $CH_3$;

$L^2$ is selected from the group consisting of a bond and $CH_2$—*, wherein "—*" indicates the attachment point to Z;

$R^2$ is selected from the group consisting of hydrogen and $CH_3$;

$R^3$ is selected from the group consisting of hydrogen and $CH_3$;

Z is phenyl, pyridyl, oxazolyl, isoxazolyl, or pyrazolyl, each of which is optionally substituted on one or more available carbons with 1-2 $R^Y$ groups; and wherein pyrazolyl may be optionally substituted on an available nitrogen with hydrogen or $CH_3$;

each $R^X$ is independently fluoro, oxo, OH, $OCH_3$, C(O)OH, or $C(O)OCH_3$;

each $R^Y$ is independently chloro, fluoro, $CHF_2$, $CF_3$, $CH_3$, $CH_2CH_3$, $CH(CH_3)_2$, $OCH_3$, $OCHF_2$, $OCF_3$, $OCH_2CF_3$, $OCH(CH_3)_2$, or CN; or 2 $R^Y$ groups on adjacent atoms, together with the atoms to which they are attached form a dioxolanyl ring, which is optionally substituted with 1-2 $R^Y$ groups.

In some embodiments, D is tetrahyropyranyl.

In some embodiments, Z is phenyl or pyridyl.

In some embodiments, each $R^Y$ is independently selected from chloro, fluoro, $CHF_2$ or $CF_3$.

In some embodiments, a disclosed compound or a pharmaceutically acceptable salt thereof is formulated as a pharmaceutically acceptable composition comprising a disclosed compound and a pharmaceutically acceptable carrier.

In some embodiments, a disclosed compound is selected from a compound set forth in Table 1 or a pharmaceutically acceptable salt, solvate, hydrate, tautomer, N-oxide or stereoisomer thereof.

In another aspect, the present invention features a method of treating a neurodegenerative disease, a leukodystrophy, cancer, an inflammatory disease, a musculoskeletal disease, a metabolic disease, a mitochondrial disease, or a disease or disorder associated with impaired function of eIF2B or components in the ISR pathway (e.g., eIF2 pathway) in a subject, wherein the method comprises administering a compound of Formula (I) or a pharmaceutically acceptable salt, solvate, hydrate, tautomer, N-oxide or stereoisomer thereof, or a composition thereof, to a subject.

In some embodiments, the method comprises the treatment of a neurodegenerative disease. In some embodiments, the neurodegenerative disease comprises vanishing white matter disease, childhood ataxia with CNS hypo-myelination, a leukodystrophy, a leukoencephalopathy, hypomyelinating or demyelinating disease, an intellectual disability syndrome, progressive supranuclear palsy, corticobasal degeneration, adrenoleukodystrophy, X-linked adrenoleukodystrophy, cerebral adrenoleukodystrophy, Pelizaeus-Merzbacher Disease, Krabbe disease, leukodystrophy due to mutation in DARS2 gene (sometimes known as lukoencephalopathy with brainstem and spinal cord involvement and lactate elevation (LBSL), DARS2-related spectrum disorders, Alzheimer's disease, amyotrophic lateral sclerosis, Creutzfeldt-Jakob disease, frontotemporal dementia, Gerstmann-Straussler-Scheinker disease, Huntington's disease, dementia (e.g., HIV-associated dementia or Lewy body dementia), kuru, Parkinson's disease, progressive nuclear palsy, a tauopathy, or a prion disease. In some embodiments, the neurodegenerative disease comprises vanishing white matter disease. In some embodiments, the neurodegenerative disease comprises a psychiatric disease such as agoraphobia, Alzheimer's disease, anorexia nervosa, amnesia, anxiety disorder, bipolar disorder, body dysmorphic disorder, bulimia nervosa, claustrophobia, depression, delusions, Diogenes syndrome, dyspraxia, insomnia, Munchausen's syndrome, narcolepsy, narcissistic personality disorder, obsessive-compulsive disorder, psychosis, phobic disorder, schizophrenia, seasonal affective disorder, schizoid personality disorder, sleepwalking, social phobia, substance abuse, tardive dyskinesia, Tourette syndrome, or trichotillomania. In some embodiments, the neurodegenerative disease comprises a disease or disorder with symptoms of cognitive impairment or cognitive decline such as Alzheimer's disease, Parkinson's disease, Huntington's disease, schizophrenia, autism, frontotemporal dementia, dementia (e.g., HIV-associated dementia or Lewy body dementia), age related dementia, chronic traumatic encephalopathy, HIV-induced neurocognitive impairment, a HIV-associated neurocognitive disorder, a hypoxic injury (e.g., premature brain injury, chronic perinatal hypoxia), traumatic brain injury, stroke, or postoperative cognitive dysfunction. In some embodiments, the neurodegenerative disease comprises an intellectual disability syndrome. In some embodiments, the neurodegenerative disease comprises mild cognitive impairment.

In some embodiments, the method comprises the treatment of cancer. In some embodiments, the cancer comprises pancreatic cancer, breast cancer, multiple myeloma, or a cancer of the secretory cells. In some embodiments, the method comprises the treatment of cancer in combination with a chemotherapeutic agent for the enhancement of memory (e.g., long term memory).

In some embodiments, the method comprises the treatment of an inflammatory disease. In some embodiments, the inflammatory disease comprises postoperative cognitive dysfunction, traumatic brain injury, arthritis (e.g., rheumatoid arthritis, psoriatic arthritis, or juvenile idiopathic arthritis), systemic lupus erythematosus (SLE), myasthenia gravis, diabetes (e.g., juvenile onset diabetes or diabetes mellitus type 1), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves' ophthalmopathy, inflammatory bowel disease, Addison's disease, vitiligo, asthma (e.g., allergic asthma), acne vulgaris, celiac disease, chronic prostatitis, pelvic inflammatory disease, reperfusion injury, sarcoidosis, transplant rejection, interstitial cystitis, or atopic dermatitis.

In some embodiments, the method comprises the treatment of a musculoskeletal disease. In some embodiments, the musculoskeletal disease comprises muscular dystrophy, multiple sclerosis, Freidrich's ataxia, a muscle wasting disorder (e.g., muscle atrophy, sarcopenia, cachexia), inclusion body myopathy, progressive muscular atrophy, motor neuron disease, carpal tunnel syndrome, epicondylitis, tendinitis, back pain, muscle pain, muscle soreness, repetitive strain disorders, or paralysis.

In some embodiments, the method comprises the treatment of a metabolic disease. In some embodiments, the metabolic disease comprises non-alcoholic steatohepatitis (NASH), non-alcoholic fatty liver disease (NAFLD), liver fibrosis, obesity, heart disease, atherosclerosis, arthritis, cystinosis, phenylketonuria, proliferative retinopathy, or Kearns-Sayre disease.

In some embodiments, the method comprises the treatment of a mitochondrial disease. In some embodiments, the mitochondrial disease is associated with, or is a result of, or is caused by mitochondrial dysfunction, one or more mitochondrial protein mutations, or one or more mitochondrial DNA mutations. In some embodiments, the mitochondrial disease is a mitochondrial myopathy. In some embodiments, the mitochondrial disease, e.g., the mitochondrial myopathy, is selected from the group consisting of Barth syndrome, chronic progressive external ophthalmoplegia (cPEO), Kearns-Sayre syndrome (KSS), Leigh syndrome (e.g., MILS, or maternally inherited Leigh syndrome), mitochondrial DNA depletion syndromes (MDDS, e.g., Alpers syndrome), mitochondrial encephalomyopathy (e.g., mitochondrial encephalomyopathy, lactic acidosis, and stroke-like episodes (MELAS)), mitochondrial neurogastrointestinal encephalomyopathy (MNGIE), myoclonus epilepsy with ragged red fibers (MERRF), neuropathy, ataxia, retinitis pigmentosa (NARP), Leber's hereditary optic neuropathy (LHON), and Pearson syndrome.

In another aspect, the present invention features a method of treating a disease or disorder related to modulation (e.g., a decrease) in eIF2B activity or level, modulation (e.g., a decrease) of eIF2α activity or level, modulation (e.g., an increase) in eIF2α phosphorylation, modulation (e.g., an increase) of phosphorylated eIF2α pathway activity, or modulation (e.g., an increase) of ISR activity in a subject, wherein the method comprises administering a compound of Formula (I) or a pharmaceutically acceptable salt, solvate, hydrate, tautomer, N-oxide or stereoisomer thereof, or a composition thereof, to a subject. In some embodiments, the disease may be caused by a mutation to a gene or protein sequence related to a member of the eIF2 pathway (e.g., the eIF2α signaling pathway or ISR pathway).

In another aspect, the present invention features a method of treating a leukodystrophy such as vanishing white matter disease (VWMD) or childhood ataxia with central nervous system hypomyelination. In some embodiments, the leukodystrophy is characterized by an amino acid mutation (e.g., an amino acid deletion, amino acid addition, or amino acid substitution) in a tRNA synthetase. In some embodiments, administration of a compound of Formula (I) enhances eIF2B activity in a subject with a leukodystrophy, such as vanishing white matter disease (VWMD) or childhood ataxia with central nervous system hypomyelination.

In another aspect, the present invention features a method of treating a disease or disorder related to an amino acid mutation (e.g., an amino acid deletion, amino acid addition, or amino acid substitution) in a gene or gene product (e.g., RNA or protein) that modulates (e.g., reduces) protein synthesis. In some embodiments, administration of a compound of Formula (I) enhances residual GEF activity of a mutant GEF complex in a subject.

In another aspect, the present invention features a composition for use in treating a neurodegenerative disease, a leukodystrophy, cancer, an inflammatory disease, a musculoskeletal disease, a metabolic disease, or a mitochondrial disease in a subject, wherein the composition comprises a compound of Formula (I) or a pharmaceutically acceptable salt, solvate, hydrate, tautomer, N-oxide or stereoisomer thereof.

In some embodiments, the neurodegenerative disease comprises vanishing white matter disease, childhood ataxia with CNS hypo-myelination, a leukodystrophy, a leukoencephalopathy, hypomyelinating or demyelinating disease, an intellectual disability syndrome, progressive supranuclear palsy, corticobasal degeneration, adrenoleukodystrophy, X-linked adrenoleukodystrophy, cerebral adrenoleukodystrophy, Pelizaeus-Merzbacher Disease, Krabbe disease, leukodystrophy due to mutation in DARS2 gene (sometimes known as lukoencephalopathy with brainstem and spinal cord involvement and lactate elevation (LBSL), DARS2-related spectrum disorders, Alzheimer's disease, amyotrophic lateral sclerosis, Creutzfeldt-Jakob disease, frontotemporal dementia, Gerstmann-Straussler-Scheinker disease, Huntington's disease, dementia (e.g., HIV-associated dementia or Lewy body dementia), kuru, Parkinson's disease, progressive nuclear palsy, a tauopathy, or a prion disease. In some embodiments, the neurodegenerative disease comprises vanishing white matter disease. In some embodiments, the neurodegenerative disease comprises a psychiatric disease such as agoraphobia, Alzheimer's disease, anorexia nervosa, amnesia, anxiety disorder, bipolar disorder, body dysmorphic disorder, bulimia nervosa, claustrophobia, depression, delusions, Diogenes syndrome, dyspraxia, insomnia, Munchausen's syndrome, narcolepsy, narcissistic personality disorder, obsessive-compulsive disorder, psychosis, phobic disorder, schizophrenia, seasonal affective disorder, schizoid personality disorder, sleepwalking, social phobia, substance abuse, tardive dyskinesia, Tourette syndrome, or trichotillomania. In some embodiments, the neurodegenerative disease comprises a disease or disorder with symptoms of cognitive impairment or cognitive decline such as Alzheimer's disease, Parkinson's disease, Huntington's disease, schizophrenia, autism, frontotemporal dementia, dementia (e.g., HIV-associated dementia or Lewy body dementia), age related dementia, chronic traumatic encephalopathy, HIV-induced neurocognitive impairment, a HIV-associated neurocognitive disorder, a hypoxic injury (e.g., premature brain injury, chronic perinatal hypoxia), traumatic brain injury, stroke, or postoperative cognitive dysfunction. In some embodiments, the neurodegenerative disease comprises an intellectual disability syndrome. In some embodiments, the neurodegenerative disease comprises mild cognitive impairment.

In some embodiments, the cancer comprises pancreatic cancer, breast cancer, multiple myeloma, or a cancer of the secretory cells. In some embodiments, the method comprises the treatment of cancer in combination with a chemotherapeutic agent for the enhancement of memory (e.g., long term memory).

In some embodiments, the inflammatory disease comprises postoperative cognitive dysfunction, traumatic brain injury, arthritis (e.g., rheumatoid arthritis, psoriatic arthritis, or juvenile idiopathic arthritis), systemic lupus erythematosus (SLE), myasthenia gravis, diabetes (e.g., juvenile onset diabetes or diabetes mellitus type 1), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves' ophthalmopathy, inflammatory bowel disease, Addison's disease, vitiligo, asthma (e.g., allergic asthma), acne vulgaris, celiac disease, chronic prostatitis, pelvic inflammatory disease, reperfusion injury, sarcoidosis, transplant rejection, interstitial cystitis, or atopic dermatitis.

In some embodiments, the musculoskeletal disease comprises muscular dystrophy, multiple sclerosis, Freidrich's ataxia, a muscle wasting disorder (e.g., muscle atrophy, sarcopenia, cachexia), inclusion body myopathy, progressive muscular atrophy, motor neuron disease, carpal tunnel syndrome, epicondylitis, tendinitis, back pain, muscle pain, muscle soreness, repetitive strain disorders, or paralysis.

In some embodiments, the metabolic disease comprises non-alcoholic steatohepatitis (NASH), non-alcoholic fatty liver disease (NAFLD), liver fibrosis, obesity, heart disease, atherosclerosis, arthritis, cystinosis, phenylketonuria, proliferative retinopathy, or Kearns-Sayre disease.

In some embodiments, the mitochondrial disease is associated with, or is a result of, or is caused by mitochondrial dysfunction, one or more mitochondrial protein mutations, or one or more mitochondrial DNA mutations. In some embodiments, the mitochondrial disease is a mitochondrial myopathy. In some embodiments, the mitochondrial disease, e.g., the mitochondrial myopathy, is selected from the group consisting of Barth syndrome, chronic progressive external ophthalmoplegia (cPEO), Kearns-Sayre syndrome (KSS), Leigh syndrome (e.g., MILS, or maternally inherited Leigh syndrome), mitochondrial DNA depletion syndromes (MDDS, e.g., Alpers syndrome), mitochondrial encephalomyopathy (e.g., mitochondrial encephalomyopathy, lactic acidosis, and stroke-like episodes (MELAS)), mitochondrial neurogastrointestinal encephalomyopathy (MNGIE), myoclonus epilepsy with ragged red fibers (MERRF), neuropathy, ataxia, retinitis pigmentosa (NARP), Leber's hereditary optic neuropathy (LHON), and Pearson syndrome.

In another aspect, the present invention features a composition for use in treating a disease or disorder related to modulation (e.g., a decrease) in eIF2B activity or level, modulation (e.g., a decrease) of eIF2α activity or level, modulation (e.g., an increase) in eIF2α phosphorylation, modulation (e.g., an increase) of phosphorylated eIF2α pathway activity, or modulation (e.g., an increase) of ISR activity in a subject, wherein the composition comprises a compound of Formula (I) or a pharmaceutically acceptable salt, solvate, hydrate, tautomer, N-oxide or stereoisomer thereof. In some embodiments, the disease may be caused by a mutation to a gene or protein sequence related to a member of the eIF2 pathway (e.g., the eIF2α signaling pathway or ISR pathway).

In another aspect, the present invention features a composition for use in treating a leukodystrophy such as vanishing white matter disease (VWMD) or childhood ataxia with central nervous system hypomyelination. In some embodiments, the leukodystrophy is characterized by an amino acid mutation (e.g., an amino acid deletion, amino acid addition, or amino acid substitution) in a tRNA synthetase. In some embodiments, the composition comprising a compound of Formula (I) enhances eIF2B activity in a subject with a leukodystrophy, such as vanishing white matter disease (VWMD) or childhood ataxia with central nervous system hypomyelination.

In another aspect, the present invention features a composition for use in treating a disease or disorder related to an amino acid mutation (e.g., an amino acid deletion, amino acid addition, or amino acid substitution) in a gene or gene product (e.g., RNA or protein) that modulates (e.g., reduces) protein synthesis. In some embodiments, the composition comprising a compound of Formula (I) enhances residual GEF activity of a mutant GEF complex in a subject.

DETAILED DESCRIPTION OF THE INVENTION

The present invention features compounds, compositions, and methods comprising a compound of Formula (I) or a pharmaceutically acceptable salt, solvate, hydrate, tautomer, N-oxide or stereoisomer thereof for use, e.g., in the modulation (e.g., activation) of eIF2B and the attenuation of the ISR signaling pathway.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound.

In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and 14C; O may be in any isotopic form, including $^{16}O$ and $^{18}O$; and the like.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_1$-$C_{20}$ alkyl"). In some embodiments, an alkyl group has 1 to 12 carbon atoms ("$C_1$-$C_{12}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$ alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_1$-10 alkyl (e.g., —$CH_3$). In certain embodiments, the alkyl group is substituted $C_{1-6}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. The term "alkenylene," by itself or as part of another substituent, means, unless otherwise stated, a divalent radical derived from an alkene. An alkylene group may be described as, e.g., a $C_1$-$C_6$-membered alkylene, wherein the term "membered" refers to the non-hydrogen atoms within the moiety.

"Alkenyl" refers to a radical of a straight-chain or branched hydrocarbon group having from 2 to 20 carbon atoms, one or more carbon-carbon double bonds, and no triple bonds ("$C_2$-$C_{20}$ alkenyl"). In some embodiments, an alkenyl group has 2 to 10 carbon atoms ("$C_2$-$C_{10}$ alkenyl"). In some embodiments, an alkenyl group has 2 to 8 carbon atoms ("$C_2$-$C_8$ alkenyl"). In some embodiments, an alkenyl group has 2 to 6 carbon atoms ("$C_2$-$C_6$ alkenyl"). In some embodiments, an alkenyl group has 2 to 5 carbon atoms ("$C_2$-$C_5$ alkenyl"). In some embodiments, an alkenyl group has 2 to 4 carbon atoms ("$C_2$-$C_4$ alkenyl"). In some embodiments, an alkenyl group has 2 to 3 carbon atoms ("$C_2$-$C_3$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_2$-4 alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-6}$ alkenyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include, but are not limited to, phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents. In certain embodiments, the aryl group is unsubstituted $C_6$-$C_{14}$ aryl. In certain embodiments, the aryl group is substituted $C_6$-$C_{14}$ aryl.

In certain embodiments, an aryl group is substituted with one or more of groups selected from halo, $C_1$-$C_8$ alkyl, halo-$C_1$-$C_8$ alkyl, haloxy-$C_1$-$C_8$ alkyl, cyano, hydroxy, alkoxy $C_1$-$C_8$ alkyl, and amino.

Examples of representative substituted aryls include the following

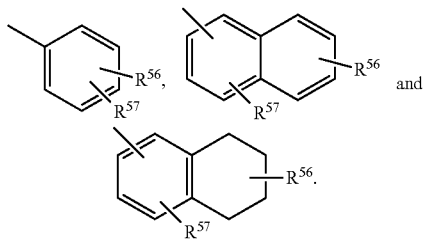

wherein one of $R^{56}$ and $R^{57}$ may be hydrogen and at least one of $R^{56}$ and $R^{57}$ is each independently selected from $C_1$-$C_8$ alkyl, halo-$C_1$-$C_8$ alkyl, 4-10 membered heterocyclyl, alkanoyl, alkoxy-$C_1$-$C_8$ alkyl, heteroaryloxy, alkylamino, arylamino, heteroarylamino, $NR^{58}COR^{59}$, $NR^{58}SOR^{59}NR^{58}SO_2R^{59}$, $C(O)Oalkyl$, $C(O)Oaryl$, $CONR^{58}R^{59}$, $CONR^{58}OR^{59}$, $NR^{58}R^{59}$, $SO_2NR^{58}R^{59}$, S-alkyl, S(O)-alkyl, $S(O)_2$-alkyl, S-aryl, S(O)-aryl, $S(O_2)$-aryl; or $R^{56}$ and $R^{57}$ may be joined to form a cyclic ring (saturated or unsaturated) from 5 to 8 atoms, optionally containing one or more heteroatoms selected from the group N, O, or S.

Other representative aryl groups having a fused heterocyclyl group include the following:

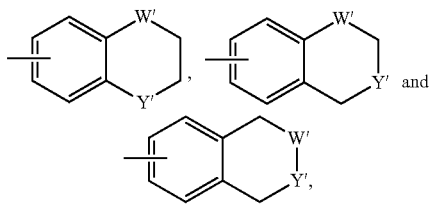

wherein each W' is selected from $C(R^{66})_2$, $NR^{66}$, O, and S; and each Y' is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

"Halo" or "halogen," independently or as part of another substituent, mean, unless otherwise stated, a fluorine (F), chlorine (Cl), bromine (Br), or iodine (I) atom. The term "halide" by itself or as part of another substituent, refers to a fluoride, chloride, bromide, or iodide atom. In certain embodiments, the halo group is either fluorine or chlorine.

Additionally, terms such as "haloalkyl" are meant to include monohaloalkyl and polyhaloalkyl. For example, the term "halo-$C_1$-$C_6$ alkyl" includes, but is not limited to, fluoromethyl, difluoromethyl, trifluoromethyl, 2,2,2-trifluoroethyl, 4-chlorobutyl, 3-bromopropyl, and the like.

The term "heteroalkyl," by itself or in combination with another term, means, unless otherwise stated, a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Exemplary heteroalkyl groups include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)_2$, $-S(O)-CH_3$, $-S(O)_2-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $-O-CH_3$, and $-O-CH_2-CH_3$. Up to two or three heteroatoms may be consecutive, such as, for example, $-CH_2-NH-OCH_3$ and $-CH_2-O-Si(CH_3)_3$. Where "heteroalkyl" is recited, followed by recitations of specific heteroalkyl groups, such as $-CH_2O$, $-NR^BR^C$, or the like, it will be understood that the terms heteroalkyl and $-CH_2O$ or $-NR^BR^C$ are not redundant or mutually exclusive. Rather, the specific heteroalkyl groups are recited to add clarity. Thus, the term "heteroalkyl" should not be interpreted herein as excluding specific heteroalkyl groups, such as $-CH_2O$, $-NR^BR^C$, or the like.

Similarly, the term "heteroalkylene," by itself or as part of another substituent, means, unless otherwise stated, a divalent radical derived from heteroalkyl, as exemplified, but not limited by, $-CH_2O-$ and $-CH_2CH_2O-$. A heteroalkylene group may be described as, e.g., a 2-7-membered heteroalkylene, wherein the term "membered" refers to the non-hydrogen atoms within the moiety. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ may represent both $-C(O)_2R'-$ and $-R'C(O)_2-$.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

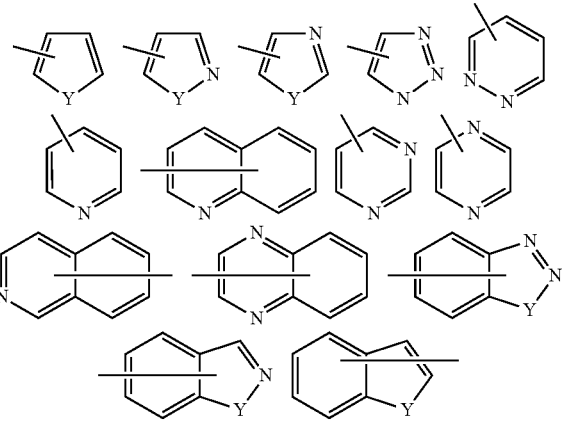

wherein each Y is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 3 to 6 ring carbon atoms ("$C_3$-$C_6$ cycloalkyl"). In some embodiments, a cycloalkyl group has 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety.

Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_8$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is a substituted $C_3$-$C_{10}$ cycloalkyl.

In some embodiments, "cycloalkyl" is a monocyclic, saturated cycloalkyl group having from 3 to 10 ring carbon atoms ("$C_3$-$C_{10}$ cycloalkyl"). In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 5 to 6 ring carbon atoms ("$C_5$-$C_6$ cycloalkyl"). In some embodiments, a cycloalkyl group has 5 to 10 ring carbon atoms ("$C_5$-$C_{10}$ cycloalkyl"). Examples of $C_5$-$C_6$ cycloalkyl groups include cyclopentyl ($C_7$) and cyclohexyl ($C_8$). Examples of $C_3$-$C_6$ cycloalkyl groups include the aforementioned $C_5$-$C_6$ cycloalkyl groups as well as cyclopropyl ($C_3$) and cyclobutyl ($C_4$). Examples of $C_3$-$C_8$ cycloalkyl groups include the aforementioned $C_3$-$C_6$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is substituted $C_3$-$C_{10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

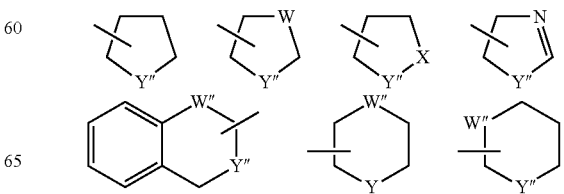

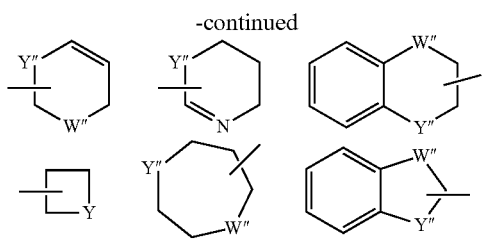

wherein each W" is selected from CR$^{67}$, C(R$^{67}$)$_2$, NR$^{67}$, O, and S; and each Y" is selected from NR$^{67}$, O, and S; and R$^{67}$ is independently hydrogen, C$_1$-C$_8$ alkyl, C$_3$-C$_{10}$ cycloalkyl, 4-10 membered heterocyclyl, C$_6$-C$_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine.

Particular examples include azetidine, piperidone and piperazone.

"Amino" refers to the radical —NR$^{70}$R$^{71}$, wherein R$^{70}$ and R$^{71}$ are each independently hydrogen, C$_1$-C$_8$ alkyl, C$_3$-C$_{10}$ cycloalkyl, 4-10 membered heterocyclyl, C$_6$-C$_{10}$ aryl, and 5-10-membered heteroaryl. In some embodiments, amino refers to NH$_2$.

"Cyano" refers to the radical —CN.
"Hydroxy" refers to the radical —OH.
Alkyl, alkenyl, alkynyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al, *Journal of Pharmaceutical Science* 66: 1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in a first buffer, e.g., in 1 mM-50 mM histidine, 0.1%-2% sucrose, 2%-7% mannitol at a pH range of 4.5 to 5.5, that is combined with a second buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer (e.g. pancreatic cancer, breast cancer, multiple myeloma, cancers of secretory cells), neurodegenerative diseases (e.g. Alzheimer's disease, Parkinson's disease, frontotemporal dementia), leukodystrophies (e.g., vanishing white matter disease, childhood ataxia with CNS hypo-myelination), postsurgical cognitive dysfunction, traumatic brain injury, stroke, spinal cord injury, intellectual disability syndromes, inflammatory diseases, musculoskeletal diseases, metabolic diseases, or diseases or disorders associated with impaired function of eIF2B or components in a signal transduction or signaling pathway including the ISR and decreased eIF2 pathway activity). For example certain methods herein treat cancer by decreasing or reducing or preventing the occurrence, growth, metastasis, or progression of cancer or decreasing a symptom of cancer; treat neurodegeneration by improving mental wellbeing, increasing mental function, slowing the decrease of mental function, decreasing dementia, delaying the onset of dementia, improving cognitive skills, decreasing the loss of cognitive skills, improving memory, decreasing the degradation of memory, decreasing a symptom of neurodegeneration or extending survival; treat vanishing white matter disease by reducing a symptom of vanishing white matter disease or reducing the loss of white matter or reducing the loss of myelin or increasing the amount of myelin or increasing the amount of white matter; treat childhood ataxia with CNS hypo-myelination by decreasing a symptom of childhood ataxia with CNS hypo-myelination or increasing the level of myelin or decreasing the loss of myelin; treat an intellectual disability syndrome by decreasing a symptom of an intellectual disability syndrome, treat an inflammatory disease by treating a symptom of the inflammatory disease; treat a musculoskeletal disease by treating a symptom of the musculoskeletal disease; or treat a metabolic disease by treating a symptom of the metabolic disease. Symptoms of a disease, disorder, or condition described herein (e.g., cancer, a neurodegenerative disease, a leukodystrophy, an inflammatory disease, a musculoskeletal disease, a metabolic disease, or a condition or disease associated with impaired function of eIF2B or components in a signal transduction pathway including the eIF2 pathway, eIF2α phosphorylation. or ISR pathway) would be known or may be determined by a person of ordinary skill in the art. The term "treating" and conjugations thereof, include prevention of an injury, pathology, condition, or disease (e.g.

preventing the development of one or more symptoms of a disease, disorder, or condition described herein).

An "effective amount" is an amount sufficient to accomplish a stated purpose (e.g. achieve the effect for which it is administered, treat a disease, reduce enzyme activity, increase enzyme activity, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

A "reduction" of a symptom or symptoms (and grammatical equivalents of this phrase) means decreasing of the severity or frequency of the symptom(s), or elimination of the symptom(s).

The term "associated" or "associated with" in the context of a substance or substance activity or function associated with a disease (e.g., a disease or disorder described herein, e.g., cancer, a neurodegenerative disease, a leukodystrophy, an inflammatory disease, a musculoskeletal disease, a metabolic disease, or a disease or disorder associated with impaired function of eIF2B or components in a signal transduction pathway including the eIF2 pathway, eIF2α phosphorylation. or ISR pathway) means that the disease is caused by (in whole or in part), or a symptom of the disease is caused by (in whole or in part) the substance or substance activity or function. For example, a symptom of a disease or condition associated with an impaired function of the eIF2B may be a symptom that results (entirely or partially) from a decrease in eIF2B activity (e.g. decrease in eIF2B activity or levels, increase in eIF2α phosphorylation or activity of phosphorylated eIF2α or reduced eIF2 activity or increase in activity of phosphorylated eIF2α signal transduction or the ISR signalling pathway). As used herein, what is described as being associated with a disease, if a causative agent, could be a target for treatment of the disease. For example, a disease associated with decreased eIF2 activity or eIF2 pathway activity, may be treated with an agent (e.g., compound as described herein) effective for increasing the level or activity of eIF2 or eIF2 pathway or a decrease in phosphorylated eIF2α activity or the ISR pathway. For example, a disease associated with phosphorylated eIF2α may be treated with an agent (e.g., compound as described herein) effective for decreasing the level of activity of phosphorylated eIF2α or a downstream component or effector of phosphorylated eIF2α. For example, a disease associated with eIF2α may be treated with an agent (e.g., compound as described herein) effective for increasing the level of activity of eIF2 or a downstream component or effector of eIF2.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. eIF2B, eIF2α, or a component of the eIF2 pathway or ISR pathway). In some embodiments contacting includes allowing a compound described herein to interact with a protein or enzyme that is involved in a signaling pathway (e.g. eIF2B, eIF2α, or a component of the eIF2 pathway or ISR pathway).

As defined herein, the term "inhibition", "inhibit", "inhibiting" and the like in reference to a protein-inhibitor (e.g., antagonist) interaction means negatively affecting (e.g., decreasing) the activity or function of the protein relative to the activity or function of the protein in the absence of the inhibitor. In some embodiments, inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a decrease in the activity of a signal transduction pathway or signaling pathway (e.g., eIF2B, eIF2α, or a component of the eIF2 pathway, pathway activated by eIF2α phosphorylation, or ISR pathway). Thus, inhibition may include, at least in part, partially or totally decreasing stimulation, decreasing or reducing activation, or inactivating, desensitizing, or down-regulating signal transduction or enzymatic activity or the amount of a protein increased in a disease (e.g. eIF2B, eIF2α, or a component of the eIF2 pathway or ISR pathway, wherein each is associated with cancer, a neurodegenerative disease, a leukodystrophy, an inflammatory disease, a musculoskeletal disease, or a metabolic disease). Inhibition may include, at least in part, partially or totally decreasing stimulation, decreasing or reducing activation, or deactivating, desensitizing, or down-regulating signal transduction or enzymatic activity or the amount of a protein (e.g. eIF2B, eIF2α, or component of the eIF2 pathway or ISR pathway) that may modulate the level of another protein or increase cell survival (e.g., decrease in phosphorylated eIF2α pathway activity may increase cell survival in cells that may or may not have an increase in phosphorylated eIF2α pathway activity relative to a non-disease control or decrease in eIF2α pathway activity may increase cell survival in cells that may or may not have an increase in eIF2α pathway activity relative to a non-disease control).

As defined herein, the term "activation", "activate", "activating" and the like in reference to a protein-activator (e.g. agonist) interaction means positively affecting (e.g. increasing) the activity or function of the protein (e.g. eIF2B, eIF2α, or component of the eIF2 pathway or ISR pathway) relative to the activity or function of the protein in the absence of the activator (e.g. compound described herein). In some embodiments, activation refers to an increase in the activity of a signal transduction pathway or signaling pathway (e.g. eIF2B, eIF2α, or component of the eIF2 pathway or ISR pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. level of eIF2B, eIF2α, or component of the eIF2 pathway or ISR pathway associated with cancer, a neurodegenerative disease, a leukodystrophy, an inflammatory disease, a musculoskeletal disease, or a metabolic disease). Activation may include, at least in part, partially or totally increasing stimulation, increasing or enabling activation, or activating, sensitizing, or up-regulating signal transduction or enzymatic activity or the amount of a protein (e.g., eIF2B, eIF2α, or component of the eIF2 pathway or ISR pathway) that may modulate the level of another protein or increase cell survival (e.g., increase in eIF2α activity may increase cell survival in cells that may or may not have a reduction in eIF2α activity relative to a non-disease control).

The term "modulation" refers to an increase or decrease in the level of a target molecule or the function of a target molecule. In some embodiments, modulation of eIF2B, eIF2α, or a component of the eIF2 pathway or ISR pathway may result in reduction of the severity of one or more symptoms of a disease associated with eIF2B, eIF2α, or a component of the eIF2 pathway or ISR pathway (e.g., cancer, a neurodegenerative disease, a leukodystrophy, an inflammatory disease, a musculoskeletal disease, or a metabolic disease) or a disease that is not caused by eIF2B, eIF2α, or a component of the eIF2 pathway or ISR pathway but may benefit from modulation of eIF2B, eIF2α, or a component of the eIF2 pathway or ISR pathway (e.g., decreasing in level or level of activity of eIF2B, eIF2α or a component of the eIF2 pathway).

The term "modulator" as used herein refers to modulation of (e.g., an increase or decrease in) the level of a target molecule or the function of a target molecule. In embodiments, a modulator of eIF2B, eIF2α, or component of the eIF2 pathway or ISR pathway is an anti-cancer agent. In embodiments, a modulator of eIF2B, eIF2α, or component of the eIF2 pathway or ISR pathway is a neuroprotectant. In embodiments, a modulator of eIF2B, eIF2α, or component of the eIF2 pathway or ISR pathway is a memory enhancing agent. In embodiments, a modulator of eIF2B, eIF2α, or component of the eIF2 pathway or ISR pathway is a memory enhancing agent (e.g., a long term memory enhancing agent). In embodiments, a modulator of eIF2B, eIF2α, or component of the eIF2 pathway or ISR pathway is an anti-inflammatory agent. In some embodiments, a modulator of eIF2B, eIF2α, or component of the eIF2 pathway or ISR pathway is a pain-relieving agent.

"Patient" or "subject in need thereof refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a domesticated animal. In some embodiments, a patient is a dog. In some embodiments, a patient is a parrot. In some embodiments, a patient is livestock animal. In some embodiments, a patient is a mammal. In some embodiments, a patient is a cat. In some embodiments, a patient is a horse. In some embodiments, a patient is bovine. In some embodiments, a patient is a canine. In some embodiments, a patient is a feline. In some embodiments, a patient is an ape. In some embodiments, a patient is a monkey. In some embodiments, a patient is a mouse. In some embodiments, a patient is an experimental animal. In some embodiments, a patient is a rat. In some embodiments, a patient is a hamster. In some embodiments, a patient is a test animal. In some embodiments, a patient is a newborn animal. In some embodiments, a patient is a newborn human. In some embodiments, a patient is a newborn mammal. In some embodiments, a patient is an elderly animal. In some embodiments, a patient is an elderly human. In some embodiments, a patient is an elderly mammal. In some embodiments, a patient is a geriatric patient.

"Disease", "disorder" or "condition" refers to a state of being or health status of a patient or subject capable of being treated with a compound, pharmaceutical composition, or method provided herein. In some embodiments, the compounds and methods described herein comprise reduction or elimination of one or more symptoms of the disease, disorder, or condition, e.g., through administration of a compound of Formula (I) or a pharmaceutically acceptable salt thereof.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., anti-cancer agent, chemotherapeutic, or treatment for a neurodegenerative disease). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation).

The term "eIF2B" as used herein refers to the heteropentameric eukaryotic translation initiation factor 2B. eIF2B is composed of five subunits: eIF2B1, eIF2B2, eIF2B3, eIF2B4 and eIF2B5. eIF2B1 refers to the protein associated with Entrez gene 1967, OMIM 606686, Uniprot Q14232, and/or RefSeq (protein) NP_001405. eIF2B2 refers to the protein associated with Entrez gene 8892, OMIM 606454, Uniprot P49770, and/or RefSeq (protein) NP_055054. eIF2B3 refers to the protein associated with Entrez gene 8891, OMIM 606273, Uniprot Q9NR50, and/or RefSeq (protein) NP_065098. eIF2B4 refers to the protein associated with Entrez gene 8890, OMIM 606687, Uniprot Q9UI10, and/or RefSeq (protein) NP_751945. eIF2B5 refers to the protein associated with Entrez gene 8893, OMIM 603945, Uniprot Q13144, and/or RefSeq (protein) NP_003898.

The terms "eIF2alpha," "eIF2α," or "eIF2α" are interchangeable and refer to the protein "eukaryotic translation initiation factor 2 alpha subunit eIF2S1". In embodiments, "eIF2alpha", "eIF2α" or "eIF2α" refer to the human protein. Included in the terms "eIF2alpha", "eIF2α" or "eIF2α" are the wildtype and mutant forms of the protein. In embodiments, "eIF2alpha", "eIF2α" or "eIF2α" refer to the protein associated with Entrez Gene 1965, OMIM 603907, UniProt P05198, and/or RefSeq (protein) NP_004085. In embodiments, the reference numbers immediately above refer to the protein and associated nucleic acids known as of the date of filing of this application.

Compounds

Disclosed herein, for example, is a compound of Formula (I):

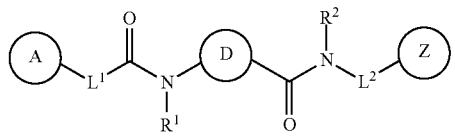

Formula (I)

or a pharmaceutically acceptable salt, solvate, hydrate, tautomer, N-oxide, or stereoisomer thereof, wherein:

D is cyclohexyl or cyclobutyl, each optionally substituted with 1-4 $R^X$;

$L^1$ is a bond, $C_1$-$C_6$ alkylene, 2-7 membered heteroalkylene, —$NR^{N1}$—, or —O—, wherein $C_1$-$C_6$ alkylene or 2-7 membered heteroalkylene is optionally substituted with 1-5 $R^{L1}$;

$R^1$ is hydrogen or $C_1$-$C_6$ alkyl;

$L^2$ is a bond, $C_1$-$C_6$ alkylene, or 2-7 membered heteroalkylene, wherein $C_1$-$C_6$ alkylene or 2-7 membered heteroalkylene is optionally substituted with 1-5 $R^{L2}$;

$R^2$ is hydrogen or $C_1$-$C_6$ alkyl; or $L^2$ and $R^2$, together with the nitrogen to which they are attached, form a 4-9 membered monocyclic, bridged bicyclic, fused bicyclic or spirocyclic heterocyclyl; wherein the 4-9 membered monocyclic, bridged bicyclic, fused bicyclic or spirocyclic heterocyclyl is optionally substituted on one or more available carbons with 1-5 $R^W$; and wherein if the 4-9 membered monocyclic, bridged bicyclic, fused bicyclic or spirocyclic heterocyclyl contains a substitutable nitrogen moiety, the substitutable nitrogen may be optionally substituted with $R^{N2}$;

one $R^Y$, $R^2$ and $L^2$, together with the nitrogen to which they are attached, form a 4-9 membered monocyclic heterocycle, wherein Z is fused to the formed 4-9 membered monocyclic heterocycle, wherein the available carbon atoms of Z are optionally substituted with 1-4 $R^Y$; and wherein if Z contains a substitutable nitrogen moiety, the substitutable nitrogen may be optionally substituted with $R^{N3}$;

A and Z are each independently phenyl or 5-6-membered heteroaryl, wherein each phenyl or 5-6-membered heteroaryl is optionally substituted on one or more available carbons with 1-5 $R^Y$; and wherein if the 5-6-membered heteroaryl contains a substitutable nitrogen moiety, the substitutable nitrogen may be optionally substituted with $R^{N3}$;

each $R^{L1}$ is independently selected from the group consisting of $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, $NR^BC(O)R^D$, —$C(O)NR^BR^C$, —$C(O)R^D$, —$C(O)OH$, —$C(O)OR^D$, —$SR^E$, —$S(O)RP$, and —$S(O)_2R^D$;

each $R^{L2}$ is independently selected from the group consisting of hydrogen, $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$N^BC(O)R^D$, —$C(O)NR^BR^C$, —$C(O)R^D$, —$C(O)OH$, —$C(O)OR^D$, —$SR^E$, —$S(O)R^D$ and —$S(O)_2R^D$;

$R^{N1}$ is selected from the group consisting of hydrogen, $C_1$-$C_6$ alkyl, hydroxy-$C_2$-$C_6$ alkyl, halo-$C_2$-$C_6$ alkyl, amino-$C_2$-$C_6$ alkyl, cyano-$C_2$-$C_6$ alkyl, —$C(O)NR^BR^C$, —$C(O)R^D$, —$C(O)OR^D$, and —$S(O)_2R^D$;

$R^{N2}$ is selected from the group consisting of hydrogen, $C_1$-$C_6$ alkyl, hydroxy-$C_2$-$C_6$ alkyl, halo-$C_2$-$C_6$ alkyl, amino-$C_2$-$C_6$ alkyl, cyano-$C_2$-$C_6$ alkyl, —$C(O)NR^BR^C$, —$C(O)R^D$, —$C(O)OR^D$, and —$S(O)_2R^D$;

$R^{N3}$ is selected from the group consisting of hydrogen, $C_1$-$C_6$ alkyl, hydroxy-$C_2$-$C_6$ alkyl, halo-$C_2$-$C_6$ alkyl, amino-$C_2$-$C_6$ alkyl, cyano-$C_2$-$C_6$ alkyl, —$C(O)NR^BR^C$, —$C(O)R^D$, —$C(O)OR^D$, and —$S(O)_2R^D$;

each $R^W$ is independently selected from the group consisting of hydrogen, $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$N^BC(O)R^D$, —$C(O)NR^BR^C$, —$C(O)R^D$, —$C(O)OH$, —$C(O)OR^D$, —$SR^E$, —$S(O)R^D$ and —$S(O)_2R^D$;

each $R^X$ is independently selected from the group consisting of hydrogen, $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$N^BC(O)R^D$, —$C(O)NR^BR^C$, —$C(O)R^D$, —$C(O)OH$, —$C(O)OR^D$, —$SR^E$, —$S(O)R^D$ and —$S(O)_2R^D$;

each $R^Y$ is independently selected from the group consisting of hydrogen, $C_1$-$C_6$ alkyl, hydroxy-$C_1$-$C_6$ alkyl, halo-$C_1$-$C_6$ alkyl, halo-$C_1$-$C_6$ alkoxy, amino-$C_1$-$C_6$ alkyl, cyano-$C_1$-$C_6$ alkyl, halo, cyano, —$OR^A$, —$NR^BR^C$, —$N^BC(O)R^D$, —$C(O)NR^BR^C$, —$C(O)R^D$, —$C(O)OH$, —$C(O)OR^D$, —$S(R^F)_m$, —$S(O)R^D$, —$S(O)_2R^D$, and $G^1$; or 2 $R^Y$ groups on adjacent atoms, together with the atoms to which they are attached, form a 3-7 membered fused cycloalkyl, 3-7-membered fused heterocyclyl, fused aryl, or 5-6 membered fused heteroaryl, each of which is optionally substituted with 1-5 $R^X$;

each $G^1$ is independently 3-7-membered cycloalkyl, 3-7-membered heterocyclyl, aryl, or 5-6-membered heteroaryl, wherein each 3-7-membered cycloalkyl, 3-7-membered heterocyclyl, aryl, or 5-6-membered heteroaryl is optionally substituted with 1-3 $R^Z$;

each $R^Z$ is independently selected from the group consisting of $C_1$-$C_6$ alkyl, hydroxy-$C_1$-$C_6$ alkyl, halo-$C_1$-$C_6$ alkyl, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, and —$S(O)_2R^D$;

$R^A$ is, at each occurrence, independently hydrogen, $C_1$-$C_6$ alkyl, halo-$C_1$-$C_6$ alkyl, —$C(O)NR^BR^C$, —$C(O)R^D$, or —$C(O)OR^D$;

each of $R^B$ and $R^C$ is independently hydrogen or $C_1$-$C_6$ alkyl; or $R^B$ and $R^C$ together with the atom to which they are attached form a 3-7-membered heterocyclyl optionally substituted with 1-3 $R^Z$;

each $R^D$ is independently $C_1$-$C_6$ alkyl or halo-$C_1$-$C_6$ alkyl;

each $R^E$ is independently hydrogen, $C_1$-$C_6$ alkyl, or halo-$C_1$-$C_6$ alkyl;

each $R^F$ is independently hydrogen, $C_1$-$C_6$ alkyl, or halo; and m is 1 when $R^F$ is hydrogen or $C_1$-$C_6$ alkyl, 3 when $R^F$ is $C_1$-$C_6$ alkyl, or 5 when $R^F$ is halo.

In some embodiments, D is selected from the group consisting of cyclobutyl and cyclohexyl, each of which is optionally substituted with 1-4 $R^X$ groups. In some embodiments, D is selected from the group consisting of:

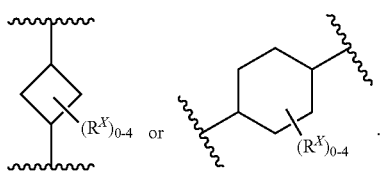

In some embodiments, D is

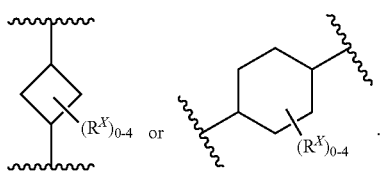

In some embodiments, each $R^X$ is independently selected from the group consisting of oxo, —$OR^A$(e.g., OH or $OCH_3$), —$C(O)OH$, —$C(O)OR^D$ (e.g., —$C(O)OCH_3$), halo, and hydroxy-$C_1$-$C_6$ alkyl.

In some embodiments, $L^1$ is a bond, 2-7 membered heteroalkylene, —$N^{N1}$—, or —O—, wherein 2-7 membered heteroalkylene is optionally substituted with 1-5 $R^{L1}$. In some embodiments, $L^1$ is a bond, 2-7 membered heteroalkylene, —$N^{N1}$—, or —O—, wherein 2-7 membered heteroalkylene is substituted with 0 $R^{L1}$. In some embodiments, $L^1$ is selected from a bond, $CH_2O$—*, $CH_2OCH_2$—*, —$NCH_3$—, —NH—, or —O—, wherein "—*" indicates the attachment point to A.

In some embodiments, $R^1$ is hydrogen or $CH_3$.

In some embodiments, each of A and Z is independently phenyl or 5-6-membered heteroaryl; wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, each of A and Z is independently phenyl, pyridyl, oxazolyl, isoxazolyl, or pyrazolyl, each of which is optionally substituted with 1-5 $R^Y$ groups.

In some embodiments, each of A and Z is selected from the group consisting of:

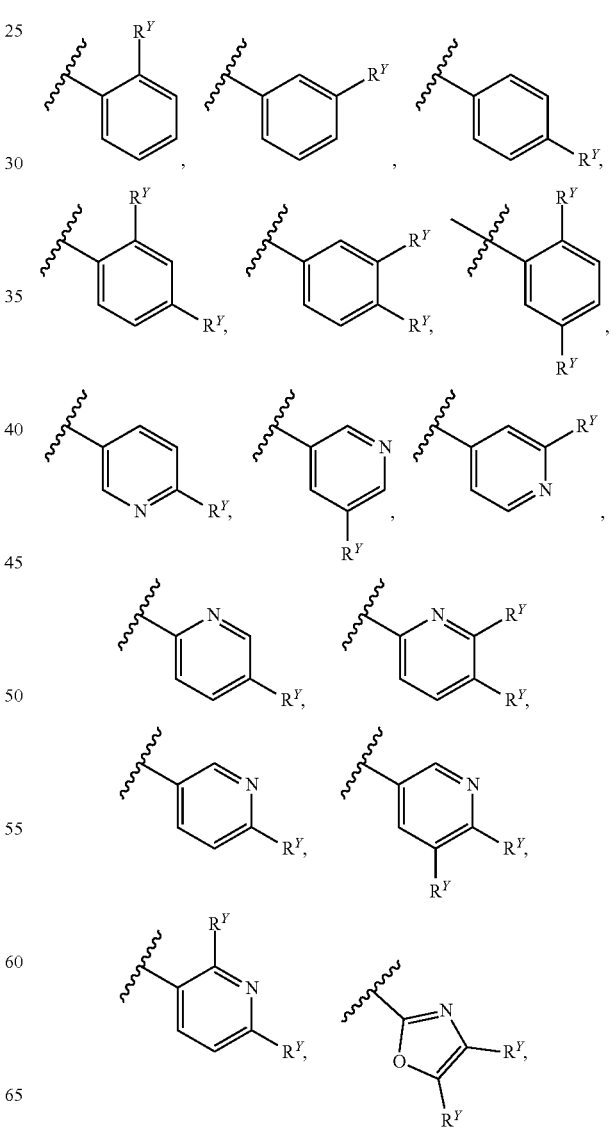

-continued

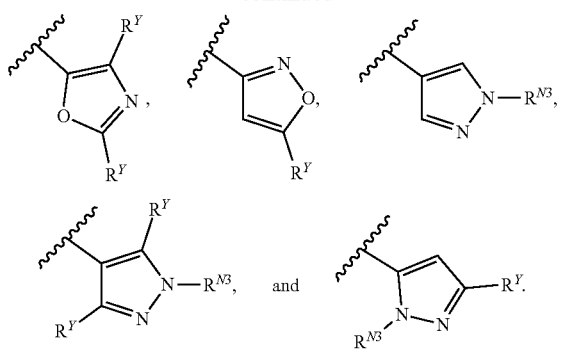

In some embodiments, A is phenyl or pyridyl, each of which is optionally substituted with 1-2 $R^Y$ groups. In some embodiments, A is selected from the group consisting of:

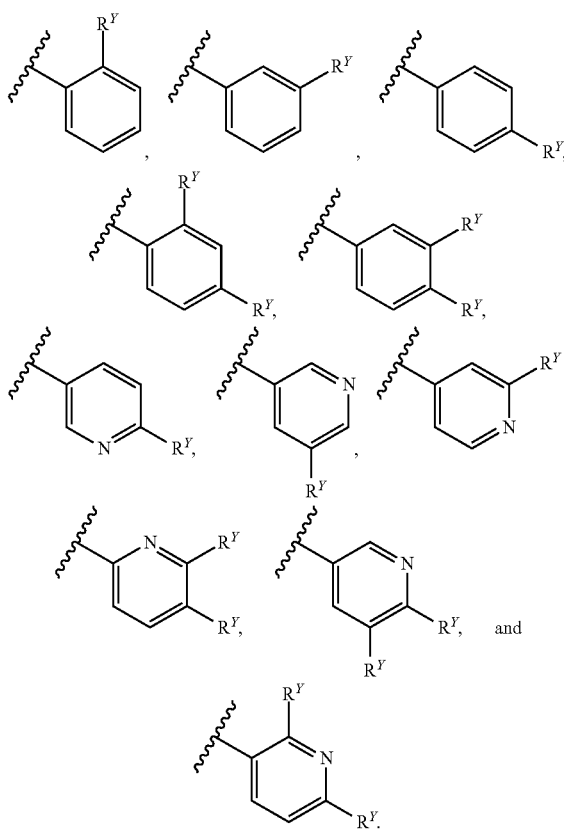

In some embodiments, Z is phenyl, pyridyl, oxazolyl, isoxazolyl, or pyrazolyl, each of which is optionally substituted with 1-2 $R^Y$ groups. In some embodiments, Z is selected from the group consisting of:

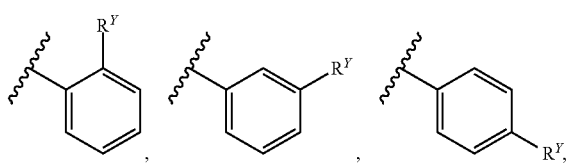

-continued

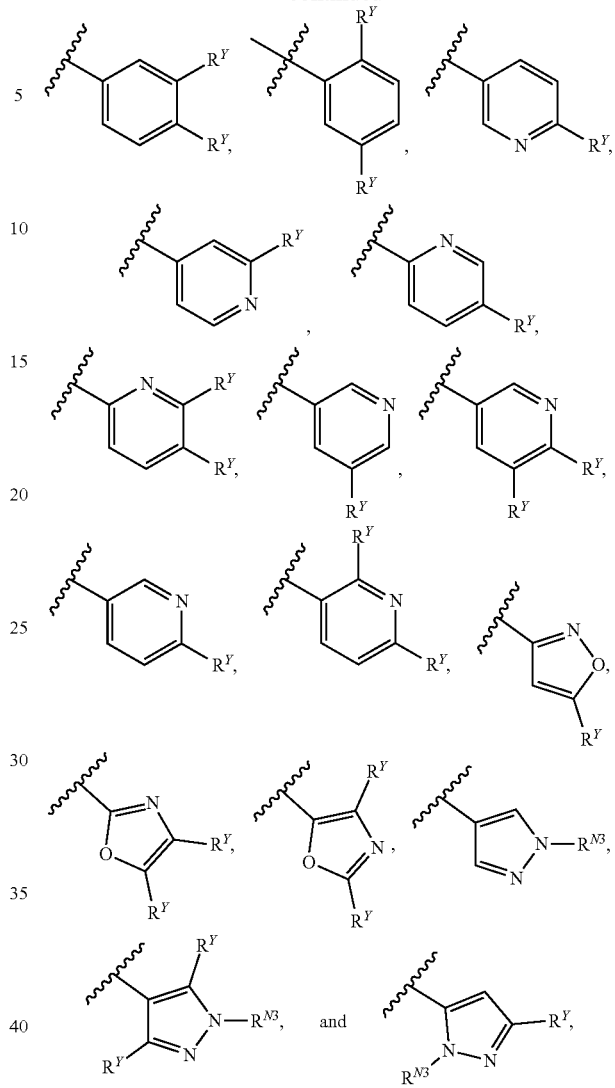

wherein $R^{N3}$ is hydrogen or $CH_3$.

In some embodiments, each $R^Y$ is independently selected from the group consisting of hydrogen, chloro, fluoro, $CHF_2$, $CF_3$, $CH_3$, $CH_2CH_3$, $CH(CH_3)_2$, $OCH_3$, $OCHF_2$, $OCF_3$, $OCH_2CF_3$, $OCH(CH_3)_2$, and CN.

In some embodiments, $L^2$ is a bond or $C_1$-$C_6$ alkylene, wherein $C_1$-$C_6$ alkylene is optionally substituted by 1-5 $R^{L1}$. In some embodiments, $L^2$ is a bond or $C_1$-$C_6$ alkylene, wherein $C_1$-$C_6$ alkylene is substituted by 0 $R^{L1}$. In some embodiments, $L^2$ is selected from a bond or $CH_2$—*, wherein "—*" indicates the attachment point to Z.

In some embodiments, $R^2$ is hydrogen or $CH_3$.

In some embodiments, $L^2$ and $R^2$, together with the nitrogen to which they are attached, form a 4-7 membered monocyclic or 7-9 membered spirocyclic heterocyclyl, each of which is optionally substituted with 1-5 $R^W$.

Is some embodiments, one $R^Y$, $R^2$ and $L^2$, together with the nitrogen to which they are attached, form a 4-9 membered monocyclic heterocycle, wherein Z is fused to the formed 4-9 membered monocyclic heterocycle, wherein the available carbon atoms of Z are optionally substituted with 1-4 $R^Y$; and wherein if Z contains a substitutable nitrogen moiety, the substitutable nitrogen may be optionally substituted with $R^{N3}$.

In some embodiments, the compound is represented by Formula (II):

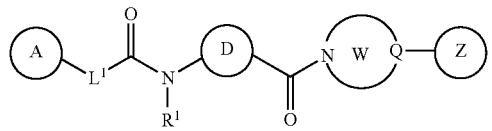

Formula (II)

wherein:

W is a 4-7 membered monocyclic or 7-9 membered spirocyclic heterocyclyl, wherein the 4-7 membered monocyclic or 7-9 membered spirocyclic heterocyclyl is optionally substituted with 1-4 $R^W$;

Q is nitrogen or C($R^Q$); and $R^Q$ is selected from the group consisting of hydrogen, hydroxyl, and $C_1$-$C_6$ alkyl; and wherein each of A, $L^1$, $R^1$, D, and Z is defined as for Formula (I).

In some embodiments, Q is nitrogen.

In some embodiments, W is a piperazine, piperazinone, or 2,6-diazaspiro[3.3]heptane moiety, each of which is optionally substituted with 1-4 $R^W$ groups, and each $R^W$ is independently selected from the group consisting of $C_1$-$C_6$ alkyl, halo-$C_1$-$C_6$ alkyl, halo, oxo, cyano, and —$OR^A$.

In some embodiments, W is selected from the group consisting of:

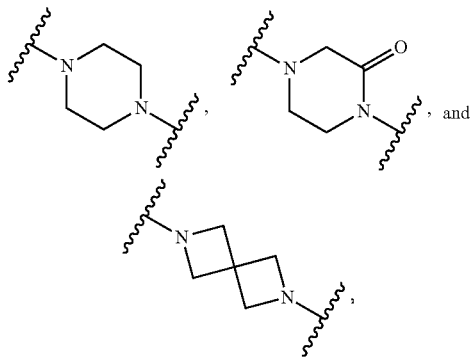

In some embodiments, Q is CH.

In some embodiments, W is an azetidine, pyrrolidine, piperidine, or 2-azaspiro[3.3]heptane moiety, each of which is optionally substituted with 1-4 $R^W$ groups, and each $R^W$ is independently $C_1$-$C_6$ alkyl, halo-$C_1$-$C_6$ alkyl, halo, oxo, cyano, or —$OR^A$.

In some embodiments, W is selected from the group consisting of:

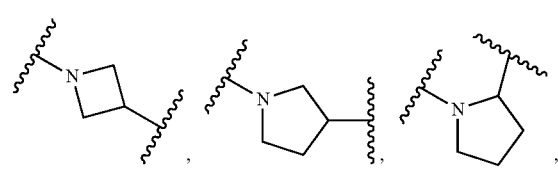

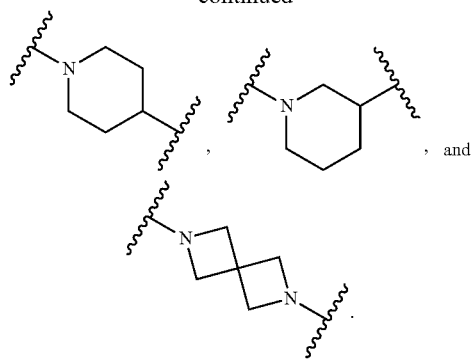

In some embodiments, the compound of Formula (I) is a compound of Formula (I-a):

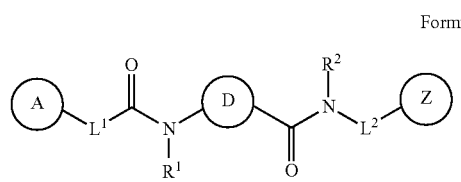

Formula (I-a)

or a pharmaceutically acceptable salt, solvate, hydrate, tautomer, N-oxide, or stereoisomer thereof, wherein:

D is cyclohexyl or cyclobutyl, each optionally substituted with 1-4 $R^X$ groups;

$L^1$ is selected from the group consisting of a bond, $CH_2O$—*, $CH_2OCH_2$—*, —$NCH_3$—, —NH—, and —O—, wherein "—*" indicates the attachment point to A;

$R^1$ is selected from the group consisting of hydrogen and $CH_3$;

$L^2$ is selected from the group consisting of a bond and $CH_2$—*, wherein "—*" indicates the attachment point to Z;

$R^2$ is selected from the group consisting of hydrogen and $CH_3$; or $L^2$ and $R^2$, together with the nitrogen to which they are attached, form an azetidine, pyrrolidine, piperidine, 2-azaspiro[3.3]heptane, piperazine, piperazinone, or 2,6-diazaspiro[3.3]heptane moiety, each of which is optionally substituted with 1-4 $R^W$ groups;

one $R^Y$, $R^2$ and $L^2$, together with the nitrogen to which they are attached, form an azetidine, pyrrolidine or piperidine, wherein Z is fused to the formed azetidine, pyrrolidine or piperidine, wherein the available carbon atoms of Z are optionally substituted with 1-4 $R^Y$; and wherein if Z contains a substitutable nitrogen moiety, the substitutable nitrogen may be optionally substituted with $R^{N3}$;

A is phenyl or pyridyl, each of which is optionally substituted with 1-5 $R^Y$ groups;

Z is phenyl, pyridyl, oxazolyl, isoxazolyl, or pyrazolyl, each of which is optionally substituted on one or more available carbons with 1-5 $R^Y$ groups; and wherein pyrazolyl may be optionally substituted on an available nitrogen with hydrogen or $CH_3$;

each $R^W$ is independently fluoro, chloro, oxo, OH, $OCH_3$, $CF_3$, $CH_3$, $CH_2CH_3$, or $CH(CH_3)_2$;

each $R^X$ is independently fluoro, oxo, OH, $OCH_3$, C(O)OH, or C(O)$OCH_3$;

each $R^Y$ is independently chloro, fluoro, $CHF_2$, $CF_3$, $CH_3$, $CH_2CH_3$, $CH(CH_3)_2$, $OCH_3$, $OCHF_2$, $OCF_3$, $OCH_2CF_3$, $OCH(CH_3)_2$, or CN; or 2 $R^Y$ groups on adjacent atoms, together with the atoms to which they are attached form a furanyl, pyrrolyl, or dioxolanyl ring, each of which is optionally substituted with 1-2 $R^X$.

In some embodiments, the compound of Formula (I) is a compound of Formula (I-b):

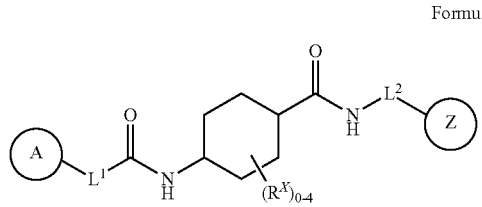

Formula (I-b)

or a pharmaceutically acceptable salt, solvate, hydrate, tautomer, N-oxide, or stereoisomer thereof, wherein each of A, Z, $L^1$, $L^2$, and $R^X$ is defined as for Formula (I).

In some embodiments, each $R^X$ is independently fluoro, oxo, OH, $OCH_3$, C(O)OH, or C(O)$OCH_3$.

In some embodiments, $L^1$ is a bond, 2-7 membered heteroalkylene, $-N^{R1}-$, or $-O-$, wherein 2-7 membered heteroalkylene is optionally substituted with 1-5 RLY. In some embodiments, $L^1$ is a bond, 2-7 membered heteroalkylene, $-NR^{N1}-$, or $-O-$, wherein 2-7 membered heteroalkylene is substituted with 0 $R^{L1}$. In some embodiments, $L^1$ is selected from a bond, $CH_2O-*$, $CH_2OCH_2-*$, $-NCH_3-$, $-NH-$, or $-O-$, wherein "—*" indicates the attachment point to A. In some embodiments, $L^2$ is a bond or $C_1$-$C_6$ alkylene, wherein $C_1$-$C_6$ alkylene is optionally substituted by 1-5 $R^{L1}$. In some embodiments, $L^2$ is a bond or $C_1$-$C_6$ alkylene, wherein $C_1$-$C_6$ alkylene is substituted by 0 $R^{L1}$. In some embodiments, $L^2$ is selected from a bond or $CH_2-*$, wherein "—*" indicates the attachment point to Z.

In some embodiments, each of A and Z is independently phenyl or 5-6-membered heteroaryl; wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, $-OR^4$, or $G^1$. In some embodiments, each of A and Z is independently phenyl, pyridyl, oxazolyl, isoxazolyl, or pyrazolyl, each of which is optionally substituted with 1-5 $R^Y$ groups.

In some embodiments, each of A and Z is selected from the group consisting of:

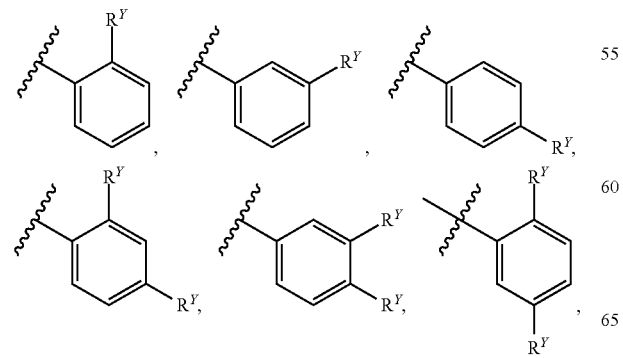

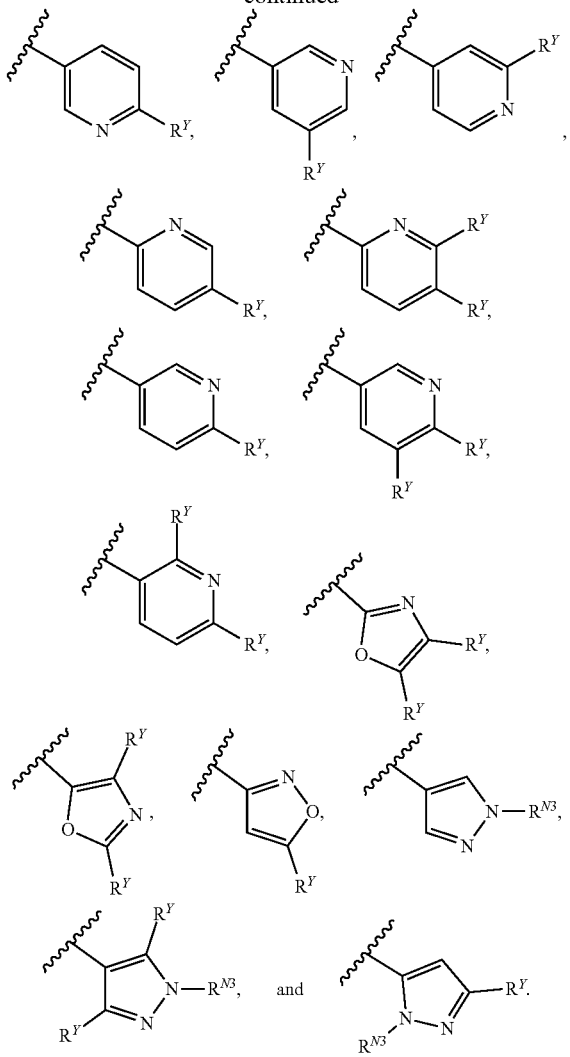

In some embodiments, A is phenyl or pyridyl, each of which is optionally substituted with 1-2 $R^Y$ groups. In some embodiments, A is selected from the group consisting of:

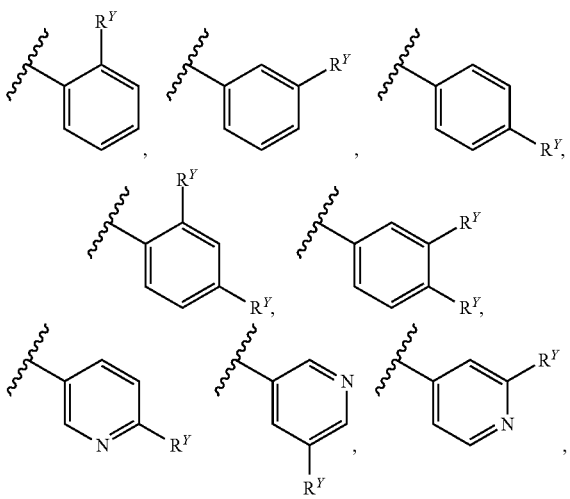

-continued

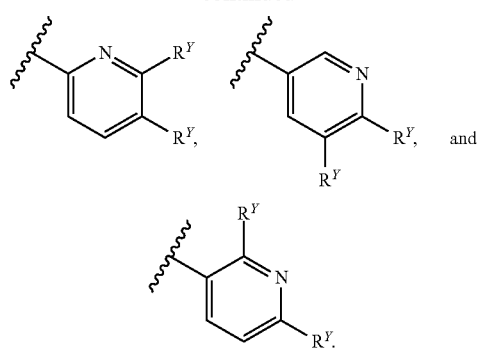

In some embodiments, Z is phenyl, pyridyl, oxazolyl, isoxazolyl, or pyrazolyl, each of which is optionally substituted with 1-2 $R^Y$ groups. In some embodiments, Z is selected from the group consisting of:

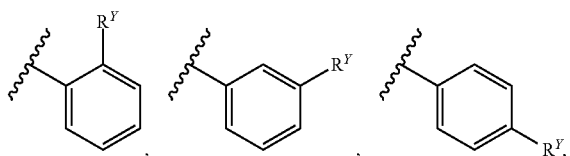

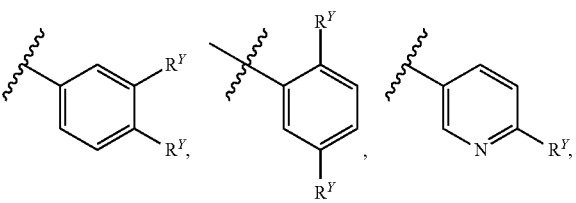

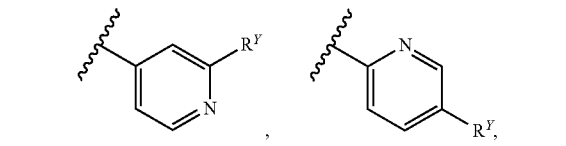

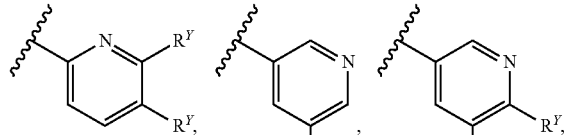

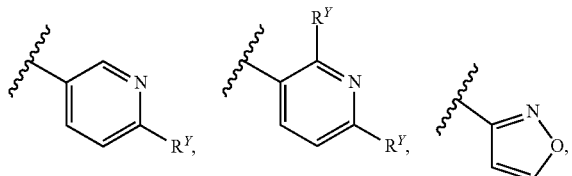

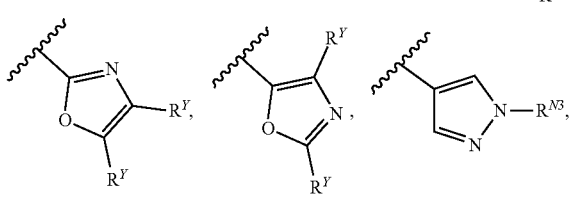

-continued

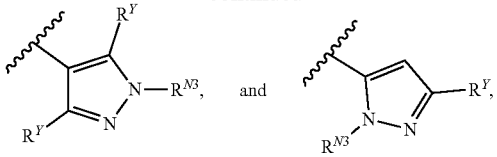

wherein $R^{N3}$ is hydrogen or $CH_3$.

In some embodiments, each $R^Y$ is independently selected from the group consisting of hydrogen, chloro, fluoro, $CHF_2$, $CF_3$, $CH_3$, $CH_2CH_3$, $CH(CH_3)_2$, $OCH_3$, $OCHF_2$, $OCF_3$, $OCH_2CF_3$, $OCH(CH_3)_2$, and CN.

In some embodiments, the compound of Formula (I) is a compound of Formula (I-c):

Formula (I-c)

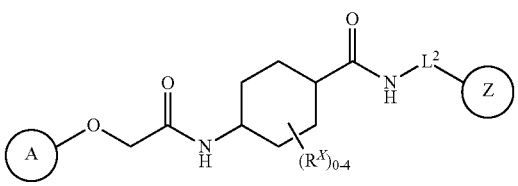

or a pharmaceutically acceptable salt, solvate, hydrate, tautomer, N-oxide, or stereoisomer thereof, wherein each of A, Z, $L^2$, and $R^X$ is defined as for Formula (I).

In some embodiments, each $R^X$ is independently fluoro, oxo, OH, $OCH_3$, C(O)OH, or C(O)$OCH_3$.

In some embodiments, each of A and Z is independently phenyl or 5-6-membered heteroaryl; wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, each of A and Z is independently phenyl, pyridyl, oxazolyl, isoxazolyl, or pyrazolyl, each of which is optionally substituted with 1-5 $R^Y$ groups.

In some embodiments, each of A and Z is selected from the group consisting of:

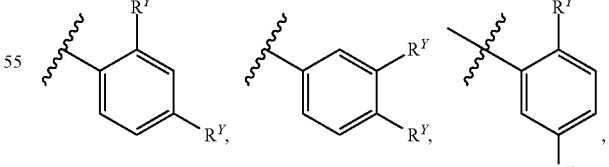

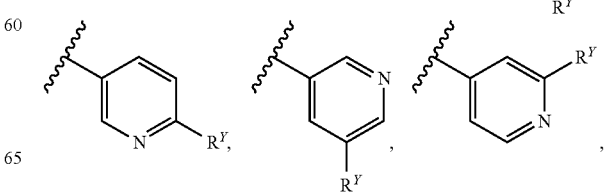

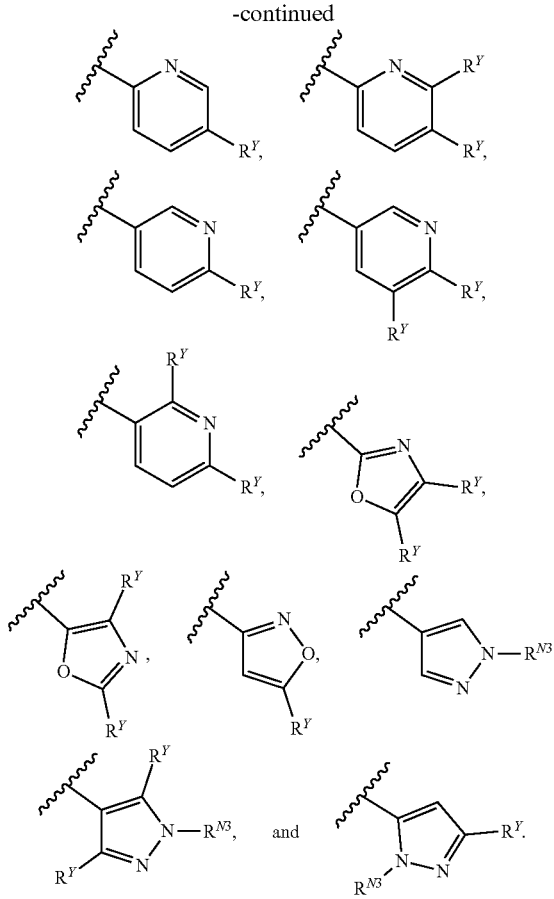
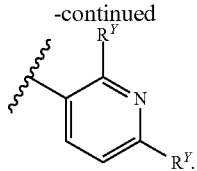
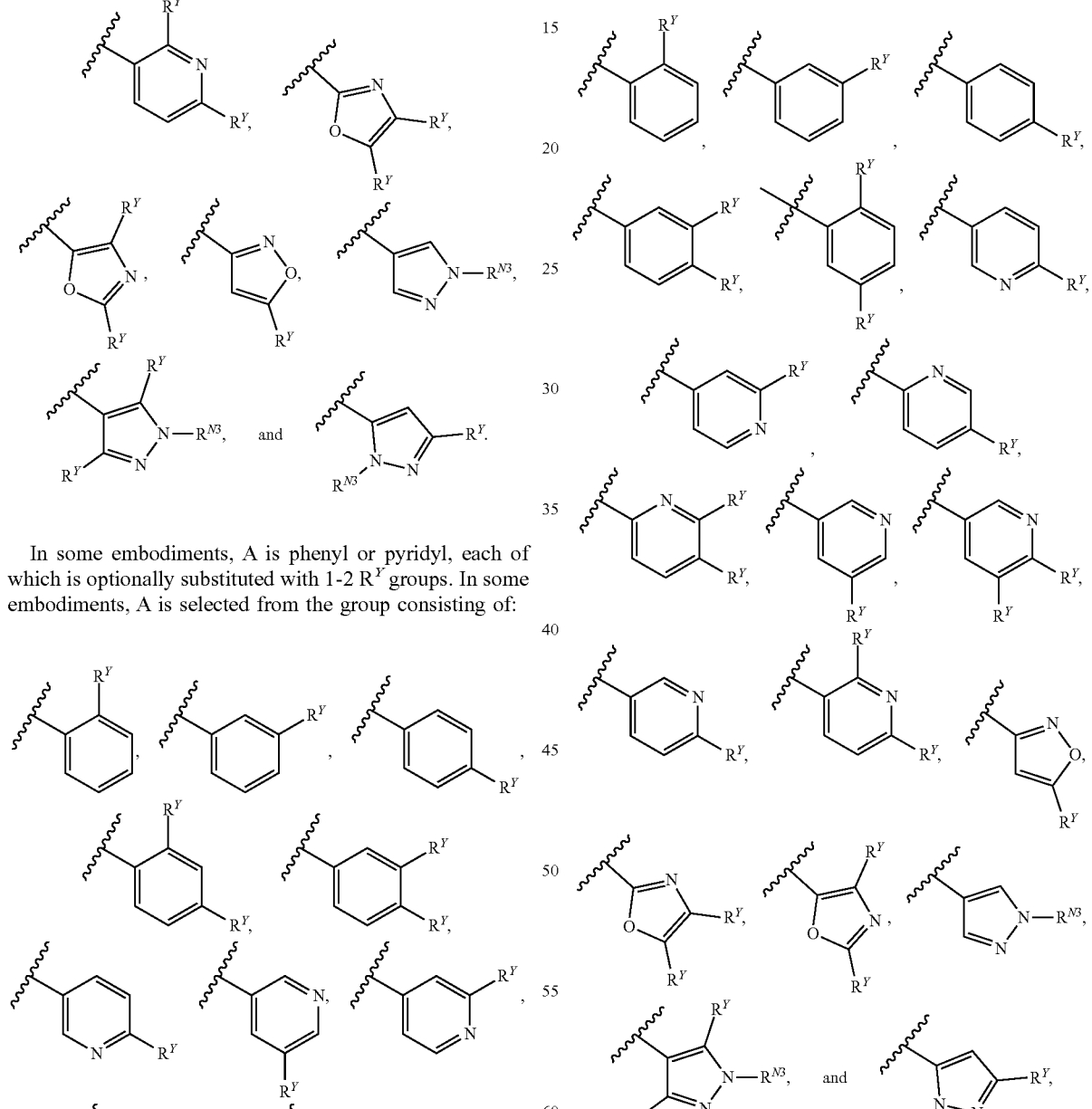

In some embodiments, A is phenyl or pyridyl, each of which is optionally substituted with 1-2 $R^Y$ groups. In some embodiments, A is selected from the group consisting of:

In some embodiments, Z is phenyl, pyridyl, oxazolyl, isoxazolyl, or pyrazolyl, each of which is optionally substituted with 1-2 $R^Y$ groups. In some embodiments, Z is selected from the group consisting of:

wherein $R^{N3}$ is hydrogen or $CH_3$.

In some embodiments, each $R^Y$ is independently selected from the group consisting of hydrogen, chloro, fluoro, $CHF_2$, $CF_3$, $CH_3$, $CH_2CH_3$, $CH(CH_3)_2$, $OCH_3$, $OCHF_2$, $OCF_3$, $OCH_2CF_3$, $OCH(CH_3)_2$, and CN.

In some embodiments, the compound of Formula (I) is a compound of Formula (I-d):

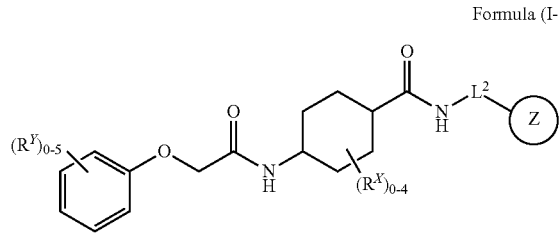

Formula (I-d)

or a pharmaceutically acceptable salt, solvate, hydrate, tautomer, N-oxide, or stereoisomer thereof, wherein each of Z, $L^2$, $R^X$, and $R^Y$ is defined as for Formula (I).

In some embodiments, each $R^X$ is independently fluoro, oxo, OH, $OCH_3$, C(O)OH, or $C(O)OCH_3$.

In some embodiments, $L^2$ is a bond or $C_1$-$C_6$ alkylene, wherein $C_1$-$C_6$ alkylene is optionally substituted by 1-5 $R^{L1}$. In some embodiments, $L^2$ is a bond or $C_1$-$C_6$ alkylene, wherein $C_1$-$C_6$ alkylene is substituted by 0 $R^{L1}$. In some embodiments, $L^2$ is selected from a bond or $CH_2$—*, wherein "—*" indicates the attachment point to Z.

In some embodiments, Z is phenyl or 5-6-membered heteroaryl; wherein 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, Z is phenyl, pyridyl, oxazolyl, isoxazolyl, or pyrazolyl, each of which is optionally substituted with 1-5 $R^Y$ groups.

In some embodiments, Z is phenyl, pyridyl, oxazolyl, isoxazolyl, or pyrazolyl, each of which is optionally substituted with 1-2 $R^Y$ groups. In some embodiments, Z is selected from the group consisting of:

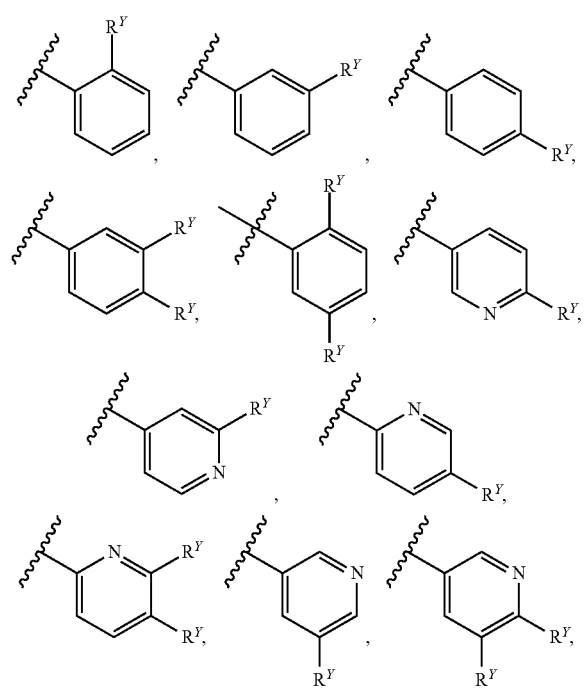

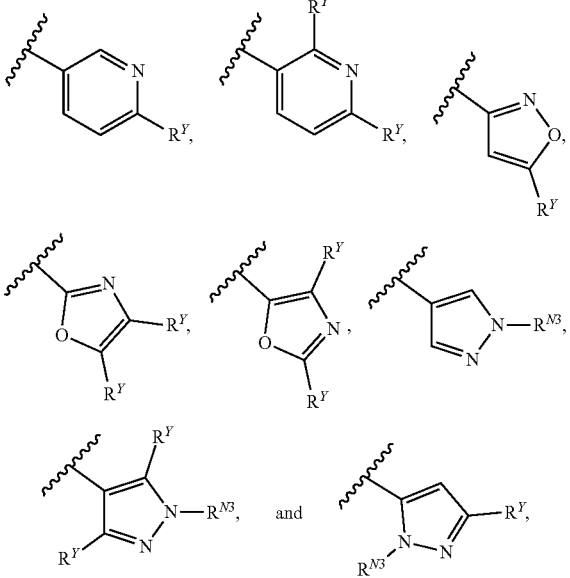

wherein $R^{N3}$ is hydrogen or $CH_3$.

In some embodiments, each $R^Y$ is independently selected from the group consisting of hydrogen, chloro, fluoro, $CHF_2$, $CF_3$, $CH_3$, $CH_2CH_3$, $CH(CH_3)_2$, $OCH_3$, $OCHF_2$, $OCF_3$, $OCH_2CF_3$, $OCH(CH_3)_2$, and CN.

In some embodiments, the compound of Formula (I) is a compound of Formula (I-e-1), Formula (I-e-2), Formula (I-e-3), Formula (I-e-4), Formula (I-e-5), Formula (I-e-6), Formula (I-e-7), Formula (I-e-8), or Formula (I-e-9):

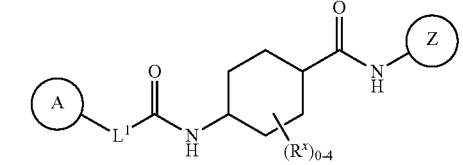

Formula (I-e-1)

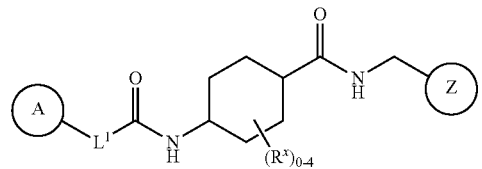

Formula (I-e-2)

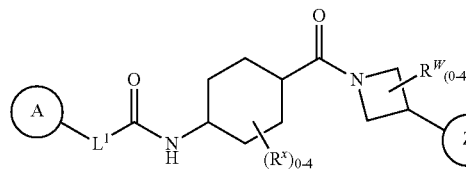

Formula (I-e-3)

-continued

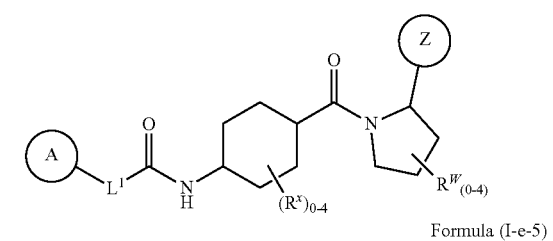

Formula (I-e-4)

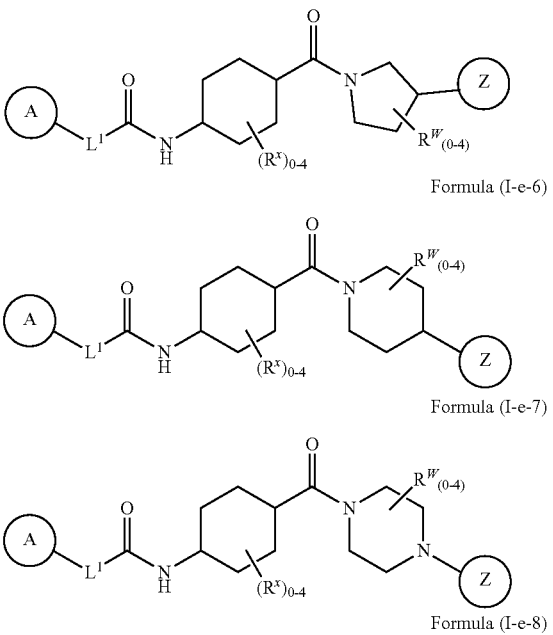

Formula (I-e-5)

Formula (I-e-6)

Formula (I-e-7)

Formula (I-e-8)

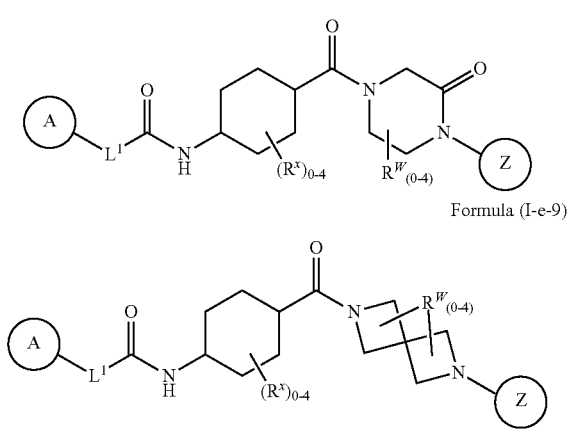

Formula (I-e-9)

or a pharmaceutically acceptable salt, solvate, hydrate, tautomer, N-oxide, or stereoisomer thereof, wherein each of A, Z, L$^1$, R$^W$ and R$^X$ is defined as for Formula (I).

In some embodiments, each R$^X$ is independently fluoro, oxo, OH, OCH$_3$, C(O)OH, or C(O)OCH$_3$.

In some embodiments, each R$^W$ is independently fluoro, chloro, oxo, OH, OCH$_3$, CF$_3$, CH$_3$, CH$_2$CH$_3$, or CH(CH$_3$)$_2$.

In some embodiments, L$^1$ is a bond, 2-7 membered heteroalkylene, —NR$^{N1}$—, or —O—, wherein 2-7 membered heteroalkylene is optionally substituted with 1-5 RLY. In some embodiments, L$^1$ is a bond, 2-7 membered heteroalkylene, —NR$^{N1}$—, or —O—, wherein 2-7 membered heteroalkylene is substituted with 0 R$^{L1}$. In some embodiments, L$^1$ is selected from a bond, CH$_2$O—*, CH$_2$OCH$_2$—*, —NCH$_3$—, —NH—, or —O—, wherein "—*" indicates the attachment point to A.

In some embodiments, each of A and Z is independently phenyl or 5-6-membered heteroaryl; wherein each phenyl or 5-6-membered heteroaryl is optionally substituted with 1-5 R$^Y$, and each R$^Y$ is independently C$_1$-C$_6$ alkyl, halo-C$_1$-C$_6$ alkyl, halo, cyano, —OR$^A$, or G$^1$. In some embodiments, each of A and Z is independently phenyl, pyridyl, oxazolyl, isoxazolyl, or pyrazolyl, each of which is optionally substituted with 1-5 R$^Y$ groups.

In some embodiments, each of A and Z is selected from the group consisting of:

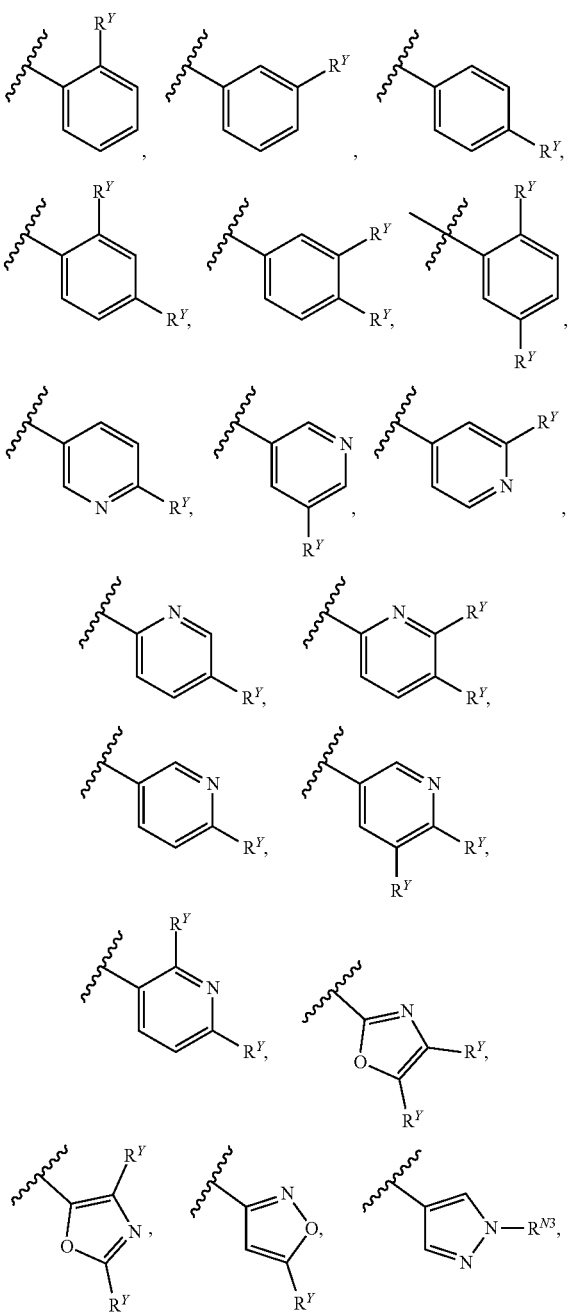

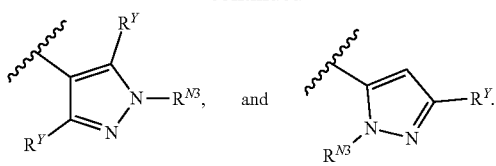

In some embodiments, A is phenyl or pyridyl, each of which is optionally substituted with 1-2 $R^Y$ groups. In some embodiments, A is selected from the group consisting of:

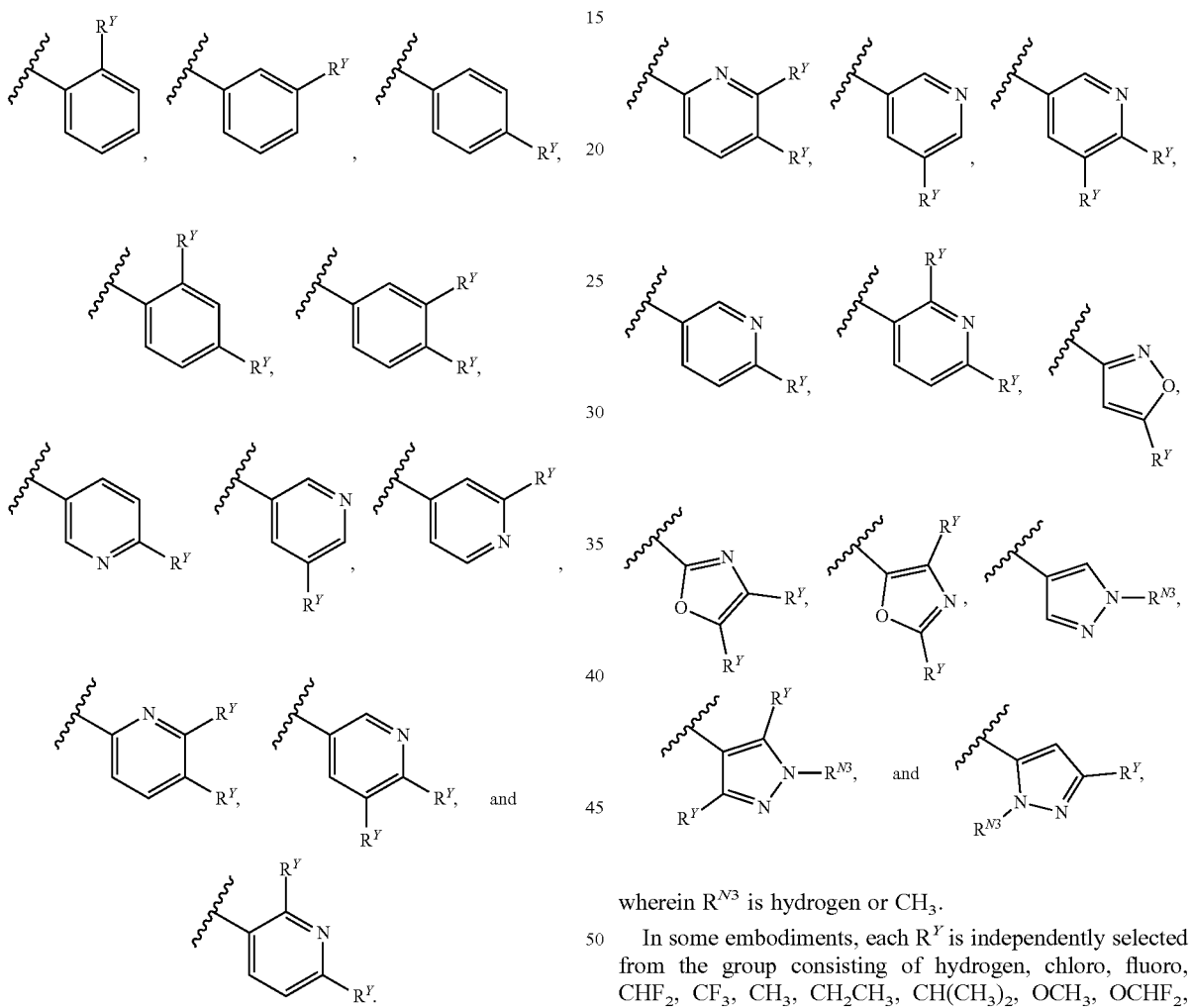

wherein $R^{N3}$ is hydrogen or $CH_3$.

In some embodiments, each $R^Y$ is independently selected from the group consisting of hydrogen, chloro, fluoro, $CHF_2$, $CF_3$, $CH_3$, $CH_2CH_3$, $CH(CH_3)_2$, $OCH_3$, $OCHF_2$, $OCF_3$, $OCH_2CF_3$, $OCH(CH_3)_2$, and CN.

In some embodiments, the compound of Formula (I) (e.g., a compound of Formula (I-a), (I-b), (I-c), (I-d), (I-e-1), (I-e-2), (I-e-3), (I-e-4), (I-e-5), (I-e-6), (I-e-7), (I-e-8), or (I-e-9)), or a pharmaceutically acceptable salt thereof is formulated as a pharmaceutically acceptable composition comprising a disclosed compound and a pharmaceutically acceptable carrier.

In some embodiments, the compound of Formula (I) (e.g., a compound of Formula (I-a), (I-b), (I-c), (I-d), (I-e-1), (I-e-2), (I-e-3), (I-e-4), (I-e-5), (I-e-6), (I-e-7), (I-e-8), or (I-e-9)), is selected from a compound set forth in Table 1 or a pharmaceutically acceptable salt, solvate, hydrate, tautomer, N-oxide or stereoisomer thereof.

In some embodiments, Z is phenyl, pyridyl, oxazolyl, isoxazolyl, or pyrazolyl, each of which is optionally substituted with 1-2 $R^Y$ groups. In some embodiments, Z is selected from the group consisting of:

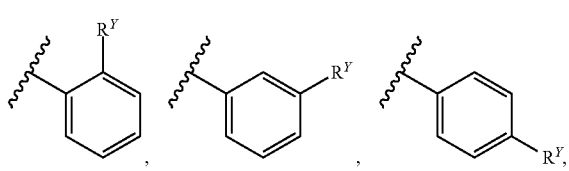

TABLE 1

Exemplary compounds of the invention

| Compound Number | Structure |
| --- | --- |
| 100 | 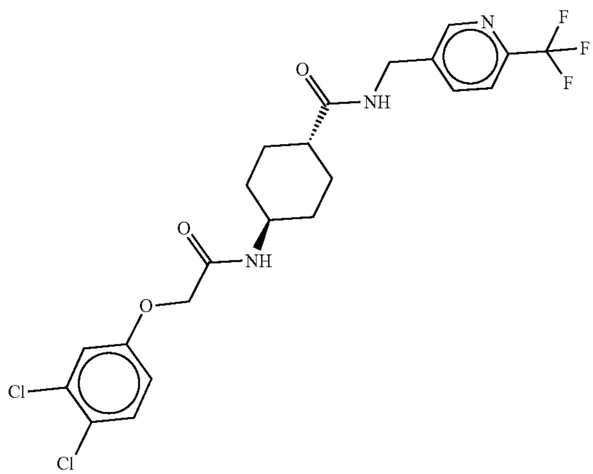 |
| 101 | 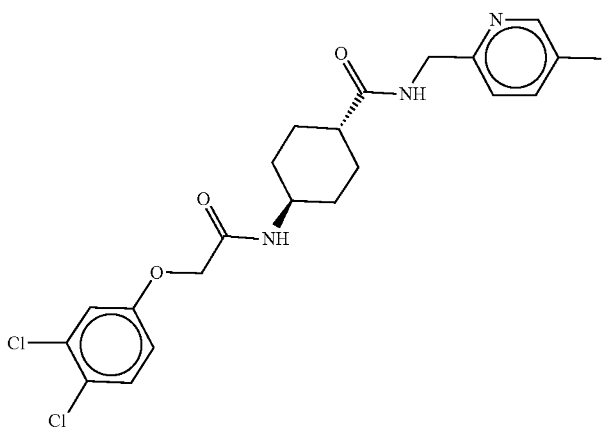 |
| 102 | 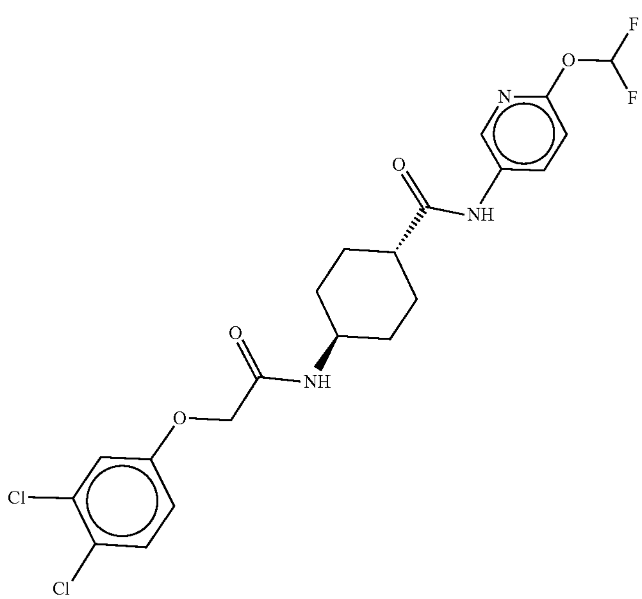 |

TABLE 1-continued
Exemplary compounds of the invention
| Compound Number | Structure |
|---|---|
| 103 | 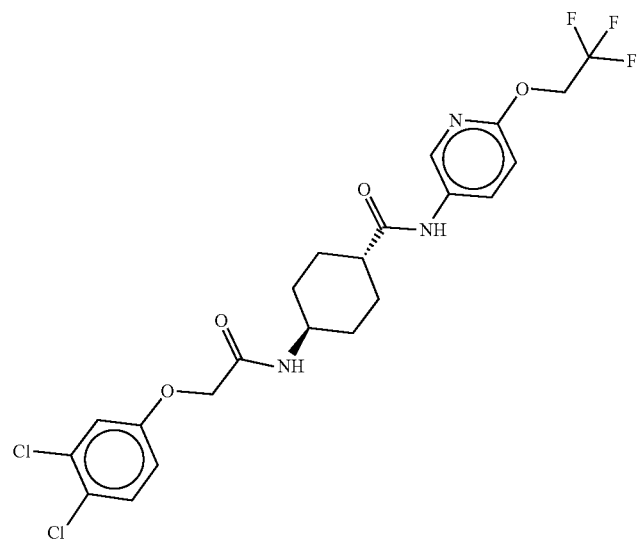 |
| 104 | 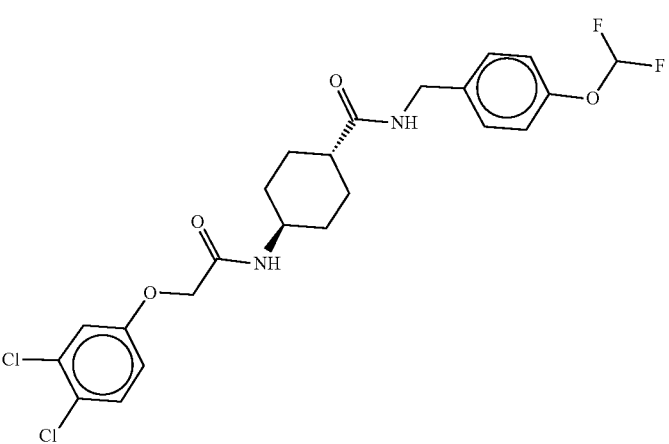 |
| 105 | 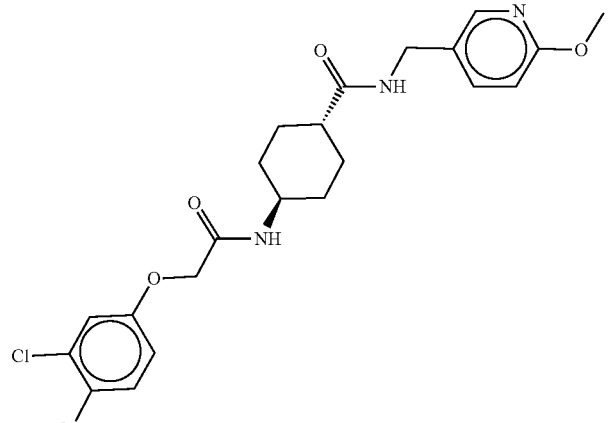 |

TABLE 1-continued

Exemplary compounds of the invention

| Compound Number | Structure |
|---|---|
| 106 | (structure) |
| 107 | (structure) |
| 108 | (structure) |

TABLE 1-continued
Exemplary compounds of the invention
| Compound Number | Structure |
|---|---|
| 109 | 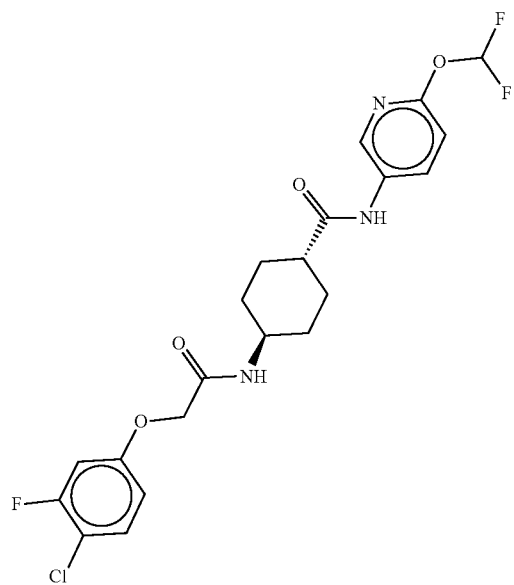 |
| 110 | 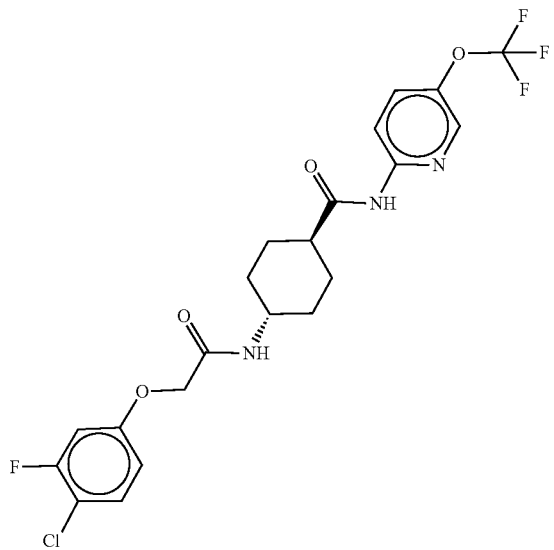 |

TABLE 1-continued
Exemplary compounds of the invention
| Compound Number | Structure |
|---|---|
| 111 | 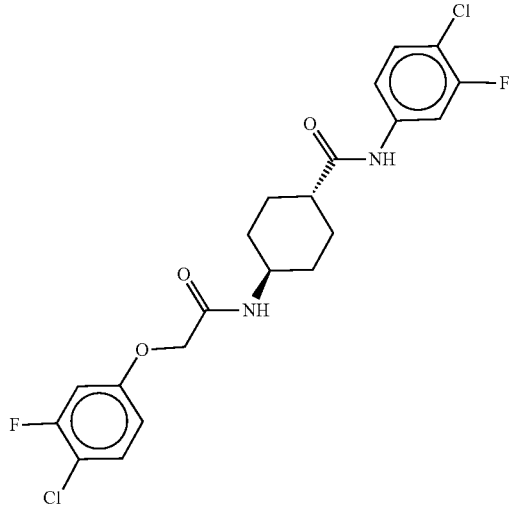 |
| 112 | 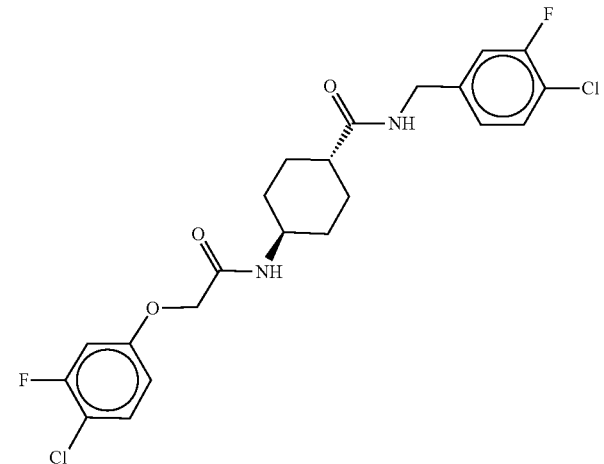 |
| 113 | 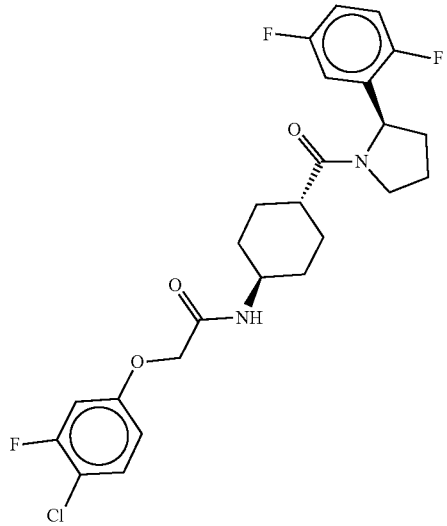 |

TABLE 1-continued
Exemplary compounds of the invention
| Compound Number | Structure |
|---|---|
| 114 | 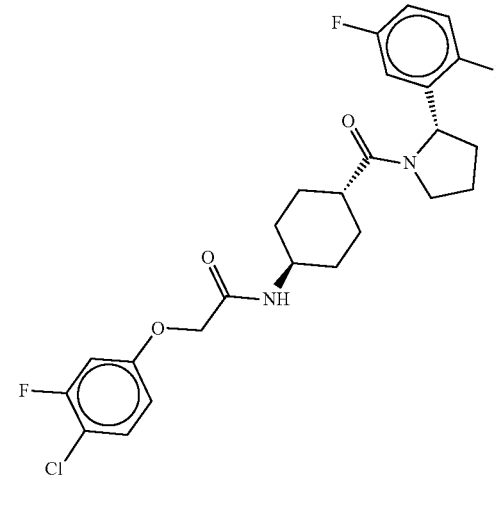 |
| 115 | 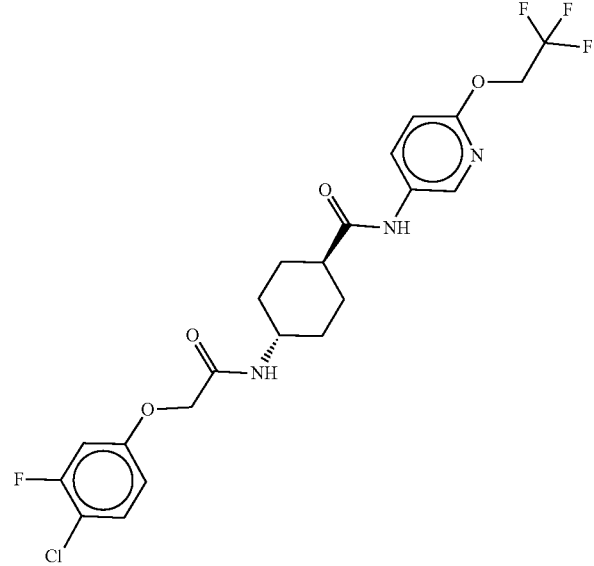 |

TABLE 1-continued
Exemplary compounds of the invention
| Compound Number | Structure |
| --- | --- |
| 116 | 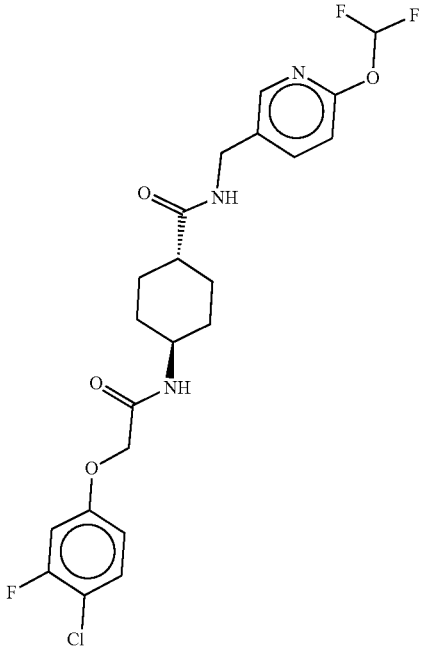 |
| 117 | 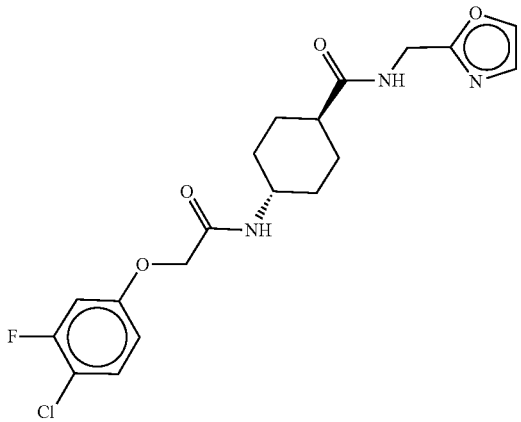 |
| 118 | 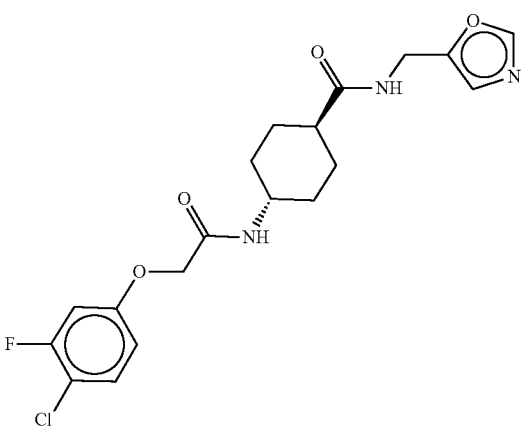 |

TABLE 1-continued
Exemplary compounds of the invention
| Compound Number | Structure |
|---|---|
| 119 | 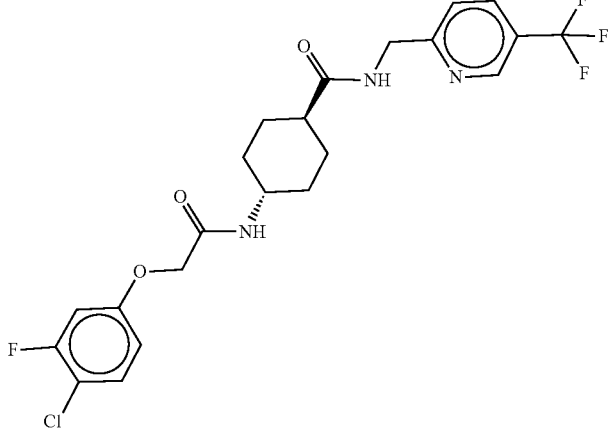 |
| 120 | 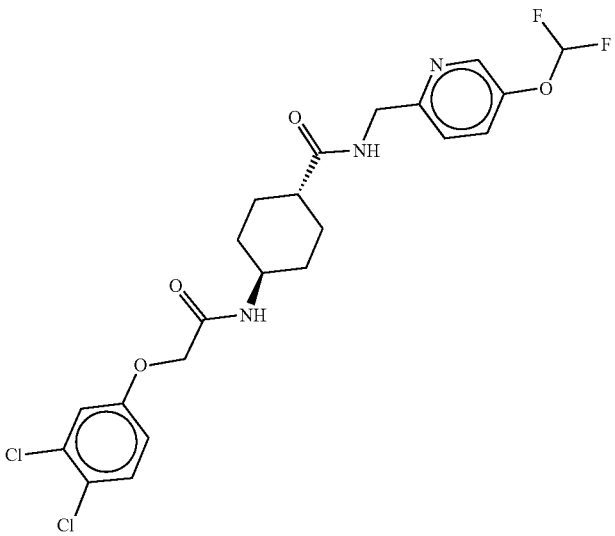 |
| 121 | 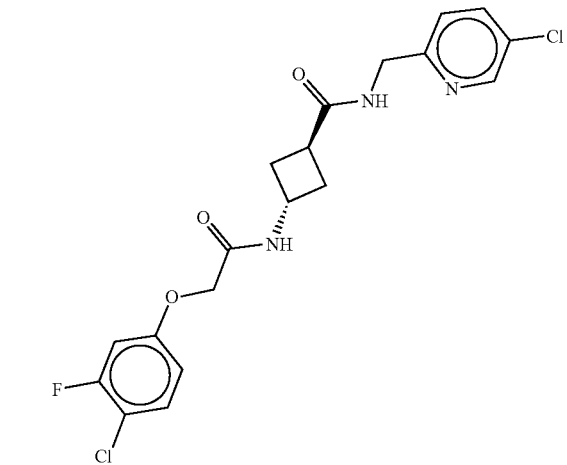 |

TABLE 1-continued
Exemplary compounds of the invention
| Compound Number | Structure |
|---|---|
| 122 | 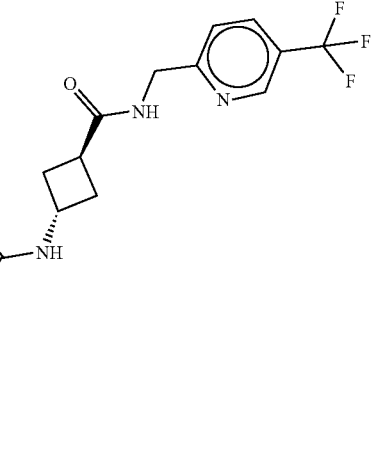 |
| 123 | 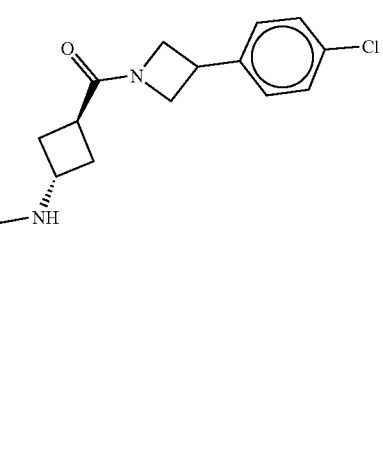 |
| 124 | 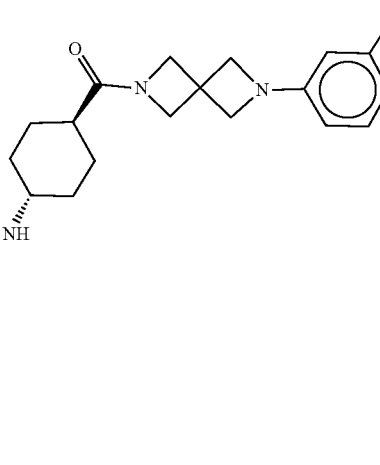 |

TABLE 1-continued
Exemplary compounds of the invention
| Compound Number | Structure |
|---|---|
| 125 | 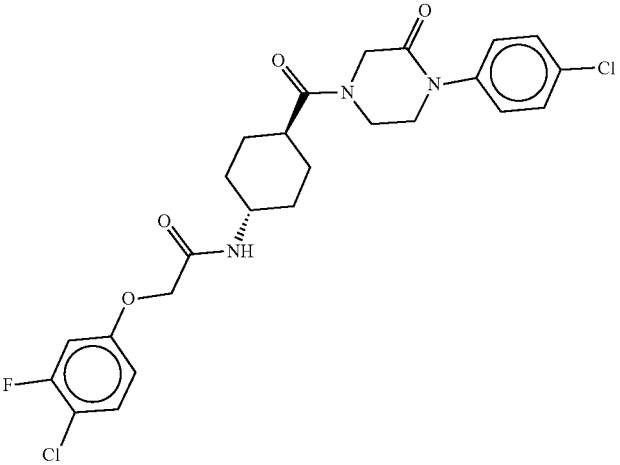 |
| 126 | 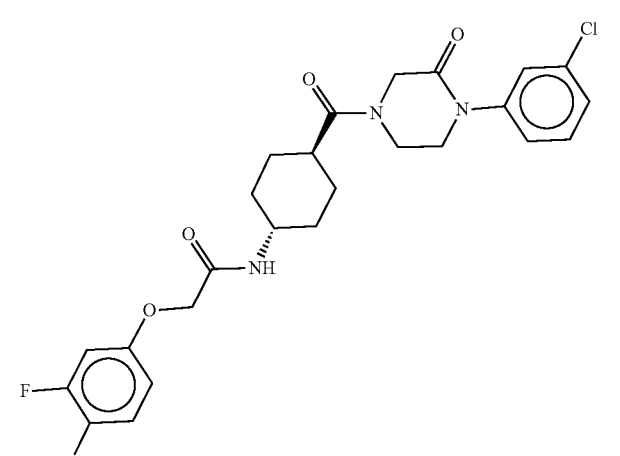 |
| 127 | 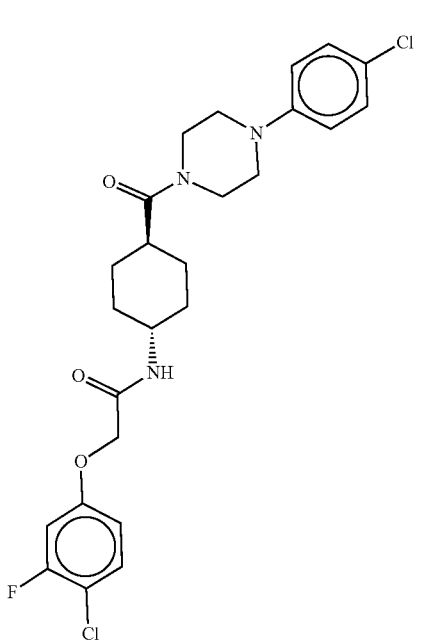 |

TABLE 1-continued
Exemplary compounds of the invention
| Compound Number | Structure |
|---|---|
| 128 | 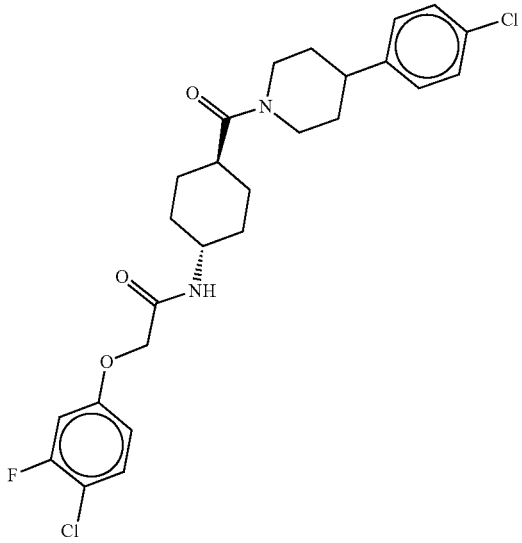 |
| 129 | 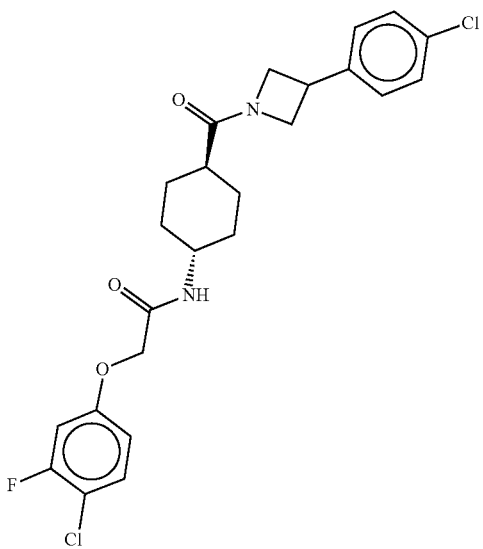 |
| 130 | 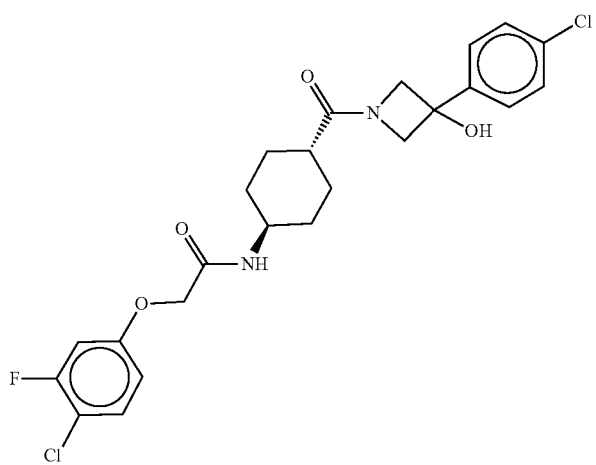 |

TABLE 1-continued
Exemplary compounds of the invention
| Compound Number | Structure |
|---|---|
| 131 | 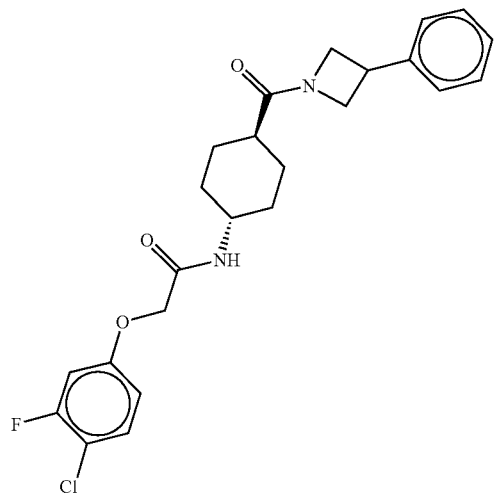 |
| 132 | 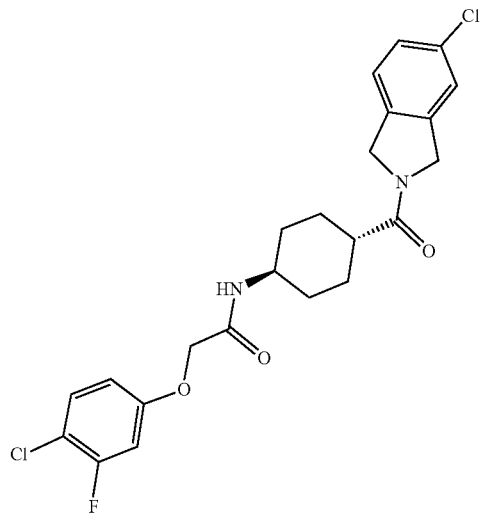 [SMILES: O=C(COc1ccc(Cl)c(F)c1)N[C@H]1CC[C@H](C(=O)N2Cc3ccc(Cl)cc3C2)CC1] |

TABLE 1-continued
Exemplary compounds of the invention
| Compound Number | Structure |
|---|---|
| 133 | 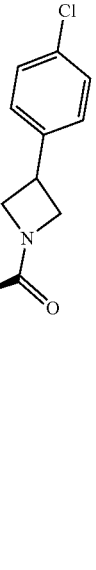 |
| 134 | 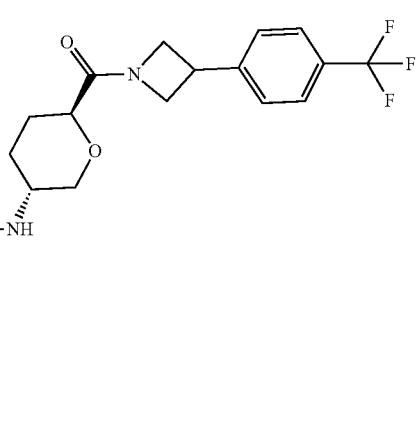 |
| 135 | 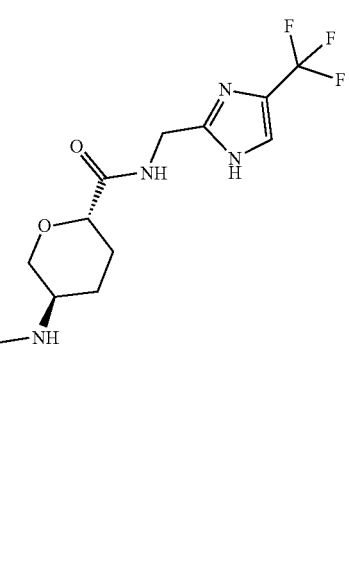 |

TABLE 1-continued
Exemplary compounds of the invention
| Compound Number | Structure |
|---|---|
| 136 | 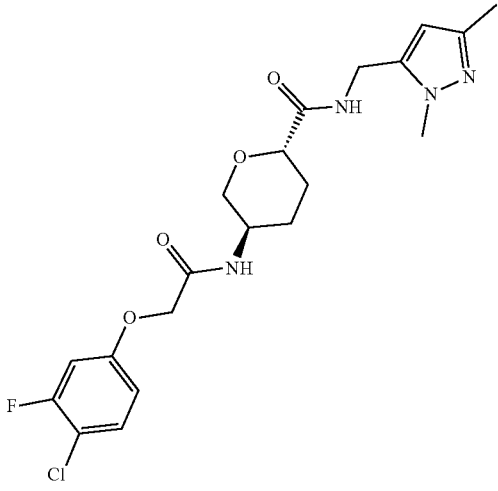 [SMILES: Cc1cc(CNC(=O)[C@@H]2CC[C@@H](NC(=O)COc3ccc(Cl)c(F)c3)CO2)n(C)n1] |
| 137 | 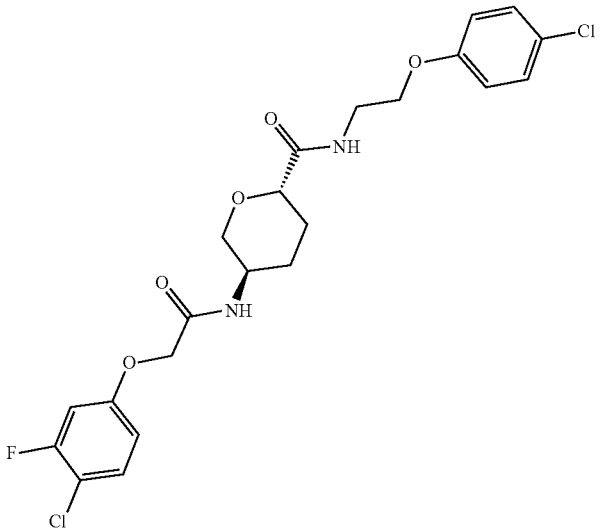 [SMILES: O=C(COc1ccc(Cl)c(F)c1)N[C@@H]1CC[C@@H](C(=O)NCCOc2ccc(Cl)cc2)OC1] |

TABLE 1-continued
Exemplary compounds of the invention
| Compound Number | Structure |
|---|---|
| 138 | 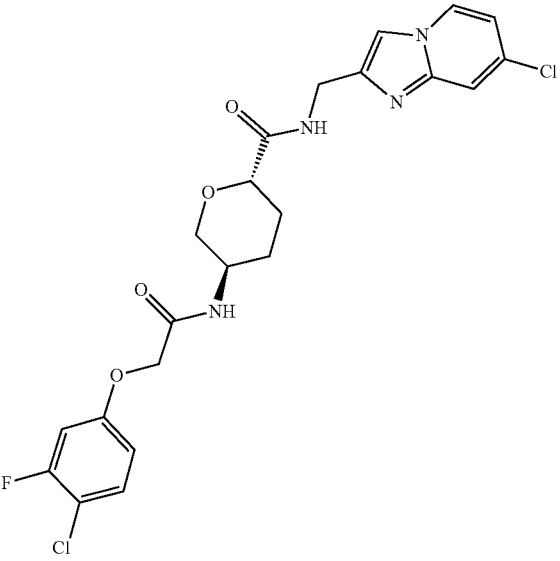 [SMILES: O=C(COc1ccc(Cl)c(F)c1)N[C@@H]1CC[C@@H](C(=O)NCc2cn3ccc(Cl)cc3n2)OC1] |
| 139 | 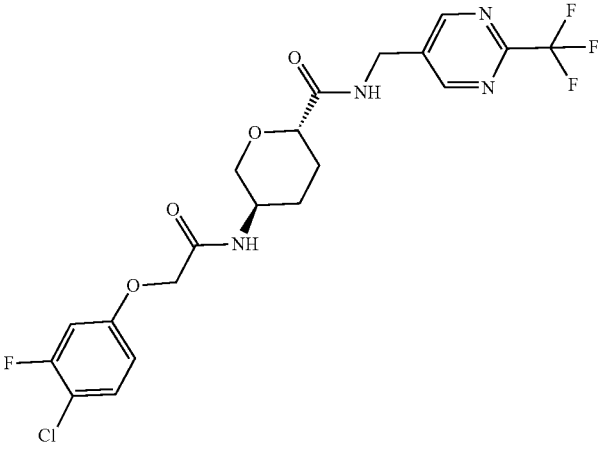 [SMILES: O=C(COc1ccc(Cl)c(F)c1)N[C@@H]1CC[C@@H](C(=O)NCc2cnc(C(F)(F)F)nc2)OC1] |
| 140 | 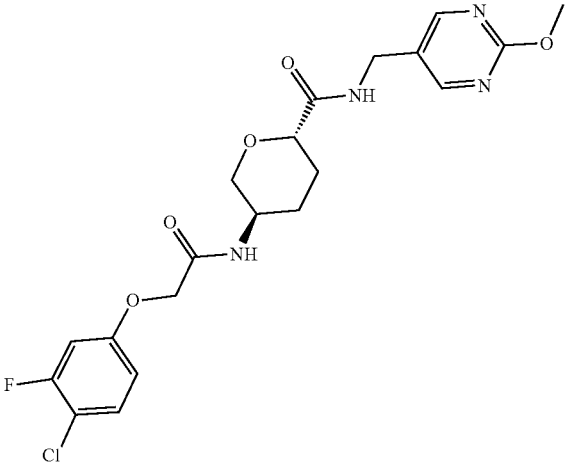 [SMILES: COc1ncc(CNC(=O)[C@@H]2CC[C@@H](NC(=O)COc3ccc(Cl)c(F)c3)CO2)cn1] |

TABLE 1-continued

Exemplary compounds of the invention

| Compound Number | Structure |
|---|---|
| 141 | 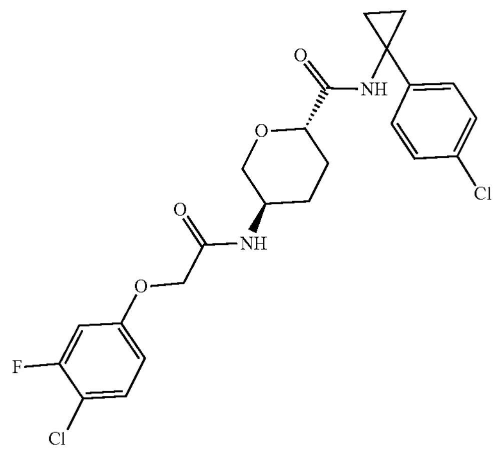 [SMILES: O=C(COc1ccc(Cl)c(F)c1)N[C@@H]1CC[C@@H](C(=O)NC2(c3ccc(Cl)cc3)CC2)OC1] |
| 142 | 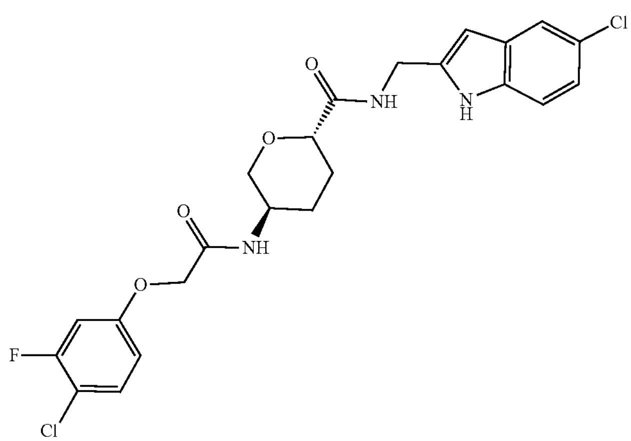 [SMILES: O=C(COc1ccc(Cl)c(F)c1)N[C@@H]1CC[C@@H](C(=O)NCc2cc3cc(Cl)ccc3[nH]2)OC1] |
| 143 | 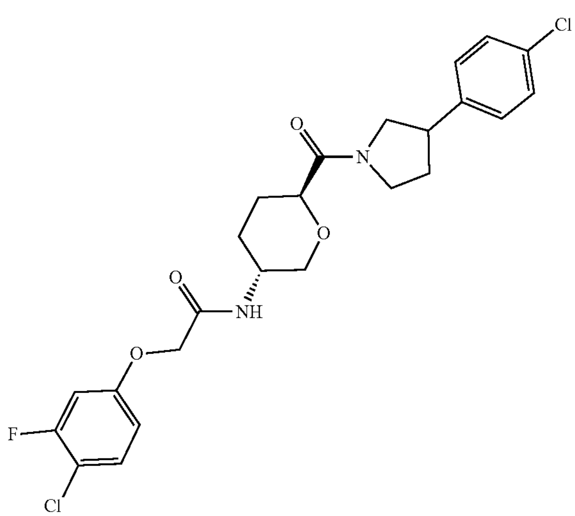 [SMILES: O=C(COc1ccc(Cl)c(F)c1)N[C@@H]1CC[C@@H](C(=O)N2CCC(c3ccc(Cl)cc3)C2)OC1] |

TABLE 1-continued
Exemplary compounds of the invention
| Compound Number | Structure |
| --- | --- |
| 144 | 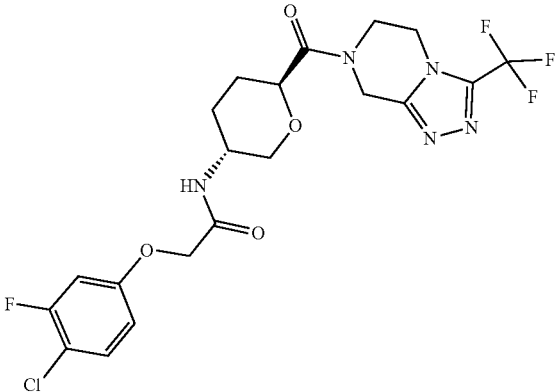 [SMILES: O=C(COc1ccc(Cl)c(F)c1)N[C@@H]1CC[C@@H](C(=O)N2CCn3c(nnc3C(F)(F)F)C2)OC1] |
| 145 | 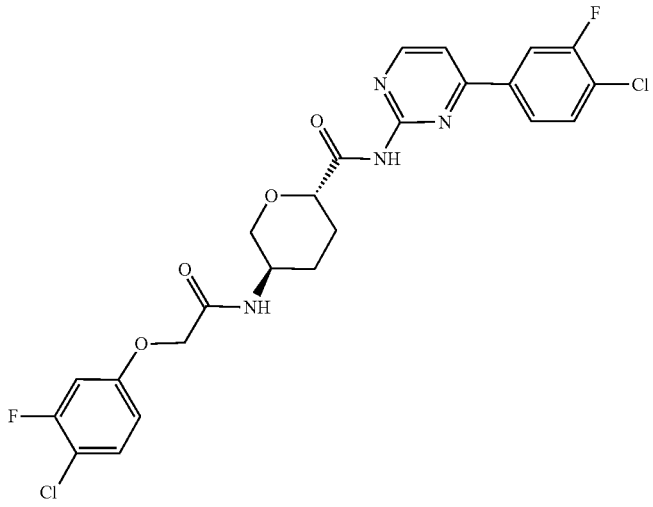 [SMILES: O=C(COc1ccc(Cl)c(F)c1)N[C@@H]1CC[C@@H](C(=O)Nc2nccc(-c3ccc(Cl)c(F)c3)n2)OC1] |
| 146 | 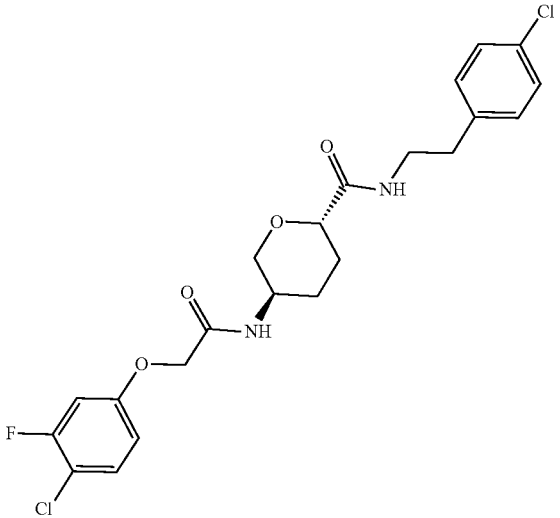 [SMILES: O=C(COc1ccc(Cl)c(F)c1)N[C@@H]1CC[C@@H](C(=O)NCCc2ccc(Cl)cc2)OC1] |

TABLE 1-continued
Exemplary compounds of the invention
| Compound Number | Structure |
|---|---|
| 147 | 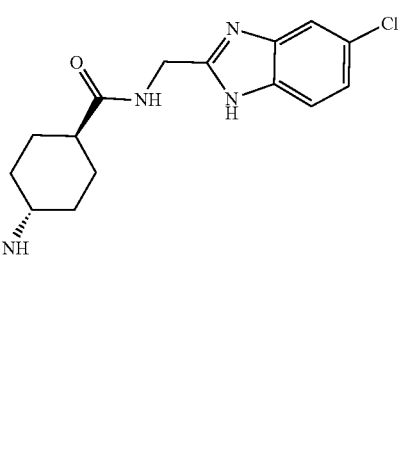 |
| 148 | 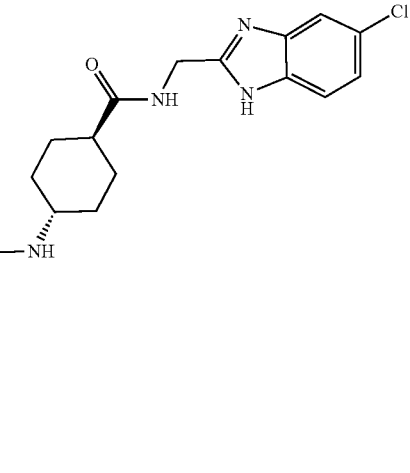 |
| 149 | 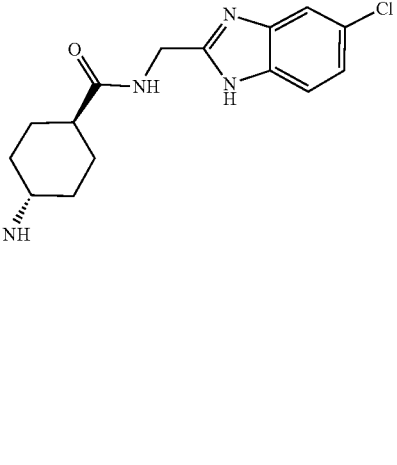 |

TABLE 1-continued
Exemplary compounds of the invention
| Compound Number | Structure |
|---|---|
| 150 | 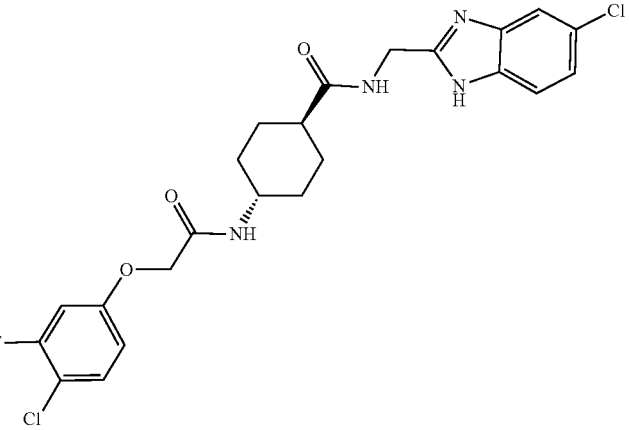 |
| 151 | 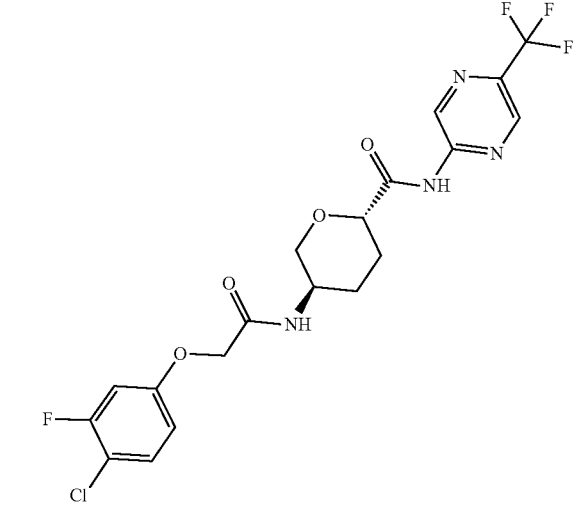 [SMILES: O=C(COc1ccc(Cl)c(F)c1)N[C@@H]1CC[C@@H](C(=O)Nc2cnc(C(F)(F)F)cn2)OC1] |
| 152 | 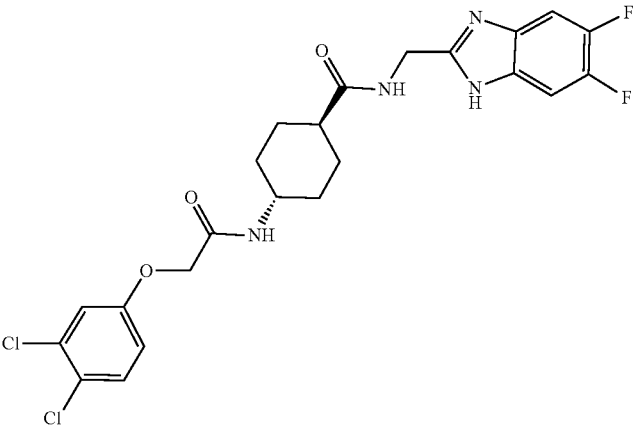 [SMILES: O=C(COc1ccc(Cl)c(Cl)c1)N[C@H]1CC[C@H](C(=O)NCc2nc3cc(F)c(F)cc3[nH]2)CC1] |

TABLE 1-continued
Exemplary compounds of the invention
| Compound Number | Structure |
|---|---|
| 153 | 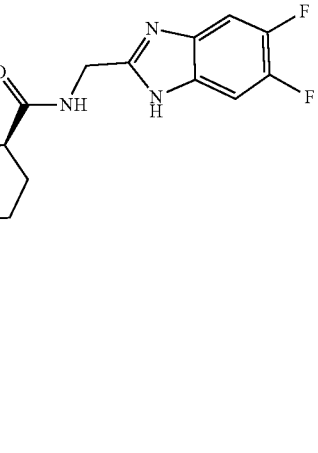 |
| 154 | 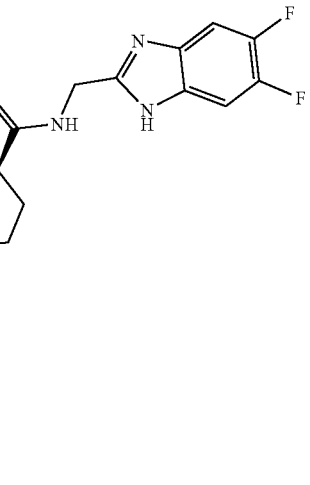 |
| 155 | 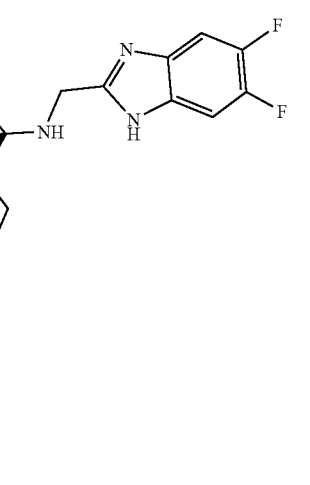 |

TABLE 1-continued
Exemplary compounds of the invention
| Compound Number | Structure |
|---|---|
| 156 | 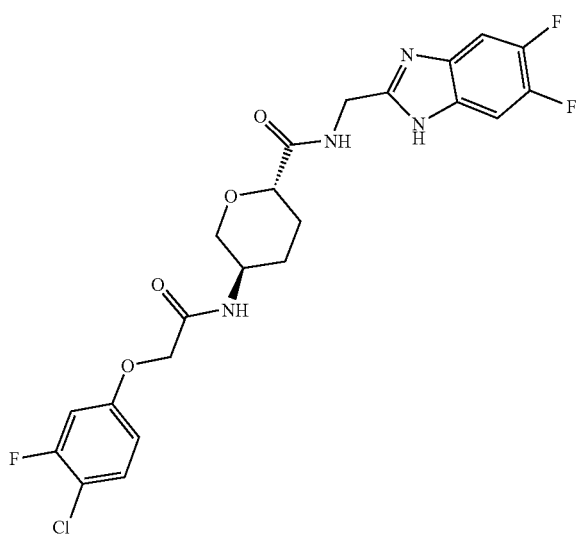 [SMILES: O=C(COc1ccc(Cl)c(F)c1)N[C@@H]1CC[C@@H](C(=O)NCc2nc3cc(F)c(F)cc3[nH]2)OC1] |
| 157 | 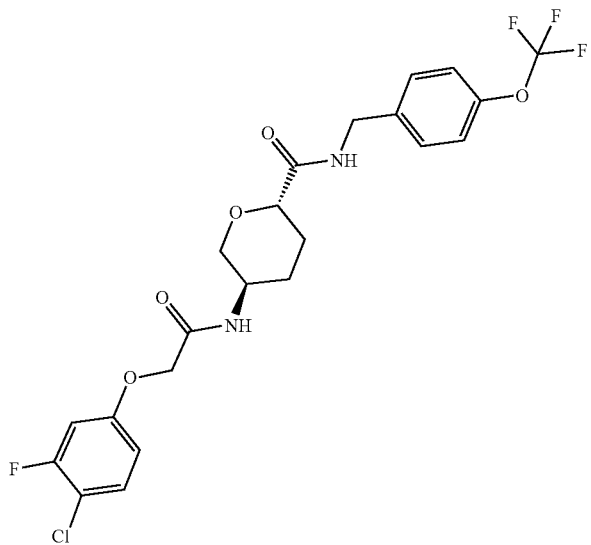 [SMILES: O=C(COc1ccc(Cl)c(F)c1)N[C@@H]1CC[C@@H](C(=O)NCc2ccc(OC(F)(F)F)cc2)OC1] |

TABLE 1-continued
Exemplary compounds of the invention
| Compound Number | Structure |
|---|---|
| 158 | 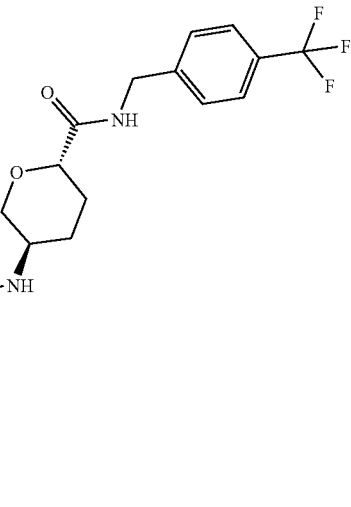 |
| 159 | 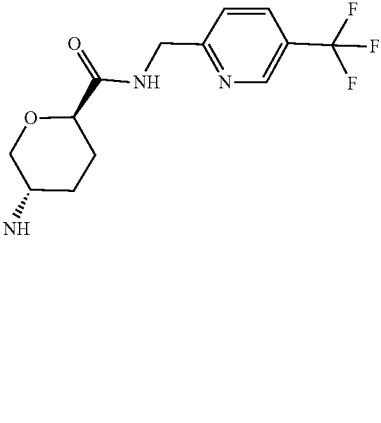 |
| 160 | 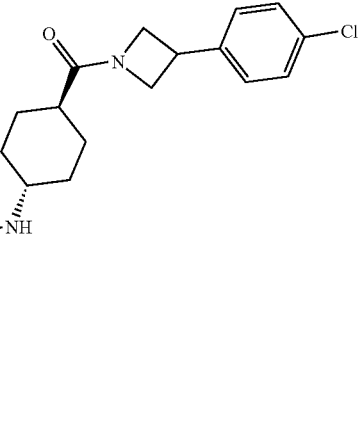 |

TABLE 1-continued
Exemplary compounds of the invention
| Compound Number | Structure |
|---|---|
| 161 | 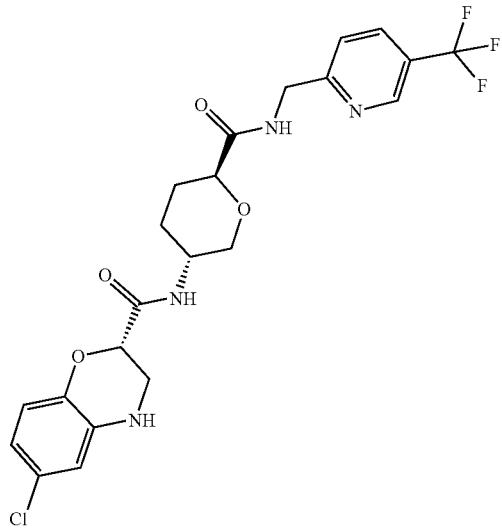 [SMILES: O=C(NCc1ccc(C(F)(F)F)cn1)[C@@H]1CC[C@@H](NC(=O)[C@@H]2CNc3cc(Cl)ccc3O2)CO1] |
| 162 | 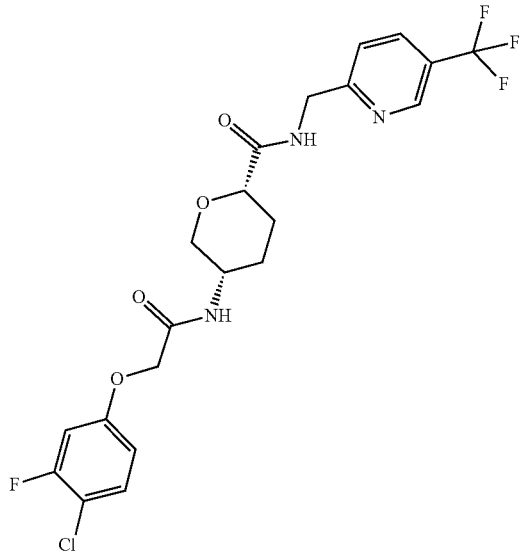 [SMILES: O=C(COc1ccc(Cl)c(F)c1)N[C@H]1CC[C@@H](C(=O)NCc2ccc(C(F)(F)F)cn2)OC1] |

TABLE 1-continued
Exemplary compounds of the invention
| Compound Number | Structure |
|---|---|
| 163 | 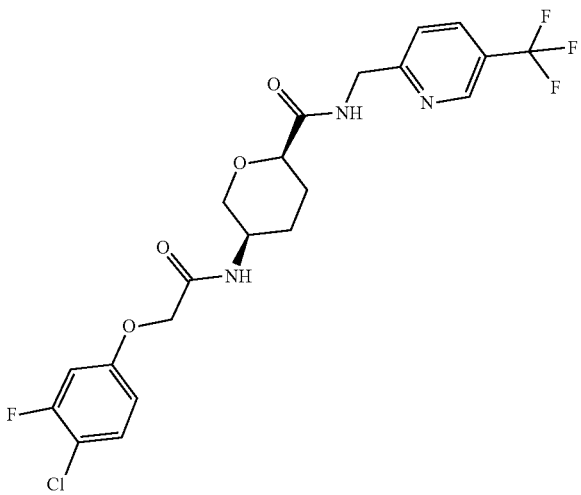 [SMILES: O=C(COc1ccc(Cl)c(F)c1)N[C@@H]1CC[C@H](C(=O)NCc2ccc(C(F)(F)F)cn2)OC1] |
| 164 | 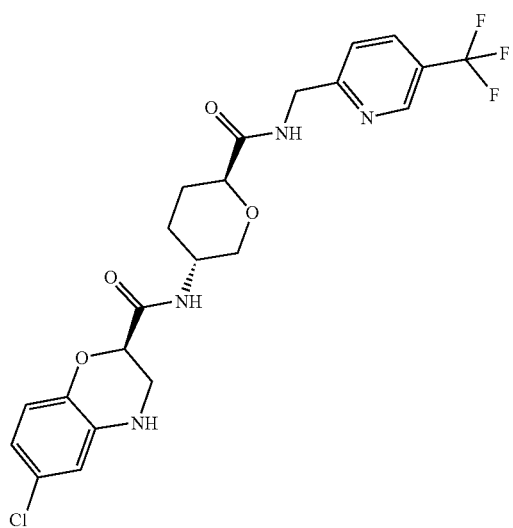 [SMILES: O=C(NCc1ccc(C(F)(F)F)cn1)[C@@H]1CC[C@@H](NC(=O)[C@H]2CNc3cc(Cl)ccc3O2)CO1] |
| 165 | 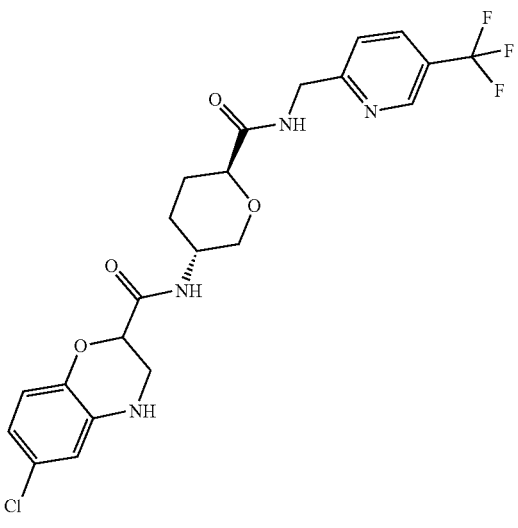 [SMILES: O=C(N[C@@H]1CC[C@@H](C(=O)NCc2ccc(C(F)(F)F)cn2)OC1)C1CNc2cc(Cl)ccc2O1] |

TABLE 1-continued
Exemplary compounds of the invention
| Compound Number | Structure |
| --- | --- |
| 166 | 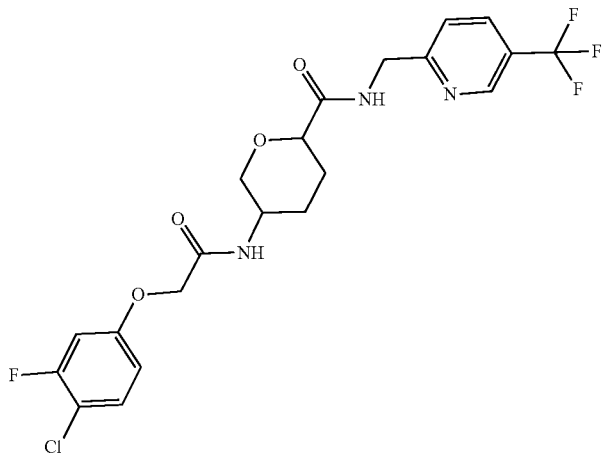 [SMILES: O=C(COc1ccc(Cl)c(F)c1)NC1CCC(C(=O)NCc2ccc(C(F)(F)F)cn2)OC1] |
| 167 | 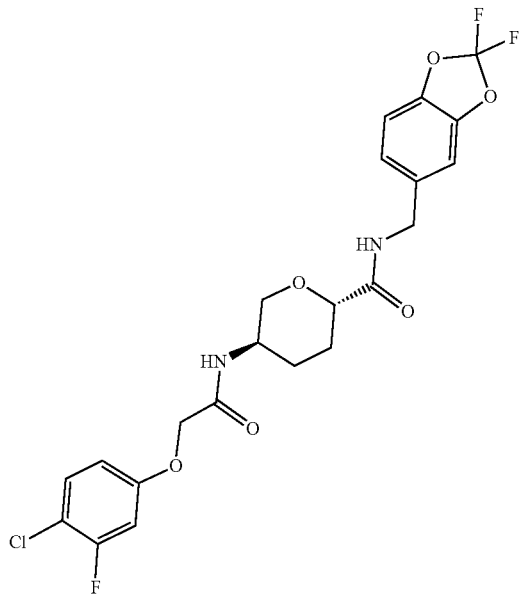 [SMILES: O=C(COc1ccc(Cl)c(F)c1)N[C@@H]1CC[C@@H](C(=O)NCc2ccc3c(c2)OC(F)(F)O3)OC1] |

TABLE 1-continued
Exemplary compounds of the invention
| Compound Number | Structure |
|---|---|
| 168 | 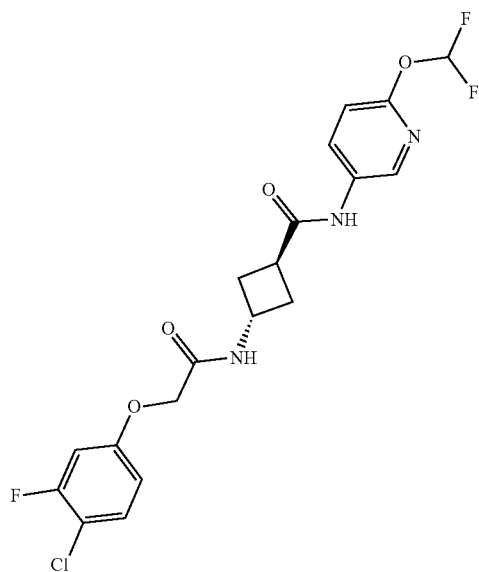 [SMILES: O=C(COc1ccc(Cl)c(F)c1)N[C@H]1C[C@H](C(=O)Nc2ccc(OC(F)F)nc2)C1] |
| 169 | 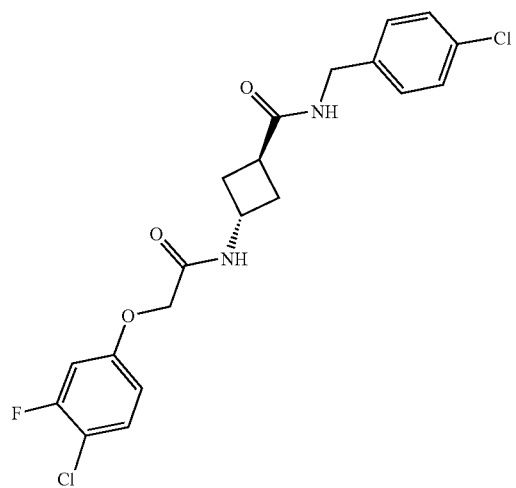 [SMILES: O=C(COc1ccc(Cl)c(F)c1)N[C@H]1C[C@H](C(=O)NCc2ccc(Cl)cc2)C1] |

TABLE 1-continued
Exemplary compounds of the invention
| Compound Number | Structure |
|---|---|
| 170 | 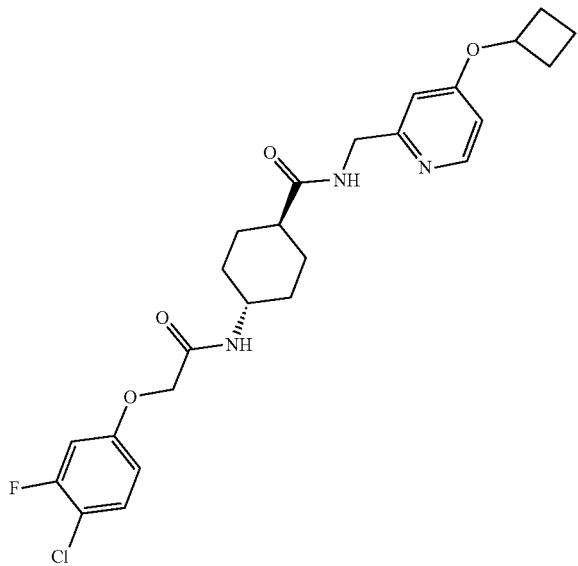 [SMILES: O=C(COc1ccc(Cl)c(F)c1)N[C@H]1CC[C@H](C(=O)NCc2cc(OC3CCC3)ccn2)CC1] |
| 171 | 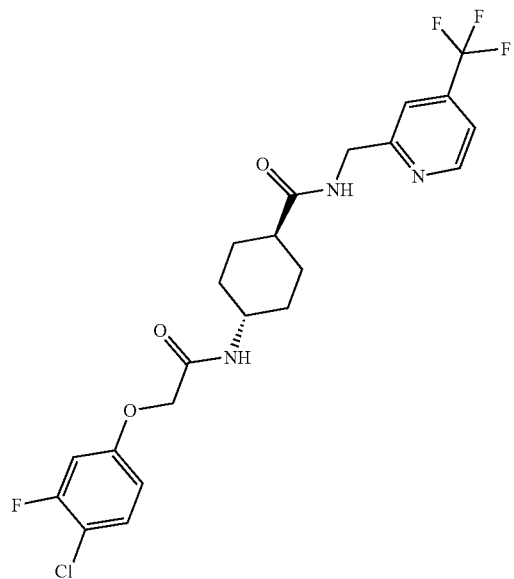 [SMILES: O=C(COc1ccc(Cl)c(F)c1)N[C@H]1CC[C@H](C(=O)NCc2cc(C(F)(F)F)ccn2)CC1] |

TABLE 1-continued
Exemplary compounds of the invention
| Compound Number | Structure |
|---|---|
| 172 | 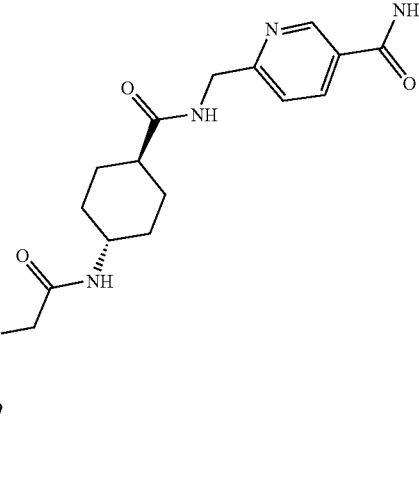 |
| 173 | 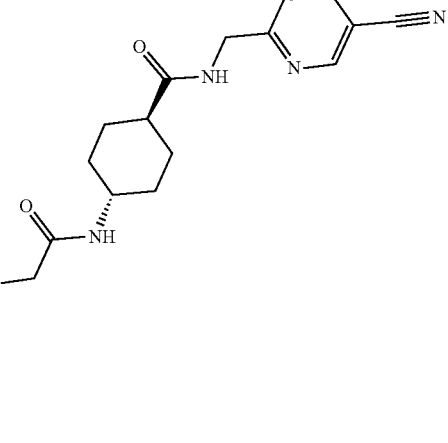 |
| 174 | 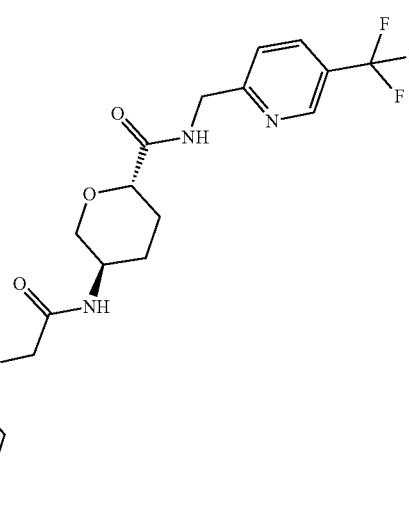 |

113
114
TABLE 1-continued
Exemplary compounds of the invention
| Compound Number | Structure |
|---|---|
| 175 | 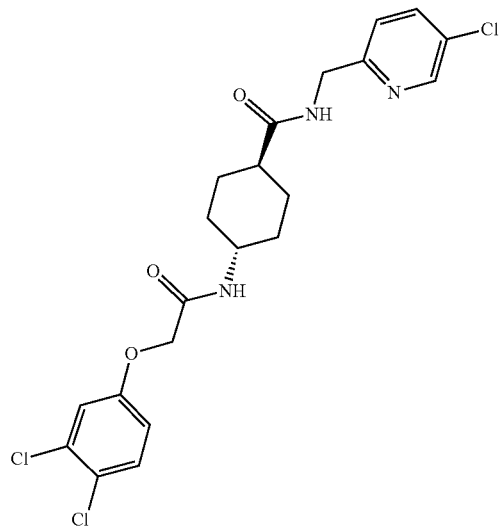 [SMILES: O=C(COc1ccc(Cl)c(Cl)c1)N[C@H]1CC[C@H](C(=O)NCc2ccc(Cl)cn2)CC1] |
| 176 | 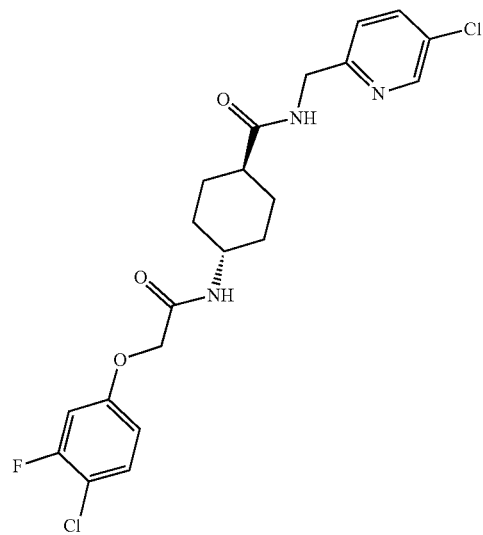 [SMILES: O=C(COc1ccc(Cl)c(F)c1)N[C@H]1CC[C@H](C(=O)NCc2ccc(Cl)cn2)CC1] |

TABLE 1-continued
Exemplary compounds of the invention
| Compound Number | Structure |
|---|---|
| 177 | 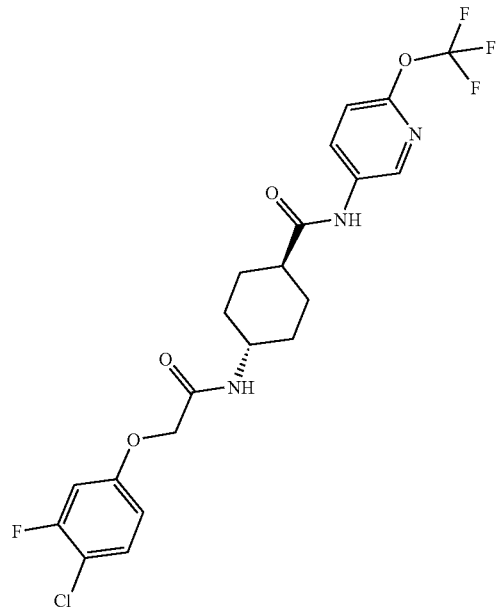 [SMILES: O=C(COc1ccc(Cl)c(F)c1)N[C@H]1CC[C@H](C(=O)Nc2ccc(OC(F)(F)F)nc2)CC1] |
| 178 | 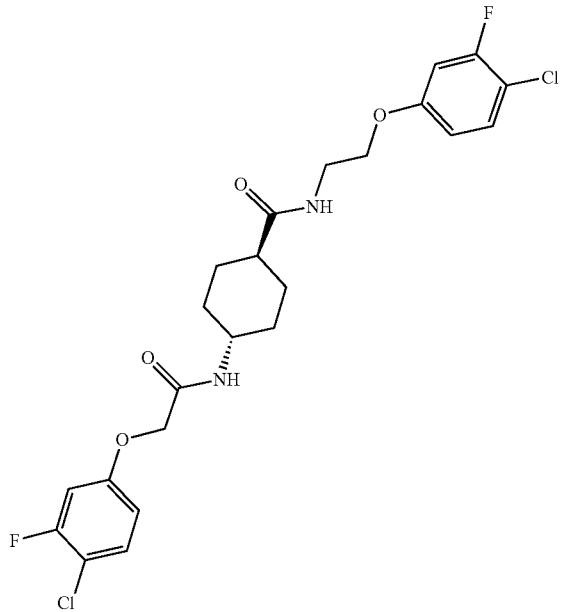 [SMILES: O=C(COc1ccc(Cl)c(F)c1)N[C@H]1CC[C@H](C(=O)NCCOc2ccc(Cl)c(F)c2)CC1] |

TABLE 1-continued
Exemplary compounds of the invention
| Compound Number | Structure |
|---|---|
| 179 | 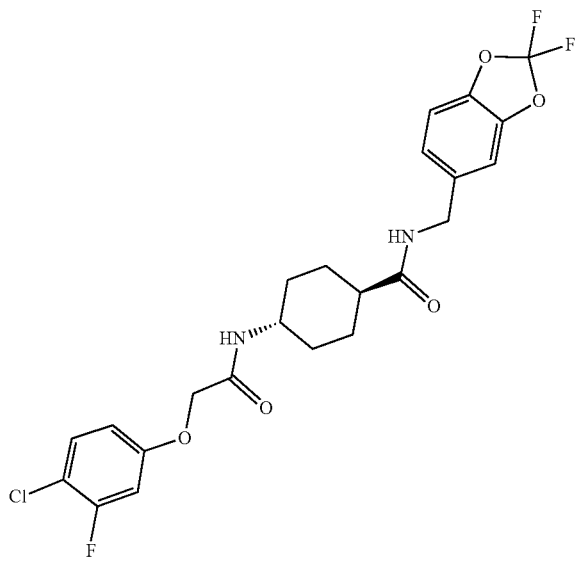 [SMILES: O=C(COc1ccc(Cl)c(F)c1)N[C@H]1CC[C@H](C(=O)NCc2ccc3c(c2)OC(F)(F)O3)CC1] |
| 180 | 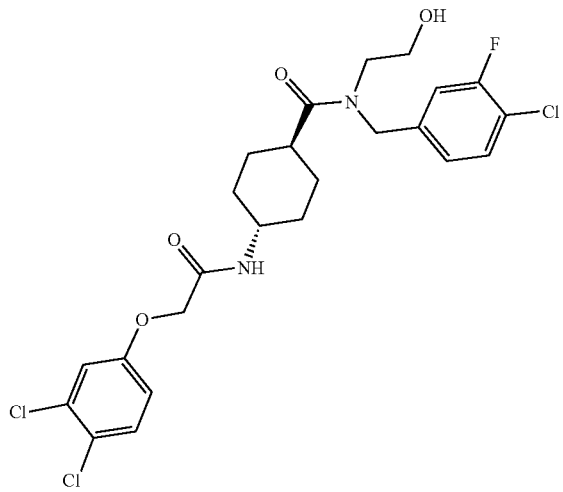 [SMILES: O=C(COc1ccc(Cl)c(Cl)c1)N[C@H]1CC[C@H](C(=O)N(CCO)Cc2ccc(Cl)c(F)c2)CC1] |
| 181 | 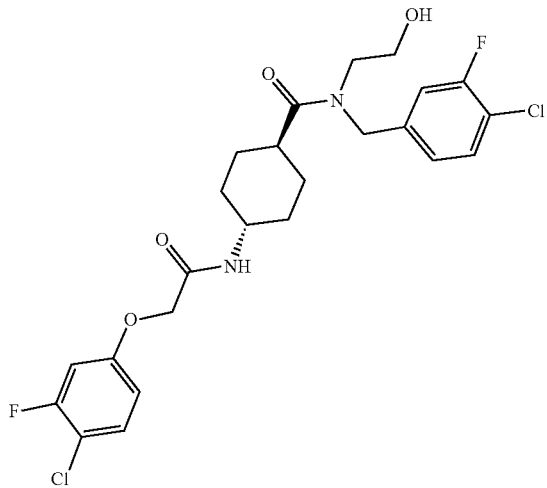 [SMILES: O=C(COc1ccc(Cl)c(F)c1)N[C@H]1CC[C@H](C(=O)N(CCO)Cc2ccc(Cl)c(F)c2)CC1] |

TABLE 1-continued
Exemplary compounds of the invention
| Compound Number | Structure |
|---|---|
| 182 | 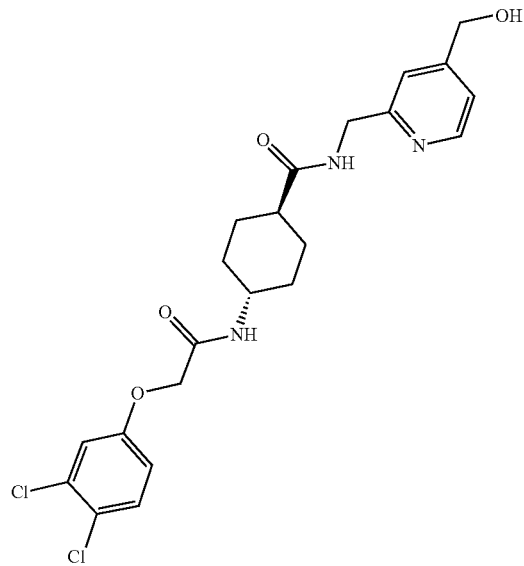 [SMILES: O=C(COc1ccc(Cl)c(Cl)c1)N[C@H]1CC[C@H](C(=O)NCc2cc(CO)ccn2)CC1] |
| 183 | 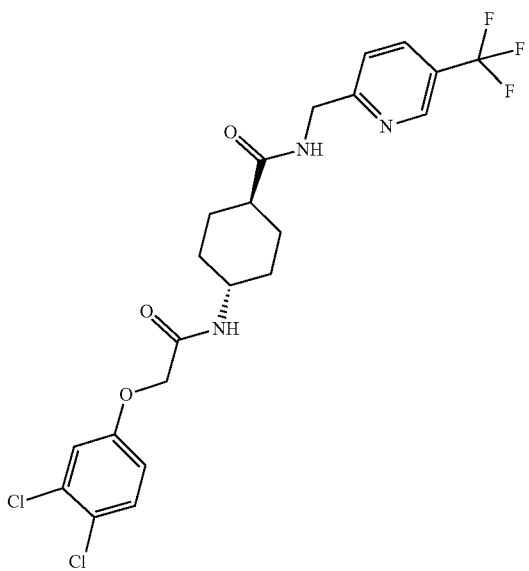 [SMILES: O=C(COc1ccc(Cl)c(Cl)c1)N[C@H]1CC[C@H](C(=O)NCc2ccc(C(F)(F)F)cn2)CC1] |

TABLE 1-continued

Exemplary compounds of the invention

| Compound Number | Structure |
|---|---|
| 184 | (structure) |
| 185 | (structure) |
| 186 | (structure) |

TABLE 1-continued

Exemplary compounds of the invention

| Compound Number | Structure |
|---|---|
| 187 | 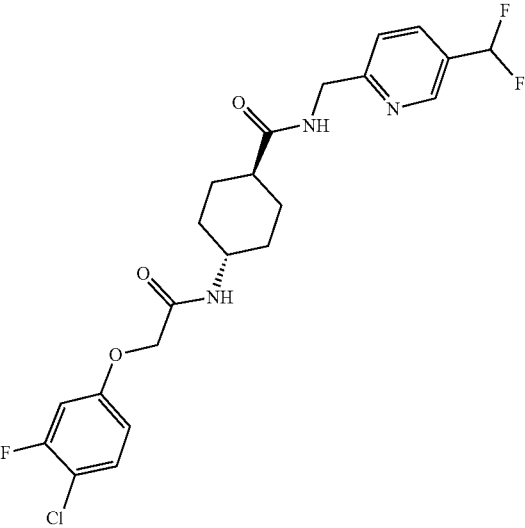 [SMILES: O=C(COc1ccc(Cl)c(F)c1)N[C@H]1CC[C@H](C(=O)NCc2ccc(C(F)F)cn2)CC1] |

Methods of Making Exemplary Compounds

The compounds of the invention may be better understood in connection with the following synthetic schemes and methods which illustrate a means by which the compounds can be prepared. The compounds of this invention can be prepared by a variety of synthetic procedures. Representative synthetic procedures are shown in, but not limited to, Schemes 1 and 2. The variables A, D, Z, $L^1$, $L^2$, $R^1$, and $R^2$ are defined as detailed herein, e.g., in the Summary.

Scheme 1: Representative scheme for synthesis of exemplary compounds of the invention.

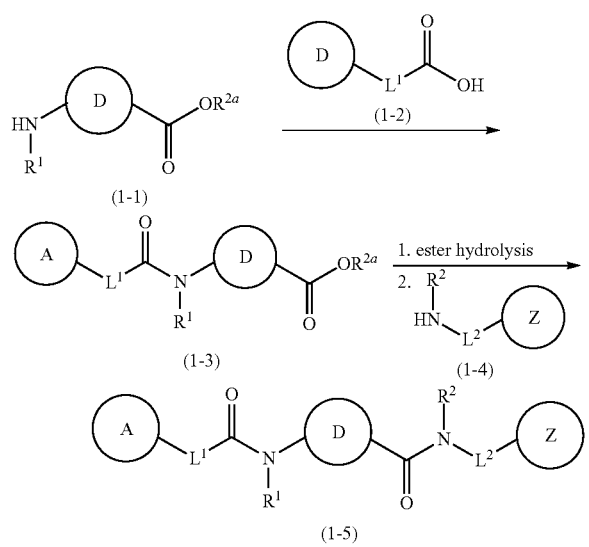

As shown in Scheme 1, compounds of formula (1-5) can be prepared from compounds of formula (1-1). Amines of formula (1-1), wherein $R^{2a}$ is $C_1$-$C_6$ alkyl, can be coupled with carboxylic acids of formula (1-2) under amide bond forming conditions to give amides of formula (1-3). Examples of conditions known to generate amides from a mixture of a carboxylic acid and an amine include but are not limited to adding a coupling reagent such as N-(3-dimethylaminopropyl)-N-ethylcarbodiimide or 1-(3-dimethylaminopropyl)-3-ethylcarbodiimide (EDC, EDAC or EDCI), 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N'N'-tetramethyluronium hexafluorophosphate or 1-[bis(dimethylamino)methylene]-1H-1,2,3-triazolo[4,5-b]pyridinium 3-oxid hexafluorophosphate or 2-(3H-[1,2,3]triazolo[4,5-b]pyridin-3-yl)-1,1,3,3-tetramethylisouronium hexafluorophosphate(V) or 2-(7-aza-1H-benzotriazole-1-yl)-1,1,3,3-tetramethyluronium hexafluorophosphate (HATU), 0-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), 2,4,6-tripropyl-1,3,5,2,4,6-trioxatriphosphinane 2,4,6-trioxide (T3P®), (1-cyano-2-ethoxy-2-oxoethylidenaminooxy)dimethylamino-morpholino-carbenium hexafluorophosphate (COMU®), and fluoro-N,N,N',N'-tetramethylformamidinium hexafluorophosphate. The coupling reagents may be added as a solid, a solution, or as the reagent bound to a solid support resin.

In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, N,N-dimethylacetamide, dimethyl sulfoxide, dichloromethane, and ethyl acetate. Alternatively, carboxylic acids of formula (1-2) can be converted to the corresponding acid chlorides by reaction with thionyl chloride, PCl₃, PCl₅, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides can then reacted with amines of formula (1-1) optionally in the presence of a base such as a tertiary amine base such as triethylamine or diisopropylethylamine or an aromatic base such as pyridine, at room temperature in a solvent such as dichloromethane to give amides of formula (1-3).

The ester moiety of compounds of formula (1-3) can be hydrolyzed under conditions known to one of skill in the art to give the corresponding carboxylic acids. The carboxylic acids can then be reacted with compounds of formula (1-4) under the amide bond forming reaction conditions described above to give compounds of formula (1-5). Alternatively, the carboxylic acids can be converted to the corresponding acid chlorides which can be reacted with compounds of formula (1-4) also as described above to give compounds of formula (1-5). Compounds of formula (1-5) are representative of compounds of formula (I).

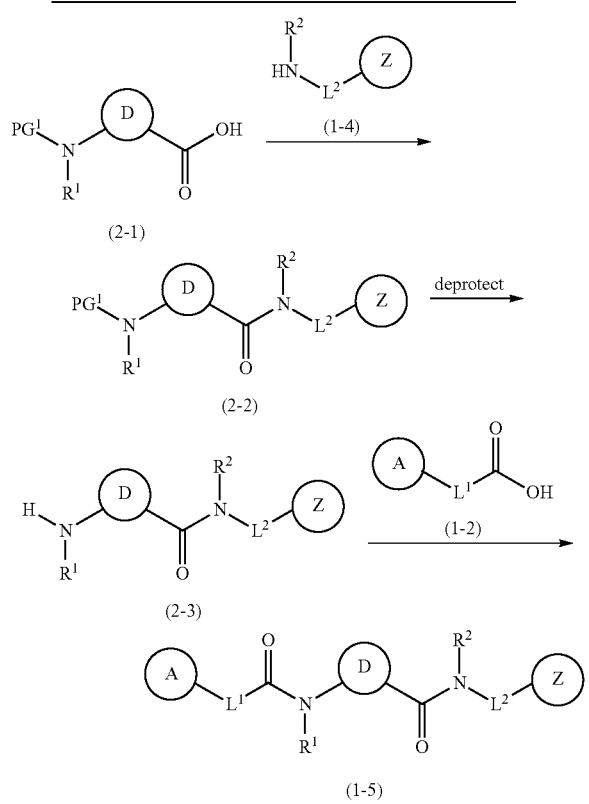

Scheme 2: Representative scheme for synthesis of exemplary compounds of the invention.

As shown in Scheme 2, compounds of formula (1-5) can alternatively be prepared from compounds of formula (2-1). Compounds of formula (2-1), wherein PG1 is an amine protecting group known to one of skill in the art, can be coupled with compounds of formula (1-4) under the amide bond forming reaction conditions described in Scheme 1 to give compounds of formula (2-2). The protecting group of compounds of formula (2-2) can be removed under conditions known to one of skill in the art and dependent upon the particular protecting group to give compounds of formula (2-3). For example, when PG1 is tert-butoxycarbonyl (Boc), treatment with trifluoroacetic acid in dichloromethane or hydrochloric acid in dioxane removes the protecting group. Compounds of formula (2-3) can be coupled with compounds of formula (1-2) under the amide bond forming reaction conditions described in Scheme 1 to give compounds of formula (1-5). Compounds of formula (1-5) are representative of compounds of formula (I).

Pharmaceutical Compositions

The present invention features pharmaceutical compositions comprising a compound of Formula (I) or a pharmaceutically acceptable salt, solvate, hydrate, tautomer, or stereoisomer thereof. In some embodiments, the pharmaceutical composition further comprises a pharmaceutically acceptable excipient. In some embodiments, the compound of Formula (I) or a pharmaceutically acceptable salt, solvate, hydrate, tautomer, stereoisomer thereof is provided in an effective amount in the pharmaceutical composition. In some embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) (the "active ingredient") into association with a carrier and/or one or more other accessory ingredients, and then, if necessary and/or desirable, shaping and/or packaging the product into a desired single- or multi-dose unit. Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of a compound of Formula (I), the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of a compound of Formula (I).

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the invention are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A compound of Formula (I) may also be in micro-encapsulated form.

The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, J. Hosp. Pharm. 46: 1576-1587, 1989). The compositions of the present invention can also be delivered as nanoparticles.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

In some embodiments, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein, e.g., a compound of Formula (I) or a pharmaceutically acceptable salt, solvate, hydrate, tautomer, or stereoisomer thereof are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound of Formula (I) or a pharmaceutically acceptable salt, solvate, hydrate, tautomer, or stereoisomer thereof for administration one or more times a day may comprise about 0.0001 mg to about 5000 mg, e.g., from about 0.0001 mg to about 4000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound of Formula (I) or a pharmaceutically acceptable salt, solvate, hydrate, tautomer, or stereoisomer thereof may be at dosage levels sufficient to deliver from about 0.001 mg/kg to about 1000 mg/kg, e.g., about 0.001 mg/kg to about 500 mg/kg, about 0.01 mg/kg to about 250 mg/kg, about 0.1 mg/kg to about 100 mg/kg, about 0.1 mg/kg to about 50 mg/kg, about 0.1 mg/kg to about 40 mg/kg, about 0.1 mg/kg to about 25 mg/kg, about 0.01 mg/kg to about 10 mg/kg, about 0.1 mg/kg to about 10 mg/kg, or about 1 mg/kg to about 50 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, e.g., a compound of Formula (I) or a pharmaceutically acceptable salt, solvate, hydrate, tautomer, or stereoisomer thereof as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and pain-relieving agents. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Pharmaceutical compositions provided by the present invention include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. eIF2B, eIF2 or component of eIF2α signal transduction pathway or component of phosphorylated eIF2α pathway or the ISR pathway), and/or reducing, eliminating, or slowing the progression of disease symptoms (e.g. symptoms of cancer a neurodegenerative disease, a leukodystrophy, an inflammatory disease, a musculoskeletal disease, a metabolic disease, or a disease or disorder associated with impaired function of eIF2B, eIF2α or a component of the eIF2 pathway or ISR pathway). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. a symptom of cancer, a neurodegenerative disease, a leukodystrophy, an inflammatory disease, a musculoskeletal disease, a metabolic disease, or a disease or disorder associated with impaired function of eIF2B, eIF2α, or a component of the eIF2 pathway or ISR pathway), kind of concurrent treatment, complications from the disease being treated or other health-related problems. Other therapeutic regimens or agents can be used in conjunction with the methods and compounds of Applicants' invention.

Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Also encompassed by the invention are kits (e.g., pharmaceutical packs). The inventive kits may be useful for preventing and/or treating a disease (e.g., cancer, a neurodegenerative disease, a leukodystrophy, an inflammatory disease, a musculoskeletal disease, a metabolic disease, or other disease or condition described herein).

The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound of Formula (I) or a pharmaceutically acceptable salt, solvate, hydrate, tautomer, or stereoisomer thereof, or a pharmaceutical composition thereof. In certain embodiments, the kits are useful in preventing and/or treating a proliferative disease in a subject. In certain embodiments, the kits further include instructions for administering a compound of Formula (I) or a pharmaceutically acceptable salt, solvate, hydrate, tautomer, or stereoisomer thereof, or a pharmaceutical composition thereof, to a subject to prevent and/or treat a disease described herein.

Methods of Treatment

The present invention features compounds, compositions, and methods comprising a compound of Formula (I) or Formula (III), or a pharmaceutically acceptable salt, co-crystal, solvate, hydrate, tautomer, ester, N-oxide or stereoisomer thereof. In some embodiments, the compounds, compositions, and methods are used in the prevention or treatment of a disease, disorder, or condition. Exemplary diseases, disorders, or conditions include, but are not limited to a neurodegenerative disease, a leukodystrophy, a cancer, an inflammatory disease, an autoimmune disease, a viral infection, a skin disease, a fibrotic disease, a hemoglobin disease, a kidney disease, a hearing loss condition, an ocular disease, a disease with mutations that leads to UPR induction, a malaria infection, a musculoskeletal disease, a metabolic disease, or a mitochondrial disease.

In some embodiments, the disease, disorder, or condition is related to (e.g., caused by) modulation of (e.g., a decrease in) eIF2B activity or level, eIF2α activity or level, or a component of the eIF2 pathway or ISR pathway. In some embodiments, the disease, disorder, or condition is related to modulation of a signaling pathway related to a component of the eIF2 pathway or ISR pathway (e.g., phosphorylation of a component of the eIF2 pathway or ISR pathway). In some embodiments, the disease, disorder, or condition is related to (e.g., caused by) neurodegeneration. In some embodiments, the disease, disorder, or condition is related to (e.g., caused by) neural cell death or dysfunction. In some embodiments, the disease, disorder, or condition is related to (e.g., caused by) glial cell death or dysfunction. In some embodiments, the disease, disorder, or condition is related to (e.g., caused by) an increase in the level or activity of eIF2B, eIF2α, or a component of the eIF2 pathway or ISR pathway. In some embodiments, the disease, disorder, or condition is related to (e.g., caused by) a decrease in the level or activity of eIF2B, eIF2α, or a component of the eIF2 pathway or ISR pathway.

In some embodiments, the disease may be caused by a mutation to a gene or protein sequence related to a member of the eIF2 pathway (e.g., eIF2B, eIF2α, or other component). Exemplary mutations include an amino acid mutation in the eIF2B1, eIF2B2, eIF2B3, eIF2B4, eIF2B5 subunits. In some embodiments, an amino acid mutation (e.g., an amino acid substitution, addition, or deletion) in a particular protein that may result in a structural change, e.g., a conformational or steric change, that affects the function of the protein. For example, in some embodiments, amino acids in and around the active site or close to a binding site (e.g., a phosphorylation site, small molecule binding site, or protein-binding site) may be mutated such that the activity of the protein is impacted. In some instances, the amino acid mutation (e.g., an amino acid substitution, addition, or deletion) may be conservative and may not substantially impact the structure or function of a protein. For example, in certain cases, the substitution of a serine residue with a threonine residue may not significantly impact the function of a protein. In other cases, the amino acid mutation may be more dramatic, such as the substitution of a charged amino acid (e.g., aspartic acid or lysine) with a large, nonpolar amino acid (e.g., phenylalanine or tryptophan) and therefore may have a substantial impact on protein function. The nature of the mutations that affect the structure of function of a gene or protein may be readily identified using standard sequencing techniques, e.g., deep sequencing techniques that are well known in the art. In some embodiments, a mutation in a member of the eIF2 pathway may affect binding or activity of a compound of Formula (I) or Formula (III), or a pharmaceutically acceptable salt, co-crystal, solvate, hydrate, tautomer, ester, N-oxide or stereoisomer thereof and thereby modulate treatment of a particular disease, disorder, or condition, or a symptom thereof.

In some embodiments, an eIF2 protein may comprise an amino acid mutation (e.g., an amino acid substitution, addition, or deletion) at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue. In some embodiments, an eIF2 protein may comprise an amino acid substitution at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue. In some embodiments, an eIF2 protein may comprise an amino acid addition at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue. In some embodiments, an eIF2 protein may comprise an amino acid deletion at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue.

In some embodiments, the eIF2 protein may comprise an amino acid mutation (e.g., an amino acid substitution, addition, or deletion) at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. In some embodiments, the eIF2 protein may comprise an amino acid substitution at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. In some embodiments, the eIF2 protein may comprise an amino acid addition at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. In some embodiments, the eIF2 protein may comprise an amino acid deletion at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. Exemplary mutations include V183F (eIF2B1 subunit), H341Q (eIF2B3), I346T (eIF2B3), R483W (eIF2B4), R113H (eIF2B5), and R195H (eIF2B5).

In some embodiments, an amino acid mutation (e.g., an amino acid substitution, addition, or deletion) in a member of the eIF2 pathway (e.g., an eIF2B protein subunit) may affect binding or activity of a compound of Formula (I) or Formula (III), or a pharmaceutically acceptable salt, co-crystal, solvate, hydrate, tautomer, ester, N-oxide or stereoisomer thereof and thereby modulate treatment of a particular disease, disorder, or condition, or a symptom thereof.

Neurodegenerative Disease

In some embodiments, the compound of Formula (I) or Formula (III), or a pharmaceutically acceptable salt, co-crystal, solvate, hydrate, tautomer, ester, N-oxide or stereoisomer thereof is used to treat a neurodegenerative disease. As used herein, the term "neurodegenerative disease" refers to a disease or condition in which the function of a subject's nervous system becomes impaired. Examples of a neurodegenerative disease that may be treated with a compound, pharmaceutical composition, or method described herein include Alexander's disease, Alper's disease, Alzheimer's disease, Amyotrophic lateral sclerosis (ALS), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Dystonia, frontotemporal dementia (FTD), Gerstmann-Straussler-Scheinker syndrome, Huntington's disease, HIV-associated dementia, Kennedy's disease, Krabbe disease, kuru, Lewy body dementia, Machado-Joseph disease (Spinocerebellar ataxia type 3), Multiple system atrophy, Multisystem proteinopathy, Narcolepsy, Neuroborreliosis, Parkinson's disease, Pelizaeus-Merzbacher Disease, Pick's disease, Primary lateral sclerosis, Prion diseases, Refsum's disease, Sandhoff disease, Schilder's disease, Subacute combined degeneration of spinal cord secondary to Pernicious Anaemia, Schizophrenia, Spinocerebellar ataxia (multiple types with varying characteristics, e.g., Spinocerebellar ataxia type 2 or Spinocerebellar ataxia type 8), Spinal muscular atrophy, Steele-Richardson-Olszewski disease, progressive supranuclear palsy, corticobasal degeneration, adrenoleukodystrophy, X-linked adrenoleukodystrophy, cerebral adrenoleukodystrophy, Pelizaeus-Merzbacher Disease, Krabbe disease, leukodystrophy due to mutation in DARS2 gene (sometimes known as lukoencephalopathy with brainstem and spinal cord involvement and lactate elevation (LBSL), DARS2-related spectrum disorders, or Tabes *dorsalis*.

In some embodiments, the neurodegenerative disease comprises vanishing white matter disease, childhood ataxia with CNS hypo-myelination, a leukodystrophy, a leukoencephalopathy, a hypomyelinating or demyelinating disease, an intellectual disability syndrome (e.g., Fragile X syndrome), Alzheimer's disease, amyotrophic lateral sclerosis (ALS), Creutzfeldt-Jakob disease, frontotemporal dementia (FTD), Gerstmann-Straussler-Scheinker disease, Huntington's disease, dementia (e.g., HIV-associated dementia or Lewy body dementia), kuru, multiple sclerosis, Parkinson's disease, or a prion disease.

In some embodiments, the neurodegenerative disease comprises vanishing white matter disease, childhood ataxia with CNS hypo-myelination, a leukodystrophy, a leukoencephalopathy, a hypomyelinating or demyelinating disease, or an intellectual disability syndrome (e.g., Fragile X syndrome).

In some embodiments, the neurodegenerative disease comprises a psychiatric disease such as agoraphobia, Alzheimer's disease, anorexia nervosa, amnesia, anxiety disorder, attention deficit disorder, bipolar disorder, body dysmorphic disorder, bulimia nervosa, claustrophobia, depression, delusions, Diogenes syndrome, dyspraxia, insomnia, Munchausen's syndrome, narcolepsy, narcissistic personality disorder, obsessive-compulsive disorder, psychosis, phobic disorder, schizophrenia, seasonal affective disorder, schizoid personality disorder, sleepwalking, social phobia, substance abuse, tardive dyskinesia, Tourette syndrome, or trichotillomania.

In some embodiments, the compound of Formula (I) or Formula (III), or a pharmaceutically acceptable salt, co-crystal, solvate, hydrate, tautomer, ester, N-oxide or stereoisomer thereof is used to treat vanishing white matter disease. Exemplary methods of treating vanishing white matter disease include, but are not limited to, reducing or eliminating a symptom of vanishing white matter disease, reducing the loss of white matter, reducing the loss of myelin, increasing the amount of myelin, or increasing the amount of white matter in a subject.

In some embodiments, the compound of Formula (I) or Formula (III), or a pharmaceutically acceptable salt, co-crystal, solvate, hydrate, tautomer, ester, N-oxide or stereoisomer thereof is used to treat childhood ataxia with CNS hypo-myelination. Exemplary methods of treating childhood ataxia with CNS hypo-myelination include, but are not limited to, reducing or eliminating a symptom of childhood ataxia with CNS hypo-myelination, increasing the level of myelin, or decreasing the loss of myelin in a subject.

In some embodiments, the compound of Formula (I) or Formula (III), or a pharmaceutically acceptable salt, co-crystal, solvate, hydrate, tautomer, ester, N-oxide or stereoisomer thereof is used to treat an intellectual disability syndrome (e.g., Fragile X syndrome). Exemplary methods of treating an intellectual disability syndrome include, but are not limited to, reducing or eliminating a symptom of an intellectual disability syndrome.

In some embodiments, the compound of Formula (I) or Formula (III), or a pharmaceutically acceptable salt, co-crystal, solvate, hydrate, tautomer, ester, N-oxide or stereoisomer thereof is used to treat neurodegeneration. Exemplary methods of treating neurodegeneration include, but are not limited to, improvement of mental wellbeing, increasing mental function, slowing the decrease of mental function, decreasing dementia, delaying the onset of dementia, improving cognitive skills, decreasing the loss of cognitive skills, improving memory, decreasing the degradation of memory, or extending survival.

In some embodiments, the compound of Formula (I) or Formula (III), or a pharmaceutically acceptable salt, co-crystal, solvate, hydrate, tautomer, ester, N-oxide or stereoisomer thereof is used to treat a leukoencephalopathy or demyelinating disease. Exemplary leukoencephalopathies include, but are not limited to, progressive multifocal leukoencephalopathy, toxic leukoencephalopathy, leukoencephalopathy with vanishing white matter, leukoencephalopathy with neuroaxonal spheroids, reversible posterior leukoencephalopathy syndrome, hypertensive leukoencephalopathy, megalencephalic leukoencephalopathy with subcortical cysts, Charcot-Marie-Tooth disorder, and Devic's disease. A leukoencephalopathy may comprise a demyelinating disease, which may be inherited or acquired. In some embodiments, an acquired demyelinating disease may be an inflammatory demyelinating disease (e.g., an infectious inflammatory demyelinating disease or a non-infectious inflammatory demyelinating disease), a toxic demyelinating disease, a metabolic demyelinating disease, a hypoxic demyelinating disease, a traumatic demyelinating disease, or an ischemic demyelinating disease (e.g., Binswanger's disease). Exemplary methods of treating a leukoencephalopathy or demyelinating disease include, but are not limited to, reducing or eliminating a symptom of a leukoencephalopathy or demyelinating disease, reducing the loss of myelin, increasing the amount of myelin, reducing the loss of white matter in a subject, or increasing the amount of white matter in a subject.

In some embodiments, the compound of Formula (I) or Formula (III), or a pharmaceutically acceptable salt, co-crystal, solvate, hydrate, tautomer, ester, N-oxide or stereoisomer thereof is used to treat a traumatic injury or a toxin-induced injury to the nervous system (e.g., the brain). Exemplary traumatic brain injuries include, but are not limited to, a brain abscess, concussion, ischemia, brain bleeding, cranial fracture, diffuse axonal injury, locked-in syndrome, or injury relating to a traumatic force or blow to the nervous system or brain that causes damage to an organ or tissue. Exemplary toxin-induced brain injuries include, but are not limited to, toxic encephalopathy, meningitis (e.g. bacterial meningitis or viral meningitis), meningoencephalitis, encephalitis (e.g., Japanese encephalitis, eastern equine encephalitis, West Nile encephalitis), Guillan-Barre syndrome, Sydenham's chorea, rabies, leprosy, neurosyphilis, a prion disease, or exposure to a chemical (e.g., arsenic, lead, toluene, ethanol, manganese, fluoride, dichlorodiphenyltrichloroethane (DDT), dichlorodiphenyldichloroethylene (DDE), tetrachloroethylene, a polybrominated diphenyl ether, a pesticide, a sodium channel inhibitor, a potassium channel inhibitor, a chloride channel inhibitor, a calcium channel inhibitor, or a blood brain barrier inhibitor).

In other embodiments, the compound of Formula (I) or Formula (III), or a pharmaceutically acceptable salt, co-crystal, solvate, hydrate, tautomer, ester, N-oxide or stereoisomer thereof is used to improve memory in a subject. Induction of memory has been shown to be facilitated by decreased and impaired by increased eIF2α phosphorylation. Regulators of translation, such as compounds disclosed herein (e.g. a compound of Formula (I) or Formula (III)), could serve as therapeutic agents that improve memory in human disorders associated with memory loss such as Alzheimer's disease and in other neurological disorders that activate the UPR or ISR in neurons and thus could have negative effects on memory consolidation such as Parkinson's disease, schizophrenia, amyotrophic lateral sclerosis (ALS) and prion diseases. In addition, a mutation in eIF27 that disrupts complex integrity linked intellectual disability (intellectual disability syndrome or ID) to impaired translation initiation in humans. Hence, two diseases with impaired eIF2 function, ID and VWM, display distinct phenotypes but both affect mainly the brain and impair learning. In some embodiments, the disease or condition is unsatisfactory memory (e.g., working memory, long term memory, short term memory, or memory consolidation).

In still other embodiments, the compound of Formula (I) or Formula (III), or a pharmaceutically acceptable salt, co-crystal, solvate, hydrate, tautomer, ester, N-oxide or stereoisomer thereof is used in a method to improve memory in a subject (e.g., working memory, long term memory, short term memory, or memory consolidation). In some embodiments, the subject is human. In some embodiments, the subject is a non-human mammal. In some embodiments, the subject is a domesticated animal. In some embodiments, the subject is a dog. In some embodiments, the subject is a bird. In some embodiments, the subject is a horse. In embodiments, the patient is a bovine. In some embodiments, the subject is a primate.

Cancer

In some embodiments, the compound of Formula (I) or Formula (III), or a pharmaceutically acceptable salt, co-crystal, solvate, hydrate, tautomer, or stereoisomer thereof is used to treat cancer. As used herein, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In some further instances, "cancer" refers to lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g., ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g., non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma (e.g., WNT-dependent pediatric medulloblastoma), Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epidermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

In some embodiments, the compound of Formula (I) or Formula (III) or a pharmaceutically acceptable salt, solvate, hydrate, tautomer, or stereoisomer thereof is used to treat pancreatic cancer, breast cancer, multiple myeloma, cancers of secretory cells. For example certain methods herein treat cancer by decreasing or reducing or preventing the occurrence, growth, metastasis, or progression of cancer. In some embodiments, the methods described herein may be used to treat cancer by decreasing or eliminating a symptom of cancer. In some embodiments, the compound of Formula (I) or Formula (III) or a pharmaceutically acceptable salt, solvate, hydrate, tautomer, or stereoisomer thereof may be used as a single agent in a composition or in combination with another agent in a composition to treat a cancer described herein (e.g., pancreatic cancer, breast cancer, multiple myeloma, cancers of secretory cells).

In some embodiments, the compounds (compounds described herein, e.g., a compound of Formula (I) or Formula (III)) and compositions (e.g., compositions comprising a compound described herein, e.g., a compound of Formula (I) or Formula (III))) are used with a cancer immunotherapy (e.g., a checkpoint blocking antibody) to treat a subject (e.g., a human subject), e.g., suffering from a disease or disorder described herein (e.g., abnormal cell growth, e.g., cancer (e.g., a cancer described herein)). The methods described herein comprise administering a compound described herein, e.g., a compound of Formula (I) or Formula (III) and an immunotherapy to a subject having abnormal cell growth such as cancer. Exemplary immunotherapies include, but are not limited to the following.

In some embodiments, the immunotherapeutic agent is a compound (e.g., a ligand, an antibody) that inhibits the immune checkpoint blockade pathway. In some embodiments, the immunotherapeutic agent is a compound that inhibits the indoleamine 2,3-dioxygenase (IDO) pathway. In some embodiments, the immunotherapeutic agent is a compound that agonizes the STING pathway. Cancer immunotherapy refers to the use of the immune system to treat cancer. Three groups of immunotherapy used to treat cancer include cell-based, antibody-based, and cytokine therapies. All groups exploit cancer cells' display of subtly different structures (e.g., molecular structure; antigens, proteins, molecules, carbohydrates) on their surface that can be detected by the immune system. Cancer immunotherapy (i.e., anti-tumor immunotherapy or anti-tumor immunotherapeutics) includes but is not limited to, immune checkpoint antibodies (e.g., PD-1 antibodies, PD-L1 antibodies, PD-L2 antibodies, CTLA-4 antibodies, TIM3 antibodies, LAG3 antibodies, TIGIT antibodies); and cancer vaccines (i.e., anti-tumor vaccines or vaccines based on neoantigens such as a peptide or RNA vaccine).

Cell-based therapies (e.g., cancer vaccines), usually involve the removal of immune cells from a subject suffering from cancer, either from the blood or from a tumor. Immune cells specific for the tumor will be activated, grown, and returned to a subject suffering from cancer where the immune cells provide an immune response against the cancer. Cell types that can be used in this way are e.g., natural killer cells, lymphokine-activated killer cells, cytotoxic T-cells, dendritic cells, CAR-T therapies (i.e., chimeric antigen receptor T-cells which are T-cells engineered to target specific antigens), TIL therapy (i.e., administration of tumor-infiltrating lymphocytes), TCR gene therapy, protein vaccines, and nucleic acid vaccines. An exemplary cell-based therapy is Provenge. In some embodiments, the cell-based therapy is a CAR-T therapy.

Interleukin-2 and interferon-alpha are examples of cytokines, proteins that regulate and coordinate the behavior of the immune system.

Cancer Vaccines with Neoantigens

Neoantigens are antigens encoded by tumor-specific mutated genes. Technological innovations have made it possible to dissect the immune response to patient-specific neoantigens that arise as a consequence of tumor-specific mutations, and emerging data suggest that recognition of such neoantigens is a major factor in the activity of clinical immunotherapies. These observations indicate that neoantigen load may form a biomarker in cancer immunotherapy. Many novel therapeutic approaches are being developed that selectively enhance T cell reactivity against this class of antigens. One approach to target neoantigens is via cancer vaccine. These vaccines can be developed using peptides or RNA, e.g., synthetic peptides or synthetic RNA.

Antibody therapies are antibody proteins produced by the immune system and that bind to a target antigen on the surface of a cell. Antibodies are typically encoded by an immunoglobulin gene or genes, or fragments thereof. In normal physiology antibodies are used by the immune system to fight pathogens. Each antibody is specific to one or a few proteins, and those that bind to cancer antigens are used, e.g., for the treatment of cancer. Antibodies are capable of specifically binding an antigen or epitope. (Fundamental Immunology, $3^{rd}$ Edition, W. E., Paul, ed., Raven Press, N.Y. (1993). Specific binding occurs to the corresponding antigen or epitope even in the presence of a heterogeneous population of proteins and other biologics. Specific binding of an antibody indicates that it binds to its target antigen or epitope with an affinity that is substantially greater than binding to irrelevant antigens. The relative difference in affinity is often at least 25% greater, more often at least 50% greater, most often at least 100% greater. The relative difference can be at least 2-fold, at least 5-fold, at least 10-fold, at least 25-fold, at least 50-fold, at least 100-fold, or at least 1000-fold, for example.

Exemplary types of antibodies include without limitation human, humanized, chimeric, monoclonal, polyclonal, single chain, antibody binding fragments, and diabodies. Once bound to a cancer antigen, antibodies can induce antibody-dependent cell-mediated cytotoxicity, activate the complement system, prevent a receptor interacting with its ligand or deliver a payload of chemotherapy or radiation, all of which can lead to cell death. Exemplary antibodies for the treatment of cancer include but are not limited to, Alemtuzumab, Bevacizumab, Bretuximab vedotin, Cetuximab, Gemtuzumab ozogamicin, Ibritumomab tiuxetan, Ipilimumab, Ofatumumab, Panitumumab, Rituximab, Tositumomab, Trastuzumab, Nivolumab, Pembrolizumab, Avelumab, durvalumab and pidilizumab.

Checkpoint Blocking Antibodies

The methods described herein comprise, in some embodiments, treating a human subject suffering from a disease or disorder described herein, the method comprising administering a composition comprising a cancer immunotherapy (e.g., an immunotherapeutic agent). In some embodiments, the immunotherapeutic agent is a compound (e.g., an inhibitor or antibody) that inhibits the immune checkpoint blockade pathway. Immune checkpoint proteins, under normal physiological conditions, maintain self-tolerance (e.g., prevent autoimmunity) and protect tissues from damage when the immune system is responding to e.g., pathogenic infection. Immune checkpoint proteins can be dysregulated by tumors as an important immune resistance mechanism. (Pardoll, Nature Rev. Cancer, 2012, 12, 252-264). Agonists of co-stimulatory receptors or antagonists of inhibitory signals (e.g., immune checkpoint proteins), provide an amplification of antigen-specific T-cell responses. Antibodies that block immune checkpoints do not target tumor cells directly but typically target lymphocyte receptors or their ligands to enhance endogenous antitumor activity.

Exemplary checkpoint blocking antibodies include but are not limited to, anti-CTLA-4, anti-PD-1, anti-LAG3 (i.e., antibodies against lymphocyte activation gene 3), and anti-TIM3 (i.e., antibodies against T-cell membrane protein 3). Exemplary anti-CTLA-4 antibodies include but are not limited to, ipilimumab and tremelimumab. Exemplary anti-PD-1 ligands include but are not limited to, PD-L1 (i.e., B7-H1 and CD274) and PD-L2 (i.e., B7-DC and CD273). Exemplary anti-PD-1 antibodies include but are not limited to, nivolumab (i.e., MDX-1106, BMS-936558, or ONO-4538)), CT-011, AMP-224, pembrolizumab (trade name Keytruda), and MK-3475. Exemplary PD-L1-specific antibodies include but are not limited to, BMS936559 (i.e., MDX-1105), MEDI4736 and MPDL-3280A. Exemplary checkpoint blocking antibodies also include but are not limited to, IMP321 and MGA271.

T-regulatory cells (e.g., CD4+, CD25+, or T-reg) are also involved in policing the distinction between self and non-self (e.g., foreign) antigens, and may represent an important mechanism in suppression of immune response in many cancers. T-reg cells can either emerge from the thymus (i.e., "natural T-reg") or can differentiate from mature T-cells under circumstances of peripheral tolerance induction (i.e., "induced T-reg"). Strategies that minimize the action of T-reg cells would therefore be expected to facilitate the immune response to tumors. (Sutmuller, van Duivernvoorde et al., 2001).

IDO Pathway Inhibitors

The IDO pathway regulates immune response by suppressing T cell function and enabling local tumor immune escape. IDO expression by antigen-presenting cells (APCs) can lead to tryptophan depletion, and resulting antigen-specific T cell energy and regulatory T cell recruitment. Some tumors even express IDO to shield themselves from the immune system. A compound that inhibits IDO or the IDO pathway thereby activating the immune system to attack the cancer (e.g., tumor in a subject). Exemplary IDO pathway inhibitors include indoximod, epacadostat and EOS200271.

STING Pathway Agonists

Stimulator of interferon genes (STING) is an adaptor protein that plays an important role in the activation of type I interferons in response to cytosolic nucleic acid ligands. Evidence indicates involvement of the STING pathway in the induction of antitumor immune response. It has been shown that activation of the STING-dependent pathway in cancer cells can result in tumor infiltration with immune cells and modulation of the anticancer immune response. STING agonists are being developed as a class of cancer therapeutics. Exemplary STING agonists include MK-1454 and ADU-S100.

Co-Stimulatory Antibodies

The methods described herein comprise, in some embodiments, treating a human subject suffering from a disease or disorder described herein, the method comprising administering a composition comprising a cancer immunotherapy (e.g., an immunotherapeutic agent). In some embodiments, the immunotherapeutic agent is a co-stimulatory inhibitor or antibody. In some embodiments, the methods described herein comprise depleting or activating anti-4-1BB, anti-OX40, anti-GITR, anti-CD27 and anti-CD40, and variants thereof.

Inventive methods of the present invention contemplate single as well as multiple administrations of a therapeutically effective amount of a compound as described herein. Compounds, e.g., a compound as described herein, can be administered at regular intervals, depending on the nature, severity and extent of the subject's condition. In some embodiments, a compound described herein is administered in a single dose. In some embodiments, a compound described herein is administered in multiple doses.

Inflammatory Disease

In some embodiments, the compound of Formula (I) or Formula (III), or a pharmaceutically acceptable salt, co-crystal, solvate, hydrate, tautomer, ester, N-oxide or stereoisomer thereof is used to treat an inflammatory disease. As used herein, the term "inflammatory disease" refers to a disease or condition characterized by aberrant inflammation (e.g. an increased level of inflammation compared to a control such as a healthy person not suffering from a disease). Examples of inflammatory diseases include post-operative cognitive dysfunction, arthritis (e.g., rheumatoid arthritis, psoriatic arthritis, juvenile idiopathic arthritis), systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves' ophthalmopathy, inflammatory bowel disease, Addison's disease, Vitiligo, asthma (e.g., allergic asthma), acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis. Proteins associated with inflammation and inflammatory diseases (e.g. aberrant expression being a symptom or cause or marker of the disease) include interleukin-6 (IL-6), interleukin-8 (IL-8), interleukin-18 (IL-18), TNF-α (tumor necrosis factor-alpha), and C-reactive protein (CRP).

In some embodiments, the inflammatory disease comprises postoperative cognitive dysfunction, arthritis (e.g., rheumatoid arthritis, psoriatic arthritis, or juvenile idiopathic arthritis), systemic lupus erythematosus (SLE), myasthenia gravis, diabetes (e.g., juvenile onset diabetes or diabetes mellitus type 1), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves' ophthalmopathy, inflammatory bowel disease, Addison's disease, vitiligo, asthma (e.g., allergic asthma), acne vulgaris, celiac disease, chronic prostatitis, pelvic inflammatory disease, reperfusion injury, sarcoidosis, transplant rejection, interstitial cystitis, atherosclerosis, or atopic dermatitis.

In some embodiments, the inflammatory disease comprises postoperative cognitive dysfunction, which refers to a decline in cognitive function (e.g. memory or executive function (e.g. working memory, reasoning, task flexibility, speed of processing, or problem solving)) following surgery.

In other embodiments, the method of treatment is a method of prevention. For example, a method of treating postsurgical cognitive dysfunction may include preventing postsurgical cognitive dysfunction or a symptom of postsurgical cognitive dysfunction or reducing the severity of a symptom of postsurgical cognitive dysfunction by administering a compound described herein prior to surgery.

In some embodiments, the compound of Formula (I) or Formula (III), or a pharmaceutically acceptable salt, co-crystal, solvate, hydrate, tautomer, ester, N-oxide or stereoisomer thereof is used to treat an inflammatory disease (e.g., an inflammatory disease described herein) by decreasing or eliminating a symptom of the disease. In some embodiments, the compound of Formula (I) or Formula (III), or a pharmaceutically acceptable salt, co-crystal, solvate, hydrate, tautomer, ester, N-oxide or stereoisomer thereof may be used as a single agent in a composition or in combination with another agent in a composition to treat an inflammatory disease (e.g., an inflammatory disease described herein).

Musculoskeletal Diseases

In some embodiments, the compound of Formula (I) or Formula (III), or a pharmaceutically acceptable salt, co-crystal, solvate, hydrate, tautomer, ester, N-oxide or stereoisomer thereof is used to treat a musculoskeletal disease. As used herein, the term "musculoskeletal disease" refers to a disease or condition in which the function of a subject's musculoskeletal system (e.g., muscles, ligaments, tendons, cartilage, or bones) becomes impaired. Exemplary musculoskeletal diseases that may be treated with a compound of Formula (I) or Formula (III), or a pharmaceutically acceptable salt, co-crystal, solvate, hydrate, tautomer, ester, N-oxide or stereoisomer thereof include muscular dystrophy (e.g., Duchenne muscular dystrophy, Becker muscular dystrophy, distal muscular dystrophy, congenital muscular dystrophy, Emery-Dreifuss muscular dystrophy, facioscapulohumeral muscular dystrophy, myotonic muscular dystrophy type 1, or myotonic muscular dystrophy type 2), limb girdle muscular dystrophy, multisystem proteinopathy, rhizomelic chondrodysplasia punctata, X-linked recessive chondrodysplasia punctata, Conradi-Hunermann syndrome, Autosomal dominant chondrodysplasia punctata, stress induced skeletal disorders (e.g., stress induced osteoporosis), multiple sclerosis, amyotrophic lateral sclerosis (ALS), primary lateral sclerosis, progressive muscular atrophy, progressive bulbar palsy, pseudobulbar palsy, spinal muscular atrophy, progressive spinobulbar muscular atrophy, spinal cord spasticity, spinal muscle atrophy, myasthenia gravis, neuralgia, fibromyalgia, Machado-Joseph disease, Paget's disease of bone, cramp fasciculation syndrome, Freidrich's ataxia, a muscle wasting disorder (e.g., muscle atrophy, sarcopenia, cachexia), an inclusion body myopathy, motor neuron disease, or paralysis.

In some embodiments, the compound of Formula (I) or Formula (III), or a pharmaceutically acceptable salt, co-crystal, solvate, hydrate, tautomer, ester, N-oxide or stereoisomer thereof is used to treat a musculoskeletal disease (e.g., a musculoskeletal disease described herein) by decreasing or eliminating a symptom of the disease. In some embodiments, the method of treatment comprises treatment of muscle pain or muscle stiffness associated with a musculoskeletal disease. In some embodiments, the compound of Formula (I) or Formula (III), or a pharmaceutically acceptable salt, co-crystal, solvate, hydrate, tautomer, ester, N-oxide or stereoisomer thereof may be used as a single agent in a composition or in combination with another agent in a composition to treat a musculoskeletal disease (e.g., a musculoskeletal disease described herein).

Metabolic Diseases

In some embodiments, the compound of Formula (I) or Formula (III), or a pharmaceutically acceptable salt, co-crystal, solvate, hydrate, tautomer, ester, N-oxide or stereoisomer thereof is used to treat metabolic disease. As used herein, the term "metabolic disease" refers to a disease or condition affecting a metabolic process in a subject. Exemplary metabolic diseases that may be treated with a compound of Formula (I) or Formula (III), or a pharmaceutically acceptable salt, co-crystal, solvate, hydrate, tautomer, ester, N-oxide or stereoisomer thereof include non-alcoholic steatohepatitis (NASH), non-alcoholic fatty liver disease (NAFLD), liver fibrosis, obesity, heart disease, atherosclerosis, arthritis, cystinosis, diabetes (e.g., Type I diabetes, Type II diabetes, or gestational diabetes), phenylketonuria, proliferative retinopathy, or Kearns-Sayre disease.

In some embodiments, the compound of Formula (I) or Formula (III), or a pharmaceutically acceptable salt, co-crystal, solvate, hydrate, tautomer, ester, N-oxide or stereoisomer thereof is used to treat a metabolic disease (e.g., a metabolic disease described herein) by decreasing or eliminating a symptom of the disease. In some embodiments, the method of treatment comprises decreasing or eliminating a symptom comprising elevated blood pressure, elevated blood sugar level, weight gain, fatigue, blurred vision, abdominal pain, flatulence, constipation, diarrhea, jaundice, and the like. In some embodiments, the compound of Formula (I) or Formula (III), or a pharmaceutically acceptable salt, solvate, hydrate, tautomer, or stereoisomer thereof may be used as a single agent in a composition or in combination with another agent in a composition to treat a metabolic disease (e.g., a musculoskeletal disease described herein).

Mitochondrial Diseases

In some embodiments, the compound of Formula (I) or Formula (III) or a pharmaceutically acceptable salt, co-crystal, solvate, hydrate, tautomer, ester, N-oxide or stereoisomer thereof is used to treat mitochondrial disease. As used herein, the term "mitochondrial disease" refers to a disease or condition affecting the mitochondria in a subject. In some embodiments, the mitochondrial disease is associated with, or is a result of, or is caused by mitochondrial dysfunction, one or more mitochondrial protein mutations, or one or more mitochondrial DNA mutations. In some embodiments, the mitochondrial disease is a mitochondrial myopathy. In some embodiments, mitochondrial diseases, e.g., the mitochondrial myopathy, that may be treated with a compound of Formula (I) or Formula (III) or a pharmaceutically acceptable salt, co-crystal, solvate, hydrate, tautomer, ester, N-oxide or stereoisomer thereof include, e.g., Barth syndrome, chronic progressive external ophthalmoplegia (cPEO), Kearns-Sayre syndrome (KSS), Leigh syndrome (e.g., MILS, or maternally inherited Leigh syndrome), mitochondrial DNA depletion syndromes (MDDS, e.g., Alpers syndrome), mitochondrial encephalomyopathy (e.g., mitochondrial encephalomyopathy, lactic acidosis, and stroke-like episodes (MELAS)), mitochondrial neurogastrointestinal encephalomyopathy (MNGIE), myoclonus epilepsy with ragged red fibers (MERRF), neuropathy, ataxia, retinitis pigmentosa (NARP), Leber's hereditary optic neuropathy (LHON), and Pearson syndrome.

In some embodiments, the compound of Formula (I) or Formula (III) or a pharmaceutically acceptable salt, co-crystal, solvate, hydrate, tautomer, ester, N-oxide or stereoisomer thereof is used to treat a mitochondrial disease described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat a mitochondrial disease described herein.

Hearing Loss

In some embodiments, the compound of Formula (I) or Formula (III) or a pharmaceutically acceptable salt, co-crystal, solvate, hydrate, tautomer, ester, N-oxide or stereoisomer thereof is used to treat hearing loss. As used herein, the term "hearing loss" or "hearing loss condition" may broadly encompass any damage to the auditory systems, organs, and cells or any impairment of an animal subject's ability to hear sound, as measured by standard methods and assessments known in the art, for example otoacoustic emission testing, pure tone testing, and auditory brainstem response testing. Exemplary hearing loss conditions that may be treated with a compound of Formula (I) or Formula (III), or a pharmaceutically acceptable salt, co-crystal, solvate, hydrate, tautomer, ester, N-oxide or stereoisomer thereof include, but are not limited to, mitochondrial nonsyndromic hearing loss and deafness, hair cell death, age-related hearing loss, noise-induced hearing loss, genetic or inherited hearing loss, hearing loss experienced as a result of ototoxic exposure, hearing loss resulting from disease, and hearing loss resulting from trauma. In some embodiments, mitochondrial nonsyndromic hearing loss and deafness is a MT-RNR1-related hearing loss. In some embodiments, the MT-RNR1-related hearing loss is the result of amino glycoside ototoxicity. In some embodiments, mitochondrial nonsyndromic hearing loss and deafness is a MT-TS1-related hearing loss. In some embodiments, mitochondrial nonsyndromic hearing loss and deafness is characterized by sensorineural hearing loss.

In some embodiments, the compound of Formula (I) or Formula (III) or a pharmaceutically acceptable salt, co-crystal, solvate, hydrate, tautomer, ester, N-oxide or stereoisomer thereof is used to treat a hearing loss condition described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat a hearing loss condition described herein.

Ocular Disease

In some embodiments, the compound of Formula (I) or Formula (III) or a pharmaceutically acceptable salt, co-crystal, solvate, hydrate, tautomer, ester, N-oxide or stereoisomer thereof is used to treat eye disease. As used herein, the term "ocular disease" may refer to a disease or condition in which the function of a subject's eye becomes impaired. Exemplary ocular diseases and conditions that may be treated with a compound of Formula (I) or Formula (III), or a pharmaceutically acceptable salt, co-crystal, solvate, hydrate, tautomer, ester, N-oxide or stereoisomer thereof include cataracts, glaucoma, endoplasmic reticulum (ER) stress, autophagy deficiency, age-related macular degeneration (AMD), or diabetic retinopathy.

In some embodiments, the compound of Formula (I) or Formula (III) or a pharmaceutically acceptable salt, co-crystal, solvate, hydrate, tautomer, ester, N-oxide or stereoisomer thereof is used to treat an ocular disease or condition described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat an ocular disease or condition described herein.

Kidney Diseases

In some embodiments, the compound of Formula (I) or Formula (III) or a pharmaceutically acceptable salt, co-crystal, solvate, hydrate, tautomer, ester, N-oxide or stereoisomer thereof is used to treat kidney disease. As used herein, the term "kidney disease" may refer to a disease or condition in which the function of a subject's kidneys becomes impaired. Exemplary kidney diseases that may be treated with a compound of Formula (I) or Formula (III), or a pharmaceutically acceptable salt, co-crystal, solvate, hydrate, tautomer, ester, N-oxide or stereoisomer thereof include Abderhalden-Kaufmann-Lignac syndrome (Nephropathic Cystinosis), Abdominal Compartment Syndrome, Acetaminophen-induced Nephrotoxicity, Acute Kidney Failure/Acute Kidney Injury, Acute Lobar Nephronia, Acute Phosphate Nephropathy, Acute Tubular Necrosis, Adenine Phosphoribosyltransferase Deficiency, Adenovirus Nephritis, Alagille Syndrome, Alport Syndrome, Amyloidosis, ANCA Vasculitis Related to Endocarditis and Other Infections, Angiomyolipoma, Analgesic Nephropathy, Anorexia Nervosa and Kidney Disease, Angiotensin Antibodies and Focal Segmental Glomerulosclerosis, Antiphospholipid Syndrome, Anti-TNF-α Therapy-related Glomerulonephritis, APOL1 Mutations, Apparent Mineralocorticoid Excess Syndrome, Aristolochic Acid Nephropathy, Chinese Herbal Nephropathy, Balkan Endemic Nephropathy, Arteriovenous Malformations and Fistulas of the Urologic Tract, Autosomal Dominant Hypocalcemia, Bardet-Biedl Syndrome, Bartter Syndrome, Bath Salts and Acute Kidney Injury, Beer Potomania, Beeturia, β-Thalassemia Renal Disease, Bile Cast Nephropathy, BK Polyoma Virus Nephropathy in the Native Kidney, Bladder Rupture, Bladder Sphincter Dyssynergia, Bladder Tamponade, Border-Crossers' Nephropathy, Bourbon Virus and Acute Kidney Injury, Burnt Sugarcane Harvesting and Acute Renal Dysfunction, Byetta and Renal Failure, Clq Nephropathy, C3 Glomerulopathy, C3 Glomerulopathy with Monoclonal Gammopathy, C4 Glomerulopathy, Calcineurin Inhibitor Nephrotoxicity, Callilepsis Laureola Poisoning, Cannabinoid Hyperemesis Acute Renal Failure, Cardiorenal syndrome, Carfilzomib-Indiced Renal Injury, CFHR5 nephropathy, Charcot-Marie-Tooth Disease with Glomerulopathy, Chinese Herbal Medicines and Nephrotoxicity, Cherry Concentrate and Acute Kidney Injury, Cholesterol Emboli, Churg-Strauss syndrome, Chyluria, Ciliopathy, Cocaine and the Kidney, Cold Diuresis, Colistin Nephrotoxicity, Collagenofibrotic Glomerulopathy, Collapsing Glomerulopathy, Collapsing Glomerulopathy Related to CMV, Combination Antiretroviral (cART) Related-Nephropathy, Congenital Anomalies of the Kidney and Urinary Tract (CAKUT), Congenital Nephrotic Syndrome, Congestive Renal Failure, Conorenal syndrome (Mainzer-Saldino Syndrome or Saldino-Mainzer Disease), Contrast Nephropathy, Copper Sulphate Intoxication, Cortical Necrosis, Crizotinib-related Acute Kidney Injury, Cryocrystalglobulinemia, Cryoglobuinemia, Crystalglobulin-Induced Nephropathy, Crystal-Induced Acute Kidney injury, Crystal-Storing Histiocytosis, Cystic Kidney Disease, Acquired, Cystinuria, Dasatinib-Induced Nephrotic-Range Proteinuria, Dense Deposit Disease (MPGN Type 2), Dent Disease (X-linked Recessive Nephrolithiasis), DHA Crystalline Nephropathy, Dialysis Disequilibrium Syndrome, Diabetes and Diabetic Kidney Disease, Diabetes Insipidus, Dietary Supplements and Renal Failure, Diffuse Mesangial Sclerosis, Diuresis, Djenkol Bean Poisoning (Djenkolism), Down Syndrome and Kidney Disease, Drugs of Abuse and Kidney Disease, Duplicated Ureter, EAST syndrome, Ebola and the Kidney, Ectopic Kidney, Ectopic Ureter, Edema, Swelling, Erdheim-Chester Disease, Fabry's Disease, Familial Hypocalciuric Hypercalcemia, Fanconi Syndrome, Fraser syndrome, Fibronectin Glomerulopathy, Fibrillary Glomerulonephritis and Immunotactoid Glomerulopathy, Fraley syndrome, Fluid Overload, Hypervolemia, Focal Segmental Glomerulosclerosis, Focal Sclerosis, Focal Glomerulosclerosis, Galloway Mowat syndrome, Giant Cell (Temporal) Arteritis with Kidney Involvement, Gestational Hypertension, Gitelman Syndrome, Glomerular Diseases, Glomerular Tubular Reflux, Glycosuria, Goodpasture Syndrome, Green Smoothie Cleanse Nephropathy, HANAC Syndrome, Harvoni (Ledipasvir with Sofosbuvir)-Induced Renal Injury, Hair Dye Ingestion and Acute Kidney Injury, Hantavirus Infection Podocytopathy, Heat Stress Nephropathy, Hematuria (Blood in Urine), Hemolytic Uremic Syndrome (HUS), Atypical Hemolytic Uremic Syndrome (aHUS), Hemophagocytic Syndrome, Hemorrhagic Cystitis, Hemorrhagic Fever with Renal Syndrome (HFRS, Hantavirus Renal Disease, Korean Hemorrhagic Fever, Epidemic Hemorrhagic Fever, Nephropathis Epidemica), Hemosiderinuria, Hemosiderosis related to Paroxysmal Nocturnal Hemoglobinuria and Hemolytic Anemia, Hepatic Glomerulopathy, Hepatic Veno-Occlusive Disease, Sinusoidal Obstruction Syndrome, Hepatitis C-Associated Renal Disease, Hepatocyte Nuclear Factor 1β-Associated Kidney Disease, Hepatorenal Syndrome, Herbal Supplements and Kidney Disease, High Altitude Renal Syndrome, High Blood Pressure and Kidney Disease, HIV-Associated Immune Complex Kidney Disease (HIVICK), HIV-Associated Nephropathy (HIVAN), HNF1β-related Autosomal Dominant Tubulointerstitial Kidney Disease, Horseshoe Kidney (Renal Fusion), Hunner's Ulcer, Hydroxychloroquine-induced Renal Phospholipidosis, Hyperaldosteronism, Hypercalcemia, Hyperkalemia, Hypermagnesemia, Hypernatremia, Hyperoxaluria, Hyperphosphatemia, Hypocalcemia, Hypocomplementemic Urticarial Vasculitic Syndrome, Hypokalemia, Hypokalemia-induced renal dysfunction, Hypokalemic Periodic Paralysis, Hypomagnesemia, Hyponatremia, Hypophosphatemia, Hypophosphatemia in Users of *Cannabis*, Hypertension, Hypertension, Monogenic, Iced Tea Nephropathy, Ifosfamide Nephrotoxicity, IgA Nephropathy, IgG4 Nephropathy, Immersion Diuresis, Immune-Checkpoint Therapy-Related Interstitial Nephritis, Infliximab-Related Renal Disease, Interstitial Cystitis, Painful Bladder Syndrome (Questionnaire), Interstitial Nephritis, Interstitial Nephritis, Karyomegalic, Ivemark's syndrome, JC Virus Nephropathy, Joubert Syndrome, Ketamine-Associated Bladder Dysfunction, Kidney Stones, Nephrolithiasis, Kombucha Tea Toxicity, Lead Nephropathy and Lead-Related Nephrotoxicity, Lecithin Cholesterol Acyltransferase Deficiency (LCAT Deficiency), Leptospirosis Renal Disease, Light Chain Deposition Disease, Monoclonal Immunoglobulin Deposition Disease, Light Chain Proximal Tubulopathy, Liddle Syndrome, Lightwood-Albright Syndrome, Lipoprotein Glomerulopathy, Lithium Nephrotoxicity, LMX1B Mutations Cause Hereditary FSGS, Loin Pain Hematuria, Lupus, Systemic Lupus Erythematosis, Lupus Kidney Disease, Lupus Nephritis, Lupus Nephritis with Antineutrophil Cytoplasmic Antibody Seropositivity, Lupus Podocytopathy, Lyme Disease-Associated Glomerulonephritis, Lysinuric Protein Intolerance, Lysozyme Nephropathy, Malarial Nephropathy, Malignancy-Associated Renal Disease, Malignant Hypertension, Malakoplakia, McKittrick-Wheelock Syndrome, MDMA (Molly; Ecstacy; 3,4-Methylenedioxymethamphetamine) and Kidney Failure, Meatal Stenosis, Medullary Cystic Kidney Disease, Urolodulin-Associated Nephropathy, Juvenile Hyperuricemic Nephropathy Type 1, Medullary Sponge Kidney, Megaureter, Melamine Toxicity and the Kidney, MELAS Syndrome, Membranoproliferative Glomerulonephritis, Membranous Nephropathy, Membranous-like Glomerulopathy with Masked IgG Kappa Deposits, MesoAmerican Nephropathy, Metabolic Acidosis, Metabolic Alkalosis, Methotrexate-related Renal Failure, Microscopic Polyangiitis, Milk-alkalai syndrome, Minimal Change Disease, Monoclonal Gammopathy of Renal Significance, Dysproteinemia, Mouthwash Toxicity, MUC1 Nephropathy, Multicystic dysplastic kidney, Multiple Myeloma, Myeloproliferative Neoplasms and Glomerulopathy, Nail-patella Syndrome, NARP Syndrome, Nephrocalcinosis, Nephrogenic Systemic Fibrosis, Nephroptosis (Floating Kidney, Renal Ptosis), Nephrotic Syndrome, Neurogenic Bladder, 9/11 and Kidney Disease, Nodular Glomerulosclerosis, Non-Gonococcal Urethritis, Nutcracker syndrome, Oligomeganephronia, Orofaciodigital Syndrome, Orotic Aciduria, Orthostatic Hypotension, Orthostatic Proteinuria, Osmotic Diuresis, Osmotic Nephrosis, Ovarian Hyperstimulation Syndrome, Oxalate Nephropathy, Page Kidney, Papillary Necrosis, Papillorenal Syndrome (Renal-Coloboma Syndrome, Isolated Renal Hypoplasia), PARN Mutations and Kidney Disease, Parvovirus B19 and the Kidney, The Peritoneal-Renal Syndrome, POEMS Syndrome, Posterior Urethral Valve, Podocyte Infolding Glomerulopathy, Post-infectious Glomerulonephritis, Post-streptococcal Glomerulonephritis, Post-infectious Glomerulonephritis, Atypical, Post-Infectious Glomerulonephritis (IgA-Dominant), Mimicking IgA Nephropathy, Polyarteritis Nodosa, Polycystic Kidney Disease, Posterior Urethral Valves, Post-Obstructive Diuresis, Preeclampsia, Propofol infusion syndrome, Proliferative Glomerulonephritis with Monoclonal IgG Deposits (Nasr Disease), Propolis (Honeybee Resin) Related Renal Failure, Proteinuria (Protein in Urine), Pseudohyperaldosteronism, Pseudohypobicarbonatemia, Pseudohypoparathyroidism, Pulmonary-Renal Syndrome, Pyelonephritis (Kidney Infection), Pyonephrosis, Pyridium and Kidney Failure, Radiation Nephropathy, Ranolazine and the Kidney, Refeeding syndrome, Reflux Nephropathy, Rapidly Progressive Glomerulonephritis, Renal Abscess, Peripnephric Abscess, Renal Agenesis, Renal Arcuate Vein Microthrombi-Associated Acute Kidney Injury, Renal Artery Aneurysm, Renal Artery Dissection, Spontaneous, Renal Artery Stenosis, Renal Cell Cancer, Renal Cyst, Renal Hypouricemia with Exercise-induced Acute Renal Failure, Renal Infarction, Renal Osteodystrophy, Renal Tubular Acidosis, Renin Mutations and Autosomal Dominant Tubulointerstitial Kidney Disease, Renin Secreting Tumors (Juxtaglomerular Cell Tumor), Reset Osmostat, Retrocaval Ureter, Retroperitoneal Fibrosis, Rhabdomyolysis, Rhabdomyolysis related to Bariatric Sugery, Rheumatoid Arthritis-Associated Renal Disease, Sarcoidosis Renal Disease, Salt Wasting, Renal and Cerebral, Schistosomiasis and Glomerular Disease, Schimke immuno-osseous dysplasia, Scleroderma Renal Crisis, Serpentine Fibula-Polycystic Kidney Syndrome, Sever Syndrome, Sickle Cell Nephropathy, Silica Exposure and Chronic Kidney Disease, Sri Lankan Farmers' Kidney Disease, Sjogren's Syndrome and Renal Disease, Synthetic Cannabinoid Use and Acute Kidney Injury, Kidney Disease Following Hematopoietic Cell Transplantation, Kidney Disease Related to Stem Cell Transplantation, TAFRO Syndrome, Tea and Toast Hyponatremia, Tenofovir-Induced Nephrotoxicity, Thin Basement Membrane Disease, Benign Familial Hematuria, Thrombotic Microangiopathy Associated with Monoclonal Gammopathy, Trench Nephritis, Trigonitis, Tuberculosis, Genitourinary, Tuberous Sclerosis, Tubular Dysgenesis, Immune Complex Tubulointerstitial Nephritis Due to Autoantibodies to the Proximal Tubule Brush Border, Tumor Lysis Syndrome, Uremia, Uremic Optic Neuropathy, Ureteritis Cystica, Ureterocele, Urethral Caruncle, Urethral Stricture, Urinary Incontinence, Urinary Tract Infection, Urinary Tract Obstruction, Urogenital Fistula, Uromodulin-Associated Kidney Disease, Vancomycin-Associated Cast Nephropathy, Vasomotor Nephropathy, Vesicointestinal Fistula, Vesicoureteral Reflux, VGEF Inhibition and Renal Thrombotic Microangiopathy, Volatile Anesthetics and Acute Kidney Injury, Von Hippel-Lindau Disease, Waldenstrom's Macroglobulinemic Glomerulonephritis, Warfarin-Related Nephropathy, Wasp Stings and Acute Kidney Injury, Wegener's Granulomatosis, Granulomatosis with Polyangiitis, West Nile Virus and Chronic Kidney Disease, Wunderlich syndrome, Zellweger Syndrome, or Cerebrohepatorenal Syndrome.

In some embodiments, the compound of Formula (I) or Formula (III) or a pharmaceutically acceptable salt, co-crystal, solvate, hydrate, tautomer, ester, N-oxide or stereoisomer thereof is used to treat a kidney disease described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat a kidney disease described herein.

Skin Diseases

In some embodiments, the compound of Formula (I) or Formula (III) or a pharmaceutically acceptable salt, co-crystal, solvate, hydrate, tautomer, ester, N-oxide or stereoisomer thereof is used to treat a skin disease. As used herein, the term "skin disease" may refer to a disease or condition affecting the skin. Exemplary skin diseases that may be treated with a compound of Formula (I) or Formula (III), or a pharmaceutically acceptable salt, co-crystal, solvate, hydrate, tautomer, ester, N-oxide or stereoisomer thereof include acne, alopecia areata, basal cell carcinoma, Bowen's disease, congenital erythropoietic *porphyria*, contact dermatitis, Darier's disease, disseminated superficial actinic porokeratosis, dystrophic epidermolysis bullosa, eczema (atopic eczema), extra-mammary Paget's disease, epidermolysis bullosa simplex, erythropoietic protoporphyria, fungal infections of nails, Hailey-Hailey disease, herpes simplex, hidradenitis suppurativa, hirsutism, hyperhidrosis, ichthyosis, impetigo, keloids, keratosis pilaris, lichen planus, lichen sclerosus, melanoma, melasma, mucous membrane pemphigoid, pemphigoid, pemphigus vulgaris, *pityriasis lichenoides*, *pityriasis rubra* pilaris, plantar warts (verrucas), polymorphic light eruption, psoriasis, plaque psoriasis, pyoderma gangrenosum, rosacea, scabies, scleroderma, shingles, squamous cell carcinoma, sweet's syndrome, urticaria and angioedema and vitiligo.

In some embodiments, the compound of Formula (I) or Formula (III) or a pharmaceutically acceptable salt, co-crystal, solvate, hydrate, tautomer, ester, N-oxide or stereoisomer thereof is used to treat a skin disease described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat a skin disease described herein.

Fibrotic Diseases

In some embodiments, the compound of Formula (I) or Formula (III) or a pharmaceutically acceptable salt, co-crystal, solvate, hydrate, tautomer, ester, N-oxide or stereoisomer thereof is used to treat a fibrotic disease. As used herein, the term "fibrotic disease" may refer to a disease or condition that is defined by the accumulation of excess extracellular matrix components. Exemplary fibrotic diseases that may be treated with a compound of Formula (I) or Formula (III), or a pharmaceutically acceptable salt, co-crystal, solvate, hydrate, tautomer, ester, N-oxide or stereoisomer thereof include adhesive capsulitis, arterial stiffness, arthrofibrosis, atrial fibrosis, cardiac fibrosis, cirrhosis, congenital hepatic fibrosis, Crohn's disease, cystic fibrosis, Dupuytren's contracture, endomyocardial fibrosis, glial scar, hepatitis C, hypertrophic cardiomyopathy, hypersensitivity pneumonitis, idiopathic pulmonary fibrosis, idiopathic interstitial pneumonia, interstitial lung disease, keloid, mediastinal fibrosis, myelofibrosis, nephrogenic systemic fibrosis, non-alcoholic fatty liver disease, old myocardial infarction, Peyronie's disease, pneumoconiosis, pneumonitis, progressive massive fibrosis, pulmonary fibrosis, radiation-induced lung injury, retroperitoneal fibrosis, scleroderma/systemic sclerosis, silicosis and ventricular remodeling.

In some embodiments, the compound of Formula (I) or Formula (III) or a pharmaceutically acceptable salt, co-crystal, solvate, hydrate, tautomer, ester, N-oxide or stereoisomer thereof is used to treat a fibrotic disease described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat a fibrotic disease described herein.

Hemoglobin Disorders

In some embodiments, the compound of Formula (I) or Formula (III) or a pharmaceutically acceptable salt, co-crystal, solvate, hydrate, tautomer, ester, N-oxide or stereoisomer thereof is used to treat a hemoglobin disease. As used herein, the terms "hemoglobin disease" or "hemoglobin disorder" may refer to a disease or condition characterized by an abnormal production or structure of the hemoglobin protein. Exemplary hemoglobin diseases that may be treated with a compound of Formula (I) or Formula (III), or a pharmaceutically acceptable salt, co-crystal, solvate, hydrate, tautomer, ester, N-oxide or stereoisomer thereof include "dominant" β-thalassemia, acquired (toxic) methemoglobinemia, carboxyhemoglobinemia, congenital Heinz body hemolytic anemia, HbH disease, HbS/β-thalassemia, HbE/β-thalassemia, HbSC disease, homozygous α-thalassemia (phenotype of α$^0$-thalassemia), Hydrops fetalis with Hb Bart's, sickle cell anemia/disease, sickle cell trait, sickle β-thalassemia disease, α$^+$-thalassemia, α$^0$-thalassemia, α-Thalassemia associated with myelodysplastic syndromes, α-Thalassemia with mental retardation syndrome (ATR), β$^0$-Thalassemia, β$^+$-Thalassemia, δ-Thalassemia, γ-Thalassemia, β-Thalassemia major, β-Thalassemia intermedia, δβ-Thalassemia, and εγδβ-Thalassemia.

In some embodiments, the compound of Formula (I) or Formula (III) or a pharmaceutically acceptable salt, co-crystal, solvate, hydrate, tautomer, ester, N-oxide or stereoisomer thereof is used to treat a hemoglobin disease described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat a hemoglobin disease described herein.

Autoimmune Diseases

In some embodiments, the compound of Formula (I) or Formula (III) or a pharmaceutically acceptable salt, co-crystal, solvate, hydrate, tautomer, ester, N-oxide or stereoisomer thereof is used to treat an autoimmune disease. As used herein, the term "autoimmune disease" may refer to a disease or condition in which the immune system of a subject attacks and damages the tissues of said subject. Exemplary kidney diseases that may be treated with a compound of Formula (I) or Formula (III), or a pharmaceutically acceptable salt, co-crystal, solvate, hydrate, tautomer, ester, N-oxide or stereoisomer thereof include Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndrome type I, Polyglandular syndrome type II, Polyglandular syndrome type III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease, and Wegener's granulomatosis (or Granulomatosis with Polyangiitis (GPA)).

In some embodiments, the compound of Formula (I) or Formula (III) or a pharmaceutically acceptable salt, co-crystal, solvate, hydrate, tautomer, ester, N-oxide or stereoisomer thereof is used to treat an autoimmune disease described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat an autoimmune disease described herein.

Viral Infections

In some embodiments, the compound of Formula (I) or Formula (III) or a pharmaceutically acceptable salt, co-crystal, solvate, hydrate, tautomer, ester, N-oxide or stereoisomer thereof is used to treat a viral infection. Exemplary viral infections that may be treated with a compound of Formula (I) or Formula (III), or a pharmaceutically acceptable salt, co-crystal, solvate, hydrate, tautomer, ester, N-oxide or stereoisomer thereof include influenza, human immunodeficiency virus (HIV) and herpes.

In some embodiments, the compound of Formula (I) or Formula (III) or a pharmaceutically acceptable salt, co-crystal, solvate, hydrate, tautomer, ester, N-oxide or stereoisomer thereof is used to treat a viral infection described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat a viral infection described herein.

Malaria Infection

In some embodiments, the compound of Formula (I) or Formula (III) or a pharmaceutically acceptable salt, co-crystal, solvate, hydrate, tautomer, ester, N-oxide or stereoisomer thereof is used to treat a malaria. As used herein, the term "malaria" may refer to a parasitic disease of protozoan of the *plasmodium* genus that causes infection of red blood cells (RBCs). Exemplary forms of malaria infection that may be treated with a compound of Formula (I) or Formula (III), or a pharmaceutically acceptable salt, co-crystal, solvate, hydrate, tautomer, ester, N-oxide or stereoisomer thereof include infection caused by *Plasmodium vivax*, *Plasmodium ovale*, *Plasmodium malariae* and *Plasmodium falciparum*. In some embodiments, the malaria infection that may be treated with a compound of Formula (I) or Formula (III), or a pharmaceutically acceptable salt, co-crystal, solvate, hydrate, tautomer, ester, N-oxide or stereoisomer thereof is resistant/recrudescent malaria.

In some embodiments, the compound of Formula (I) or Formula (III) or a pharmaceutically acceptable salt, co-crystal, solvate, hydrate, tautomer, ester, N-oxide or stereoisomer thereof is used to treat a malaria infection described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat a malaria infection described herein.

Diseases with Mutations Leading to Unfolded Protein Response (UPR) Induction

In some embodiments, the compound of Formula (I) or Formula (III) or a pharmaceutically acceptable salt, co-crystal, solvate, hydrate, tautomer, ester, N-oxide or stereoisomer thereof is used to treat a disease with mutations that leads to UPR induction. Exemplary disease with mutations that lead to UPR induction include Marinesco-Sjogren syndrome, neuropathic pain, diabetic neuropathic pain, noise induced hearing loss, non-syndromic sensorineural hearing loss, age-related hearing loss, Wolfram syndrome, Darier White disease, Usher syndrome, collagenopathies, Thin basement nephropathy, Alport syndrome, skeletal chondrodysplasia, metaphyseal chondrodysplasia type Schmid, and Pseudochondrodysplasia.

In some embodiments, the compound of Formula (I) or Formula (III) or a pharmaceutically acceptable salt, co-crystal, solvate, hydrate, tautomer, ester, N-oxide or stereoisomer thereof is used to treat a disease with mutations that leads to UPR induction described herein by decreasing or eliminating a symptom of the disease. In some embodiments, the compound of Formula (I) or Formula (III) or a pharmaceutically acceptable salt, co-crystal, solvate, hydrate, tautomer, ester, N-oxide or stereoisomer thereof may be used as a single agent in a composition or in combination with another agent in a composition to treat a disease with mutations that leads to UPR induction described herein.

Methods of Modulating Protein Production

In another aspect, disclosed herein is a method of modulating the expression of eIF2B, eIF2α, a component of the eIF2 pathway, component of the ISR pathway or any combination thereof in a cell, the method comprising contacting the cell with an effective amount of a compound of Formula (I) or Formula (III), or a pharmaceutically acceptable salt, co-crystal, solvate, hydrate, tautomer, ester, N-oxide or stereoisomer thereof, thereby modulating the expression of eIF2B, eIF2α, a component of the eIF2 pathway, component of the ISR pathway or any combination thereof in the cell. In some embodiments, contacting the compound of Formula (I) or Formula (III), or a pharmaceutically acceptable salt, co-crystal, solvate, hydrate, tautomer, ester, N-oxide or stereoisomer thereof with the cell increases the expression of eIF2B, eIF2α, a component of the eIF2 pathway, component of the ISR pathway or any combination thereof in the cell. In some embodiments, contacting the compound of Formula (I) or Formula (III), or a pharmaceutically acceptable salt, co-crystal, solvate, hydrate, tautomer, ester, N-oxide or stereoisomer thereof with the cell decreases the expression of eIF2B, eIF2α, a component of the eIF2 pathway, component of the ISR pathway or any combination thereof in the cell.

In another aspect, disclosed herein is a method of preventing or treating a condition, disease or disorder described herein in a patient in need thereof, the method comprising administering to the patient an effective amount of a compound of Formula (I) or Formula (III), or a pharmaceutically acceptable salt, co-crystal, solvate, hydrate, tautomer, ester, N-oxide or stereoisomer thereof, wherein the compound of Formula (I) or Formula (III), or a pharmaceutically acceptable salt, co-crystal, solvate, hydrate, tautomer, ester, N-oxide or stereoisomer thereof modulates the expression of eIF2B, eIF2α, a component of the eIF2 pathway, component of the ISR pathway or any combination thereof by the patient's cells, thereby treating the condition, disease or disorder. In some embodiments, the condition, disease or disorder is characterized by aberrant expression of eIF2B, eIF2α, a component of the eIF2 pathway, component of the ISR pathway or any combination thereof by the patient's cells. In some embodiments, the compound of Formula (I) or Formula (III), or a pharmaceutically acceptable salt, co-crystal, solvate, hydrate, tautomer, ester, N-oxide or stereoisomer thereof increases the expression of eIF2B, eIF2α, a component of the eIF2 pathway, component of the ISR pathway or any combination thereof by the patient's cells, thereby treating the condition, disease or disorder. In some embodiments, the compound of Formula (I) or Formula (III), or a pharmaceutically acceptable salt, co-crystal, solvate, hydrate, tautomer, ester, N-oxide or stereoisomer thereof decreases the expression of eIF2B, eIF2α, a component of the eIF2 pathway, component of the ISR pathway or any combination thereof by the patient's cells, thereby treating the condition, disease or disorder.

In another aspect, disclosed herein is a method of modulating the activity of eIF2B, eIF2α, a component of the eIF2 pathway, component of the ISR pathway or any combination thereof in a cell, the method comprising contacting the cell with an effective amount of a compound of Formula (I) or Formula (III), or a pharmaceutically acceptable salt, co-crystal, solvate, hydrate, tautomer, ester, N-oxide or stereoisomer thereof, thereby modulating the activity of eIF2B, eIF2α, a component of the eIF2 pathway, component of the ISR pathway or any combination thereof in the cell. In some embodiments, contacting the compound of Formula (I) or Formula (III), or a pharmaceutically acceptable salt, co-crystal, solvate, hydrate, tautomer, ester, N-oxide or stereoisomer thereof with the cell increases the activity of eIF2B, eIF2α, a component of the eIF2 pathway, component of the ISR pathway or any combination thereof in the cell. In some embodiments, contacting the compound of Formula (I) or Formula (III), or a pharmaceutically acceptable salt, co-crystal, solvate, hydrate, tautomer, ester, N-oxide or stereoisomer thereof with the cell decreases the activity of eIF2B, eIF2α, a component of the eIF2 pathway, component of the ISR pathway or any combination thereof in the cell.

In another aspect, disclosed herein is a method of preventing or treating a condition, disease or disorder described herein in a patient in need thereof, the method comprising administering to the patient an effective amount of a compound of Formula (I) or Formula (III), or a pharmaceutically acceptable salt, co-crystal, solvate, hydrate, tautomer, ester, N-oxide or stereoisomer thereof, wherein the compound of Formula (I) or Formula (III), or a pharmaceutically acceptable salt, co-crystal, solvate, hydrate, tautomer, ester, N-oxide or stereoisomer thereof modulates the activity of eIF2B, eIF2α, a component of the eIF2 pathway, component of the ISR pathway or any combination thereof by the patients cells, thereby treating the condition, disease or disorder. In some embodiments, the condition, disease or disorder is characterized by aberrant activity of eIF2B, eIF2α, a component of the eIF2 pathway, component of the ISR pathway or any combination thereof in the patient's cells. In some embodiments, the compound of Formula (I) or Formula (III), or a pharmaceutically acceptable salt, co-crystal, solvate, hydrate, tautomer, ester, N-oxide or stereoisomer thereof increases the activity of eIF2B, eIF2α, a component of the eIF2 pathway, component of the ISR pathway or any combination thereof in the patient's cells, thereby treating the condition, disease or disorder. In some embodiments, the compound of Formula (I) or Formula (III), or a pharmaceutically acceptable salt, co-crystal, solvate, hydrate, tautomer, ester, N-oxide or stereoisomer thereof decreases the activity of eIF2B, eIF2α, a component of the eIF2 pathway, component of the ISR pathway or any combination thereof in the patient's cells, thereby treating the condition, disease or disorder.

In some embodiments, administering an effective amount of a compound of Formula (I) or Formula (III), or a pharmaceutically acceptable salt, co-crystal, solvate, hydrate, tautomer, ester, N-oxide or stereoisomer thereof, wherein the compound of Formula (I) or Formula (III), or a pharmaceutically acceptable salt, co-crystal, solvate, hydrate, tautomer, ester, N-oxide or stereoisomer thereof modulates both the expression and the activity of eIF2B, eIF2α, a component of the eIF2 pathway, component of the ISR pathway or any combination thereof in the patients cells, thereby treating the condition, disease or disorder.

In some embodiments, the compound of Formula (I) or Formula (III) is chemically modified, prior to (ex vivo) or after (in vivo) contacting with a cell, forming a biologically active compound that modulates the expression and/or activity of eIF2B, eIF2α, a component of the eIF2 pathway, component of the ISR pathway or any combination thereof in the cell. In some embodiments, the compound of Formula (I) or Formula (III) is metabolized by the patient forming a biologically active compound that modulates the expression and/or activity of eIF2B, eIF2α, a component of the eIF2 pathway, component of the ISR pathway or any combination thereof in the patients cells, thereby treating a condition, disease or disorder disclosed herein. In some embodiments, the biologically active compound is the compound of Formula (III).

In one aspect, disclosed herein is a method of treating a disease related to a modulation of eIF2B activity or levels, eIF2α activity or levels, or the activity or levels of a component of the eIF2 pathway or the ISR pathway in a patient in need thereof, comprising administering to the patient an effective amount of a compound of Formula (I) or Formula (III). In some embodiments, the modulation comprises an increase in eIF2B activity or levels, increase in eIF2α activity or levels, or increase in activity or levels of a component of the eIF2 pathway or the ISR pathway. In some embodiments, the disease may be caused by a mutation to a gene or protein sequence related to a member of the eIF2 pathway (e.g., the eIF2α signaling pathway).

Methods of Increasing Protein Activity and Production

In another aspect, the compound of Formula (I) or Formula (III), or a pharmaceutically acceptable salt, co-crystal, solvate, hydrate, tautomer, ester, N-oxide or stereoisomer thereof may be useful in applications where increasing production output of eIF2B, eIF2α, a component of the eIF2 pathway, a component of the ISR pathway or any combination thereof is desirable, such as in vitro cell free systems for protein production.

In some embodiments, the present invention features a method of increasing expression of eIF2B, eIF2α, a component of the eIF2 pathway, a component of the ISR pathway or any combination thereof by a cell or in vitro expression system, the method comprising contacting the cell or in vitro expression system with an effective amount of a compound of Formula (I) or Formula (III), or a pharmaceutically acceptable salt, co-crystal, solvate, hydrate, tautomer, ester, N-oxide or stereoisomer thereof. In some embodiments, the method is a method of increasing the expression of eIF2B, eIF2α, a component of the eIF2 pathway, a component of the ISR pathway or any combination thereof by a cell comprising contacting the cell with an effective amount of a compound described herein (e.g., the compound of Formula (I) or Formula (III), or a pharmaceutically acceptable salt, co-crystal, solvate, hydrate, tautomer, ester, N-oxide or stereoisomer thereof). In other embodiments, the method is a method of increasing the expression of eIF2B, eIF2α, a component of the eIF2 pathway, a component of the ISR pathway or any combination thereof by an in vitro protein expression system comprising contacting the in vitro expression system with a compound described herein (e.g. the compound of Formula (I) or Formula (III), or a pharmaceutically acceptable salt, co-crystal, solvate, hydrate, tautomer, ester, N-oxide or stereoisomer thereof). In some embodiments, contacting the cell or in vitro expression system with an effective amount of a compound of Formula (I) or Formula (III), or a pharmaceutically acceptable salt, co-crystal, solvate, hydrate, tautomer, ester, N-oxide or stereoisomer thereof increases expression of eIF2B, eIF2α, a component of the eIF2 pathway, a component of the ISR pathway or any combination thereof in the cell or in vitro expression system by about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%. In some embodiments, contacting the cell or in vitro expression system with an effective amount of a compound of Formula (I) or Formula (III), or a pharmaceutically acceptable salt, co-crystal, solvate, hydrate, tautomer, ester, N-oxide or stereoisomer thereof increases expression of eIF2B, eIF2α, a component of the eIF2 pathway, a component of the ISR pathway or any combination thereof in the cell or in vitro expression system by about 1-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, about 200-fold, about 300-fold, about 400-fold, about 500-fold, about 600-fold about 700-fold, about 800-fold, about 900-fold, about 1000-fold, about 10000-fold, about 100000-fold, or about 1000000-fold.

In some embodiments, the present invention features a method of increasing the expression of eIF2B, eIF2α, a component of the eIF2 pathway, a component of the ISR pathway or any combination thereof by a patient cells, the method comprising administering to the patient an effective amount of a compound of Formula (I) or Formula (III), or a pharmaceutically acceptable salt, co-crystal, solvate, hydrate, tautomer, ester, N-oxide or stereoisomer thereof, wherein the patient has been diagnosed with a disease, disorder, or condition disclosed herein and wherein the disease, disorder or condition is characterized by aberrant expression of eIF2B, eIF2α, a component of the eIF2 pathway, a component of the ISR pathway or any combination thereof (e.g., a leukodystrophy, a leukoencephalopathy, a hypomyelinating or demyelinating disease, muscle-wasting disease, or sarcopenia). In some embodiments, administering to the patient in need thereof an effective amount of a compound of Formula (I) or Formula (III), or a pharmaceutically acceptable salt, co-crystal, solvate, hydrate, tautomer, ester, N-oxide or stereoisomer thereof increases the expression of eIF2B, eIF2α, a component of the eIF2 pathway, a component of the ISR pathway or any combination thereof by the patients cells about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%, thereby treating the disease, disorder or condition. In some embodiments, administering to the patient in need thereof an effective amount of a compound of Formula (I) or Formula (III), or a pharmaceutically acceptable salt, co-crystal, solvate, hydrate, tautomer, ester, N-oxide or stereoisomer thereof increases expression of eIF2B, eIF2α, a component of the eIF2 pathway, a component of the ISR pathway or any combination thereof by the patients cells about 1-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, about 200-fold, about 300-fold, about 400-fold, about 500-fold, about 600-fold about 700-fold, about 800-fold, about 900-fold, about 1000-fold, about 10000-fold, about 100000-fold, or about 1000000-fold, thereby treating the disease, disorder or condition.

In another aspect, the compound of Formula (I) or Formula (III), or a pharmaceutically acceptable salt, co-crystal, solvate, hydrate, tautomer, ester, N-oxide or stereoisomer thereof may be useful in applications where increasing the activity of eIF2B, eIF2α, a component of the eIF2 pathway, a component of the ISR pathway or any combination thereof is desirable.

In some embodiments, the present invention features a method of increasing the activity of eIF2B, eIF2α, a component of the eIF2 pathway, a component of the ISR pathway or any combination thereof in a cell, the method comprising contacting the cell with an effective amount of a compound of Formula (I) or Formula (III), or a pharmaceutically acceptable salt, co-crystal, solvate, hydrate, tautomer, ester, N-oxide or stereoisomer thereof. In some embodiments, contacting the cell with an effective amount of a compound of Formula (I) or Formula (III), or a pharmaceutically acceptable salt, co-crystal, solvate, hydrate, tautomer, ester, N-oxide or stereoisomer thereof increases the activity of eIF2B, eIF2α, a component of the eIF2 pathway, a component of the ISR pathway or any combination thereof in the cell by about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%. In some embodiments, contacting the cell with an effective amount of a compound of Formula (I) or Formula (III), or a pharmaceutically acceptable salt, co-crystal, solvate, hydrate, tautomer, ester, N-oxide or stereoisomer thereof increases the activity of eIF2B, eIF2α, a component of the eIF2 pathway, a component of the ISR pathway or any combination thereof in the cell by about 1-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, about 200-fold, about 300-fold, about 400-fold, about 500-fold, about 600-fold about 700-fold, about 800-fold, about 900-fold, about 1000-fold, about 10000-fold, about 100000-fold, or about 1000000-fold.

In some embodiments, the present invention features a method of increasing the activity of eIF2B, eIF2α, a component of the eIF2 pathway, a component of the ISR pathway or any combination thereof in a patient in need thereof, the method comprising administering to the patient an effective amount of a compound of Formula (I) or Formula (III), or a pharmaceutically acceptable salt, co-crystal, solvate, hydrate, tautomer, ester, N-oxide or stereoisomer thereof, wherein the patient has been diagnosed with a disease, disorder, or condition disclosed herein and wherein the disease, disorder or condition is characterized by lowered levels of protein activity. In some embodiments, administering to the patient in need thereof an effective amount of a compound of Formula (I) or Formula (III), or a pharmaceutically acceptable salt, co-crystal, solvate, hydrate, tautomer, ester, N-oxide or stereoisomer thereof increases the activity of eIF2B, eIF2α, a component of the eIF2 pathway, a component of the ISR pathway or any combination thereof in the patient by about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%, thereby treating the disease, disorder or condition.

In some embodiments, administering to the patient in need thereof an effective amount of a compound of Formula (I) or Formula (III), or a pharmaceutically acceptable salt, co-crystal, solvate, hydrate, tautomer, ester, N-oxide or stereoisomer thereof increases the activity of eIF2B, eIF2α, a component of the eIF2 pathway, a component of the ISR pathway or any combination thereof in the patient by about 1-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, about 200-fold, about 300-fold, about 400-fold, about 500-fold, about 600-fold about 700-fold, about 800-fold, about 900-fold, about 1000-fold, about 10000-fold, about 100000-fold, or about 1000000-fold, thereby treating the disease, disorder or condition.

In some embodiments, the compound of Formula (I) or Formula (III) is chemically modified, prior to (ex vivo) or after (in vivo) contacting with the cell or in vitro expression system, forming a biologically active compound that increases the expression and/or activity of eIF2B, eIF2α, a component of the eIF2 pathway, component of the ISR pathway or any combination thereof in the cells and/or in vitro expression system. In some embodiments, the compound of Formula (I) or Formula (III) is metabolized by the patient forming a biologically active compound that increases the expression and/or activity of eIF2B, eIF2α, a component of the eIF2 pathway, component of the ISR pathway or any combination thereof in the patients cells, thereby treating a condition, disease or disorder disclosed herein. In some embodiments, the biologically active compound is the compound of Formula (III).

Methods of Decreasing Protein Activity and Production

In another aspect, the compound of Formula (I) or Formula (III), or a pharmaceutically acceptable salt, co-crystal, solvate, hydrate, tautomer, ester, N-oxide or stereoisomer thereof may be useful in applications where decreasing production output of eIF2B, eIF2α, a component of the eIF2 pathway, a component of the ISR pathway or any combination thereof is desirable.

In some embodiments, the present invention features a method of decreasing expression of eIF2B, eIF2α, a component of the eIF2 pathway, a component of the ISR pathway or any combination thereof in a cell, the method comprising contacting the cells with an effective amount of a compound of Formula (I) or Formula (III), or a pharmaceutically acceptable salt, co-crystal, solvate, hydrate, tautomer, ester, N-oxide or stereoisomer thereof. In some embodiments, contacting the cells with an effective amount of a compound of Formula (I) or Formula (III), or a pharmaceutically acceptable salt, co-crystal, solvate, hydrate, tautomer, ester, N-oxide or stereoisomer thereof decreases expression of eIF2B, eIF2α, a component of the eIF2 pathway, a component of the ISR pathway or any combination thereof in the cell by about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%.

In some embodiments, the present invention features a method of decreasing the expression of eIF2B, eIF2α, a component of the eIF2 pathway, a component of the ISR pathway or any combination thereof in a patient in need thereof, the method comprising administering to the patient an effective amount of a compound of Formula (I) or Formula (III), or a pharmaceutically acceptable salt, co-crystal, solvate, hydrate, tautomer, ester, N-oxide or stereoisomer thereof, wherein the patient has been diagnosed with a disease, disorder, or condition described herein and wherein the disease, disorder or condition is characterized by increased levels of protein production. In some embodiments, administering to the patient in need thereof an effective amount of a compound of Formula (I) or Formula (III), or a pharmaceutically acceptable salt, co-crystal, solvate, hydrate, tautomer, ester, N-oxide or stereoisomer thereof decreases the expression of eIF2B, eIF2α, a component of the eIF2 pathway, a component of the ISR pathway or any combination thereof in the patient by about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%, thereby treating the disease, disorder or condition.

In another aspect, the compound of Formula (I) or Formula (III), or a pharmaceutically acceptable salt, co-crystal, solvate, hydrate, tautomer, ester, N-oxide or stereoisomer thereof may be useful in applications where decreasing the activity of eIF2B, eIF2α, a component of the eIF2 pathway, a component of the ISR pathway or any combination thereof is desirable.

In some embodiments, the present invention features a method of decreasing the activity of eIF2B, eIF2α, a component of the eIF2 pathway, a component of the ISR pathway or any combination thereof in a cell, the method comprising contacting the cell with an effective amount of a compound of Formula (I) or Formula (III), or a pharmaceutically acceptable salt, co-crystal, solvate, hydrate, tautomer, ester, N-oxide or stereoisomer thereof. In some embodiments, contacting the cell with an effective amount of a compound of Formula (I) or Formula (III), or a pharmaceutically acceptable salt, co-crystal, solvate, hydrate, tautomer, ester, N-oxide or stereoisomer thereof decreases the activity of eIF2B, eIF2α, a component of the eIF2 pathway, a component of the ISR pathway or any combination thereof in the cell by about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%, thereby treating the disease, disorder or condition.

In some embodiments, the present invention features a method of decreasing the activity of eIF2B, eIF2α, a component of the eIF2 pathway, a component of the ISR pathway or any combination thereof in a patient in need thereof, the method comprising administering to the patient an effective amount of a compound of Formula (I) or Formula (III), or a pharmaceutically acceptable salt, co-crystal, solvate, hydrate, tautomer, ester, N-oxide or stereoisomer thereof, wherein the patient has been diagnosed with a disease, disorder, or condition described herein and wherein the disease, disorder or condition is characterized by increased levels of protein activity. In some embodiments, administering to the patient in need thereof an effective amount of a compound of Formula (I) or Formula (III), or a pharmaceutically acceptable salt, co-crystal, solvate, hydrate, tautomer, ester, N-oxide or stereoisomer thereof decreases the activity of eIF2B, eIF2α, a component of the eIF2 pathway, a component of the ISR pathway or any combination thereof in the patient by about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%, thereby treating the disease, disorder or condition.

In some embodiments, the compound of Formula (I) or Formula (III) is chemically modified, prior to (ex vivo) or after (in vivo) contacting with a cell, forming a biologically active compound that decreases the expression and/or activity of eIF2B, eIF2α, a component of the eIF2 pathway, component of the ISR pathway or any combination thereof in the cell. In some embodiments, the compound of Formula (I) or Formula (III) is metabolized by the patient forming a biologically active compound that decreases the expression and/or activity of eIF2B, eIF2α, a component of the eIF2 pathway, component of the ISR pathway or any combination thereof in the patients cells, thereby treating a condition, disease or disorder disclosed herein. In some embodiments, the biologically active compound is the compound of Formula (I) or Formula (III).

In some embodiments, the compounds set forth herein are provided as pharmaceutical compositions including a compound of Formula (I) or a pharmaceutically acceptable salt, solvate, hydrate, tautomer, or stereoisomer thereof and a pharmaceutically acceptable excipient. In embodiments of the method, a compound of Formula (I) or a pharmaceutically acceptable salt, solvate, hydrate, tautomer, or stereoisomer thereof, is co-administered with a second agent (e.g. therapeutic agent). In other embodiments of the method, a compound of Formula (I) or a pharmaceutically acceptable salt, solvate, hydrate, tautomer, or stereoisomer thereof, is co-administered with a second agent (e.g. therapeutic agent), which is administered in a therapeutically effective amount. In embodiments, the second agent is an agent for improving memory.

Combination Therapy

In one aspect, the present invention features a pharmaceutical composition comprising a compound of Formula (I) or a pharmaceutically acceptable salt, solvate, hydrate, tautomer, or stereoisomer thereof as well as a second agent (e.g. a second therapeutic agent). In some embodiments, the pharmaceutical composition includes a second agent (e.g. a second therapeutic agent) in a therapeutically effective amount. In some embodiments, the second agent is an agent for treating cancer, a neurodegenerative disease, a leukodystrophy, an inflammatory disease, a musculoskeletal disease, a metabolic disease, or a disease or disorder associated with impaired function of eIF2B, eIF2α, or a component of the eIF2 pathway or ISR pathway.

The compounds described herein can be used in combination with one another, with other active agents known to be useful in treating cancer, a neurodegenerative disease, an inflammatory disease, a musculoskeletal disease, a metabolic disease, or a disease or disorder associated with impaired function of eIF2B, eIF2α, or a component of the eIF2 pathway or ISR pathway or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for a cancer, a neurodegenerative disease, a leukodystrophy, an inflammatory disease, a musculoskeletal disease, a metabolic disease, or a disease or disorder associated with impaired function of eIF2B, eIF2α, or a component of the eIF2 pathway or ISR pathway.

In embodiments, the second agent is an anti-cancer agent. In embodiments, the second agent is a chemotherapeutic. In embodiments, the second agent is an agent for improving memory. In embodiments, the second agent is an agent for treating a neurodegenerative disease. In embodiments, the second agent is an agent for treating a leukodystrophy. In embodiments, the second agent is an agent for treating vanishing white matter disease. In embodiments, the second agent is an agent for treating childhood ataxia with CNS hypo-myelination. In embodiments, the second agent is an agent for treating an intellectual disability syndrome. In embodiments, the second agent is an agent for treating pancreatic cancer. In embodiments, the second agent is an agent for treating breast cancer. In embodiments, the second agent is an agent for treating multiple myeloma. In embodiments, the second agent is an agent for treating myeloma. In embodiments, the second agent is an agent for treating a cancer of a secretory cell. In embodiments, the second agent is an agent for reducing eIF2α phosphorylation. In embodiments, the second agent is an agent for inhibiting a pathway activated by eIF2α phosphorylation. In embodiments, the second agent is an agent for inhibiting a pathway activated by eIF2α. In embodiments, the second agent is an agent for inhibiting the integrated stress response. In embodiments, the second agent is an anti-inflammatory agent. In embodiments, the second agent is an agent for treating postsurgical cognitive dysfunction. In embodiments, the second agent is an agent for treating traumatic brain injury. In embodiments, the second agent is an agent for treating a musculoskeletal disease. In embodiments, the second agent is an agent for treating a metabolic disease. In embodiments, the second agent is an anti-diabetic agent.

Anti-Cancer Agents

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anticancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 1 1-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone Bl; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-n1; interferon alfa-n3; interferon beta-la; interferon gamma-lb; iprop latin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol, i.e. paclitaxel), Taxotere, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and SC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-1 12378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A 1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tularik, i.e. T-900607), RPR-115781 (Aventis), Eleutherobins (such as Desmethyleleutherobin, Desaetyleleutherobin, Iso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y $^{87}$Y, $^{90}$Y, $^{105}$Rh, $^{111m}$Ag, $^{111m}$In, $^{117m}$Sn, $^{149}$Pm, $^{153}$Sm, $^{166}$Ho $^{177}$Lu, $^{186}$Re, $^{188}$Re, $^{211}$At, and $^{212}$Bi, optionally conjugated to antibodies directed against tumor antigens.

Additional Agents

In some embodiments, the second agent for use in combination with a compound (e.g., a compound of Formula (I)) or composition thereof described herein is an agent for use in treating a neurodegenerative disease, a leukodystrophy, an inflammatory disease, a musculoskeletal disease, or a metabolic disease. In some embodiments, a second agent for use in combination with a compound (e.g., a compound of Formula (I)) or composition thereof described herein is an agent approved by the FDA or similar regulatory agency of a country other than the USA, for treating a disease, disorder, or condition described herein.

In some embodiments, a second agent for use in treating a neurodegenerative disease, a leukodystrophy, an inflammatory disease, a musculoskeletal disease, or a metabolic disease includes, but is not limited to, an anti-psychotic drug, anti-depressive drug, anti-anxiety drug, analgesic, a stimulant, a sedative, a pain reliever, an anti-inflammatory agent, a benzodiazepine, a cholinesterase inhibitor, a nonsteroidal anti-inflammatory drug (NSAID), a corticosteroid, a MAO inhibitor, a beta-blocker, a calcium channel blocker, an antacid, or other agent.

Exemplary second agents may include donepezil, galantamine, rivastigmine, memantine, levodopa, dopamine, pramipexole, ropinirole, rotigotine, doxapram, oxazepam, quetiapine, selegiline, rasagiline, entacapone, benztropine, trihexyphenidyl, riluzole, diazepam, chlorodiazepoxide, lorazepam, alprazolam, buspirone, gepirone, ispapirone, hydroxyzine, propranolol, hydroxyzine, midazolam, trifluoperazine, methylphenidate, atomoxetine, methylphenidate, pemoline, perphenazine, divalproex, valproic acid, sertraline, fluoxetine, citalopram, escitalopram, paroxetine, fluvoxamine, trazodone, desvenlafaxine, duloxetine, venlafaxine, amitriptyline, amoxapine, clomipramine, desipramine, imipramine, nortriptyline, protriptyline, trimipramine, maprotiline, bupropion, nefazodone, vortioxetine, lithium, clozapine, fluphenazine, haloperidol, paliperidone, loxapine, thiothixene, pimozide, thioridazine, risperidone, aspirin, ibuprofen, naproxen, acetaminophen, azathioprine, methotrexate, mycophenolic acid, leflunomide, dibenzoylmethane, cilostazol, pentoxifylline, duloxetine, a cannabinoid (e.g, nabilone), simethicone, magaldrate, aluminum salts, calcium salts, sodium salts, magnesium salts, alginic acid, acarbose, albiglutide, alogliptin, metformin, insulin, lisinopril, atenolol, atorvastatin, fluvastatin, lovastatin, pitavastatin, simvastatin, rosuvastatin, and the like.

Naturally derived agents or supplements may also be used in conjunction with a compound of Formula (I) or a composition thereof to treat a neurodegenerative disease, an inflammatory disease, a musculoskeletal disease, or a metabolic disease. Exemplary naturally derived agents or supplements include omega-3 fatty acids, carnitine, citicoline, curcumin, gingko, vitamin E, vitamin B (e.g., vitamin B5, vitamin B6, or vitamin B12), huperzine A, phosphatidylserine, rosemary, caffeine, melatonin, chamomile, St. John's wort, tryptophan, and the like.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthetic Protocols

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures. General scheme relating to methods of making exemplary compounds of the invention are additionally described in the section entitled Methods of Making Compounds.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Abbreviations

APCI for atmospheric pressure chemical ionization; COMU for (1-cyano-2-ethoxy-2-oxoethylidenaminooxy)dimethylamino-morpholino-carbenium hexafluorophosphate; DCI for desorption chemical ionization; DMSO for dimethyl sulfoxide; ESI for electrospray ionization; HATU for 1-[bis(dimethylamino)methylene]-1H-1,2,3-triazolo[4,5-b]pyridinium 3-oxid hexafluorophosphate; HPLC for high performance liquid chromatography; LC/MS for liquid chromatography/mass spectrometry; MS for mass spectrum; NMR for nuclear magnetic resonance; psi for pounds per square inch; TLC for thin-layer chromatography; and XPhos for 2-(dicyclohexylphosphino)-2',4',6'-triisopropylbiphenyl.

Example 1: (1r,4r)-4-[2-(3,4-dichlorophenoxy)acetamido]-N-{[6-(trifluoromethyl)pyridin-3-yl]methyl}cyclohexane-1-carboxamide (Compound 100)

Example 1A: methyl (1 r,4r)-4-[2-(3,4-dichlorophenoxy)acetamido]cyclohexane-1-carboxylate Methyl trans-4-aminocyclohexanecarboxylate (0.6 g, 3.82 mmol, AMRI), 2-(3,4-dichlorophenoxy)acetic acid (0.886 g, 4.01 mmol, Aldrich) and trimethylamine (2.13 mL, 15.27 mmol) were combined with N,N-dimethylformamide (10 mL), and the mixture was stirred at ambient temperature. 1-[Bis(dimethylamino)methylene]-1H-1,2,3-triazolo[4,5-b]pyridinium 3-oxid hexafluorophosphate (HATU, 1.741 g, 4.58 mmol) was added. After stirring for 1 hour, the reaction mixture was filtered through a glass microfiber frit and purified by preparative HPLC [YMC TriArt™ C18 Hybrid 20 μm column, 25×150 mm, flow rate 80 mL/minute, 5-100% gradient of acetonitrile in buffer (0.025 M aqueous ammonium bicarbonate, adjusted to pH 10 with ammonium hydroxide)] to give the title compound (1.1 g, 3.05 mmol, 80% yield). MS (ESI$^+$) m/z 360 (M+H)$^+$.

Example 1B: (1r,4r)-4-[2-(3,4-dichlorophenoxy)acetamido]cyclohexane-1-carboxylic acid The product of Example 1A (1.1 g, 3.05 mmol) was dissolved in CH$_3$OH (10 mL). NaOH (2.5 M aqueous solution, 3.05 mL) was added. After stirring at ambient temperature for 18 hours, the reaction mixture was filtered through a glass microfiber frit and purified by preparative HPLC [YMC TriArt™ C18 Hybrid 20 μm column, 50×150 mm, flow rate 70 mL/minute, 5-100% gradient of acetonitrile in buffer (0.1% trifluoroacetic acid)] to give the title compound (0.9 g, 2.60 mmol, 85% yield). MS (ESI$^+$) m/z 346 (M+H)$^+$.

Example 1C: (1r,4r)-4-[2-(3,4-dichlorophenoxy)acetamido]-N-{[6-(trifluoromethyl)pyridin-3-yl]methyl}cyclohexane-1-carboxamide The product of Example 1B (45 mg, 0.13 mmol), (6-(trifluoromethyl)pyridin-3-yl)methanamine (22.89 mg, 0.130 mmol, Matrix) and triethylamine (0.054 mL, 0.39 mmol) were combined with N,N-dimethylformamide (2 mL), and the mixture was stirred at ambient temperature. 1-[Bis(dimethylamino)methylene]-1H-1,2,3-triazolo[4,5-b]pyridinium 3-oxid hexafluorophosphate (HATU, 54.4 mg, 0.14 mmol) was added. After stirring for 1 hour, the reaction mixture was filtered through a glass microfiber frit and purified by preparative HPLC [YMC TriArt™ C18 Hybrid 5 μm column, 50×100 mm, flow rate 70 mL/minute, 5-100% gradient of acetonitrile in buffer (0.025 M aqueous ammonium bicarbonate, adjusted to pH 10 with ammonium hydroxide)] to give the title compound (38 mg, 0.075 mmol, 58% yield). $^1$H NMR (501 MHz, DMSO-d$_6$) δ ppm 8.66-8.62 (m, 1H), 8.42 (t, J=6.0 Hz, 1H), 7.95 (d, J=8.1 Hz, 1H), 7.92-7.84 (m, 2H), 7.54 (d, J=8.9 Hz, 1H), 7.25 (d, J=2.9 Hz, 1H), 6.98 (dd, J=9.0, 2.9 Hz, 1H), 4.50 (s, 2H), 4.37 (d, J=5.9 Hz, 2H), 3.63-3.54 (m, 1H), 2.18-2.09 (m, 1H), 1.85-1.74 (m, 4H), 1.48-1.37 (m, 2H), 1.33-1.22 (m, 2H); MS (ESI$^+$) m/z 504 (M+H)$^+$.

Example 2: (1r,4r)-4-[2-(3,4-dichlorophenoxy)acetamido]-N-[(5-methylpyridin-2-yl)methyl]cyclohexane-1-carboxamide (Compound 101)

The reaction and purification conditions described in Example 1C substituting (5-methylpyridin-2-yl)methanamine hydrochloride (ArkPharm) for (6-(trifluoromethyl)pyridin-3-yl)methanamine gave the title compound. $^1$H NMR (501 MHz, DMSO-d$_6$) δ ppm 8.33-8.31 (m, 1H), 8.30 (t, J=6.0 Hz, 1H), 7.96 (d, J=8.1 Hz, 1H), 7.59-7.52 (m, 2H), 7.25 (d, J=2.9 Hz, 1H), 7.12 (d, J=8.0 Hz, 1H), 6.98 (dd, J=8.9, 2.9 Hz, 1H), 4.50 (s, 2H), 4.29 (d, J=6.0 Hz, 2H), 3.64-3.53 (m, 1H), 2.26 (s, 3H), 2.22-2.12 (m, 1H), 1.85-1.74 (m, 4H), 1.50-1.36 (m, 2H), 1.34-1.22 (m, 2H); MS (ESI+) m/z 450 (M+H)$^+$.

Example 3: (1r,4r)-4-[2-(3,4-dichlorophenoxy)acetamido]-N-[6-(difluoromethoxy)pyridin-3-yl]cyclohexane-1-carboxamide (Compound 102)

The product of Example 1B (65 mg, 0.19 mmol) and bis(tetramethylene)fluoroformamidinium (89 mg, 0.28 mmol) were charged to a sealed tube (5 mL) and a mixture of dichloromethane (469 μL) and N,N-diisopropylethylamine (148 μL, 0.85 mmol) was added in one portion. The resulting mixture was stirred at ambient temperature for 30 minutes and 6-(difluoromethoxy)pyridin-3-amine (34.6 mg, 0.22 mmol, Enamine) was added. The tube was sealed and stirred at 75° C. for 18 hours. The reaction mixture was cooled to ambient temperature and then concentrated under reduced pressure. The residue was taken up in N,N-dimethylformamide (3 mL), filtered through a glass microfiber frit and purified by preparative HPLC [YMC TriArt™ C18 Hybrid 5 μm column, 50×100 mm, flow rate 70 mL/minute, 5-100% gradient of acetonitrile in buffer (0.1% trifluoroacetic acid)] to give the title compound (0.02 g, 0.033 mmol, 18% yield). $^1$H NMR (400 MHz, DMSO-d$_6$) δ ppm 10.04 (s, 1H), 8.42 (d, J=2.7 Hz, 1H), 8.06 (dd, J=8.9, 2.7 Hz, 1H), 7.95 (d, J=8.0 Hz, 1H), 7.58 (t, J=73.2 Hz, 1H), 7.51 (d, J=9.0 Hz, 1H), 7.23 (d, J=2.9 Hz, 1H), 7.02 (d, J=8.8 Hz, 1H), 6.96 (dd, J=9.0, 2.9 Hz, 1H), 4.48 (s, 2H), 3.66-3.53 (m, 1H), 2.33-2.20 (m, 1H), 1.91-1.76 (m, 4H), 1.55-1.37 (m, 2H), 1.37-1.20 (m, 2H); MS (APCI⁺) m/z 488 (M+H)⁺.

Example 4: (1r,4r)-4-[2-(3,4-dichlorophenoxy)acetamido]-N-[6-(2,2,2-trifluoroethoxy)pyridin-3-yl]cyclohexane-1-carboxamide (Compound 103)

The reaction and purification conditions described in Example 3 substituting 6-(2,2,2-trifluoroethoxy)pyridin-3-amine (Enamine) for 6-(difluoromethoxy)pyridin-3-amine gave the title compound. ¹H NMR (400 MHz, DMSO-d₆) δ ppm 9.91 (s, 1H), 8.37 (dd, J=2.7, 0.7 Hz, 1H), 7.99-7.91 (m, 2H), 7.51 (d, J=9.0 Hz, 1H), 7.23 (d, J=2.9 Hz, 1H), 6.96 (dd, J=8.9, 2.9 Hz, 1H), 6.91 (d, J=8.8 Hz, 1H), 4.90 (q, J=9.1 Hz, 2H), 4.48 (s, 2H), 3.58 (n, J=11.4, 7.6, 5.7 Hz, 1H), 2.31-2.19 (m, 1H), 1.96-1.72 (m, 4H), 1.53-1.38 (m, 2H), 1.37-1.21 (m, 2H); MS (APCI⁺) m/z 520 (M+H)⁺.

Example 5: (1r,4r)-4-[2-(3,4-dichlorophenoxy)acetamido]-N-{[4-(difluoromethoxy)phenyl]methyl}cyclohexane-1-carboxamide (Compound 104)

The reaction and purification conditions described in Example 1C substituting 4-(difluoromethoxy)benzylamine (Aldrich) for (6-(trifluoromethyl)pyridin-3-yl)methanamine gave the title compound. ¹H NMR (501 MHz, DMSO-d₆) δ ppm 8.26 (t, J=6.0 Hz, 1H), 7.95 (d, J=8.1 Hz, 1H), 7.54 (d, J=9.0 Hz, 1H), 7.29-7.24 (m, 3H), 7.18 (t, J=74.2 Hz, 1H), 7.14-7.09 (m, 2H), 6.98 (dd, J=8.9, 2.9 Hz, 1H), 4.50 (s, 2H), 4.23 (d, J=5.9 Hz, 2H), 3.58 (dtt, J=11.7, 7.7, 3.8 Hz, 1H), 2.12 (tt, J=11.8, 3.2 Hz, 1H), 1.87-1.71 (m, 4H), 1.48-1.37 (m, 2H), 1.33-1.20 (m, 2H); MS (ESI⁺) m/z 501 (M+H)⁺.

Example 6: (1r,4r)-4-[2-(3,4-dichlorophenoxy)acetamido]-N-[(6-methoxypyridin-3-yl)methyl]cyclohexane-1-carboxamide (Compound 105)

The reaction and purification conditions described in Example 1C substituting (6-methoxypyridin-3-yl)methanamine, hydrochloric acid (Anichem) for (6-(trifluoromethyl)pyridin-3-yl)methanamine gave the title compound. ¹H NMR (400 MHz, DMSO-d₆) δ ppm 8.22 (t, J=5.9 Hz, 1H), 8.02 (d, J=2.4 Hz, 1H), 7.94 (d, J=8.1 Hz, 1H), 7.58-7.51 (m, 2H), 7.25 (d, J=3.0 Hz, 1H), 6.98 (dd, J=8.9, 2.9 Hz, 1H), 6.77 (d, J=8.5 Hz, 1H), 4.50 (s, 2H), 4.17 (d, J=5.8 Hz, 2H), 3.82 (s, 3H), 3.64-3.51 (m, 1H), 2.17-2.03 (m, 1H), 1.83-1.70 (m, 4H), 1.48-1.35 (m, 2H), 1.33-1.19 (m, 2H); MS (ESI⁺) m/z 466 (M+H)⁺.

Example 7: (1r,4r)-4-[2-(3,4-dichlorophenoxy)acetamido]-N-methyl-N-[(pyridin-3-yl)methyl]cyclohexane-1-carboxamide (Compound 106)

The reaction and purification conditions described in Example 1C substituting N-methyl-N-(3-pyridylmethyl)amine (Alfa) for (6-(trifluoromethyl)pyridin-3-yl)methanamine gave the title compound. ¹H NMR (400 MHz, DMSO-d₆) δ ppm 8.22 (t, J=5.9 Hz, 1H), 8.02 (d, J=2.4 Hz, 1H), 7.94 (d, J=8.1 Hz, 1H), 7.58-7.51 (m, 2H), 7.25 (d, J=3.0 Hz, 1H), 6.98 (dd, J=8.9, 2.9 Hz, 1H), 6.77 (d, J=8.5 Hz, 1H), 4.50 (s, 2H), 4.17 (d, J=5.8 Hz, 2H), 3.82 (s, 3H), 3.64-3.51 (m, 1H), 2.17-2.03 (m, 1H), 1.83-1.70 (m, 4H), 1.48-1.35 (m, 2H), 1.33-1.19 (m, 2H); MS (ESI⁺) m/z 466 (M+H)⁺.

Example 8: (1r,4r)-4-[2-(4-chloro-3-fluorophenoxy)acetamido]-N-{[5-(difluoromethoxy)pyridin-2-yl]methyl}cyclohexane-1-carboxamide (Compound 107)

Example 8A: (1r,4r)-4-(2-(4-chloro-3-fluorophenoxy)acetamido)cyclohexanecarboxylic acid The reaction and purification conditions described in Example 1A and Example 1B substituting 2-(4-chloro-3-fluorophenoxy)acetic acid (CombiBlock) for 2-(3,4-dichlorophenoxy)acetic acid gave the title compound. MS (APCI⁺) m/z 330 (M+H)⁺.

Example 8B: (1r,4r)-4-[2-(4-chloro-3-fluorophenoxy)acetamido]-N-{[5-(difluoromethoxy)pyridin-2-yl]methyl}cyclohexane-1-carboxamide The reaction and purification conditions described in Example 1C substituting [5-(difluoromethoxy)pyridin-2-yl]methanamine (Enamine) for (6-(trifluoromethyl)pyridin-3-yl)methanamine and the product of Example 8A for the product of Example 1B gave the title compound. ¹H NMR (400 MHz, DMSO-d₆) δ ppm 8.41-8.34 (m, 2H), 7.95 (d, J=8.1 Hz, 1H), 7.63 (dd, J=8.6, 2.9 Hz, 1H), 7.49 (t, J=8.9 Hz, 1H), 7.33-7.28 (m, 1H), 7.27 (t, J=73.5 Hz, 1H), 7.07 (dd, J=11.4, 2.9 Hz, 1H), 6.85 (ddd, J=9.0, 2.9, 1.2 Hz, 1H), 4.49 (s, 2H), 4.33 (d, J=5.9 Hz, 2H), 3.65-3.53 (m, 1H), 2.23-2.10 (m, 1H), 1.89-1.74 (m, 4H), 1.52-1.36 (m, 2H), 1.35-1.21 (m, 2H); MS (ESI⁺) m/z 486 (M+H)⁺.

Example 9: (1r,4r)-4-[2-(4-chloro-3-fluorophenoxy)acetamido]-N-[(5-methylpyridin-3-yl)methyl]cyclohexane-1-carboxamide (Compound 108)

The reaction and purification conditions described in Example 1C substituting (5-methylpyridin-3-yl)methanamine (Enamine) for (6-(trifluoromethyl)pyridin-3-yl)methanamine and the product of Example 8A for the product of Example 1B gave the title compound. ¹H NMR (500 MHz, DMSO-d₆) δ ppm 8.33-8.23 (m, 3H), 7.95 (d, J=8.1 Hz, 1H), 7.49 (t, J=8.9 Hz, 1H), 7.42 (tq, J=2.1, 0.7 Hz, 1H), 7.07 (dd, J=11.4, 2.8 Hz, 1H), 6.85 (ddd, J=9.0, 2.9, 1.2 Hz, 1H), 4.49 (s, 2H), 4.23 (d, J=5.8 Hz, 2H), 3.58 (tdt, J=11.8, 7.9, 3.9 Hz, 1H), 2.29-2.27 (m, 3H), 2.12 (tt, J=11.9, 3.3 Hz, 1H), 1.84-1.73 (m, 4H), 1.49-1.37 (m, 2H), 1.33-1.21 (m, 2H); MS (ESI⁺) m/z 434 (M+H)⁺.

Example 10: (1r,4r)-4-[2-(4-chloro-3-fluorophenoxy)acetamido]-N-[6-(difluoromethoxy)pyridin-3-yl]cyclohexane-1-carboxamide (Compound 109)

The reaction and purification conditions described in Example 1C substituting 6-(difluoromethoxy)pyridin-3-amine (Enamine) for (6-(trifluoromethyl)pyridin-3-yl)methanamine, the product of Example 8A for the product of Example 1B, and (1-cyano-2-ethoxy-2-oxoethylidenaminooxy)dimethylamino-morpholino-carbenium hexafluorophosphate (COMU) for 1-[bis(dimethylamino)methylene]-1H-1,2,3-triazolo[4,5-b]pyridinium 3-oxid hexafluorophosphate (HATU) gave the title compound. ¹H NMR (501 MHz, DMSO-d₆) δ ppm 10.08 (s, 1H), 8.46 (dd, J=2.7, 0.7 Hz, 1H), 8.09 (dd, J=8.8, 2.7 Hz, 1H), 7.98 (d, J=8.1 Hz, 1H), 7.62 (s, J=73.2 Hz, 1H), 7.54-7.45 (m, 1H), 7.10-7.03 (m, 2H), 6.86 (ddd, J=9.0, 2.9, 1.2 Hz, 1H), 4.51 (s, 2H), 3.62 (tdt, J=11.6, 7.8, 3.9 Hz, 1H), 2.29 (tt, J=12.0, 3.4 Hz, 1H), 1.93-1.80 (m, 4H), 1.55-1.44 (m, 2H), 1.39-1.27 (m, 2H); MS (ESI⁺) m/z 472 (M+H)⁺.

Example 11: (1r,4r)-4-[2-(4-chloro-3-fluorophenoxy)acetamido]-N-[5-(trifluoromethoxy)pyridin-2-yl]cyclohexane-1-carboxamide (Compound 110)

One drop of N,N-dimethylformamide was added to a suspension of the product of Example 8A (40 mg, 0.12 mmol) in dichloromethane (2 mL). Oxalyl chloride (2.0 M in dichloromethane, 0.121 mL) was added in one portion. After stirring at ambient temperature for 20 minutes, the resulting solution was concentrated under reduced pressure. The residue was then taken up in pyridine (1 mL) and transferred to a solution of 5-(trifluoromethoxy)pyridin-2-amine (24.9 mg, 0.14 mmol, Astatech) in a solvent mixture of N,N-dimethylformamide (1.0 mL) and pyridine (1.0 mL). The reaction mixture was stirred for 30 minutes, filtered through a glass microfiber frit, and purified by preparative HPLC [YMC TriArt™ C18 Hybrid 5 µm column, 50×100 mm, flow rate 70 mL/minute, 5-100% gradient of acetonitrile in buffer (0.025 M aqueous ammonium bicarbonate, adjusted to pH 10 with ammonium hydroxide)] to give the title compound (13 mg, 0.027 mmol, 22% yield). ¹H NMR (501 MHz, DMSO-d₆) δ ppm 10.67 (s, 1H), 8.40 (dt, J=2.9, 0.7 Hz, 1H), 8.21 (dd, J=9.1, 0.7 Hz, 1H), 7.99 (d, J=8.1 Hz, 1H), 7.87 (ddd, J=9.2, 3.0, 1.1 Hz, 1H), 7.50 (t, J=8.9 Hz, 1H), 7.07 (dd, J=11.4, 2.8 Hz, 1H), 6.86 (ddd, J=9.0, 2.9, 1.2 Hz, 1H), 4.50 (s, 2H), 3.67-3.57 (m, 1H), 2.54-2.43 (m, 1H), 1.91-1.77 (m, 4H), 1.53-1.42 (m, 2H), 1.39-1.24 (m, 2H); MS (ESI⁺) m/z 490 (M+H)⁺.

Example 12: (1r,4r)-4-[2-(4-chloro-3-fluorophenoxy)acetamido]-N-(4-chloro-3-fluorophenyl)cyclohexane-1-carboxamide (Compound 111)

The reaction and purification conditions described in Example 1C substituting 4-chloro-3-fluoroaniline (Oakwood) for (6-(trifluoromethyl)pyridin-3-yl)methanamine, the product of Example 8A for the product of Example 1B, and (1-cyano-2-ethoxy-2-oxoethylidenaminooxy)dimethylamino-morpholino-carbenium hexafluorophosphate (COMU) for 1-[bis(dimethylamino)methylene]-1H-1,2,3-triazolo[4,5-b]pyridinium 3-oxid hexafluorophosphate (HATU) gave the title compound. ¹H NMR (400 MHz, DMSO-d₆) δ ppm 10.15 (s, 1H), 7.98 (d, J=8.1 Hz, 1H), 7.79 (dd, J=12.1, 2.4 Hz, 1H), 7.54-7.45 (m, 2H), 7.33 (ddd, J=8.8, 2.4, 1.0 Hz, 1H), 7.07 (dd, J=11.4, 2.8 Hz, 1H), 6.86 (ddd, J=9.1, 2.9, 1.2 Hz, 1H), 4.50 (s, 2H), 3.67-3.55 (m, 1H), 2.33-2.22 (m, 1H), 1.92-1.78 (m, 4H), 1.57-1.41 (m, 2H), 1.39-1.23 (m, 2H); MS (ESI⁺) m/z 457 (M+H)⁺.

Example 13: (1r,4r)-4-[2-(4-chloro-3-fluorophenoxy)acetamido]-N-[(4-chloro-3-fluorophenyl)methyl]cyclohexane-1-carboxamide (Compound 112)

The reaction and purification conditions described in Example 1C substituting (4-chloro-3-fluorophenyl)methanamine (Alfa) for (6-(trifluoromethyl)pyridin-3-yl)methanamine, the product of Example 8A for the product of Example 1B, and (1-cyano-2-ethoxy-2-oxoethylidenaminooxy)dimethylamino-morpholino-carbenium hexafluorophosphate (COMU) for 1-[bis(dimethylamino)methylene]-1H-1,2,3-triazolo[4,5-b]pyridinium 3-oxid hexafluorophosphate (HATU) gave the title compound. ¹H NMR (400 MHz, DMSO-d₆) δ ppm 8.32 (t, J=6.0 Hz, 1H), 7.95 (d, J=8.1 Hz, 1H), 7.58-7.45 (m, 2H), 7.23 (dd, J=10.5, 2.0 Hz, 1H), 7.11-7.04 (m, 2H), 6.85 (ddd, J=9.0, 2.9, 1.2 Hz, 1H), 4.49 (s, 2H), 4.25 (d, J=6.0 Hz, 2H), 3.64-3.53 (m, 1H), 2.20-2.07 (m, 1H), 1.85-1.73 (m, 4H), 1.51-1.36 (m, 2H), 1.34-1.20 (m, 2H); MS (ESI⁺) m/z 471 (M+H)⁺.

Example 14: 2-(4-chloro-3-fluorophenoxy)-N-{(1R,4r)-4-[(2R)-2-(2,5-difluorophenyl)pyrrolidine-1-carbonyl]cyclohexyl}acetamide (Compound 113)

The reaction and purification conditions described in Example 1C substituting (R)-2-(2,5-difluorophenyl)pyrrolidine (Enamine) for (6-(trifluoromethyl)pyridin-3-yl)methanamine and the product of Example 8A for the product of Example 1B gave the title compound. ¹H NMR (120° C., 400 MHz, DMSO-d₆) δ ppm 7.45-7.30 (m, 2H), 7.17-7.07 (m, 1H), 7.06-6.99 (m, 1H), 6.97 (dd, J=11.3, 2.8 Hz, 1H), 6.90-6.79 (m, 2H), 5.19-5.10 (m, 1H), 4.44 (s, 2H), 3.81-3.47 (m, 3H), 2.43-2.21 (m, 2H), 2.04-1.62 (m, 7H), 1.50-1.09 (m, 4H); MS (APCI*) m/z 495 (M+H)⁺.

Example 15: 2-(4-chloro-3-fluorophenoxy)-N-{(1S,4r)-4-[(2S)-2-(2,5-difluorophenyl)pyrrolidine-1-carbonyl]cyclohexyl}acetamide (Compound 114)

The reaction and purification conditions described in Example 1C substituting (S)-2-(2,5-difluorophenyl)pyrrolidine (Enamine) for (6-(trifluoromethyl)pyridin-3-yl)methanamine and the product of Example 8A for the product of Example 1B gave the title compound. ¹H NMR (120° C., 400 MHz, DMSO-d₆) δ ppm 7.50-7.28 (m, 2H), 7.18-7.07 (m, 1H), 7.07-6.99 (m, OH), 6.97 (dd, J=11.3, 2.8 Hz, 1H), 6.88-6.80 (m, 2H), 5.24-5.07 (m, 1H), 4.44 (s, 2H), 3.78-3.48 (m, 3H), 2.41-2.20 (m, 2H), 2.00-1.58 (m, 8H), 1.38 (tq, J=24.8, 13.6 Hz, 4H); MS (APCI⁺) m/z 495 (M+H)⁺.

Example 16: (1r,4r)-4-[2-(4-chloro-3-fluorophenoxy)acetamido]-N-[6-(2,2,2-trifluoroethoxy)pyridin-3-yl]cyclohexane-1-carboxamide (Compound 115)

The reaction and purification conditions described in Example 1C substituting 6-(2,2,2-trifluoroethoxy)pyridin-3-amine (Enamine) for (6-(trifluoromethyl)pyridin-3-yl)methanamine and the product of Example 8A for the product of Example 1B gave the title compound. ¹H NMR (400 MHz, DMSO-d₆) δ ppm 9.95 (s, 1H), 8.40 (dd, J=2.7, 0.7 Hz, 1H), 8.02-7.95 (m, 2H), 7.50 (t, J=8.9 Hz, 1H), 7.07 (dd, J=11.4, 2.9 Hz, 1H), 6.95 (dd, J=8.9, 0.7 Hz, 1H), 6.86 (ddd, J=9.0, 2.9, 1.2 Hz, 1H), 4.93 (q, J=9.1 Hz, 2H), 4.51 (s, 2H), 3.68-3.54 (m, 1H), 2.36-2.21 (m, 1H), 1.95-1.77 (m, 4H), 1.58-1.40 (m, 2H), 1.40-1.23 (m, 2H); MS (ESI⁺) m/z 504 (M+H)⁺.

Example 17: (1r,4r)-4-[2-(4-chloro-3-fluorophenoxy)acetamido]-N-{[6-(difluoromethoxy)pyridin-3-yl]methyl}cyclohexane-1-carboxamide (Compound 116)

The reaction and purification conditions described in Example 1C substituting (6-(difluoromethoxy)pyridin-3-yl)methanamine (ArkPharm) for (6-(trifluoromethyl)pyridin-3-yl)methanamine and the product of Example 8A for the product of Example 1B gave the title compound. ¹H NMR (501 MHz, DMSO-d₆) δ ppm 8.31 (t, J=5.9 Hz, 1H), 8.11 (dd, J=2.4, 0.8 Hz, 1H), 7.95 (d, J=8.1 Hz, 1H), 7.76 (dd, J=8.5, 2.5 Hz, 1H), 7.68 (t, J=73.0 Hz, 1H), 7.49 (t, J=8.9

Hz, 1H), 7.08-7.03 (m, 2H), 6.85 (ddd, J=9.0, 2.9, 1.2 Hz, 1H), 4.49 (s, 2H), 4.24 (d, J=5.9 Hz, 2H), 3.64-3.52 (m, 1H), 2.10 (tt, J=12.0, 3.4 Hz, 1H), 1.84-1.74 (m, 4H), 1.42 (qd, J=13.6, 12.8, 3.7 Hz, 2H), 1.32-1.21 (m, 2H); MS (ESI$^+$) m/z 486 (M+H)$^+$.

Example 18: (1r,4r)-4-[2-(4-chloro-3-fluorophenoxy)acetamido]-N-[(1,3-oxazol-2-yl)methyl]cyclohexane-1-carboxamide (Compound 117)

The reaction and purification conditions described in Example 1C substituting oxazol-2-ylmethanamine hydrochloride (JW-Pharmlab) for (6-(trifluoromethyl)pyridin-3-yl)methanamine and the product of Example 8A for the product of Example 1B gave the title compound. $^1$H NMR (400 MHz, DMSO-d$_6$) δ ppm 8.39 (t, J=5.8 Hz, 1H), 8.02 (d, J=0.9 Hz, 1H), 7.95 (d, J=8.1 Hz, 1H), 7.49 (t, J=8.9 Hz, 1H), 7.14 (d, J=0.8 Hz, 1H), 7.06 (dd, J=11.4, 2.8 Hz, 1H), 6.85 (ddd, J=9.0, 2.9, 1.2 Hz, 1H), 4.49 (s, 2H), 4.35 (d, J=5.8 Hz, 2H), 3.63-3.52 (m, 1H), 2.19-2.07 (m, 1H), 1.84-1.73 (m, 4H), 1.47-1.34 (m, 2H), 1.32-1.20 (m, 2H); MS (ESI$^+$) m/z 410 (M+H)$^+$.

Example 19: (1r,4r)-4-[2-(4-chloro-3-fluorophenoxy)acetamido]-N-[(1,3-oxazol-5-yl)methyl]cyclohexane-1-carboxamide (Compound 118)

The reaction and purification conditions described in Example 1C substituting oxazol-5-ylmethanamine hydrochloride (JW-Pharmlab) for (6-(trifluoromethyl)pyridin-3-yl)methanamine and the product of Example 8A for the product of Example 1B gave the title compound. $^1$H NMR (501 MHz, DMSO-d$_6$) δ ppm 8.28-8.25 (m, 2H), 7.94 (d, J=8.1 Hz, 1H), 7.49 (t, J=8.9 Hz, 1H), 7.06 (dd, J=11.4, 2.8 Hz, 1H), 6.98-6.94 (m, 1H), 6.85 (ddd, J=9.0, 2.9, 1.2 Hz, 1H), 4.49 (s, 2H), 4.31 (dd, J=5.7, 1.0 Hz, 2H), 3.61-3.53 (m, 1H), 2.13-2.04 (m, 1H), 1.84-1.71 (m, 4H), 1.47-1.36 (m, 2H), 1.30-1.19 (m, 2H); MS (ESI$^+$) m/z 410 (M+H)$^+$.

Example 20: (1r,4r)-4-[2-(4-chloro-3-fluorophenoxy)acetamido]-N-{[5-(trifluoromethyl)pyridin-2-yl]methyl}cyclohexane-1-carboxamide (Compound 119)

The reaction and purification conditions described in Example 1C substituting (5-(trifluoromethyl)pyridin-2-yl)methanamine hydrochloride (Pharmablock) for (6-(trifluoromethyl)pyridin-3-yl)methanamine and the product of Example 8A for the product of Example 1B gave the title compound. $^1$H NMR (400 MHz, DMSO-d$_6$) δ ppm 8.91-8.86 (m, 1H), 8.47 (t, J=6.0 Hz, 1H), 8.20-8.12 (m, 1H), 7.96 (d, J=8.1 Hz, 1H), 7.49 (t, J=8.9 Hz, 1H), 7.45 (d, J=8.3 Hz, 1H), 7.07 (dd, J=11.4, 2.9 Hz, 1H), 6.85 (ddd, J=9.0, 2.9, 1.2 Hz, 1H), 4.50 (s, 2H), 4.43 (d, J=5.9 Hz, 2H), 3.59 (dtt, J=11.6, 7.7, 3.9 Hz, 1H), 2.19 (tt, J=12.0, 3.3 Hz, 1H), 1.88-1.74 (m, 4H), 1.51-1.37 (m, 2H), 1.36-1.22 (m, 2H); MS (ESI$^+$) m/z 488 (M+H)$^+$.

Example 21: (1r,4r)-4-[2-(3,4-dichlorophenoxy)acetamido]-N-{[5-(difluoromethoxy)pyridin-2-yl]methyl}cyclohexane-1-carboxamide (Compound 120)

The reaction and purification conditions described in Example 1C substituting (5-(difluoromethoxy)pyridin-2-yl)methanamine (Enamine) for (6-(trifluoromethyl)pyridin-3-yl)methanamine gave the title compound. $^1$H NMR (501 MHz, DMSO-d$_6$) δ ppm 8.39 (d, J=2.9 Hz, 1H), 8.37 (t, J=6.0 Hz, 1H), 7.95 (d, J=8.1 Hz, 1H), 7.63 (dd, J=8.6, 2.8 Hz, 1H), 7.54 (d, J=8.9 Hz, 1H), 7.32-7.29 (m, 1H), 7.27 (t, J=73.5 Hz, 1H), 7.25 (d, J=2.9 Hz, 1H), 6.98 (dd, J=8.9, 2.9 Hz, 1H), 4.50 (s, 2H), 4.33 (d, J=5.9 Hz, 2H), 3.64-3.53 (m, 1H), 2.17 (tt, J=11.9, 3.0 Hz, 1H), 1.85-1.76 (m, 4H), 1.50-1.38 (m, 2H), 1.34-1.22 (m, 2H); MS (ESI$^+$) m/z 502 (M+H)$^+$.

Example 22: (1r,3r)-3-[2-(4-chloro-3-fluorophenoxy)acetamido]-N-[(5-chloropyridin-2-yl)methyl]cyclobutane-1-carboxamide (Compound 121)

Example 22A: methyl (1r,3r)-3-[2-(4-chloro-3-fluorophenoxy)acetamido]cyclobutane-1-carboxylate The reaction and purification conditions described in Example 1A substituting 2-(4-chloro-3-fluorophenoxy)acetic acid (CombiBlock) for 2-(3,4-dichlorophenoxy)acetic acid and methyl trans-3-amino-cyclobutanecarboxylate hydrochloride (Pharmablock) for methyl trans-4-aminocyclohexanecarboxylate gave the title compound. MS (ESI$^+$) m/z 316 (M+H)$^+$.

Example 22B: (1r,3r)-3-[2-(4-chloro-3-fluorophenoxy)acetamido]cyclobutane-1-carboxylic acid, 4 sodium chloride The product of Example 22A (0.7 g, 2.22 mmol) was dissolved in CH$_3$OH (10 mL). Aqueous NaOH solution (2.5 N, 3.55 mL) was added. After stirring at 40° C. for 1 hour, aqueous HCl solution (6.0 N, 2.22 mmol) was added in one portion. The resulting solution was concentrated under reduced pressure to give the title compound (1.2 g, 2.1 mmol, 95% yield). MS (ESI$^+$) m/z 302 (M+H)$^+$.

Example 22C: (1r,3r)-3-[2-(4-chloro-3-fluorophenoxy)acetamido]-N-[(5-chloropyridin-2-yl)methyl]cyclobutane-1-carboxamide The reaction and purification conditions described in Example 1C substituting (5-chloropyridin-2-yl)methanamine hydrochloride (Frontier) for (6-(trifluoromethyl)pyridin-3-yl)methanamine and the product of Example 22B for the product of Example 1B gave the title compound. $^1$H NMR (501 MHz, DMSO-d$_6$) δ ppm 8.54 (dd, J=2.5, 0.7 Hz, 1H), 8.40 (t, J=6.0 Hz, 1H), 8.36 (d, J=7.8 Hz, 1H), 7.89 (dd, J=8.4, 2.6 Hz, 1H), 7.50 (t, J=8.9 Hz, 1H), 7.29 (dd, J=8.4, 0.7 Hz, 1H), 7.08 (dd, J=11.4, 2.8 Hz, 1H), 6.86 (ddd, J=9.0, 2.9, 1.2 Hz, 1H), 4.49 (s, 2H), 4.48-4.39 (m, 1H), 4.36 (d, J=5.9 Hz, 2H), 3.01-2.94 (m, 1H), 2.39-2.32 (m, 2H), 2.27-2.19 (m, 2H); MS (APCI$^+$) m/z 426 (M+H)$^+$.

Example 23: (1r,3r)-3-[2-(4-chloro-3-fluorophenoxy)acetamido]-N-{[5-(trifluoromethyl)pyridin-2-yl]methyl}cyclobutane-1-carboxamide (Compound 122)

The reaction and purification conditions described in Example 1C substituting (5-(trifluoromethyl)pyridin-2-yl)methanamine hydrochloride (Pharmablock) for (6-(trifluoromethyl)pyridin-3-yl)methanamine and the product of Example 22B for the product of Example 1B gave the title compound. $^1$H NMR (501 MHz, DMSO-d$_6$) δ ppm 8.91-8.88 (m, 1H), 8.49 (t, J=6.0 Hz, 1H), 8.37 (d, J=7.8 Hz, 1H), 8.18 (ddd, J=8.2, 2.4, 0.8 Hz, 1H), 7.52-7.46 (m, 2H), 7.08 (dd, J=11.4, 2.9 Hz, 1H), 6.86 (ddd, J=9.0, 2.9, 1.2 Hz, 1H), 4.49 (s, 2H), 4.49-4.39 (m, 3H), 3.00 (ttd, J=9.4, 3.8, 1.1 Hz, 1H), 2.41-2.34 (m, 2H), 2.29-2.20 (m, 2H); MS (APCI*) m/z 460 (M+H)⁺.

Example 24: 2-(4-chloro-3-fluorophenoxy)-N-{(1r, 3r)-3-[3-(4-chlorophenyl)azetidine-1-carbonyl] cyclobutyl}acetamide (Compound 123)

The reaction and purification conditions described in Example 1C substituting 3-(4-chlorophenyl)azetidine (Enamine) for (6-(trifluoromethyl)pyridin-3-yl)methanamine and the product of Example 22B for the product of Example 1B gave the title compound. ¹H NMR (400 MHz, DMSO-d₆) δ ppm 8.40 (d, J=7.7 Hz, 1H), 7.50 (t, J=8.9 Hz, 1H), 7.44-7.36 (m, 4H), 7.08 (dd, J=11.4, 2.8 Hz, 1H), 6.86 (ddd, J=8.9, 2.9, 1.2 Hz, 1H), 4.50 (s, 2H), 4.46-4.33 (m, 2H), 4.31-4.23 (m, 1H), 4.00 (dd, J=8.2, 5.4 Hz, 1H), 3.89-3.79 (m, 2H), 3.03-2.95 (m, 1H), 2.44-2.32 (m, 2H), 2.27-2.16 (m, 2H); MS (APCI⁺) m/z 450 (M+H)⁺.

Example 25: 2-(4-chloro-3-fluorophenoxy)-N-{(1r, 4r)-4-[6-(4-chloro-3-fluorophenyl)-2,6-diazaspiro [3.3]heptane-2-carbonyl]cyclohexyl}acetamide (Compound 124)

Example 25A: tert-butyl 6-(4-chloro-3-fluorophenyl)-2,6-diazaspiro[3.3]heptane-2-carboxylate Tris(dibenzylideneacetone)dipalladium(0) (47.6 mg, 0.05 mmol), 2-(dicyclohexylphosphino)-2',4',6'-triisopropylbiphenyl (XPhos, 49.6 mg, 0.10 mmol), 4-chloro-3-fluoroiodobenzene (400 mg, 1.56 mmol, Aldrich), tert-butyl 2,6-diazaspiro[3.3]heptane-2-carboxylate, oxalic acid, (300 mg, 1.04 mmol, ArkPharm) and cesium carbonate (1017 mg, 3.12 mmol) were suspended in dioxane (12 mL). The reaction mixture was stirred at 98° C. for 18 hours and then cooled to ambient temperature. The crude reaction mixture was combined with 5 g of diatomaceous earth and concentrated under reduced pressure to a free flowing powder. The powder was directly purified by reversed-phase flash chromatography [Interchim® PuriFlash® C18XS 30 μm 175 g column, flow rate 100 mL/minute, 5-100% gradient of acetonitrile in buffer (0.025 M aqueous ammonium bicarbonate, adjusted to pH 10 with ammonium hydroxide)] to give the title compound (0.27 g, 0.83 mmol, 79% yield). ¹H NMR (400 MHz, DMSO-d₆) δ ppm 7.29 (t, J=8.6 Hz, 1H), 6.42 (dd, J=11.7, 2.6 Hz, 1H), 6.25 (ddd, J=8.8, 2.6, 0.8 Hz, 1H), 4.01 (s, 4H), 3.94 (s, 4H), 1.38 (s, 9H); MS (ESI⁺) m/z 327 (M+H)⁺.

Example 25B: 2-(4-chloro-3-fluorophenyl)-2,6-diazaspiro[3.3]heptane

Trifluoroacetic acid (1.0 mL, 13.0 mmol) was added to a solution of the product of Example 25A (0.27 g, 0.83 mmol) in dichloromethane (1.0 mL). After stirring at ambient temperature for 30 minutes, the reaction mixture was concentrated under reduced pressure. The residue was taken up in CH₃OH (3 mL), filtered through a glass microfiber frit and purified by preparative HPLC [YMC TriArt™ C18 Hybrid 5 μm column, 50×100 mm, flow rate 140 mL/minute, 5-100% gradient of acetonitrile in buffer (0.025 M aqueous ammonium bicarbonate, adjusted to pH 10 with ammonium hydroxide)] to give the title compound (0.16 g, 0.71 mmol, 85% yield). MS (APCI⁺) m/z 227 (M+H)⁺.

Example 25C: 2-(4-chloro-3-fluorophenoxy)-N-{ (1r,4r)-4-[6-(4-chloro-3-fluorophenyl)-2,6-diazaspiro [3.3]heptane-2-carbonyl]cyclohexyl}acetamide The reaction and purification conditions described in Example 1C substituting the product of Example 25B for (6-(trifluoromethyl)pyridin-3-yl)methanamine and the product of Example 8A for the product of Example 1B gave the title compound. ¹H NMR (501 MHz, DMSO-d₆) δ ppm 7.94 (d, J=8.0 Hz, 1H), 7.49 (t, J=8.9 Hz, 1H), 7.30 (t, J=8.6 Hz, 1H), 7.05 (dd, J=11.4, 2.8 Hz, 1H), 6.84 (ddd, J=8.9, 2.8, 1.1 Hz, 1H), 6.44 (dd, J=11.7, 2.5 Hz, 1H), 6.32-6.21 (m, 1H), 4.49 (s, 2H), 4.34 (s, 2H), 4.00 (s, 2H), 3.97 (s, 4H), 3.61-3.50 (m, 1H), 2.14-2.07 (m, 1H), 1.83-1.76 (m, 2H), 1.73-1.66 (m, 2H), 1.41-1.20 (m, 4H); MS (APCI⁺) m/z 538 (M+H)⁺.

Example 26: 2-(4-chloro-3-fluorophenoxy)-N-{(1r, 4r)-4-[4-(4-chlorophenyl)-3-oxopiperazine-1-carbonyl]cyclohexyl}acetamide (Compound 125)

The reaction and purification conditions described in Example 1C substituting 1-(4-chlorophenyl)piperazin-2-one (ArkPharm) for (6-(trifluoromethyl)pyridin-3-yl)methanamine and the product of Example 8A for the product of Example 1B gave the title compound. ¹H NMR (120° C., 501 MHz, DMSO-d₆) δ ppm 7.43-7.35 (m, 6H), 6.98 (dd, J=11.3, 2.8 Hz, 1H), 6.83 (ddd, J=9.0, 2.9, 1.2 Hz, 1H), 4.47 (s, 2H), 4.22 (s, 2H), 3.84 (dd, J=6.5, 4.3 Hz, 2H), 3.74 (dd, J=6.4, 4.4 Hz, 2H), 3.65-3.54 (m, 1H), 2.56 (tt, J=11.4, 3.5 Hz, 1H), 1.92-1.83 (m, 2H), 1.82-1.73 (m, 2H), 1.57-1.44 (m, 2H), 1.42-1.30 (m, 2H); MS (APCI⁺) m/z 522 (M+H)⁺.

Example 27: 2-(4-chloro-3-fluorophenoxy)-N-{(1r, 4r)-4-[4-(3-chlorophenyl)-3-oxopiperazine-1-carbonyl]cyclohexyl}acetamide (Compound 126)

The reaction and purification conditions described in Example 1C substituting 1-(3-chlorophenyl)piperazin-2-one (ArkPharm) for (6-(trifluoromethyl)pyridin-3-yl)methanamine, and the product of Example 8A for the product of Example 1B gave the title compound. ¹H NMR (120° C., 400 MHz, DMSO-d₆) δ ppm 7.46 (t, J=2.1 Hz, 1H), 7.43-7.35 (m, 3H), 7.33-7.29 (m, 1H), 7.29-7.25 (m, 1H), 6.98 (dd, J=11.3, 2.9 Hz, 1H), 6.83 (ddd, J=8.9, 2.9, 1.2 Hz, 1H), 4.47 (s, 2H), 4.22 (s, 2H), 3.87-3.82 (m, 2H), 3.79-3.73 (m, 2H), 3.66-3.55 (m, 1H), 2.57 (tt, J=11.5, 3.6 Hz, 1H), 1.93-1.84 (m, 2H), 1.83-1.73 (m, 2H), 1.56-1.44 (m, 2H), 1.42-1.30 (m, 2H); MS (APCI⁺) m/z 522 (M+H)⁺.

Example 28: 2-(4-chloro-3-fluorophenoxy)-N-{(1r, 4r)-4-[4-(4-chlorophenyl)piperazine-1-carbonyl] cyclohexyl}acetamide (Compound 127)

The reaction and purification conditions described in Example 1C substituting 1-(4-chlorophenyl)piperazine (Aldrich) for (6-(trifluoromethyl)pyridin-3-yl)methanamine and the product of Example 8A for the product of Example 1B gave the title compound. ¹H NMR (501 MHz, DMSO-d₆) δ ppm 7.97 (d, J=7.9 Hz, 1H), 7.49 (t, J=8.9 Hz, 1H), 7.28-7.23 (m, 2H), 7.06 (dd, J=11.4, 2.8 Hz, 1H), 7.00-6.94 (m, 2H), 6.84 (ddd, J=9.0, 3.0, 1.1 Hz, 1H), 4.50 (s, 2H), 3.67-3.54 (m, 5H), 3.20-3.05 (m, 4H), 2.58 (tt, J=10.9, 3.0 Hz, 1H), 1.84-1.77 (m, 2H), 1.76-1.68 (m, 2H), 1.48-1.29 (m, 4H); MS (APCI⁺) m/z 508 (M+H)⁺.

Example 29: 2-(4-chloro-3-fluorophenoxy)-N-{(1r,4r)-4-[4-(4-chlorophenyl)piperidine-1-carbonyl]cyclohexyl}acetamide (Compound 128)

The reaction and purification conditions described in Example 1C substituting 4-(4-chlorophenyl)piperidine (Aldrich) for (6-(trifluoromethyl)pyridin-3-yl)methanamine and the product of Example 8A for the product of Example 1B gave the title compound. $^1$H NMR (400 MHz, DMSO-$d_6$) δ ppm 7.96 (d, J=7.9 Hz, 1H), 7.49 (t, J=8.9 Hz, 1H), 7.37-7.32 (m, 2H), 7.31-7.25 (m, 2H), 7.06 (dd, J=11.4, 2.8 Hz, 1H), 6.84 (ddd, J=9.0, 2.8, 1.2 Hz, 1H), 4.55 (d, J=13.7 Hz, 1H), 4.50 (s, 2H), 4.05 (d, J=13.4 Hz, 1H), 3.64-3.51 (m, 1H), 3.10 (t, J=12.9 Hz, 1H), 2.79 (tt, J=12.2, 3.6 Hz, 1H), 2.61-2.52 (m, 2H), 1.87-1.65 (m, 6H), 1.59-1.26 (m, 6H); MS (APCI$^+$) m/z 507 (M+H)$^+$.

Example 30: 2-(4-chloro-3-fluorophenoxy)-N-{(1r,4r)-4-[3-(4-chlorophenyl)azetidine-1-carbonyl]cyclohexyl}acetamide (Compound 129)

The reaction and purification conditions described in Example 1C substituting 3-(4-chlorophenyl)azetidine, hydrochloride (Astatech) for (6-(trifluoromethyl)pyridin-3-yl)methanamine and the product of Example 8A for the product of Example 1B gave the title compound. $^1$H NMR (400 MHz, DMSO-$d_6$) δ ppm 7.94 (d, J=8.0 Hz, 1H), 7.49 (t, J=8.9 Hz, 1H), 7.44-7.37 (m, 4H), 7.05 (dd, J=11.4, 2.8 Hz, 1H), 6.84 (ddd, J=8.9, 2.8, 1.2 Hz, 1H), 4.56 (t, J=8.5 Hz, 1H), 4.49 (s, 2H), 4.23 (t, J=8.9 Hz, 1H), 4.15 (dd, J=8.5, 5.9 Hz, 1H), 3.89-3.80 (m, 1H), 3.80-3.74 (m, 1H), 3.62-3.50 (m, 1H), 2.21-2.11 (m, 1H), 1.85-1.68 (m, 4H), 1.46-1.18 (m, 4H); MS (APCI$^+$) m/z 479 (M+H)$^+$.

Example 31: 2-(4-chloro-3-fluorophenoxy)-N-{(1r,4r)-4-[3-(4-chlorophenyl)-3-hydroxyazetidine-1-carbonyl]cyclohexyl}acetamide (Compound 130)

The reaction and purification conditions described in Example 1C substituting 3-(4-chlorophenyl)azetidin-3-ol, trifluoroacetic acid (Enamine) for (6-(trifluoromethyl)pyridin-3-yl)methanamine and the product of Example 8A for the product of Example 1B gave the title compound. $^1$H NMR (400 MHz, DMSO-$d_6$) δ ppm 7.95 (d, J=8.0 Hz, 1H), 7.55-7.41 (m, 5H), 7.05 (dd, J=11.4, 2.9 Hz, 1H), 6.84 (ddd, J=9.0, 2.9, 1.2 Hz, 1H), 6.49 (s, 1H), 4.50 (s, 2H), 4.43-4.26 (m, 2H), 4.05-3.96 (m, 2H), 3.63-3.50 (m, 1H), 2.26-2.15 (m, 1H), 1.86-1.69 (m, 4H), 1.48-1.21 (m, 4H); MS (APCI$^+$) m/z 495 (M+H)$^+$.

Example 32: 2-(4-chloro-3-fluorophenoxy)-N-[(1r,4r)-4-(3-phenylazetidine-1-carbonyl)cyclohexyl]acetamide (Compound 131)

The reaction and purification conditions described in Example 1C substituting 3-phenylazetidine hydrochloride (ASW MedChem, Inc.) for (6-(trifluoromethyl)pyridin-3-yl)methanamine and the product of Example 8A for the product of Example 1B gave the title compound. $^1$H NMR (400 MHz, DMSO-$d_6$) δ ppm 7.94 (d, J=8.0 Hz, 1H), 7.49 (t, J=8.9 Hz, 1H), 7.40-7.33 (m, 4H), 7.30-7.23 (m, 1H), 7.06 (dd, J=11.4, 2.9 Hz, 1H), 6.84 (ddd, J=9.0, 2.9, 1.2 Hz, 1H), 4.57 (t, J=8.3 Hz, 1H), 4.50 (s, 2H), 4.29-4.20 (m, 1H), 4.20-4.11 (m, 1H), 3.89-3.75 (m, 2H), 3.63-3.50 (m, 1H), 2.18 (tt, J=11.6, 3.4 Hz, 1H), 1.84-1.69 (m, 4H), 1.46-1.22 (m, 4H); MS (APCI$^+$) m/z 445 (M+H)$^+$.

Example 33: N-[(1r,4r)-4-(5-chloro-1,3-dihydro-2H-isoindole-2-carbonyl)cyclohexyl]-2-(4-chloro-3-fluorophenoxy)acetamide (Compound 132)

The reaction and purification conditions described in Example 1C substituting 5-chloroisoindoline, hydrobromic acid (Milestone PharmTech) for (6-(trifluoromethyl)pyridin-3-yl)methanamine and the product of Example 8A for the product of Example 1B gave the title compound. $^1$H NMR (120° C., 400 MHz, DMSO-$d_6$) δ ppm 7.44-7.35 (m, 3H), 7.34-7.26 (m, 2H), 6.99 (dd, J=11.3, 2.8 Hz, 1H), 6.84 (ddd, J=8.8, 2.9, 1.1 Hz, 1H), 4.74 (br s, 4H), 4.47 (s, 2H), 3.68-3.55 (m, 1H), 2.49-2.41 (m, 1H), 1.95-1.78 (m, 4H), 1.58-1.44 (m, 2H), 1.42-1.28 (m, 2H); MS (ESI$^+$) m/z 465 (M+H)$^+$.

Example 34: 2-(4-chloro-3-fluorophenoxy)-N-{(1s,4s)-4-[3-(4-chlorophenyl)azetidine-1-carbonyl]cyclohexyl}acetamide (Compound 133)

Example 34A: methyl (1s,4s)-4-[2-(4-chloro-3-fluorophenoxy)acetamido]cyclohexane-1-carboxylate The reaction and purification conditions described in Example 1A substituting 2-(4-chloro-3-fluorophenoxy)acetic acid (CombiBlock) for 2-(3,4-dichlorophenoxy)acetic acid and methyl cis-4-aminocyclohexanecarboxylate hydrochloride (ArkPharm) for methyl trans-4-aminocyclohexanecarboxylate gave the title compound. $^1$H NMR (400 MHz, DMSO-$d_6$) δ ppm 7.95 (d, J=7.8 Hz, 1H), 7.48 (t, J=8.9 Hz, 1H), 7.05 (dd, J=11.4, 2.8 Hz, 1H), 6.83 (ddd, J=8.9, 2.9, 1.2 Hz, 1H), 4.51 (s, 2H), 3.81-3.68 (m, 1H), 3.62 (s, 3H), 2.55-2.51 (m, 1H), 1.92-1.81 (m, 2H), 1.64-1.53 (m, 4H), 1.53-1.42 (m, 2H); MS (ESI$^+$) m/z 344 (M+H)$^+$.

Example 34B: (1s,4s)-4-[2-(4-chloro-3-fluorophenoxy)acetamido]cyclohexane-1-carboxylic acid The product of Example 34A (0.26 g, 0.76 mmol) was dissolved in methanol (3 mL). Aqueous NaOH (2.5 M, 0.91 mL) was added. After stirring at 50° C. for 2 hours, the reaction mixture was filtered through a glass microfiber frit and directly purified by preparative HPLC [YMC TriArt™ C18 Hybrid 5 μm column, 50×100 mm, flow rate 140 mL/minute, 5-100% gradient of acetonitrile in buffer (0.1% trifluoroacetic acid)] to give the title compound (0.21 g, 0.64 mmol, 84% yield). $^1$H NMR (400 MHz, DMSO-$d_6$) δ ppm 12.12 (br s, 1H), 7.96 (d, J=7.7 Hz, 1H), 7.48 (t, J=8.9 Hz, 1H), 7.05 (dd, J=11.4, 2.9 Hz, 1H), 6.83 (ddd, J=9.0, 3.0, 1.2 Hz, 1H), 4.51 (s, 2H), 3.79-3.69 (m, 1H), 2.44-2.36 (m, 1H), 1.93-1.80 (m, 2H), 1.61-1.44 (m, 6H); MS (ESI$^+$) m/z 330 (M+H)$^+$.

Example 34C: 2-(4-chloro-3-fluorophenoxy)-N-{(1s,4s)-4-[3-(4-chlorophenyl)azetidine-1-carbonyl]cyclohexyl}acetamide The reaction and purification conditions described in Example 1C substituting 3-(4-chlorophenyl)azetidine (Enamine) for (6-(trifluoromethyl)pyridin-3-yl)methanamine and the product of Example 34B for the product of Example 1B gave the title compound. $^1$H NMR (400 MHz, DMSO-$d_6$) δ ppm 8.01 (d, J=7.4 Hz, 1H), 7.48 (t, J=8.9 Hz, 1H), 7.44-7.36 (m, 4H), 7.04 (dd, J=11.4, 2.9 Hz, 1H), 6.82 (ddd, J=9.0, 2.9, 1.2 Hz, 1H), 4.57-4.52 (m, 1H), 4.24 (t, J=8.9 Hz, 1H), 4.14 (dd, J=8.4, 5.9 Hz, 1H), 3.90-3.74 (m, 3H), 2.39-2.30 (m, 1H), 1.76-1.62 (m, 4H), 1.59-1.45 (m, 4H); MS (APCI$^+$) m/z 479 (M+H)$^+$.

Example 35: 2-(4-chloro-3-fluorophenoxy)-N-[(3R, 6S)-6-{3-[4-(trifluoromethyl)phenyl]azetidine-1-carbonyl}oxan-3-yl]acetamide (Compound 134)

Example 35A: tert-butyl ((3R,6S)-6-(3-(4-(trifluoromethyl)phenyl)azetidine-1-carbonyl)tetrahydro-2H-pyran-3-yl)carbamate To a mixture of (2S,5R)-5-((tert-butoxycarbonyl)amino)tetrahydro-2H-pyran-2-carboxylic acid (0.060 g, 0.25 mmol) and 3-(4-(trifluoromethyl)phenyl)azetidine hydrochloride (0.061 g, 0.26 mmol) in N,N-dimethylformamide (1.4 mL) was added triethylamine (0.14 mL, 0.98 mmol) followed by (1-[bis(dimethylamino)methylene]-1H-1,2,3-triazolo[4,5-b]pyridinium 3-oxid hexafluorophosphate) (HATU, 0.10 g, 0.27 mmol). This reaction mixture was allowed to stir at ambient temperature overnight, was diluted with N,N-dimethylformamide/water (1.5 mL, 3:1), filtered, and purified by preparative HPLC (Waters XBridge™ C18 5 μm OBD column, 30×100 mm, flow rate 40 mL/minute, 5-100% gradient of acetonitrile in 0.1% trifluoroacetic acid/water) to give the title compound as a trifluoroacetic acid salt (0.15 g, 0.28 mmol, 112% yield). MS (ESI$^+$) m/z 429 (M+H)$^+$.

Example 35B: ((2S,5R)-5-aminotetrahydro-2H-pyran-2-yl)(3-(4-(trifluoromethyl)phenyl)azetidin-1-yl)methanone To a solution of Example 35A (0.173 g, 0.404 mmol) in dichloromethane (0.42 mL) was added trifluoroacetic acid (0.22 mL, 2.8 mmol), and the resulting mixture was stirred at ambient temperature for 5 hours and was then concentrated to afford the title compound, which was carried forward without purification. MS (ESI$^+$) m/z 328 (M+H)$^+$.

Example 35C: 2-(4-chloro-3-fluorophenoxy)-N-[(3R,6S)-6-{3-[4-(trifluoromethyl)phenyl]azetidine-1-carbonyl}oxan-3-yl]acetamide (Compound 134)

The methodologies described in Example 35A substituting Example 35B for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. $^1$H NMR (400 MHz, DMSO-d$_6$) δ ppm 8.01 (dd, J=7.9, 2.4 Hz, 1H), 7.76-7.69 (m, 2H), 7.59 (d, J=8.1 Hz, 2H), 7.49 (t, J=8.9 Hz, 1H), 7.06 (dd, J=11.4, 2.9 Hz, 1H), 6.84 (dt, J=8.9, 1.8 Hz, 1H), 4.69 (td, J=9.0, 4.9 Hz, 1H), 4.52 (s, 2H), 4.36-4.22 (m, 2H), 4.04-3.71 (m, 5H), 3.14 (td, J=10.3, 1.4 Hz, 1H), 1.94-1.82 (m, 2H), 1.70-1.49 (m, 2H); MS (ESI$^+$) m/z 514 (M+H)$^+$.

Example 36: (2S,5R)-5-[2-(4-chloro-3-fluorophenoxy)acetamido]-N-{[4-(trifluoromethyl)-1H-imidazol-2-yl]methyl}oxane-2-carboxamide (Compound 135)

Example 36A: tert-butyl ((3R,6S)-6-(((4-(trifluoromethyl)-1H-imidazol-2-yl)methyl)carbamoyl)tetrahydro-2H-pyran-3-yl)carbamate The methodologies described in Example 35A substituting (4-(trifluoromethyl)-1H-imidazol-2-yl)methanamine dihydrochloride for 3-(4-(trifluoromethyl)phenyl)azetidine hydrochloride gave the title compound. $^1$H NMR (400 MHz, DMSO-d$_6$) δ ppm 8.15 (t, J=5.9 Hz, 1H), 7.62 (d, J=1.5 Hz, 1H), 6.81 (d, J=7.9 Hz, 1H), 4.36 (dd, J=15.6, 6.1 Hz, 1H), 4.27 (dd, J=15.6, 5.8 Hz, 1H), 3.90 (dd, J=10.7, 4.5 Hz, 1H), 3.75-3.67 (m, 1H), 3.05 (t, J=10.6 Hz, 1H), 1.96 (dt, J=9.4, 3.1 Hz, 1H), 1.93-1.86 (m, 1H), 1.51-1.39 (m, 2H), 1.38 (s, 9H); MS (ESI$^+$) m/z 392 (M+H)$^+$.

Example 36B: (2S,5R)-5-amino-N-((4-(trifluoromethyl)-1H-imidazol-2-yl)methyl)tetrahydro-2H-pyran-2-carboxamide The methodologies described in Example 35B substituting Example 36A for Example 35A gave the title compound. MS (ESI$^+$) m/z 292 (M+H)$^+$.

Example 36C: (2S,5R)-5-[2-(4-chloro-3-fluorophenoxy)acetamido]-N-{[4-(trifluoromethyl)-1H-imidazol-2-yl]methyl}oxane-2-carboxamide The methodologies described in Example 35A substituting Example 36B for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. $^1$H NMR (501 MHz, DMSO-d$_6$) δ ppm 12.40 (s, 1H), 8.19 (t, J=5.9 Hz, 1H), 8.03 (d, J=8.0 Hz, 1H), 7.63 (d, J=1.5 Hz, 1H), 7.49 (t, J=8.9 Hz, 1H), 7.07 (dd, J=11.3, 2.9 Hz, 1H), 6.85 (ddd, J=9.0, 3.0, 1.2 Hz, 1H), 4.53 (d, J=1.7 Hz, 2H), 4.37 (dd, J=15.5, 6.2 Hz, 1H), 4.28 (dd, J=15.6, 5.8 Hz, 1H), 3.91 (ddd, J=10.7, 4.8, 1.9 Hz, 1H), 3.85-3.74 (m, 2H), 3.19 (t, J=10.6 Hz, 1H), 2.01 (dq, J=13.2, 3.2 Hz, 1H), 1.95-1.87 (m, 1H), 1.60 (qd, J=12.5, 3.8 Hz, 1H), 1.54-1.43 (m, 1H); MS (ESI$^+$) m/z 479 (M+H)$^+$.

Example 37: (2S,5R)-5-[2-(4-chloro-3-fluorophenoxy)acetamido]-N-[(1,3-dimethyl-1H-pyrazol-5-yl)methyl]oxane-2-carboxamide (Compound 136)

Example 37A: tert-butyl ((3R,6S)-6-(((1,3-dimethyl-1H-pyrazol-5-yl)methyl)carbamoyl)tetrahydro-2H-pyran-3-yl)carbamate The methodologies described in Example 35A substituting (1,3-dimethyl-1H-pyrazol-5-yl)methanamine for 3-(4-(trifluoromethyl)phenyl)azetidine hydrochloride gave the title compound. MS (ESI$^+$) m/z 353 (M+H)$^+$.

Example 37B: (2S,5R)-5-amino-N-((1,3-dimethyl-1H-pyrazol-5-yl)methyl)tetrahydro-2H-pyran-2-carboxamide The methodologies described in Example 35B substituting Example 37A for Example 35A gave the title compound. MS (ESI$^+$) m/z 253 (M+H)$^+$.

Example 37C: (2S,5R)-5-[2-(4-chloro-3-fluorophenoxy)acetamido]-N-[(1,3-dimethyl-1H-pyrazol-5-yl)methyl]oxane-2-carboxamide The methodologies described in Example 35A substituting Example 37B for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. $^1$H NMR (501 MHz, DMSO-d$_6$) δ ppm 8.25 (t, J=6.0 Hz, 1H), 8.05 (d, J=8.0 Hz, 1H), 7.49 (t, J=8.9 Hz, 1H), 7.06 (dd, J=11.3, 2.8 Hz, 1H), 6.85 (ddd, J=8.9, 2.9, 1.2 Hz, 1H), 5.97 (s, 1H), 4.53 (d, J=1.7 Hz, 2H), 4.28 (d, J=6.1 Hz, 2H), 3.91 (ddd, J=10.7, 4.7, 1.9 Hz, 1H), 3.79 (td, J=11.4, 3.3 Hz, 2H), 3.74 (s, 3H), 3.18 (t, J=10.6 Hz, 1H), 2.13 (s, 3H), 2.01 (dt, J=13.3, 3.2 Hz, 1H), 1.96-1.88 (m, 1H), 1.61 (qd, J=12.7, 3.9 Hz, 1H), 1.52-1.40 (m, 1H); MS (ESI$^+$) m/z 439 (M+H)$^+$.

Example 38: (2S,5R)-5-[2-(4-chloro-3-fluorophenoxy)acetamido]-N-[2-(4-chlorophenoxy)ethyl]oxane-2-carboxamide (Compound 137)

Example 38A: tert-butyl ((3R,6S)-6-((2-(4-chlorophenoxy)ethyl)carbamoyl)tetrahydro-2H-pyran-3-yl)carbamate The methodologies described in Example 35A substituting 2-(4-chlorophenoxy)ethanamine hydrochloride for 3-(4-(trifluoromethyl)phenyl)azetidine hydrochloride and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. MS (ESI$^+$) m/z 399 (M+H)$^+$.

Example 38B: (2S,5R)-5-amino-N-(2-(4-chlorophenoxy)ethyl)tetrahydro-2H-pyran-2-carboxamide The methodologies described in Example 35B substituting Example 38A for Example 35A gave the title compound. MS (ESI$^+$) m/z 299 (M+H)$^+$.

Example 38C: (2S,5R)-5-[2-(4-chloro-3-fluorophenoxy)acetamido]-N-[2-(4-chlorophenoxy)ethyl]oxane-2-carboxamide The methodologies described in Example 35A substituting Example 38B for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. $^1$H NMR (400 MHz, DMSO-d$_6$) δ ppm 8.02 (d, J=8.0 Hz, 1H), 7.83 (t, J=5.8 Hz, 1H), 7.49 (t, J=8.9 Hz, 1H), 7.36-7.27 (m, 2H), 7.06 (dd, J=11.4, 2.8 Hz, 1H), 7.00-6.92 (m, 2H), 6.85 (ddd, J=8.8, 2.8, 1.2 Hz, 1H), 4.52 (d, J=1.1 Hz, 2H), 4.00 (t, J=6.0 Hz, 2H), 3.89 (ddd, J=10.6, 4.8, 1.9 Hz, 1H), 3.75 (ddd, J=16.7, 9.4, 3.2 Hz, 2H), 3.49-3.40 (m, 2H), 3.17 (t, J=10.6 Hz, 1H), 2.00 (dd, J=13.0, 3.1 Hz, 1H), 1.94-1.85 (m, 1H), 1.59 (qd, J=12.5, 3.9 Hz, 1H), 1.48-1.33 (m, 1H); MS (ESI$^+$) m/z 485 (M+H)$^+$.

Example 39: (2S,5R)-5-[2-(4-chloro-3-fluorophenoxy)acetamido]-N-[(7-chloroimidazo[1,2-a]pyridin-2-yl)methyl]oxane-2-carboxamide (Compound 138)

Example 39A: tert-butyl ((3R,6S)-6-(((7-chloroimidazo[1,2-a]pyridin-2-yl)methyl)carbamoyl)tetrahydro-2H-pyran-3-yl)carbamate The methodologies described in Example 35A substituting (7-chloroimidazo[1,2-a]pyridin-2-yl)methanamine hydrochloride for 3-(4-(trifluoromethyl)phenyl)azetidine hydrochloride and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. MS (ESI$^+$) m/z 409 (M+H)$^+$.

Example 39B: (2S,5R)-5-amino-N-((7-chloroimidazo[1,2-a]pyridin-2-yl)methyl)tetrahydro-2H-pyran-2-carboxamide The methodologies described in Example 35B substituting Example 39A for Example 35A gave the title compound. MS (ESI$^+$) m/z 309 (M+H)$^+$.

Example 39C: (2S,5R)-5-[2-(4-chloro-3-fluorophenoxy)acetamido]-N-[(7-chloroimidazo[1,2-a]pyridin-2-yl)methyl]oxane-2-carboxamide The methodologies described in Example 35A substituting Example 39B for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (501 MHz, DMSO-d$_6$) δ ppm 8.54 (dd, J=7.3, 0.8 Hz, 1H), 8.12 (t, J=6.0 Hz, 1H), 8.03 (d, J=8.0 Hz, 1H), 7.75 (d, J=0.8 Hz, 1H), 7.64 (dt, J=2.1, 0.8 Hz, 1H), 7.50 (t, J=8.9 Hz, 1H), 7.07 (dd, J=11.4, 2.8 Hz, 1H), 6.94 (dd, J=7.3, 2.1 Hz, 1H), 6.85 (ddd, J=9.0, 2.9, 1.2 Hz, 1H), 4.52 (d, J=1.7 Hz, 2H), 4.38 (d, J=5.8 Hz, 2H), 3.94-3.87 (m, 1H), 3.78 (dd, J=11.5, 2.6 Hz, 1H), 3.18 (t, J=10.6 Hz, 1H), 2.03 (dd, J=13.1, 3.1 Hz, 1H), 1.91 (d, J=12.5 Hz, 1H), 1.61 (qd, J=12.4, 3.8 Hz, 1H), 1.49 (qd, J=13.2, 3.7 Hz, 1H); MS (ESI$^+$) m/z 495 (M+H)$^+$.

Example 40: (2S,5R)-5-[2-(4-chloro-3-fluorophenoxy)acetamido]-N-{[2-(trifluoromethyl)pyrimidin-5-yl]methyl}oxane-2-carboxamide (Compound 139)

Example 40A: tert-butyl ((3R,6S)-6-(((2-(trifluoromethyl)pyrimidin-5-yl)methyl)carbamoyl)tetrahydro-2H-pyran-3-yl)carbamate The methodologies described in Example 35A substituting (2-(trifluoromethyl)pyrimidin-5-yl)methanamine for 3-(4-(trifluoromethyl)phenyl)azetidine hydrochloride and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. MS (ESI$^+$) m/z 305 (M-C(O)OC(CH$_3$)$_3$+H)$^+$.

Example 40B: (2S,5R)-5-amino-N-((2-(trifluoromethyl)pyrimidin-5-yl)methyl)tetrahydro-2H-pyran-2-carboxamide The methodologies described in Example 35B substituting Example 40A for Example 35A gave the title compound. MS (ESI$^+$) m/z 305 (M+H)$^+$.

Example 40C: (2S,5R)-5-[2-(4-chloro-3-fluorophenoxy)acetamido]-N-{[2-(trifluoromethyl)pyrimidin-5-yl]methyl}oxane-2-carboxamide The methodologies described in Example 35A substituting Example 40B for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (400 MHz, DMSO-$d_6$) δ ppm 8.93 (s, 2H), 8.50 (t, J=6.1 Hz, 1H), 8.04 (d, J=8.0 Hz, 1H), 7.49 (t, J=8.9 Hz, 1H), 7.07 (dd, J=11.4, 2.8 Hz, 1H), 6.85 (ddd, J=9.0, 2.8, 1.2 Hz, 1H), 4.52 (d, J=1.1 Hz, 2H), 4.47-4.34 (m, 2H), 3.91 (ddd, J=10.6, 4.7, 1.9 Hz, 1H), 3.80 (ddd, J=17.9, 10.9, 6.5 Hz, 2H), 3.19 (t, J=10.6 Hz, 1H), 2.06-1.96 (m, 1H), 1.90 (dd, J=11.0, 5.2 Hz, 1H), 1.60 (qd, J=12.4, 3.6 Hz, 1H), 1.53-1.39 (m, 1H); MS (ESI$^+$) m/z 491 (M+H)$^+$.

Example 41: (2S,5R)-5-[2-(4-chloro-3-fluorophenoxy)acetamido]-N-[(2-methoxypyrimidin-5-yl)methyl]oxane-2-carboxamide (Compound 140)

Example 41A: tert-butyl ((3R,6S)-6-(((2-methoxypyrimidin-5-yl)methyl)carbamoyl)tetrahydro-2H-pyran-3-yl)carbamate The methodologies described in Example 35A substituting (2-methoxypyrimidin-5-yl)methanamine for 3-(4-(trifluoromethyl)phenyl)azetidine hydrochloride and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. MS (ESI$^+$) m/z 367 (M+H)$^+$.

Example 41B: (2S,5R)-5-amino-N-((2-methoxypyrimidin-5-yl)methyl)tetrahydro-2H-pyran-2-carboxamide The methodologies described in Example 35B substituting Example 41A for Example 35A gave the title compound. MS (ESI$^+$) m/z 267 (M+H)$^+$.

Example 41C: (2S,5R)-5-[2-(4-chloro-3-fluorophenoxy)acetamido]-N-[(2-methoxypyrimidin-5-yl)methyl]oxane-2-carboxamide The methodologies described in Example 35A substituting Example 41B for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (400 MHz, DMSO-$d_6$) δ ppm 8.49 (s, 2H), 8.35 (t, J=6.1 Hz, 1H), 8.04 (d, J=7.9 Hz, 1H), 7.49 (t, J=8.9 Hz, 1H), 7.07 (dd, J=11.4, 2.9 Hz, 1H), 6.85 (ddd, J=8.9, 2.9, 1.2 Hz, 1H), 4.53 (d, J=1.1 Hz, 2H), 4.30-4.15 (m, 2H), 3.95-3.89 (m, 1H), 3.90 (s, 3H), 3.78 (ddd, J=11.4, 8.6, 3.3 Hz, 2H), 3.19 (t, J=10.6 Hz, 1H), 2.01 (dt, J=13.3, 3.2 Hz, 1H), 1.96-1.87 (m, 1H), 1.61 (qd, J=12.6, 3.8 Hz, 1H), 1.51-1.36 (m, 1H); MS (ESI$^+$) m/z 453 (M+H)$^+$.

Example 42: (2S,5R)-5-[2-(4-chloro-3-fluorophenoxy)acetamido]-N-[1-(4-chlorophenyl)cyclopropyl]oxane-2-carboxamide (Compound 141)

Example 42A: tert-butyl ((3R,6S)-6-((1-(4-chlorophenyl)cyclopropyl)carbamoyl)tetrahydro-2H-pyran-3-yl)carbamate The methodologies described in Example 35A substituting 1-(4-chlorophenyl)cyclopropanamine for 3-(4-(trifluoromethyl)phenyl)azetidine hydrochloride and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. MS (ESI$^+$) m/z 395 (M+H)$^+$.

Example 42B: (2S,5R)-5-amino-N-(1-(4-chlorophenyl)cyclopropyl)tetrahydro-2H-pyran-2-carboxamide The methodologies described in Example 35B substituting Example 42A for Example 35A gave the title compound. MS (ESI$^+$) m/z 295 (M+H)$^+$.

Example 42C: (2S,5R)-5-[2-(4-chloro-3-fluorophenoxy)acetamido]-N-[1-(4-chlorophenyl)cyclopropyl]oxane-2-carboxamide The methodologies described in Example 35A substituting Example 42B for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (501 MHz, DMSO-$d_6$) δ ppm 8.48 (s, 1H), 8.03 (d, J=8.0 Hz, 1H), 7.49 (t, J=8.9 Hz, 1H), 7.34-7.27 (m, 2H), 7.17-7.11 (m, 2H), 7.07 (dd, J=11.4, 2.9 Hz, 1H), 6.85 (ddd, J=8.9, 2.9, 1.2 Hz, 1H), 4.53 (d, J=1.9 Hz, 2H), 3.91 (ddd, J=10.7, 4.7, 1.9 Hz, 1H), 3.85-3.76 (m, 1H), 3.73 (dd, J=11.4, 2.4 Hz, 1H), 3.17 (t, J=10.6 Hz, 1H), 2.03-1.84 (m, 2H), 1.65-1.54 (m, 1H), 1.54-1.42 (m, 1H), 1.21-1.10 (m, 4H); MS (ESI$^+$) m/z 481 (M+H)$^+$.

Example 43: (2S,5R)-5-[2-(4-chloro-3-fluorophenoxy)acetamido]-N-[(5-chloro-1H-indol-2-yl)methyl]oxane-2-carboxamide (Compound 142)

Example 43A: tert-butyl ((3R,6S)-6-(((5-chloro-1H-indol-2-yl)methyl)carbamoyl)tetrahydro-2H-pyran-3-yl)carbamate The methodologies described in Example 35A substituting (5-chloro-1H-indol-2-yl)methanamine hydrochloride for 3-(4-(trifluoromethyl)phenyl)azetidine hydrochloride and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (501 MHz, DMSO-$d_6$) δ ppm 11.04 (s, 1H), 8.16 (s, 1H), 7.48 (d, J=2.0 Hz, 1H), 7.34 (d, J=8.5 Hz, 1H), 7.01 (dd, J=8.6, 2.1 Hz, 1H), 6.82 (s, 1H), 6.20 (s, 1H), 4.40 (dd, J=13.4, 6.0 Hz, 2H), 3.90 (m, 1H), 3.71 (d, J=9.2 Hz, 1H), 3.06 (d, J=10.6 Hz, 1H), 2.03 (m, 1H), 1.43 (m, 1H), 1.38 (s, 9H); MS (ESI$^+$) m/z 408 (M+H)$^+$.

Example 43B: (2S,5R)-5-amino-N-((5-chloro-1H-indol-2-yl)methyl)tetrahydro-2H-pyran-2-carboxamide The methodologies described in Example 35B substituting Example 43A for Example 35A gave the title compound. MS (ESI$^+$) m/z 308 (M+H)$^+$.

Example 43C: (2S,5R)-5-[2-(4-chloro-3-fluorophenoxy)acetamido]-N-[(5-chloro-1H-indol-2-yl)methyl]oxane-2-carboxamide The methodologies described in Example 35A substituting Example 43B for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 µm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (501 MHz, DMSO-d$_6$) δ ppm 11.05 (s, 1H), 8.20 (t, J=6.1 Hz, 1H), 8.03 (d, J=7.9 Hz, 1H), 7.53-7.46 (m, 2H), 7.37-7.31 (m, 1H), 7.07 (dd, J=11.4, 2.9 Hz, 1H), 7.01 (dd, J=8.6, 2.1 Hz, 1H), 6.88-6.82 (m, 1H), 6.21 (s, 1H), 4.52 (d, J=1.7 Hz, 2H), 4.44 (dd, J=15.4, 6.2 Hz, 1H), 4.38 (dd, J=15.5, 5.9 Hz, 1H), 3.90 (dd, J=10.2, 5.1 Hz, 1H), 3.79 (dd, J=11.5, 2.7 Hz, 2H), 3.18 (t, J=10.6 Hz, 1H), 2.04 (d, J=26.9 Hz, 1H), 1.91 (d, J=12.5 Hz, 1H), 1.60 (dd, J=12.2, 3.9 Hz, 1H), 1.53-1.45 (m, 1H); MS (ESI$^+$) m/z 494 (M+H)$^+$.

Example 44: 2-(4-chloro-3-fluorophenoxy)-N-{(3R,6S)-6-[3-(4-chlorophenyl)pyrrolidine-1-carbonyl]oxan-3-yl}acetamide (Compound 143)

Example 44A: tert-butyl ((3R,6S)-6-(3-(4-chlorophenyl)pyrrolidine-1-carbonyl)tetrahydro-2H-pyran-3-yl)carbamate The methodologies described in Example 35A substituting 3-(4-chlorophenyl)pyrrolidine hydrochloride for 3-(4-(trifluoromethyl)phenyl)azetidine hydrochloride and purifying by preparative HPLC [Waters XBridge™ C18 5 µm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. MS (ESI$^+$) m/z 409 (M+H)$^+$.

Example 44B: ((2S,5R)-5-aminotetrahydro-2H-pyran-2-yl)(3-(4-chlorophenyl)pyrrolidin-1-yl)methanone The methodologies described in Example 35B substituting Example 44A for Example 35A gave the title compound. MS (ESI$^+$) m/z 309 (M+H)$^+$.

Example 44C: 2-(4-chloro-3-fluorophenoxy)-N-{(3R,6S)-6-[3-(4-chlorophenyl)pyrrolidine-1-carbonyl]oxan-3-yl}acetamide The methodologies described in Example 35A substituting Example 44B for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 µm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (400 MHz, DMSO-d$_6$) δ ppm 8.01 (t, J=8.0 Hz, 1H), 7.49 (td, J=8.9, 4.8 Hz, 1H), 7.43-7.29 (m, 4H), 7.06 (ddd, J=11.5, 6.5, 2.8 Hz, 1H), 6.84 (dddd, J=9.0, 7.8, 2.9, 1.3 Hz, 1H), 4.52 (d, J=5.5 Hz, 2H), 4.00 (ddt, J=15.9, 10.0, 5.9 Hz, 2H), 3.87-3.72 (m, 1H), 3.24-3.10 (m, 2H), 2.29 (m, 1H), 2.19 (m, 1H), 2.07 (s, 1H), 2.03-1.84 (m, 3H), 1.75 (d, J=16.0 Hz, 3H), 1.71-1.52 (m, 1H); MS (ESI$^+$) m/z 495 (M+H)$^+$.

Example 45: 2-(4-chloro-3-fluorophenoxy)-N-{(3R,6S)-6-[3-(trifluoromethyl)-5,6-dihydro[1,2,4]triazolo[4,3-a]pyrazine-7(8H)-carbonyl]oxan-3-yl}acetamide (Compound 144)

Example 45A: tert-butyl ((3R,6S)-6-(3-(trifluoromethyl)-5,6,7,8-tetrahydro-[1,2,4]triazolo[4,3-a]pyrazine-7-carbonyl)tetrahydro-2H-pyran-3-yl)carbamate The methodologies described in Example 35A substituting 3-(trifluoromethyl)-5,6,7,8-tetrahydro-[1,2,4]triazolo[4,3-a]pyrazine hydrochloride for 3-(4-(trifluoromethyl)phenyl)azetidine hydrochloride and purifying by preparative HPLC [Waters XBridge™ C18 5 µm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. MS (ESI$^+$) m/z 420 (M+H)$^+$.

Example 45B: ((2S,5R)-5-aminotetrahydro-2H-pyran-2-yl)(3-(trifluoromethyl)-5,6-dihydro-[1,2,4]triazolo[4,3-a]pyrazin-7(8H)-yl)methanone The methodologies described in Example 35B substituting Example 45A for Example 35A gave the title compound. MS (ESI$^+$) m/z 320 (M+H)$^+$.

Example 45C: 2-(4-chloro-3-fluorophenoxy)-N-{(3R,6S)-6-[3-(trifluoromethyl)-5,6-dihydro[1,2,4]triazolo[4,3-a]pyrazine-7(8H)-carbonyl]oxan-3-yl}acetamide The methodologies described in Example 35A substituting Example 45B for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 µm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (501 MHz, DMSO-d$_6$) δ ppm 8.05 (d, J=7.8 Hz, 1H), 7.50 (t, J=8.9 Hz, 1H), 7.06 (dd, J=11.3, 2.8 Hz, 1H), 6.85 (ddd, J=9.0, 2.9, 1.2 Hz, 1H), 5.11-4.97 (m, 1H), 4.97-4.78 (m, 1H), 4.54 (d, J=0.9 Hz, 2H), 4.26 (q, J=13.0, 9.3 Hz, 1H), 4.20-4.09 (m, 1H), 4.08-3.94 (m, 1H), 3.85 (d, J=10.2 Hz, 1H), 3.75 (ddt, J=15.6, 11.0, 5.7 Hz, 1H), 3.32-3.22 (m, 1H), 2.07 (s, 1H), 1.94 (d, J=12.2 Hz, 1H), 1.78 (dd, J=8.7, 4.8 Hz, 1H), 1.73 (s, 2H), 1.60 (qd, J=12.1, 4.7 Hz, 1H); MS (ESI$^+$) m/z 506 (M+H)$^+$.

Example 46: (2S,5R)-5-[2-(4-chloro-3-fluorophenoxy)acetamido]-N-[4-(4-chloro-3-fluorophenyl)pyrimidin-2-yl]oxane-2-carboxamide (Compound 145)

4-(4-chloro-3-fluorophenyl)pyrimidin-2-amine

A Suzuki coupling between 4-bromopyridimidin-2-amine (1 equivalent) and 2-(4-chloro-3-fluorophenyl)-4,4,5,5-tetramethyl-1,3,2-dioxaborolane (3 equivalents), using 2 M sodium carbonate (3 equivalents) and tetrakis(triphenylphosphine) palladium(0) (0.1 equivalent) in heated tetrahydrofuran (90-100° C.) provides the title compound.

Example 46A: tert-butyl ((3R,6S)-6-((4-(4-chloro-3-fluorophenyl)pyrimidin-2-yl)carbamoyl)tetrahydro-2H-pyran-3-yl)carbamate The methodologies described in Example 35A substituting 4-(4-chloro-3-fluorophenyl)pyrimidin-2-amine for 3-(4-(trifluoromethyl)phenyl)azetidine hydrochloride and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (400 MHz, DMSO-$d_6$) δ ppm 9.97 (s, 1H), 8.79 (d, J=5.3 Hz, 1H), 8.26 (dd, J=10.8, 2.0 Hz, 1H), 8.12 (ddd, J=8.4, 2.1, 0.7 Hz, 1H), 7.88 (d, J=5.3 Hz, 1H), 7.80 (dd, J=8.5, 7.7 Hz, 1H), 6.84 (d, J=7.8 Hz, 1H), 4.04-3.92 (m, 2H), 3.12 (t, J=10.7 Hz, 1H), 2.05-1.97 (m, 1H), 1.94 (d, J=12.1 Hz, 1H), 1.67-1.56 (m, 1H), 1.55-1.39 (m, 2H), 1.39 (s, 9H); MS (ESI$^+$) m/z 451 (M+H)$^+$.

Example 46B: (2S,5R)-5-amino-N-(4-(4-chloro-3-fluorophenyl)pyrimidin-2-yl)tetrahydro-2H-pyran-2-carboxamide The methodologies described in Example 35B substituting Example 46A for Example 35A gave the title compound. MS (ESI$^+$) m/z 351 (M+H)$^+$.

Example 46C: (2S,5R)-5-[2-(4-chloro-3-fluorophenoxy)acetamido]-N-[4-(4-chloro-3-fluorophenyl)pyrimidin-2-yl]oxane-2-carboxamide The methodologies described in Example 35A substituting Example 46B for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (400 MHz, DMSO-$d_6$, diagnostic peaks) δ ppm 10.00 (s, 1H), 8.79 (d, J=5.3 Hz, 1H), 8.26 (d, J=10.9 Hz, 1H), 8.13 (d, J=7.9 Hz, 1H), 8.05 (s, 1H), 7.88 (d, J=5.3 Hz, 1H), 7.81 (d, J=7.8 Hz, 1H), 7.49 (d, J=9.0 Hz, 1H), 7.08 (dd, J=11.3, 2.9 Hz, 1H), 4.54 (s, 3H), 4.06 (m, 1H), 2.04 (m, 2H), 1.65 (m, 2H), 1.24 (m, 2H); MS (ESI$^+$) m/z 537 (M+H)$^+$.

Example 47: (2S,5R)-5-[2-(4-chloro-3-fluorophenoxy)acetamido]-N-[2-(4-chlorophenyl)ethyl]oxane-2-carboxamide (Compound 146)

Example 47A: tert-butyl ((3R,6S)-6-((4-chlorophenethyl)carbamoyl)tetrahydro-2H-pyran-3-yl)carbamate The methodologies described in Example 35A substituting 2-(4-chlorophenyl)ethanamine for 3-(4-(trifluoromethyl)phenyl)azetidine hydrochloride and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (501 MHz, DMSO-$d_6$) δ ppm 7.69 (t, J=5.9 Hz, 1H), 7.36-7.30 (m, 2H), 7.24-7.18 (m, 2H), 6.80 (d, J=7.8 Hz, 1H), 3.90-3.83 (m, 1H), 3.59 (dd, J=11.4, 2.4 Hz, 1H), 3.28 (dt, J=8.4, 6.8 Hz, 2H), 3.02 (t, J=10.6 Hz, 1H), 2.72 (t, J=7.3 Hz, 2H), 1.95-1.84 (m, 2H), 1.38 (s, 9H), 1.31 (tdd, J=12.8, 11.1, 3.2 Hz, 1H); MS (ESI$^+$) m/z 283 (M-C(O))C(CH$_3$)$_3$+H)$^+$.

Example 47B: (2S,5R)-5-amino-N-(4-chlorophenethyl)tetrahydro-2H-pyran-2-carboxamide The methodologies described in Example 35B substituting Example 47A for Example 35A gave the title compound. MS (ESI$^+$) m/z 283 (M+H)$^+$.

Example 47C: (2S,5R)-5-[2-(4-chloro-3-fluorophenoxy)acetamido]-N-[2-(4-chlorophenyl)ethyl]oxane-2-carboxamide The methodologies described in Example 35A substituting Example 47B for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (400 MHz, DMSO-$d_6$) δ ppm 8.02 (d, J=7.9 Hz, 1H), 7.74 (t, J=5.9 Hz, 1H), 7.49 (t, J=8.9 Hz, 1H), 7.37-7.29 (m, 2H), 7.25-7.18 (m, 2H), 7.07 (dd, J=11.4, 2.9 Hz, 1H), 6.85 (ddd, J=9.0, 2.8, 1.2 Hz, 1H), 4.52 (d, J=1.2 Hz, 2H), 3.88 (ddd, J=10.6, 4.8, 1.9 Hz, 1H), 3.77 (dtd, J=15.3, 8.2, 7.4, 4.3 Hz, 1H), 3.68 (dd, J=11.5, 2.4 Hz, 1H), 3.30 (q, J=6.8 Hz, 2H), 3.16 (t, J=10.6 Hz, 1H), 2.73 (t, J=7.3 Hz, 2H), 1.97 (dq, J=13.2, 3.3 Hz, 1H), 1.92-1.84 (m, 1H), 1.58 (qd, J=12.6, 3.9 Hz, 1H), 1.37 (tdd, J=13.1, 11.4, 3.8 Hz, 1H); MS (ESI$^+$) m/z 469 (M+H)$^+$.

Example 48: (1r,4r)-N-[(5-chloro-1H-benzimidazol-2-yl)methyl]-4-(2-{[6-(trifluoromethyl)pyridin-3-yl]oxy}acetamido)cyclohexane-1-carboxamide (Compound 147)

Example 48A: tert-butyl 2-((6-(trifluoromethyl)pyridin-3-yl)oxy)acetate

A mixture of 6-(trifluoromethyl)pyridin-3-ol (Combi-Blocks, 10 g, 60.1 mmol), potassium carbonate (16.61 g, 120 mmol) and tert-butyl bromoacetate (9.25 mL, 63.1 mmol) in N,N-dimethylformamide (100 mL) was warmed to 65° C. and was allowed to stir for 16 hours. The mixture was cooled to ambient temperature, quenched with saturated, aqueous NaHCO$_3$ (40 mL) and diluted with ethyl acetate (40 mL) and water (20 mL). The layers were separated, and the aqueous layer was extracted with ethyl acetate (3×15 mL). The combined organic layers were dried over anhydrous sodium sulfate and concentrated under reduced pressure. The resulting residue was purified via column chromatography (SiO$_2$, 1$_5$-2$_5$% ethyl acetate/heptanes) to give the title compound (16.2 g, 58.4 mmol, 97% yield). MS (ESI$^+$) m/z 278 (M+H)$^+$.

Example 48B:
2-((6-(trifluoromethyl)pyridin-3-yl)oxy)acetic acid

To a solution of the product of Example 48A (16.2 g, 58.4 mmol) in dichloromethane (100 mL) at ambient temperature was added trifluoroacetic acid (45.0 mL, 584 mmol). This mixture was allowed to stir at ambient temperature for 4 hours and then concentrated under reduced pressure and azeotroped with toluene to give solids which were precipitated from ethyl acetate/heptane to give the title compound (12.25 g, 55.4 mmol, 95% yield). MS (DCI) m/z 239 (M+NH$_4$)$^+$.

Example 48C: tert-butyl ((1r,4r)-4-(((5-chloro-1H-benzo[d]imidazol-2-yl)methyl)carbamoyl)cyclohexyl)carbamate trans-4-((tert-Butoxycarbonyl)amino)cyclohexanecarboxylic acid (193 mg, 0.79 mmol, Ark Pharm), (5-chloro-1H-benzo[d]imidazol-2-yl)methanamine (120 mg, 0.66 mmol, ChemBridge) and trimethylamine (0.368 mL, 2.64 mmol) were combined with N,N-dimethylformamide (2 mL) and stirred at ambient temperature. 1-[Bis(dimethylamino)methylene]-1H-1,2,3-triazolo[4,5-b]pyridinium 3-oxid hexafluorophosphate (HATU, 301 mg, 0.79 mmol) was added in one portion. After stirring for 1 hour, water (0.2 mL) was added. The resulting solution was filtered through a glass microfiber frit and purified by preparative HPLC [YMC TriArt™ C18 Hybrid 5 μm column, 50×100 mm, flow rate 140 mL/minute, 5-100% gradient of acetonitrile in buffer (0.025 M aqueous ammonium bicarbonate, adjusted to pH 10 with ammonium hydroxide)] to give the title compound (182 mg, 0.45 mmol, 68% yield). MS (ESI$^+$) m/z 407 (M+H)$^+$.

Example 48D: (1r,4r)-N-[(5-chloro-1H-benzimidazol-2-yl)methyl]-4-(2-{[6-(trifluoromethyl)pyridin-3-yl]oxy}acetamido)cyclohexane-1-carboxamide Trifluoroacetic acid (0.2 mL) was added to a dichloromethane (0.3 mL) solution of the product of Example 48C (40 mg, 0.10 mmol). The resulting reaction mixture was stirred at ambient temperature for 30 minutes and then concentrated under reduced pressure. To the resulting residue was added N,N-dimethylformamide (1.5 mL), triethylamine (0.082 mL), the product of Example 48B (32.6 mg, 0.15 mmol) and 1-[bis(dimethylamino)methylene]-1H-1,2,3-triazolo[4,5-b]pyridinium 3-oxid hexafluorophosphate (HATU, 56.1 mg, 0.5 mmol) in sequential order. The mixture was stirred at ambient temperature for 1 hour and then water (0.5 mL) was added. The resulting solution was filtered through a glass microfiber frit and purified by preparative HPLC [YMC TriArt™ C18 Hybrid 5 μm column, 50×100 mm, flow rate 140 mL/minute, 5-100% gradient of acetonitrile in buffer (0.025 M aqueous ammonium bicarbonate, adjusted to pH 10 with ammonium hydroxide)] to give the title compound (16 mg, 0.03 mmol, 32% yield). $^1$H NMR (400 MHz, DMSO-d$_6$) δ ppm 8.43 (d, J=2.8 Hz, 1H), 8.37 (t, J=5.6 Hz, 1H), 8.02 (d, J=8.0 Hz, 1H), 7.82 (d, J=8.8 Hz, 1H), 7.54-7.49 (m, 2H), 7.46 (d, J=8.5 Hz, 1H), 7.12 (dd, J=8.6, 2.1 Hz, 1H), 4.63 (s, 2H), 4.41 (d, J=5.6 Hz, 2H), 3.60-3.52 (m, 1H), 2.14 (tt, J=12.0, 3.3 Hz, 1H), 1.87-1.73 (m, 4H), 1.40 (qd, J=13.2, 3.4 Hz, 2H), 1.24 (qd, J=13.0, 12.5, 3.7 Hz, 2H); MS (APCI$^+$) m/z 510 (M+H)$^+$.

Example 49: (1r,4r)-N-[(5-chloro-1H-benzimidazol-2-yl)methyl]-4-{2-[(2,2-difluoro-2H-1,3-benzodioxol-5-yl)oxy]acetamido}cyclohexane-1-carboxamide (Compound 148)

Example 49A: 2-((2,2-difluorobenzo[d][1,3]dioxol-5-yl)oxy)acetic acid

The reaction and purification conditions described in Examples 48A and 48B, substituting 2,2-difluorobenzo[d][1,3]dioxol-5-ol (AstaTech) for 6-(trifluoromethyl)pyridin-3-ol gave the title compound. $^1$H NMR (400 MHz, DMSO-d$_6$) δ ppm 13.05 (s, 1H), 7.30 (d, J=8.8 Hz, 1H), 7.14 (d, J=2.6 Hz, 1H), 6.73 (dd, J=8.8, 2.6 Hz, 1H), 4.70 (s, 2H).

Example 49B: (1r,4r)-N-[(5-chloro-1H-benzimidazol-2-yl)methyl]-4-{2-[(2,2-difluoro-2H-1,3-benzodioxol-5-yl)oxy]acetamido}cyclohexane-1-carboxamide The reaction and purification conditions described in Example 48D substituting the product of Example 49A for the product of Example 48B gave the title compound. $^1$H NMR (400 MHz, DMSO-d$_6$) δ ppm 12.34 (br s, 1H), 8.42 (t, J=5.7 Hz, 1H), 7.93 (d, J=8.1 Hz, 1H), 7.57-7.53 (m, 1H), 7.50 (d, J=8.5 Hz, 1H), 7.32 (d, J=8.9 Hz, 1H), 7.17 (dd, J=8.5, 2.1 Hz, 1H), 7.13 (d, J=2.6 Hz, 1H), 6.77 (dd, J=8.9, 2.6 Hz, 1H), 4.51-4.40 (m, 4H), 3.65-3.55 (m, 1H), 2.18 (tt, J=12.0, 3.3 Hz, 1H), 1.89-1.76 (m, 4H), 1.50-1.37 (m, 2H), 1.34-1.23 (m, 2H); MS (ESI$^+$) m/z 521 (M+H)$^+$.

Example 50: (1r,4r)-N-[(5-chloro-1H-benzimidazol-2-yl)methyl]-4-[2-(3,4-difluorophenoxy)acetamido]cyclohexane-1-carboxamide (Compound 149)

The reaction and purification conditions described in Example 48D substituting 2-(3,4-difluorophenoxy)acetic acid (Combi-Blocks) for the product of Example 48B gave the title compound. $^1$H NMR (400 MHz, DMSO-d$_6$) δ ppm 8.41 (t, J=5.7 Hz, 1H), 7.93 (d, J=8.1 Hz, 1H), 7.54 (d, J=2.1 Hz, 1H), 7.50 (d, J=8.5 Hz, 1H), 7.41-7.32 (m, 1H), 7.16 (dd, J=8.5, 2.1 Hz, 1H), 7.08 (ddd, J=12.6, 6.7, 3.0 Hz, 1H), 6.82-6.77 (m, 1H), 4.47-4.44 (m, 4H), 3.63-3.53 (m, 1H), 2.17 (tt, J=11.9, 3.4 Hz, 1H), 1.89-1.75 (m, 4H), 1.44 (qd, J=13.8, 13.3, 3.5 Hz, 2H), 1.28 (qd, J=12.9, 12.3, 3.7 Hz, 2H); MS (ESI$^+$) m/z 477 (M+H)$^+$.

Example 51: (1r,4r)-N-[(5-chloro-1H-benzimidazol-2-yl)methyl]-4-[2-(4-chloro-3-fluorophenoxy)acetamido]cyclohexane-1-carboxamide (Compound 150)

The title compound was prepared using the methodologies described above. $^1$H NMR (400 MHz, DMSO-d$_6$) δ ppm 12.27 (br s, 1H), 8.38 (t, J=5.7 Hz, 1H), 7.91 (d, J=8.1 Hz, 1H), 7.52-7.42 (m, 3H), 7.13 (dd, J=8.5, 2.0 Hz, 1H), 7.03 (dd, J=11.4, 2.9 Hz, 1H), 6.81 (ddd, J=9.0, 2.9, 1.2 Hz, 1H), 4.45 (s, 2H), 4.42 (d, J=5.6 Hz, 2H), 3.62-3.49 (m, 1H), 2.14 (tt, J=12.0, 3.3 Hz, 1H), 1.85-1.72 (m, 4H), 1.48-1.33 (m, 2H), 1.31-1.18 (m, 2H); MS (APCI⁺) m/z 493 (M+H)⁺.

Example 52: (2S,5R)-5-[2-(4-chloro-3-fluorophenoxy)acetamido]-N-[5-(trifluoromethyl)pyrazin-2-yl]oxane-2-carboxamide (Compound 151)

Example 52A: tert-butyl ((3R,6S)-6-((5-(trifluoromethyl)pyrazin-2-yl)carbamoyl)tetrahydro-2H-pyran-3-yl)carbamate The methodologies described in Example 35A substituting 5-(trifluoromethyl)pyrazin-2-amine for 3-(4-(trifluoromethyl)phenyl)azetidine hydrochloride and purifying by preparative HPLC [Waters XBridge™ C18 5 µm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. MS (ESI⁺) m/z 391 (M+H)⁺.

Example 52B: (2S,5R)-5-amino-N-(5-(trifluoromethyl)pyrazin-2-yl)tetrahydro-2H-pyran-2-carboxamide The methodologies described in Example 35B substituting Example 52A for Example 35A gave the title compound. MS (ESI⁺) m/z 291 (M+H)⁺.

Example 52C: (2S,5R)-5-[2-(4-chloro-3-fluorophenoxy)acetamido]-N-[5-(trifluoromethyl)pyrazin-2-yl]oxane-2-carboxamide The methodologies described in Example 35A substituting Example 52B for 3-(4-(trifluoromethyl)phenyl)azetidine hydrochloride and substituting 2-(4-chloro-3-fluoro-phenoxy)acetic acid for (2S,5R)-5-((tert-butoxycarbonyl)amino)tetrahydro-2H-pyran-2-carboxylic acid gave the title compound. ¹H NMR (400 MHz, DMSO-d₆) δ ppm 10.69 (s, 1H), 9.41 (d, J=1.5 Hz, 1H), 8.94 (dd, J=1.4, 0.7 Hz, 1H), 8.06 (d, J=8.1 Hz, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.54 (s, 2H), 4.14 4.06 (m, 1H), 3.99-3.90 (m, 1H), 3.86 (d, J=10.9 Hz, 1H), 3.25 (t, J=10.5 Hz, 1H), 2.03 (d, J=12.2 Hz, 1H), 1.96 (s, 1H), 1.75-1.56 (m, 2H); MS (ESI⁺) m/z 477 (M+H)⁺.

Example 53: (1r,4r)-4-[2-(3,4-dichlorophenoxy)acetamido]-N-[(5,6-difluoro-1H-benzimidazol-2-yl)methyl]cyclohexane-1-carboxamide (Compound 152)

The title compound was prepared using the methodologies described above. ¹H NMR (400 MHz, DMSO-d₆) δ ppm 12.25 (s, 1H), 8.37 (t, J=5.7 Hz, 1H), 7.92 (d, J=8.2 Hz, 1H), 7.54-7.45 (m, 3H), 7.21 (d, J=2.9 Hz, 1H), 6.94 (dd, J=8.9, 2.9 Hz, 1H), 4.46 (s, 2H), 4.40 (d, J=5.6 Hz, 2H), 3.63-3.50 (m, 1H), 2.17-2.09 (m, 1H), 1.85-1.71 (m, 4H), 1.46-1.33 (m, 2H), 1.31-1.16 (m, 2H); MS (APCI⁺) m/z 511 (M+H)⁺.

Example 54: (1r,4r)-4-[2-(4-chloro-3-fluorophenoxy)acetamido]-N-[(5,6-difluoro-1H-benzimidazol-2-yl)methyl]cyclohexane-1-carboxamide (Compound 153)

The title compound was prepared using the methodologies described above. ¹H NMR (400 MHz, DMSO-d₆) δ ppm 12.26 (s, 1H), 8.40 (t, J=5.7 Hz, 1H), 7.95 (d, J=8.1 Hz, 1H), 7.56-7.50 (m, 2H), 7.49 (t, J=8.9 Hz, 1H), 7.06 (dd, J=11.4, 2.8 Hz, 1H), 6.85 (ddd, J=9.0, 2.9, 1.2 Hz, 1H), 4.49 (s, 2H), 4.44 (d, J=5.6 Hz, 2H), 3.65-3.51 (m, 1H), 2.17 (tt, J=12.0, 3.3 Hz, 1H), 1.88-1.76 (m, 4H), 1.51-1.37 (m, 2H), 1.34-1.21 (m, 2H); MS (APCI⁺) m/z 495 (M+H)⁺.

Example 55: (1r,4r)-N-[(5,6-difluoro-1H-benzimidazol-2-yl)methyl]-4-[2-(3,4-difluorophenoxy)acetamido]cyclohexane-1-carboxamide (Compound 154)

The title compound was prepared using the methodologies described above. ¹H NMR (501 MHz, DMSO-d₆) δ ppm 12.33 (s, 1H), 8.41 (t, J=5.7 Hz, 1H), 7.93 (d, J=8.1 Hz, 1H), 7.56-7.50 (m, 2H), 7.36 (dt, J=10.7, 9.3 Hz, 1H), 7.08 (ddd, J=12.6, 6.7, 3.0 Hz, 1H), 6.84-6.77 (m, 1H), 4.46 (s, 2H), 4.44 (d, J=5.7 Hz, 2H), 3.59 (tdt, J=11.7, 7.9, 3.9 Hz, 1H), 2.17 (tt, J=12.0, 3.3 Hz, 1H), 1.86-1.77 (m, 4H), 1.43 (qd, J=14.2, 13.6, 3.7 Hz, 2H), 1.34-1.23 (m, 2H); MS (APCI⁺) m/z 479 (M+H)⁺.

Example 56: (1r,4r)-4-[2-(4-chlorophenoxy)acetamido]-N-[(5,6-difluoro-1H-benzimidazol-2-yl)methyl]cyclohexane-1-carboxamide (Compound 155)

The title compound was prepared using the methodologies described above. ¹H NMR (400 MHz, DMSO-d₆) δ ppm 12.32 (s, 1H), 8.40 (t, J=5.7 Hz, 1H), 7.92 (d, J=8.1 Hz, 1H), 7.57-7.49 (m, 2H), 7.37-7.30 (m, 2H), 7.02-6.94 (m, 2H), 4.45-4.42 (m, 4H), 3.64-3.53 (m, 1H), 2.21-2.11 (m, 1H), 1.88-1.76 (m, 4H), 1.50-1.36 (m, 2H), 1.34-1.20 (m, 2H); MS (APCI⁺) m/z 477 (M+H)⁺.

Example 57: (2S,5R)-5-[2-(4-chloro-3-fluorophenoxy)acetamido]-N-[(5,6-difluoro-1H-benzimidazol-2-yl)methyl]oxane-2-carboxamide (Compound 156)

Example 57A: tert-butyl ((3R,6S)-6-(((5,6-difluoro-1H-benzo[d]imidazol-2-yl)methyl)carbamoyl)tetrahydro-2H-pyran-3-yl)carbamate The methodologies described in Example 35A substituting (5,6-difluoro-1H-benzo[d]imidazol-2-yl)methanamine for 3-(4-(trifluoromethyl)phenyl)azetidine hydrochloride gave the title compound. MS (ESI⁺) m/z 411 (M+H)⁺.

Example 57B: (2S,5R)-5-amino-N-((5,6-difluoro-1H-benzo[d]imidazol-2-yl)methyl)tetrahydro-2H-pyran-2-carboxamide The methodologies described in Example 35B substituting Example 57A for Example 35A gave the title compound. MS (ESI⁺) m/z 311 (M+H)⁺.

Example 57C: (2S,5R)-5-[2-(4-chloro-3-fluorophenoxy)acetamido]-N-[(5,6-difluoro-1H-benzimidazol-2-yl)methyl]oxane-2-carboxamide The methodologies described in Example 35A substituting Example 57B for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. ¹H NMR (501 MHz, DMSO-d₆) δ ppm 8.30 (s, 1H), 8.04 (d, J=8.3 Hz, 1H), 7.57-7.53 (m, 2H), 7.50 (t, J=8.9 Hz, 1H), 7.10-7.04 (m, 1H), 6.85 (d, J=10.4 Hz, 1H), 4.53 (d, J=1.6 Hz, 2H), 4.52-4.40 (m, 2H), 3.91 (m, 1H), 3.81 (m, 1H), 2.03 (d, J=12.6 Hz, 1H), 1.91 (m, 1H), 1.56 (dd, J=55.0, 13.4 Hz, 2H), 1.23 (d, J=6.9 Hz, 1H); MS (ESI$^+$) m/z 497 (M+H)$^+$.

Example 58: (2S,5R)-5-[2-(4-chloro-3-fluorophenoxy)acetamido]-N-{[4-(trifluoromethoxy)phenyl]methyl}oxane-2-carboxamide (Compound 157)

Example 58A: tert-butyl ((3R,6S)-6-((4-(trifluoromethoxy)benzyl)carbamoyl)tetrahydro-2H-pyran-3-yl)carbamate The methodologies described in Example 35A substituting (4-(trifluoromethoxy)phenyl)methanamine for 3-(4-(trifluoromethyl)phenyl)azetidine hydrochloride gave the title compound. MS (ESI$^+$) m/z 419 (M+H)$^+$.

Example 58B: (2S,5R)-5-amino-N-(4-(trifluoromethoxy)benzyl)tetrahydro-2H-pyran-2-carboxamide The methodologies described in Example 35B substituting Example 58A for Example 35A gave the title compound. MS (ESI$^+$) m/z 319 (M+H)$^+$.

Example 58C: (2S,5R)-5-[2-(4-chloro-3-fluorophenoxy)acetamido]-N-{[4-(trifluoromethoxy)phenyl]methyl}oxane-2-carboxamide The methodologies described in Example 35A substituting Example 58B for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. $^1$H NMR (501 MHz, DMSO-d$_6$) δ ppm 8.34 (t, J=6.3 Hz, 1H), 8.03 (d, J=8.0 Hz, 1H), 7.49 (t, J=8.9 Hz, 1H), 7.39-7.33 (m, 2H), 7.33-7.27 (m, 2H), 7.07 (dd, J=11.3, 2.8 Hz, 1H), 6.85 (ddd, J=9.0, 2.9, 1.2 Hz, 1H), 6.52 (s, 1H), 4.52 (d, J=1.7 Hz, 2H), 4.34-4.23 (m, 1H), 3.90 (dd, J=10.7, 4.0 Hz, 1H), 3.78 (dd, J=11.4, 2.4 Hz, 1H), 3.18 (t, J=10.6 Hz, 1H), 2.02 (dd, J=13.2, 3.1 Hz, 1H), 1.91 (d, J=12.6 Hz, 1H), 1.60 (qd, J=12.6, 3.9 Hz, 1H), 1.52-1.40 (m, 1H); MS (ESI$^+$) m/z 505 (M+H)$^+$.

Example 59: (2S,5R)-5-[2-(4-chloro-3-fluorophenoxy)acetamido]-N-{[4-(trifluoromethyl)phenyl]methyl}oxane-2-carboxamide (Compound 158)

Example 59A: tert-butyl ((3R,6S)-6-((4-(trifluoromethyl)benzyl)carbamoyl)tetrahydro-2H-pyran-3-yl)carbamate The methodologies described in Example 35A substituting (4-(trifluoromethyl)phenyl)methanamine hydrochloride for 3-(4-(trifluoromethyl)phenyl)azetidine hydrochloride gave the title compound. MS (ESI$^+$) m/z 403 (M+H)$^+$.

Example 59B: (2S,5R)-5-amino-N-(4-(trifluoromethyl)benzyl)tetrahydro-2H-pyran-2-carboxamide The methodologies described in Example 35B substituting Example 59A for Example 35A gave the title compound. MS (ESI$^+$) m/z 303 (M+H)$^+$.

Example 59C: (2S,5R)-5-[2-(4-chloro-3-fluorophenoxy)acetamido]-N-{[4-(trifluoromethyl)phenyl]methyl}oxane-2-carboxamide The methodologies described in Example 35A substituting Example 59B for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. $^1$H NMR (501 MHz, DMSO-d$_6$) δ ppm 8.41 (t, J=6.3 Hz, 1H), 8.04 (d, J=8.1 Hz, 1H), 7.67 (d, J=8.1 Hz, 2H), 7.50 (t, J=8.9 Hz, 1H), 7.45 (d, J=8.0 Hz, 2H), 7.07 (dd, J=11.4, 2.9 Hz, 1H), 6.85 (ddd, J=9.1, 2.8, 1.2 Hz, 1H), 4.52 (d, J=1.7 Hz, 2H), 4.35 (d, J=6.5 Hz, 2H), 3.94-3.88 (m, 1H), 3.79 (dd, J=11.4, 2.5 Hz, 1H), 3.19 (t, J=10.7 Hz, 1H), 2.02 (d, J=12.8 Hz, 1H), 1.90 (s, 1H), 1.67-1.52 (m, 1H), 1.52-1.37 (m, 1H); MS (ESI$^+$) m/z 488 (M+H)$^+$.

Example 60: (2R,5S)-5-[2-(4-chloro-3-fluorophenoxy)acetamido]-N-{[5-(trifluoromethyl)pyridin-2-yl]methyl}oxane-2-carboxamide (Compound 159)

Example 60A: (R)-(2-((tert-butoxycarbonyl)amino)-3-methoxy-3-oxopropyl)zinc(II) iodide A mixture of zinc (20.9 g, 319 mmol) and 12 (1.08 g, 4.25 mmol) was heated with a heat gun under vacuum for 10 minutes, and then reaction vessel was filled with argon. Then a solution of (R)-methyl 2-((tert-butoxycarbonyl)amino)-3-iodopropanoate (35 g, 106 mmol) in N,N-dimethylformamide (70 mL) was added at 0° C., and the reaction mixture was stirred at 25° C. for 2 hours. The mixture was filtered and used in the next step directly.

Example 60B: (S)-methyl 2-((tert-butoxycarbonyl)amino)hex-5-enoate

To a mixture of copper(I) bromide (3.05 g, 21.3 mmol) in N,N-dimethylformamide (70 mL) was added 3-bromoprop-1-ene (19.3 g, 160 mmol) at 20° C., followed by Example 60A (42 g, 106 mmol) at −15° C. under argon. The reaction mixture was stirred at −15-20° C. for 16 hours, and was diluted with ethyl acetate (200 mL) and 1 M Na$_2$S$_2$O$_3$ (200 mL). The organic layer was washed with water (200 mL) and brine (200 mL), dried over Na$_2$SO$_4$, and concentrated. The residue was purified by column chromatography on silica gel (petroleum ether/ethyl acetate=10:1 to 1:1) to give the title compound (25 g, 98 mmol, 71% yield). $^1$H NMR (400 MHz, CDCl$_3$) δ ppm 5.79 (ddt, J=17.03, 10.31, 6.50, 6.50 Hz, 1H) 4.99-5.08 (m, 2H) 4.22-4.39 (m, 1H) 3.74 (s, 3H) 2.07-2.18 (m, 2H) 1.84-1.97 (m, 1H) 1.65-1.78 (m, 1H) 1.45 (s, 9H).

Example 60C: (S)-tert-butyl (1-hydroxyhex-5-en-2-yl)carbamate

To a mixture of LiBH$_4$ (0.627 g, 28.8 mmol) in tetrahydrofuran (35 mL) was added Example 60B (7 g, 29 mmol) in tetrahydrofuran (35 mL), and the reaction mixture was stirred at 20° C. for 5 hours. The mixture was quenched by water (100 mL) and extracted with ethyl acetate (2×200 mL). The combined organic layers were washed with brine (50 mL), dried over Na$_2$SO$_4$ and concentrated to give the title compound (22 g, 97 mmol, 94% yield). $^1$H NMR (400 MHz, CDCl3) δ ppm 5.72-5.92 (m, 1H) 4.94-5.11 (m, 2H) 4.67 (br s, 1H) 3.48-3.72 (m, 3H) 2.07-2.20 (m, 2H) 1.51-1.66 (m, 2H) 1.45 (s, 9H).

Example 60D: tert-butyl ((2S)-1-hydroxy-4-(oxiran-2-yl)butan-2-yl)carbamate

To a solution of Example 60C (2 g, 9.3 mmol) in dichloromethane (20 mL) was added 3-chloroperoxybenzoic acid (m-CPBA, 2.204 g, 10.22 mmol) at 0° C., and the reaction mixture was stirred at 0-20° C. for 16 hours. The reaction mixture was washed with saturated $NaHCO_3$ (2×200 mL), saturated $Na_2SO_3$ (2×100 mL), and brine (200 mL), dried over $Na_2SO_4$ and concentrated. The residue was purified by column chromatography ($SiO_2$, petroleum ether/ethyl acetate=10:1 to 1:1) to give the title compound (13 g, 53 mmol, 52% yield). $^1$H NMR (400 MHz, $CDCl_3$) δ ppm 4.72-4.92 (m, 1H) 3.50-3.72 (m, 3H) 2.89-2.97 (m, 1H) 2.73-2.80 (m, 1H) 2.50 (dt, J=5.07, 2.76 Hz, 1H) 1.64-1.74 (m, 2H) 1.49-1.63 (m, 2H) 1.43 (s, 9H).

Example 60E: tert-butyl ((3S,6R)-6-(hydroxymethyl)tetrahydro-2H-pyran-3-yl)carbamate To a solution of Example 60D (5.5 g, 24 mmol) in dichloromethane (60 mL) was added ((1S,4R)-7,7-dimethyl-2-oxobicyclo[2.2.1]heptan-1-yl)methanesulfonic acid (0.552 g, 2.38 mmol) at 0° C., and the mixture was stirred at 0-25° C. for 16 hours. Then the reaction mixture was washed with saturated $NaHCO_3$ (100 mL), dried over $Na_2SO_4$, and concentrated. The residue was purified by column chromatography ($SiO_2$, petroleum ether/ethyl acetate=5:1 to 2:1) to give the impure title compound. This compound was triturated with petroleum ether (60 mL) and ethyl acetate (20 mL), the solid was collected by filtration, and the filter cake was dried to the title compound (4 g, 16.4 mmol, 35% yield). $^1$H NMR (400 MHz, $CDCl_3$) δ ppm 4.26 (br s, 1H) 4.12 (ddd, J=10.69, 4.74, 1.98 Hz, 1H) 3.56-3.70 (m, 2H) 3.48-3.56 (m, 1H) 3.33-3.41 (m, 1H) 3.03 (t, J=10.69 Hz, 1H) 2.12 (br d, J=12.35 Hz, 1H) 1.98 (br s, 1H) 1.59-1.68 (m, 1H) 1.40-1.53 (m, 10H) 1.30 (qd, J=12.35, 3.75 Hz, 1H).

Example 60F: (2R,5S)-5-((tert-butoxycarbonyl)amino)tetrahydro-2H-pyran-2-carboxylic acid To a solution of Example 60E (1.7 g, 7.4 mmol) in dichloromethane (15 mL), acetonitrile (15 mL) and water (15 mL) was added ruthenium(III) chloride hydrate (0.083 g, 0.37 mmol) and sodium periodate (6.29 g, 29.4 mmol) at 0° C. The reaction mixture was stirred at 0° C. for 6 hours, and then saturated $NaHSO_3$ was added, and the mixture was extracted with dichloromethane (3×100 mL). The combined organic layers were washed with brine (3×100 mL), dried over $Na_2SO_4$, and concentrated to give the title compound (3.1 g, 12.6 mmol, 86% yield). $^1$H NMR (400 MHz, DMSO-$d_6$) δ ppm 12.59 (br s, 1H) 6.81 (br d, J=7.72 Hz, 1H) 3.79-3.88 (m, 1H) 3.71-3.78 (m, 1H) 3.32 (br s, 1H) 2.99 (t, J=10.58 Hz, 1H) 1.81-1.96 (m, 2H) 1.40-1.56 (m, 2H) 1.37 (s, 9H).

Example 60G: tert-butyl ((3S,6R)-6-(((5-(trifluoromethyl)pyridin-2-yl)methyl)carbamoyl)tetrahydro-2H-pyran-3-yl)carbamate The methodologies described in Example 35A substituting (5-(trifluoromethyl)pyridin-2-yl)methanamine hydrochloride for 3-(4-(trifluoromethyl)phenyl)azetidine hydrochloride and substituting (2R,5S)-5-((tert-butoxycarbonyl)amino)tetrahydro-2H-pyran-2-carboxylic acid (Example 60F) for (2S,5R)-5-((tert-butoxycarbonyl)amino)tetrahydro-2H-pyran-2-carboxylic acid gave the title compound. MS (ESI$^+$) m/z 404 (M+H)$^+$.

Example 60H: (2R,5S)-5-amino-N-((5-(trifluoromethyl)pyridin-2-yl)methyl)tetrahydro-2H-pyran-2-carboxamide The methodologies described in Example 35B substituting Example 60G for Example 35A gave the title compound. MS (ESI$^+$) m/z 304 (M+H)$^+$.

Example 60I. (2R,5S)-5-[2-(4-chloro-3-fluorophenoxy)acetamido]-N-{[5-(trifluoromethyl)pyridin-2-yl]methyl}oxane-2-carboxamide The methodologies described in Example 35A substituting Example 60H for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. $^1$H NMR (400 MHz, DMSO-$d_6$) δ ppm 8.89 (s, 1H), 8.43 (t, J=6.0 Hz, 1H), 8.20-8.13 (m, 1H), 8.05 (d, J=8.0 Hz, 1H), 7.54-7.43 (m, 2H), 7.07 (dd, J=11.3, 2.9 Hz, 1H), 6.85 (dd, J=9.0, 2.8 Hz, 1H), 4.53 (s, 2H), 4.47 (d, J=6.1 Hz, 2H), 3.93 (dd, J=10.0, 4.4 Hz, 1H), 3.87-3.80 (m, 1H), 3.21 (t, J=10.6 Hz, 3H), 2.04 (d, J=13.3 Hz, 1H), 1.92 (d, J=12.5 Hz, 1H), 1.66-1.44 (m, 1H); MS (ESI$^+$) m/z 490 (M+H)$^+$.

Example 61: 2-(4-chloro-3-fluorophenoxy)-N-{(3R,6S)-6-[3-(4-chlorophenyl)azetidine-1-carbonyl]oxan-3-yl}acetamide (Compound 160)

Example 61A: tert-butyl ((3R,6S)-6-(3-(4-chlorophenyl)azetidine-]-carbonyl)tetrahydro-2H-pyran-3-yl)carbamate The methodologies described in Example 35A substituting 3-(4-chlorophenyl)azetidine 2,2,2-trifluoroacetate for 3-(4-(trifluoromethyl)phenyl)azetidine hydrochloride gave the title compound. $^1$H NMR (400 MHz, DMSO-$d_6$) δ ppm 7.45-7.34 (m, 4H), 6.80 (d, J=7.9 Hz, 1H), 4.63 (td, J=8.8, 3.2 Hz, 1H), 4.26 (t, J=8.8 Hz, 1H), 4.19 (dd, J=9.4, 5.9 Hz, 1H), 3.92-3.81 (m, 1H), 3.85 (s, 1H), 3.85-3.77 (m, 2H), 2.99 (t, J=10.6 Hz, 1H), 1.88 (d, J=12.5 Hz, 1H), 1.81 (dt, J=13.4, 3.4 Hz, 1H), 1.56 (qd, J=13.0, 3.6 Hz, 1H), 1.43 (dd, J=12.3, 3.8 Hz, 1H), 1.37 (s, 9H); MS (ESI$^+$) m/z 395 (M+H)$^+$.

Example 61B: ((2S,5R)-5-aminotetrahydro-2H-pyran-2-yl)(3-(4-chlorophenyl)azetidin-1-yl)methanone The methodologies described in Example 35B substituting Example 61A for Example 35A gave the title compound. MS (ESI$^+$) m/z 295 (M+H)$^+$.

Example 61C: 2-(4-chloro-3-fluorophenoxy)-N-{(3R,6S)-6-[3-(4-chlorophenyl)azetidine-]-carbonyl]oxan-3-yl}acetamide The methodologies described in Example 35A substituting Example 61B for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. ¹H NMR (400 MHz, DMSO-d₆) δ ppm 8.00 (dd, J=7.8, 2.2 Hz, 1H), 7.49 (t, J=8.9 Hz, 1H), 7.45-7.35 (m, 4H), 7.06 (dd, J=11.4, 2.9 Hz, 1H), 6.84 (ddd, J=8.9, 2.9, 1.1 Hz, 1H), 4.65 (td, J=8.6, 4.8 Hz, 1H), 4.52 (s, 2H), 4.31-4.17 (m, 2H), 3.93-3.65 (m, 3H), 3.20-3.08 (m, 1H), 1.94-1.81 (m, 2H), 1.62 (d, J=13.5 Hz, 1H), 1.58-1.49 (m, 1H); MS (ESI⁺) m/z 481 (M+H)⁺.

Example 62: (2S)-6-chloro-N-[(3R,6S)-6-({[5-(trifluoromethyl)pyridin-2-yl]methyl}carbamoyl)oxan-3-yl]-3,4-dihydro-2H-1,4-benzoxazine-2-carboxamide (Compound 161)

Example 66 was purified by chiral SFC (supercritical fluid chromatography) using a Chiralcel® OD-H column eluting with 30% CH₃OH in CO₂ with a flow rate of 70 g/minute to give the title compound (first enantiomer eluted out of the column, 0.005 g, 0.010 mmol, 45% yield). The absolute stereochemistry of this title compounds was arbitrarily assigned. ¹H NMR (400 MHz, DMSO-d₆) δ ppm 8.89 (s, 1H), 8.43 (t, J=6.0 Hz, 1H), 8.17 (dd, J=8.5, 2.3 Hz, 1H), 7.94 (d, J=8.0 Hz, 1H), 7.46 (d, J=8.2 Hz, 1H), 6.78 (d, J=8.5 Hz, 1H), 6.61 (d, J=2.6 Hz, 1H), 6.51 (dd, J=8.5, 2.5 Hz, 1H), 6.18 (s, 1H), 5.75 (s, 1H), 4.46 (dd, J=8.1, 4.0 Hz, 3H), 4.04 (s, 1H), 3.90-3.78 (m, 2H), 3.19 (q, J=9.7, 9.0 Hz, 2H), 2.03 (d, J=13.5 Hz, 1H), 1.93 (d, J=12.5 Hz, 1H), 1.70-1.62 (m, 1H), 1.50 (d, J=12.5 Hz, 1H), 1.19 (d, J=35.5 Hz, 1H); MS (ESI⁺) m/z 499 (M+H)⁺.

Example 63: (2S,5S)-5-[2-(4-chloro-3-fluorophenoxy)acetamido]-N-{[5-(trifluoromethyl) pyridin-2-yl]methyl}oxane-2-carboxamide (Compound 162)

Example 67 was purified by chiral SFC (supercritical fluid chromatography) using a Chiralcel® OD-H column eluting with 25% CH₃OH in CO₂ with a flow rate of 70 g/minute to give the title compound (second enantiomer eluted out of the column, 0.030 g, 0.061 mmol, 55% yield). The absolute stereochemistry of this title compounds was arbitrarily assigned. ¹H NMR (501 MHz, DMSO-d₆) δ ppm 8.92-8.87 (m, 1H), 8.45 (t, J=6.0 Hz, 1H), 8.19-8.13 (m, 1H), 8.08 (d, J=7.3 Hz, 1H), 7.52-7.43 (m, 2H), 7.06 (dd, J=11.4, 2.9 Hz, 1H), 6.84 (ddd, J=9.0, 2.9, 1.2 Hz, 1H), 4.60 (d, J=1.3 Hz, 2H), 4.56 (dd, J=16.9, 5.8 Hz, 1H), 4.46 (dd, J=16.5, 5.8 Hz, 1H), 3.98 (t, J=6.1 Hz, 1H), 3.87-3.79 (m, 2H), 3.68 (dd, J=11.5, 2.3 Hz, 1H), 1.84-1.72 (m, 4H); MS (ESI⁺) m/z 490 (M+H)⁺.

Example 64: (2R,5R)-5-[2-(4-chloro-3-fluorophenoxy)acetamido]-N-{[5-(trifluoromethyl)pyridin-2-yl]methyl}oxane-2-carboxamide (Compound 163)

Example 67 was purified by chiral SFC (supercritical fluid chromatography) using a Chiralcel® OD-H column eluting with 25% CH₃OH in CO₂ with a flow rate of 70 g/minute to give the title compound (first enantiomer eluted out of the column, 0.031 g, 0.061 mmol, 55% yield). The absolute stereochemistry of this title compounds was arbitrarily assigned. ¹H NMR (500 MHz, DMSO-d₆) δ ppm 8.92-8.88 (m, 1H), 8.47 (t, J=6.1 Hz, 1H), 8.16 (dd, J=8.4, 2.4 Hz, 1H), 8.11 (d, J=7.3 Hz, 1H), 7.52-7.44 (m, 2H), 7.07 (dd, J=11.4, 2.9 Hz, 1H), 6.84 (ddd, J=8.9, 2.9, 1.2 Hz, 1H), 4.60 (d, J=1.4 Hz, 2H), 4.59-4.51 (m, 1H), 4.46 (dd, J=16.5, 5.9 Hz, 1H), 3.98 (dd, J=7.5, 4.8 Hz, 1H), 3.87-3.79 (m, 2H), 3.71-3.65 (m, 1H), 3.17 (d, J=5.1 Hz, 1H), 1.84-1.74 (m, 1H), 1.78 (s, 3H); MS (ESI⁺) m/z 490 (M+H)⁺.

Example 65: (2R)-6-chloro-N-[(3R,6S)-6-({[5-(trifluoromethyl)pyridin-2-yl]methyl}carbamoyl)oxan-3-yl]-3,4-dihydro-2H-1,4-benzoxazine-2-carboxamide (Compound 164)

Example 66 was purified by chiral SFC (supercritical fluid chromatography) using a Chiralcel® OD-H column eluting with 30% CH₃OH in CO₂ with a flow rate of 70 g/minute to give the title compound (second enantiomer eluted out of the column, 0.005 g, 0.010 mmol, 45% yield). The absolute stereochemistry of this title compounds was arbitrarily assigned. ¹H NMR (501 MHz, DMSO-d₆) δ ppm 8.89 (s, 1H), 8.43 (t, J=6.1 Hz, 1H), 8.17 (d, J=10.5 Hz, 1H), 7.91 (d, J=8.1 Hz, 1H), 7.46 (d, J=8.3 Hz, 1H), 6.79 (d, J=8.5 Hz, 1H), 6.61 (d, J=2.5 Hz, 1H), 6.51 (dd, J=8.5, 2.5 Hz, 1H), 6.18 (s, 1H), 4.47 (t, J=5.9 Hz, 3H), 4.05 (m, 1H), 3.93 (d, J=11.0 Hz, 1H), 3.84-3.74 (m, 1H), 2.02 (d, J=13.4 Hz, 1H), 1.84 (s, 1H), 1.72-1.41 (m, 1H), 1.24 (s, 1H), 1.15 (s, 1H).; MS (ESI⁺) m/z 499 (M+H)⁺.

Example 66: 6-chloro-N-[(3R,6S)-6-({[5-(trifluoromethyl)pyridin-2-yl]methyl}carbamoyl)oxan-3-yl]-3,4-dihydro-2H-1,4-benzoxazine-2-carboxamide (Compound 165)

Example 66A: ethyl 6-chloro-3,4-dihydro-2H-benzo[b][1,4]oxazine-2-carboxylate To a solution of 2-amino-4-chlorophenol (2.00 g, 13.9 mmol) in acetone (77 mL) was added potassium carbonate (5.39 g, 39.0 mmol), followed by ethyl 2,3-dibromopropanoate (2.2 mL, 15 mmol). The reaction mixture was refluxed for 16 hours, cooled to ambient temperature, filtered, and concentrated to give the title compound without further purification. MS (ESI⁺) m/z 242 (M+H)⁺.

Example 66B: 6-chloro-3,4-dihydro-2H-benzo[b][1,4]oxazine-2-carboxylic acid To a solution of Example 66A (6.36 g, 26.3 mmol) in methanol/water (26.3 mL, 1:1) was added NaOH (5 N aqueous solution, 26.3 mL), and the mixture stirred for 4 hours. The mixture was concentrated, and the residue was acidified with HCl (1 N). The resultant mixture was concentrated again and carried forward without purification. MS (ESI⁺) m/z 214 (M+H)⁺.

Example 66C: tert-butyl ((3R,6S)-6-(((5-(trifluoromethyl)pyridin-2-yl)methyl)carbamoyl)tetrahydro-2H-pyran-3-yl)carbamate The methodologies described in Example 35A substituting (5-(trifluoromethyl)pyridin-2-yl)methanamine hydrochloride for 3-(4-(trifluoromethyl)phenyl)azetidine hydrochloride gave the title compound. MS (ESI⁺) m/z 404 (M+H)⁺.

Example 66D: (2S,5R)-5-amino-N-((5-(trifluoromethyl)pyridin-2-yl)methyl)tetrahydro-2H-pyran-2-carboxamide The methodologies described in Example 35B substituting Example 66C for Example 35A gave the title compound. MS (ESI⁺) m/z 304 (M+H)⁺.

Example 66E: rac-6-chloro-N-[(3R,6S)-6-({[5-(trifluoromethyl)pyridin-2-yl]methyl}carbamoyl)oxan-3-yl]-3,4-dihydro-2H-1,4-benzoxazine-2-carboxamide The methodologies described in Example 35A substituting Example 66D for 3-(4-(trifluoromethyl)phenyl)azetidine hydrochloride and substituting Example 66B for (2S,5R)-5-((tert-butoxycarbonyl)amino)tetrahydro-2H-pyran-2-carboxylic acid gave the title compound. $^1$H NMR (501 MHz, DMSO-$d_6$, diagnostic peaks) δ ppm 8.89 (d, J=2.3 Hz, 1H), 8.43 (t, J=5.9 Hz, 1H), 8.17 (dd, J=8.2, 2.4 Hz, 1H), 7.93 (dd, J=18.2, 8.1 Hz, 1H), 7.46 (d, J=8.2 Hz, 1H), 6.79 (dd, J=8.5, 2.2 Hz, 1H), 6.61 (d, J=2.6 Hz, 1H), 6.51 (dd, J=8.0, 2.7 Hz, 1H), 4.51-4.43 (m, 3H), 3.91 (dddd, J=28.3, 10.7, 4.8, 1.9 Hz, 1H), 3.98-3.72 (m, 2H), 3.30-3.17 (m, 2H), 2.03 (tt, J=9.7, 3.2 Hz, 1H), 1.89 (ddd, J=40.3, 13.4, 5.3 Hz, 1H), 1.69-1.58 (m, 1H), 1.56 1.45 (m, 1H); MS (ESI$^+$) m/z 499 (M+H)$^+$.

Example 67: 5-[2-(4-chloro-3-fluorophenoxy)acetamido]-N-{[5-(trifluoromethyl)pyridin-2-yl]methyl}oxane-2-carboxamide (Compound 166)

Example 67A: tert-butyl (6-(((5-(trifluoromethyl)pyridin-2-yl)methyl)carbamoyl)tetrahydro-2H-pyran-3-yl)carbamate The methodologies described in Example 35A substituting (5-(trifluoromethyl)pyridine-2-yl)methanamine hydrochloride for 3-(4-(trifluoromethyl)phenyl)azetidine hydrochloride and substituting 5-((tert-butoxycarbonyl)amino)tetrahydro-2H-pyran-2-carboxylic acid for (2S,5R)-5-((tert-butoxycarbonyl)amino)tetrahydro-2H-pyran-2-carboxylic acid gave the title compound. $^1$H NMR (400 MHz, DMSO-$d_6$) δ ppm 8.90 (dt, J=2.1, 1.0 Hz, 1H), 8.50 (dt, J=24.5, 6.1 Hz, 1H), 8.18 (dd, J=8.5, 2.4 Hz, 1H), 7.49 (d, J=8.2 Hz, 1H), 6.99 (d, J=7.3 Hz, 1H), 4.49 (qd, J=16.6, 6.2 Hz, 2H), 3.99-3.86 (m, 1H), 3.86-3.67 (m, 1H), 3.60 (dd, J=11.6, 2.4 Hz, 1H), 3.50 (s, 1H), 1.89-1.64 (m, 3H), 1.40 (s, 9H); MS (ESI$^+$) m/z 404 (M+H)$^+$.

Example 67B: 5-amino-N-((5-(trifluoromethyl)pyridin-2-yl)methyl)tetrahydro-2H-pyran-2-carboxamide The methodologies described in Example 35B substituting Example 67A for Example 35A gave the title compound. MS (ESI$^+$) m/z 304 (M+H)$^+$.

Example 67C: 5-[2-(4-chloro-3-fluorophenoxy)acetamido]-N-{[5-(trifluoromethyl)pyridin-2-yl]methyl}oxane-2-carboxamide The methodologies described in Example 35A substituting Example 67B for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. $^1$H NMR (400 MHz, DMSO-$d_6$) δ ppm 8.89 (d, J=2.3 Hz, 1H), 8.46 (t, J=6.1 Hz, 1H), 8.16 (dd, J=8.3, 2.4 Hz, 1H), 8.11 (d, J=7.3 Hz, 1H), 7.53-7.42 (m, 2H), 7.06 (dd, J=11.4, 2.8 Hz, 1H), 6.85 (dd, J=9.1, 2.9 Hz, 1H), 4.60 (s, 2H), 4.61 4.41 (m, 2H), 3.99 (q, J=4.5 Hz, 1H), 3.89-3.78 (m, 2H), 3.73-3.65 (m, 1H), 1.88-1.70 (m, 4H); MS (ESI$^+$) m/z 490 (M+H)$^+$.

Example 68: (2S,5R)-5-[2-(4-chloro-3-fluorophenoxy)acetamido]-N-[(2,2-difluoro-2H-1,3-benzodioxol-5-yl)methyl]oxane-2-carboxamide (Compound 167)

Example 68A: tert-butyl ((3R,6S)-6-(((2,2-difluorobenzo[d][1,3]dioxol-5-yl)methyl)carbamoyl)tetrahydro-2H-pyran-3-yl)carbamate The methodologies described in Example 35A substituting (2,2-difluorobenzo[d][1,3]dioxol-5-yl)methanamine for 3-(4-(trifluoromethyl)phenyl)azetidine hydrochloride gave the title compound. MS (ESI$^+$) m/z 415 (M+H)$^+$.

Example 68B: (2S,5R)-5-amino-N-((2,2-difluorobenzo[d][1,3]dioxol-5-yl)methyl)tetrahydro-2H-pyran-2-carboxamide The methodologies described in Example 35B substituting Example 68A for Example 35A gave the title compound. MS (ESI$^+$) m/z 315 (M+H)$^+$.

Example 68C: (2S,5R)-5-[2-(4-chloro-3-fluorophenoxy)acetamido]-N-[(2,2-difluoro-2H-1,3-benzodioxol-5-yl)methyl]oxane-2-carboxamide The methodologies described in Example 35A substituting Example 68B for 3-(4-(trifluoromethyl)phenyl)azetidine hydrochloride and substituting 2-(4-chloro-3-fluorophenoxy)acetic acid for (2S,5R)-5-((tert-butoxycarbonyl)amino)tetrahydro-2H-pyran-2-carboxylic acid gave the title compound. $^1$H NMR (400 MHz, DMSO-$d_6$) δ ppm 8.32 (t, J=6.3 Hz, 1H), 8.02 (d, J=7.9 Hz, 1H), 7.49 (t, J=8.9 Hz, 1H), 7.33 (d, J=8.2 Hz, 1H), 7.26 (d, J=1.6 Hz, 1H), 7.07 (ddd, J=10.0, 6.1, 2.2 Hz, 2H), 6.89-6.81 (m, 1H), 4.52 (d, J=1.2 Hz, 2H), 4.34-4.19 (m, 2H), 3.89 (dd, J=10.8, 4.6 Hz, 1H), 3.77 (dd, J=11.5, 2.4 Hz, 1H), 3.17 (t, J=10.5 Hz, 2H), 2.01 (d, J=13.3 Hz, 1H), 1.90 (d, J=12.4 Hz, 1H), 1.67-1.53 (m, 1H), 1.52-1.41 (m, 1H); MS (ESI$^+$) m/z 501 (M+H)$^+$.

Example 69: (1r,3r)-3-[2-(4-chloro-3-fluorophenoxy)acetamido]-N-[6-(difluoromethoxy)pyridin-3-yl]cyclobutane-1-carboxamide (Compound 168)

The reaction and purification conditions described in Example 1C substituting 6-(difluoromethoxy)pyridin-3-amine (Enamine) for (6-(trifluoromethyl)pyridin-3-yl)methanamine, and the product of Example 22B for the product of Example 1B gave the title compound. $^1$H NMR (400 MHz, DMSO-$d_6$) δ ppm 10.09 (s, 1H), 8.47 (d, J=2.7 Hz, 1H), 8.40 (d, J=7.8 Hz, 1H), 8.11 (dd, J=8.8, 2.7 Hz, 1H), 7.63 (t, J=73.2 Hz, 1H), 7.51 (t, J=8.9 Hz, 1H), 7.12-7.05 (m, 2H), 6.87 (ddd, J=8.9, 2.8, 1.2 Hz, 1H), 4.51 (s, 2H), 4.50-4.41 (m, 1H), 3.11 (ddt, J=12.4, 8.6, 3.6 Hz, 1H), 2.49-2.40 (m, 2H), 2.38-2.26 (m, 2H); MS (ESI$^+$) m/z 444 (M+H)$^+$.

Example 70: (1r,3r)-3-[2-(4-chloro-3-fluorophenoxy)acetamido]-N-[(4-chlorophenyl)methyl]cyclobutane-1-carboxamide (Compound 169)

The title compound was prepared using the methodologies described above. $^1$H NMR (501 MHz, DMSO-$d_6$) δ ppm 8.35 (d, J=7.8 Hz, 1H), 8.31 (t, J=6.0 Hz, 1H), 7.50 (t, J=8.9 Hz, 1H), 7.40-7.35 (m, 2H), 7.29-7.23 (m, 2H), 7.08 (dd, J=11.3, 2.9 Hz, 1H), 6.86 (ddd, J=9.0, 2.9, 1.2 Hz, 1H), 4.49 (s, 2H), 4.48-4.39 (m, 1H), 4.26 (d, J=5.9 Hz, 2H), 2.96-2.89 (m, 1H), 2.38-2.31 (m, 2H), 2.26-2.18 (m, 2H); MS (APCI⁺) m/z 425 (M+H)⁺.

Example 71: (1r,4r)-4-[2-(4-chloro-3-fluorophenoxy)acetamido]-N-{[4-(cyclobutyloxy)pyridin-2-yl]methyl}cyclohexane-1-carboxamide (Compound 170)

The reaction and purification conditions described in Example 1C substituting (4-cyclobutoxypyridin-2-yl)methanamine (Enamine) for (6-(trifluoromethyl)pyridin-3-yl)methanamine, and the product of Example 8A for the product of Example 1B gave the title compound. ¹H NMR (400 MHz, DMSO-d₆) δ ppm 8.31-8.24 (m, 2H), 7.95 (d, J=8.0 Hz, 1H), 7.49 (t, J=8.9 Hz, 1H), 7.07 (dd, J=11.4, 2.8 Hz, 1H), 6.85 (ddd, J=9.0, 2.9, 1.2 Hz, 1H), 6.73 (dd, J=5.7, 2.4 Hz, 1H), 6.66-6.64 (m, 1H), 4.74 (p, J=7.2 Hz, 1H), 4.50 (s, 2H), 4.26 (d, J=5.9 Hz, 2H), 3.65-3.53 (m, 1H), 2.47-2.38 (m, 2H), 2.23-2.13 (m, 1H), 2.10-1.98 (m, 2H), 1.87-1.74 (m, 5H), 1.72-1.58 (m, 1H), 1.51-1.40 (m, 2H), 1.35-1.21 (m, 2H); MS (APCI⁺) m/z 490 (M+H)⁺.

Example 72: (1r,4r)-4-[2-(4-chloro-3-fluorophenoxy)acetamido]-N-{[4-(trifluoromethyl)pyridin-2-yl]methyl}cyclohexane-1-carboxamide (Compound 171)

The title compound was prepared using the methodologies described above. ¹H NMR (400 MHz, DMSO-d₆) δ ppm 8.79 (d, J=5.2 Hz, 1H), 8.46 (t, J=6.0 Hz, 1H), 7.96 (d, J=8.1 Hz, 1H), 7.66-7.62 (m, 1H), 7.54-7.52 (m, 1H), 7.49 (t, J=8.9 Hz, 1H), 7.07 (dd, J=11.4, 2.9 Hz, 1H), 6.85 (ddd, J=9.0, 2.9, 1.2 Hz, 1H), 4.50 (s, 2H), 4.45 (d, J=5.9 Hz, 2H), 3.64-3.52 (m, 1H), 2.25-2.15 (m, 1H), 1.86-1.75 (m, 4H), 1.51-1.37 (m, 2H), 1.35-1.23 (m, 2H); MS (APCI⁺) m/z 488 (M+H)⁺.

Example 73: 6-[({(1r,4r)-4-[2-(4-chloro-3-fluorophenoxy)acetamido]cyclohexane-1-carbonyl}amino)methyl]pyridine-3-carboxamide (Compound 172)

The reaction and purification conditions described in Example 1C substituting 6-(aminomethyl)nicotinamide (Ark Pharm) for (6-(trifluoromethyl)pyridin-3-yl)methanamine, and the product of Example 8A for the product of Example 1B gave the title compound. ¹H NMR (400 MHz, DMSO-d₆) δ ppm 8.94 (dd, J=2.3, 0.8 Hz, 1H), 8.40 (t, J=6.0 Hz, 1H), 8.16 (dd, J=8.1, 2.3 Hz, 1H), 8.10 (s, 1H), 7.95 (d, J=8.1 Hz, 1H), 7.52 (s, 1H), 7.52-7.45 (m, 1H), 7.30 (dd, J=8.2, 0.8 Hz, 1H), 7.07 (dd, J=11.4, 2.8 Hz, 1H), 6.85 (ddd, J=9.0, 2.9, 1.2 Hz, 1H), 4.49 (s, 2H), 4.38 (d, J=5.9 Hz, 2H), 3.65-3.52 (m, 1H), 2.24-2.13 (m, 1H), 1.87-1.77 (m, 4H), 1.51-1.38 (m, 2H), 1.35-1.22 (m, 2H); MS (APCI⁺) m/z 463 (M+H)⁺.

Example 74: (1r,4r)-N-[(5-cyanopyridin-2-yl)methyl]-4-[2-(3,4-dichlorophenoxy)acetamido]cyclohexane-1-carboxamide (Compound 173)

The title compound was prepared using the methodologies described above. ¹H NMR (400 MHz, DMSO-d₆) δ ppm 8.96-8.93 (m, 1H), 8.46 (t, J=6.0 Hz, 1H), 8.26 (dd, J=8.2, 2.1 Hz, 1H), 7.96 (d, J=8.1 Hz, 1H), 7.54 (d, J=9.0 Hz, 1H), 7.41 (d, J=8.2 Hz, 1H), 7.25 (d, J=2.9 Hz, 1H), 6.98 (dd, J=9.0, 2.9 Hz, 1H), 4.51 (s, 2H), 4.41 (d, J=5.9 Hz, 2H), 3.64-3.52 (m, 1H), 2.19 (tt, J=11.9, 3.3 Hz, 1H), 1.88-1.77 (m, 4H), 1.51-1.37 (m, 2H), 1.35-1.23 (m, 2H); MS (ESI⁺) m/z 461 (M+H)⁺.

Example 75: (2S,5R)-5-[2-(3,4-dichlorophenoxy)acetamido]-N-{[5-(trifluoromethyl)pyridin-2-yl]methyl}oxane-2-carboxamide (Compound 174)

The methodologies described in Example 35A substituting Example 66D for 3-(4-(trifluoromethyl)phenyl)azetidine hydrochloride and substituting 2-(3,4-dichlorophenoxy)acetic acid for (2S,5R)-5-((tert-butoxycarbonyl)amino)tetrahydro-2H-pyran-2-carboxylic acid gave the title compound. ¹H NMR (400 MHz, DMSO-d₆) δ ppm 8.89 (dt, J=2.0, 1.0 Hz, 1H), 8.43 (t, J=6.1 Hz, 1H), 8.20-8.13 (m, 1H), 8.05 (d, J=8.0 Hz, 1H), 7.55 (d, J=8.9 Hz, 1H), 7.47 (d, J=8.2 Hz, 1H), 7.26 (d, J=3.0 Hz, 1H), 6.99 (dd, J=9.0, 2.9 Hz, 1H), 4.55 (d, J=1.0 Hz, 2H), 4.47 (d, J=6.0 Hz, 2H), 3.93 (ddd, J=10.7, 4.8, 1.9 Hz, 1H), 3.83 (ddd, J=11.4, 8.2, 3.3 Hz, 2H), 3.22 (t, J=10.6 Hz, 1H), 2.10-1.98 (m, 1H), 1.98-1.86 (m, 1H), 1.71-1.41 (m, 2H); MS (ESI⁺) m/z 506 (M+H)⁺.

Example 76: (1r,4r)-N-[(5-chloropyridin-2-yl)methyl]-4-[2-(3,4-dichlorophenoxy)acetamido]cyclohexane-1-carboxamide (Compound 175)

The title compound was prepared using the methodologies described above. ¹H NMR (400 MHz, DMSO-d₆) δ ppm 8.53 (d, J=2.6 Hz, 1H), 8.38 (t, J=6.0 Hz, 1H), 7.96 (d, J=8.1 Hz, 1H), 7.88 (dd, J=8.4, 2.5 Hz, 1H), 7.54 (d, J=8.9 Hz, 1H), 7.29-7.24 (m, 2H), 6.98 (dd, J=8.9, 2.9 Hz, 1H), 4.50 (s, 2H), 4.33 (d, J=6.0 Hz, 2H), 3.65-3.53 (m, 1H), 2.21-2.13 (m, 1H), 1.87-1.76 (m, 4H), 1.50-1.37 (m, 2H), 1.34-1.22 (m, 2H); MS (ESI⁺) m/z 470, 472 (M+H)⁺.

Example 77: (1r,4r)-4-[2-(4-chloro-3-fluorophenoxy)acetamido]-N-[(5-chloropyridin-2-yl)methyl]cyclohexane-1-carboxamide (Compound 176)

The title compound was prepared using the methodologies described above. ¹H NMR (501 MHz, DMSO-d₆) δ ppm 8.53 (dd, J=2.6, 0.6 Hz, 1H), 8.38 (t, J=6.0 Hz, 1H), 7.95 (d, J=8.1 Hz, 1H), 7.88 (dd, J=8.4, 2.6 Hz, 1H), 7.49 (t, J=8.9 Hz, 1H), 7.27 (dd, J=8.4, 0.7 Hz, 1H), 7.07 (dd, J=11.4, 2.8 Hz, 1H), 6.85 (ddd, J=9.0, 2.9, 1.2 Hz, 1H), 4.49 (s, 2H), 4.32 (d, J=5.9 Hz, 2H), 3.63-3.53 (m, 1H), 2.20-2.13 (m, 1H), 1.86-1.77 (m, 4H), 1.49-1.38 (m, 2H), 1.33-1.23 (m, 2H); MS (ESI⁺) m/z 454 (M+H)⁺.

Example 78: (1r,4r)-4-[2-(4-chloro-3-fluorophenoxy)acetamido]-N-[6-(trifluoromethoxy)pyridin-3-yl]cyclohexane-1-carboxamide (Compound 177)

The title compound was prepared using the methodologies described above. ¹H NMR (400 MHz, DMSO-d₆) δ ppm 10.23 (s, 1H), 8.53 (dd, J=2.8, 0.6 Hz, 1H), 8.22 (dd, J=8.9, 2.8 Hz, 1H), 7.99 (d, J=8.1 Hz, 1H), 7.50 (t, J=8.9 Hz, 1H), 7.28 (d, J=8.8 Hz, 1H), 7.07 (dd, J=11.4, 2.8 Hz, 1H), 6.86 (ddd, J=9.0, 2.9, 1.2 Hz, 1H), 4.51 (s, 2H), 3.68-3.57 (m, 1H), 2.31 (tt, J=12.0, 3.1 Hz, 1H), 1.94-1.81 (m, 4H), 1.57-1.45 (m, 2H), 1.39-1.26 (m, 2H); MS (ESI⁺) m/z 490 (M+H)⁺.

Example 79: (1r,4r)-4-[2-(4-chloro-3-fluorophenoxy)acetamido]-N-[2-(4-chloro-3-fluorophenoxy)ethyl]cyclohexane-1-carboxamide (Compound 178)

The reaction and purification conditions described in Example 1C substituting 2-(4-chloro-3-fluorophenoxy)

ethanamine (Enamine) for (6-(trifluoromethyl)pyridin-3-yl) methanamine, and the product of Example 8A for the product of Example 1B gave the title compound. $^1$H NMR (400 MHz, DMSO-$d_6$) δ ppm 7.99-7.90 (m, 2H), 7.49 (t, J=8.9 Hz, 1H), 7.46 (t, J=8.9 Hz, 1H), 7.08 (t, J=2.5 Hz, 1H), 7.05 (dd, J=2.8, 2.1 Hz, 1H), 6.87-6.81 (m, 2H), 4.48 (s, 2H), 4.00 (t, J=5.7 Hz, 2H), 3.62-3.50 (m, 1H), 3.39 (q, J=5.6 Hz, 2H), 2.12-2.02 (m, 1H), 1.83-1.68 (m, 4H), 1.45-1.33 (m, 2H), 1.30-1.17 (m, 2H); MS (ESI$^+$) m/z 501 (M+H)$^+$.

Example 80: (1r,4r)-4-[2-(4-chloro-3-fluorophenoxy)acetamido]-N-[(2,2-difluoro-2H-1,3-benzodioxol-5-yl)methyl]cyclohexane-1-carboxamide (Compound 179)

The reaction and purification conditions described in Example 1C substituting (2,2-difluorobenzo[d][1,3]dioxol-5-yl)methanamine (Enamine) for (6-(trifluoromethyl)pyridin-3-yl)methanamine, and the product of Example 8A for the product of Example 1B gave the title compound. $^1$H NMR (400 MHz, DMSO-$d_6$) δ ppm 8.29 (t, J=6.0 Hz, 1H), 7.94 (d, J=8.1 Hz, 1H), 7.49 (t, J=8.9 Hz, 1H), 7.34 (d, J=8.3 Hz, 1H), 7.24 (d, J=1.8 Hz, 1H), 7.10-7.02 (m, 2H), 6.85 (ddd, J=9.0, 2.9, 1.2 Hz, 1H), 4.49 (s, 2H), 4.25 (d, J=5.9 Hz, 2H), 3.63-3.52 (m, 1H), 2.16-2.06 (m, 1H), 1.83-1.73 (m, 4H), 1.49-1.34 (m, 2H), 1.34-1.18 (m, 2H); MS (ESI$^+$) m/z 499 (M+H)$^+$.

Example 81: (1r,4r)-N-[(4-chloro-3-fluorophenyl) methyl]-4-[2-(3,4-dichlorophenoxy)acetamido]-N-(2-hydroxyethyl)cyclohexane-1-carboxamide (Compound 180)

Example 81A: 2-((4-chloro-3-fluorobenzyl)amino)ethanol

To a solution of (4-chloro-3-fluorophenyl)methanamine (266 mg, 1.67 mmol, Alfa) in a methanol buffer (3.6 weight % sodium acetate trihydrate and 2.4 weight % acetic acid in methanol, 15 mL) was added 1,4-dioxane-2,5-diol (100 mg, 0.833 mmol, Aldrich) in one portion followed by sodium cyanoborohydride (105 mg, 1.67 mmol) and trifluoroacetic acid (0.1 mL). After stirring at ambient temperature for 10 minutes, the reaction mixture was concentrated under reduced pressure to less than 5 mL and was filtered through a glass microfiber frit, and then purified by preparative HPLC [YMC TriArt™ C18 Hybrid 5 μm column, 50×100 mm, flow rate 140 mL/minute, 5-100% gradient of acetonitrile in buffer (0.025 M aqueous ammonium bicarbonate, adjusted to pH 10 with ammonium hydroxide)] to give the title compound (0.18 g, 0.88 mmol, 53.0% yield). MS (ESI$^+$) m/z 204 (M+H)$^+$.

Example 81B: (1r,4r)-N-[(4-chloro-3-fluorophenyl) methyl]-4-[2-(3,4-dichlorophenoxy)acetamido]-N-(2-hydroxyethyl)cyclohexane-1-carboxamide The reaction and purification conditions described in Example 1C substituting the product of Example 81A for (6-(trifluoromethyl)pyridin-3-yl)methanamine gave the title compound. $^1$H NMR (120° C., 501 MHz, DMSO-$d_6$) δ ppm 7.49-7.44 (m, 2H), 7.44-7.39 (m, 1H), 7.20 (d, J=2.9 Hz, 1H), 7.17-7.13 (m, 1H), 7.07-7.03 (m, 1H), 6.96 (dd, J=8.9, 2.9 Hz, 1H), 4.56 (s, 2H), 4.46 (s, 2H), 4.37 (br s, 1H), 3.63-3.54 (m, 1H), 3.52 (q, J=5.7 Hz, 2H), 3.38 (t, J=5.9 Hz, 2H), 2.65-2.54 (m, 1H), 1.88-1.81 (m, 2H), 1.78-1.67 (m, 2H), 1.50 (qd, J=13.4, 3.4 Hz, 2H), 1.36-1.24 (m, 2H); MS (ESI$^+$) m/z 531, 533 (M+H)$^+$.

Example 82: (1r,4r)-4-[2-(4-chloro-3-fluorophenoxy)acetamido]-N-[(4-chloro-3-fluorophenyl) methyl]-N-(2-hydroxyethyl)cyclohexane-1-carboxamide (Compound 181)

The reaction and purification conditions described in Example 1C substituting the product of Example 81A for (6-(trifluoromethyl)pyridin-3-yl)methanamine, and the product of Example 8A for the product of Example 1B gave the title compound. $^1$H NMR (120° C., 501 MHz, DMSO-$d_6$) δ ppm 7.46 (t, J=8.0 Hz, 1H), 7.43-7.38 (m, 2H), 7.15 (dd, J=10.5, 1.9 Hz, 1H), 7.07-7.03 (m, 1H), 6.98 (dd, J=11.3, 2.8 Hz, 1H), 6.83 (ddd, J=9.0, 2.9, 1.3 Hz, 1H), 4.56 (s, 2H), 4.46 (s, 2H), 4.37 (br s, 1H), 3.63-3.54 (m, 1H), 3.52 (q, J=5.6 Hz, 2H), 3.38 (t, J=5.9 Hz, 2H), 2.68-2.51 (m, 1H), 1.89-1.81 (m, 2H), 1.78-1.67 (m, 2H), 1.50 (qd, J=13.4, 3.4 Hz, 2H), 1.37-1.25 (m, 2H); MS (ESI$^+$) m/z 515 (M+H)$^+$.

Example 83: (1r,4r)-4-[2-(3,4-dichlorophenoxy) acetamido]-N-{[4-(hydroxymethyl)pyridin-2-yl] methyl}cyclohexane-1-carboxamide (Compound 182)

The reaction and purification conditions described in Example 1C substituting (2-(aminomethyl)pyridin-4-yl) methanol (Princeton) for (6-(trifluoromethyl)pyridin-3-yl) methanamine gave the title compound. $^1$H NMR (400 MHz, DMSO-$d_6$) δ ppm 8.40 (dd, J=5.0, 0.8 Hz, 1H), 8.33 (t, J=6.0 Hz, 1H), 7.96 (d, J=8.2 Hz, 1H), 7.54 (d, J=8.9 Hz, 1H), 7.25 (d, J=2.9 Hz, 1H), 7.19 (s, 1H), 7.18-7.14 (m, 1H), 6.98 (dd, J=9.0, 2.9 Hz, 1H), 5.41 (br s, 1H), 4.54-4.48 (m, 4H), 4.32 (d, J=5.9 Hz, 2H), 3.65-3.53 (m, 1H), 2.23-2.13 (m, 1H), 1.85-1.76 (m, 4H), 1.52-1.38 (m, 2H), 1.35-1.21 (m, 2H); MS (APCI$^+$) m/z 466 (M+H)$^+$.

Example 84: (1r,4r)-4-[2-(3,4-dichlorophenoxy) acetamido]-N-{[5-(trifluoromethyl)pyridin-2-yl] methyl}cyclohexane-1-carboxamide (Compound 183)

The title compound was prepared using the methodologies described above. $^1$H NMR (501 MHz, DMSO-$d_6$) δ ppm 8.89-8.87 (m, 1H), 8.47 (t, J=6.0 Hz, 1H), 8.17 (dd, J=8.1, 2.6 Hz, 1H), 7.96 (d, J=8.1 Hz, 1H), 7.54 (d, J=8.9 Hz, 1H), 7.45 (d, J=8.3 Hz, 1H), 7.25 (d, J=2.9 Hz, 1H), 6.98 (dd, J=8.9, 2.9 Hz, 1H), 4.50 (s, 2H), 4.43 (d, J=5.9 Hz, 2H), 3.64-3.56 (m, 1H), 2.23-2.15 (m, 1H), 1.88-1.77 (m, 4H), 1.51-1.38 (m, 2H), 1.34-1.24 (m, 2H); MS (ESI$^+$) m/z 504 (M+H)$^+$.

Example 85: (1r,4r)-4-[2-(3,4-dichlorophenoxy) acetamido]-N-{[5-(difluoromethyl)pyridin-2-yl] methyl}cyclohexane-1-carboxamide (Compound 184)

The title compound was prepared using the methodologies described above. $^1$H NMR (400 MHz, DMSO-$d_6$) δ ppm 8.71-8.67 (m, 1H), 8.42 (t, J=6.0 Hz, 1H), 7.99-7.93 (m, 2H), 7.54 (d, J=8.9 Hz, 1H), 7.37 (d, J=8.2 Hz, 1H), 7.27-6.95 (m, 3H), 4.50 (s, 2H), 4.39 (d, J=5.9 Hz, 2H), 3.67-3.52 (m, 1H), 2.23-2.12 (m, 1H), 1.89-1.75 (m, 4H), 1.50-1.37 (m, 2H), 1.34-1.19 (m, 2H); MS (ESI$^+$) m/z 468 (M+H)$^+$.

Example 86: (2S,5R)-5-[2-(4-chloro-3-fluorophenoxy)acetamido]-N-[(4-chloro-3-fluorophenyl)methyl]oxane-2-carboxamide (Compound 185)

Example 86A: tert-butyl ((3R,6S)-6-((4-chloro-3-fluorobenzyl)carbamoyl)tetrahydro-2H-pyran-3-yl)carbamate The methodologies described in Example 35A substituting (4-chloro-3-fluorophenyl)methanamine for 3-(4-(trifluoromethyl)phenyl)azetidine hydrochloride gave the title compound. MS (ESI$^+$) m/z 331 (M-C(O)OC(CH$_3$)$_3$+H)$^+$.

Example 86B: (2S,5R)-5-amino-N-(4-chloro-3-fluorobenzyl)tetrahydro-2H-pyran-2-carboxamide The methodologies described in Example 35B substituting Example 86A for Example 35A gave the title compound. MS (ESI$^+$) m/z 287 (M+H)$^+$.

Example 86C: (2S,5R)-5-[2-(4-chloro-3-fluorophenoxy)acetamido]-N-[(4-chloro-3-fluorophenyl)methyl]oxane-2-carboxamide The methodologies described in Example 35A substituting Example 86B for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (400 MHz, DMSO-d$_6$) δ ppm 8.36 (t, J=6.4 Hz, 1H), 8.02 (d, J=8.0 Hz, 1H), 7.56-7.45 (m, 2H), 7.24 (d, J=11.0 Hz, 1H), 7.15-7.03 (m, 2H), 6.85 (dt, J=8.9, 1.5 Hz, 1H), 4.52 (d, J=1.2 Hz, 2H), 4.26 (dd, J=6.2, 3.7 Hz, 2H), 3.90 (dd, J=10.6, 4.1 Hz, 1H), 3.79 (dd, J=11.5, 2.6 Hz, 2H), 3.18 (t, J=10.6 Hz, 1H), 2.01 (d, J=13.1 Hz, 1H), 1.90 (d, J=12.3 Hz, 1H), 1.69-1.52 (m, 1H), 1.52-1.37 (m, 1H); MS (ESI$^+$) m/z 473 (M+H)$^+$.

Example 87: (2S,5R)-5-[2-(4-chloro-3-fluorophenoxy)acetamido]-N-{[5-(trifluoromethyl)pyridin-2-yl]methyl}oxane-2-carboxamide (Compound 186)

The methodologies described in Example 35A substituting Example 66D for 3-(4-(trifluoromethyl)phenyl)azetidine hydrochloride, substituting 2-(4-chloro-3-fluorophenoxy)acetic acid for (2S,5R)-5-((tert-butoxycarbonyl)amino)tetrahydro-2H-pyran-2-carboxylic acid, and purifying by preparative HPLC [Waters XBridge™ C18 5 μm OBD column, 30×100 mm, flow rate 40 mL/minute, 5-100% gradient of acetonitrile in buffer (0.025 M aqueous ammonium bicarbonate, adjusted to pH 10 with ammonium hydroxide)] gave the title compound. $^1$H NMR (400 MHz, DMSO-d$_6$) δ ppm 1H NMR (501 MHz, DMSO-d$_6$) δ ppm 8.89 (s, 1H), 8.43 (t, J=6.1 Hz, 1H), 8.17 (dd, J=8.3, 2.4 Hz, 1H), 8.05 (d, J=8.0 Hz, 1H), 7.54-7.44 (m, 2H), 7.07 (dd, J=11.3, 2.9 Hz, 1H), 6.85 (ddd, J=9.0, 2.9, 1.1 Hz, 1H), 4.53 (d, J=1.8 Hz, 2H), 4.47 (d, J=6.1 Hz, 2H), 3.93 (ddd, J=10.6, 4.9, 1.8 Hz, 1H), 3.87-3.79 (m, 2H), 3.21 (t, J=10.6 Hz, 1H), 2.11-2.00 (m, 1H), 1.92 (d, J=12.3 Hz, 1H), 1.62 (qd, J=12.5, 3.8 Hz, 1H), 1.50 (qd, J=13.1, 3.6 Hz, 1H); MS (ESI$^+$) m/z 490 (M+H)$^+$.

Example 88: (1r,4r)-4-[2-(4-chloro-3-fluorophenoxy)acetamido]-N-{[5-(difluoromethyl)pyridin-2-yl]methyl}cyclohexane-1-carboxamide (Compound 187)

The title compound was prepared using the methodologies described above. $^1$H NMR (400 MHz, DMSO-d$_6$) δ ppm 8.71-8.68 (m, 1H), 8.42 (t, J=6.0 Hz, 1H), 7.99-7.93 (m, 2H), 7.49 (t, J=8.9 Hz, 1H), 7.37 (d, J=8.1 Hz, 1H), 7.13 (t, J=55.3 Hz, 1H), 7.07 (dd, J=11.4, 2.8 Hz, 1H), 6.85 (ddd, J=9.0, 2.9, 1.2 Hz, 1H), 4.49 (s, 2H), 4.39 (d, J=5.9 Hz, 2H), 3.65-3.53 (m, 1H), 2.25-2.13 (m, 1H), 1.87-1.75 (m, 4H), 1.50-1.38 (m, 2H), 1.35-1.21 (m, 2H); MS (ESI$^+$) m/z 470 (M+H)$^+$.

Example 89: Activity of Exemplary Compounds in an In Vitro Model of Vanishing Cell White Matter Disease (VWMD)

In order to test exemplary compounds of the invention in a cellular context, a stable VWMD cell line was first constructed. The ATF4 reporter was prepared by fusing the human full-length ATF4 5'-UTR (NCBI Accession No. BC022088.2) in front of the firefly luciferase (FLuc) coding sequence lacking the initiator methionine as described in Sidrauski et al (eLife 2013). The construct was used to produce recombinant retroviruses using standard methods and the resulting viral supernatant was used to transduce HEK293T cells, which were then subsequently selected with puromycin to generate a stable cell line.

HEK293T cells carrying the ATF4 luciferase reporter were plated on polylysine coated 384-well plates (Greiner Bio-one) at 30,000 cells per well. Cells were treated the next day with 1 μg/mL tunicamycin and 200 nM of a compound of Formula (I) for 7 hours. Luminescence was measured using One Glo (Promega) as specified by the manufacturer. Cells were maintained in DMEM with L-glutamine supplemented with 10% heat-inactivated FBS (Gibco) and Antibiotic-Antimycotic solution (Gibco).

Table 2 below summarizes the EC$_{50}$ data obtained using the ATF4-Luc assay for exemplary compounds of the invention. In this table, "A" represents an EC$_{50}$ of less than 10 nM; "B" an EC$_{50}$ of between 10 nM and 50 nM; "C" an EC$_{50}$ of between 50 nM and 250 nM; "D" an EC$_{50}$ of between 250 nM and 500 nM; "E" an EC$_{50}$ of between 500 nM and 2 μM; "F" an EC$_{50}$ of greater than 2 μM; and "G" indicates that data is not available.

TABLE 2

| EC$_{50}$ values of exemplary compounds of the invention in the ATF4-Luc assay. | |
|---|---|
| Compound No. | ATF4-Luc EC$_{50}$ |
| 100 | B |
| 101 | F |
| 102 | A |
| 103 | F |
| 104 | C |
| 105 | F |
| 106 | F |
| 107 | B |
| 108 | F |
| 109 | A |
| 110 | B |
| 111 | B |
| 112 | A |
| 113 | F |
| 114 | F |

TABLE 2-continued

EC$_{50}$ values of exemplary compounds of the invention in the ATF4-Luc assay.

| Compound No. | ATF4-Luc EC$_{50}$ |
|---|---|
| 115 | E |
| 116 | C |
| 117 | F |
| 118 | F |
| 119 | A |
| 120 | B |
| 121 | D |
| 122 | E |
| 123 | D |
| 124 | F |
| 125 | D |
| 126 | E |
| 127 | F |
| 128 | F |
| 129 | A |
| 130 | C |
| 131 | B |
| 132 | B |
| 133 | F |
| 134 | A |
| 135 | C |
| 136 | F |
| 137 | B |
| 138 | B |
| 139 | D |
| 140 | F |
| 141 | F |
| 142 | C |
| 143 | E |
| 144 | F |
| 145 | E |
| 146 | C |
| 147 | F |
| 148 | C |
| 149 | C |
| 150 | B |
| 151 | G |
| 152 | F |
| 153 | F |
| 154 | F |
| 155 | E |
| 156 | C |
| 157 | C |
| 158 | C |
| 159 | B |
| 160 | B |
| 161 | D |
| 162 | F |
| 163 | F |
| 164 | C |
| 165 | C |
| 166 | F |
| 167 | C |
| 168 | F |
| 169 | F |
| 170 | F |
| 171 | C |
| 172 | F |
| 173 | C |
| 174 | B |
| 175 | C |
| 176 | F |
| 177 | A |
| 178 | B |
| 179 | B |
| 180 | E |
| 181 | E |
| 182 | F |
| 183 | A |
| 184 | B |
| 185 | B |
| 186 | B |
| 187 | B |

Table 2: EC$_{50}$ values of exemplary compounds of the invention in the ATF4-Luc assay.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

Methods of Making Exemplary Compounds

The compounds of the invention may be better understood in connection with the following synthetic schemes and methods which illustrate a means by which the compounds can be prepared. The compounds of this invention can be prepared by a variety of synthetic

We claim:

1. A compound of Formula (I):

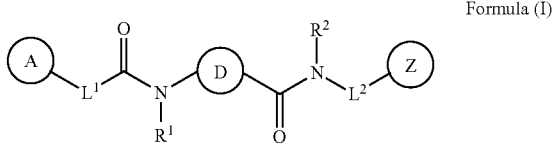

Formula (I)

or a pharmaceutically acceptable salt thereof, wherein:

D is cyclobutyl optionally substituted with 1-4 $R^X$;

$L^1$ is a bond, $C_1$-$C_6$ alkylene, 2-7 membered heteroalkylene, —$NR^{N1}$—, or —O—, wherein $C_1$-$C_6$ alkylene or 2-7 membered heteroalkylene is optionally substituted with 1-5 $R^{L1}$;

$R^1$ is hydrogen, hydroxy-$C_1$-$C_6$ alkyl, or $C_1$-$C_6$ alkyl;

$L^2$ is a bond, $C_1$-$C_6$ alkylene, or 2-7 membered heteroalkylene, wherein $C_1$-$C_6$ alkylene or 2-7 membered heteroalkylene is optionally substituted with 1-5 $R^{L2}$;

$R^2$ is hydrogen, hydroxy-$C_1$-$C_6$ alkyl, or $C_1$-$C_6$ alkyl; or $L^2$ and $R^2$, together with the nitrogen to which they are attached, form a 4-9 membered monocyclic, bridged bicyclic, fused bicyclic, or spirocyclic heterocyclyl; wherein the 4-9 membered monocyclic, bridged bicyclic, fused bicyclic, or spirocyclic heterocyclyl is optionally substituted on one or more available carbons with 1-5 $R^W$; and wherein if the 4-9 membered monocyclic, bridged bicyclic, fused bicyclic, or spirocyclic heterocyclyl contains a substitutable nitrogen moiety, the substitutable nitrogen may be optionally substituted with $R^{N2}$;

A and Z are each independently phenyl or 5-6-membered heteroaryl, wherein each phenyl or 5-6-membered heteroaryl is optionally substituted on one or more available carbons with 1-5 $R^Y$; and wherein if the 5-6-membered heteroaryl contains a substitutable nitrogen moiety, the substitutable nitrogen may be optionally substituted with $R^{N3}$; or one $R^Y$, $R^2$, and $L^2$, together with the nitrogen to which $R^2$ and $L^2$ are attached, form a 4-9 membered monocyclic heterocycle, wherein Z is fused to the formed 4-9 membered monocyclic heterocycle, wherein the available carbon atoms of Z are optionally substituted with 1-4 $R^Y$; and wherein if Z contains a substitutable nitrogen moiety, the substitutable nitrogen may be optionally substituted with $R^{N3}$;

each $R^{L1}$ is independently selected from the group consisting of $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$NR^BC(O)R^D$, —$C(O)NR^BR^C$, —$C(O)R^D$, —C(O)OH, —$C(O)OR^D$, —$SR^E$, —$S(O)R^D$, and —$S(O)_2R^D$;

2 geminal $R^{L2}$ groups together with the carbon to which they are attached form a cyclopropyl moiety; or each $R^{L2}$ is independently selected from the group consisting of hydrogen, $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, $NR^BC(O)R^D$, —$C(O)NR^BR^C$, —$C(O)R^D$, —C(O)OH, —$C(O)OR^D$, —$SR^E$, —$S(O)R^D$, and —$S(O)_2R^D$;

$R^{N1}$ is selected from the group consisting of hydrogen, $C_1$-$C_6$ alkyl, hydroxy-$C_2$-$C_6$ alkyl, halo-$C_2$-$C_6$ alkyl, amino-$C_2$-$C_6$ alkyl, cyano-$C_2$-$C_6$ alkyl, —$C(O)NR^BR^C$, —$C(O)R^D$, —$C(O)OR^D$, and —$S(O)_2R^D$;

$R^{N2}$ is selected from the group consisting of hydrogen, $C_1$-$C_6$ alkyl, hydroxy-$C_2$-$C_6$ alkyl, halo-$C_2$-$C_6$ alkyl, amino-$C_2$-$C_6$ alkyl, cyano-$C_2$-$C_6$ alkyl, —$C(O)NR^BR^C$, —$C(O)R^D$, —$C(O)OR^D$, and —$S(O)_2R^D$;

$R^{N3}$ is selected from the group consisting of hydrogen, $C_1$-$C_6$ alkyl, hydroxy-$C_2$-$C_6$ alkyl, halo-$C_2$-$C_6$ alkyl, amino-$C_2$-$C_6$ alkyl, cyano-$C_2$-$C_6$ alkyl, —$C(O)NR^BR^C$, —$C(O)R^D$, —$C(O)OR^D$, and —$S(O)_2R^D$;

each $R^W$ is independently selected from the group consisting of hydrogen, $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$NR^BC(O)R^D$, —$C(O)NR^BR^C$, —$C(O)R^D$, —C(O)OH, —$C(O)OR^D$, —$SR^E$, —$S(O)R^D$, and —$S(O)_2R^D$;

each $R^X$ is independently selected from the group consisting of hydrogen, $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$NR^BC(O)R^D$, —$C(O)NR^BR^C$, —$C(O)R^D$, —C(O)OH, —$C(O)OR^D$, —$SR^E$, —$S(O)R^D$, and —$S(O)_2R^D$;

each $R^Y$ is independently selected from the group consisting of hydrogen, $C_1$-$C_6$ alkyl, hydroxy-$C_1$-$C_6$ alkyl, halo-$C_1$-$C_6$ alkyl, halo-$C_1$-$C_6$ alkoxy, amino-$C_1$-$C_6$ alkyl, cyano-$C_1$-$C_6$ alkyl, —O—$C_1$-$C_6$ cycloalkyl, halo, cyano, —$OR^A$, —$NR^BR^C$, —$NR^BC(O)R^D$, —$C(O)NR^BR^C$, —$C(O)R^D$, —C(O)OH, —$C(O)OR^D$, —$S(R^F)_m$, —$S(O)R^D$, —$S(O)_2R^D$, and $G^1$; or 2 $R^Y$ groups or one $R^Y$ and one $R^{N3}$ on adjacent atoms, together with the atoms to which they are attached, form a 3-7 membered fused cycloalkyl, 3-7-membered fused heterocyclyl, fused aryl, or 5-6 membered fused heteroaryl, each of which is optionally substituted with 1-5 $R^X$;

each $G^1$ is independently 3-7-membered cycloalkyl, 3-7-membered heterocyclyl, aryl, or 5-6-membered heteroaryl, wherein each 3-7-membered cycloalkyl, 3-7-membered heterocyclyl, aryl, or 5-6-membered heteroaryl is optionally substituted with 1-3 $R^Z$;

each $R^Z$ is independently selected from the group consisting of $C_1$-$C_6$ alkyl, hydroxy-$C_1$-$C_6$ alkyl, halo-$C_1$-$C_6$ alkyl, halo, cyano, —$OR^A$, —$NR^BR^C$, —$NR^BC(O)R^D$, —$C(O)NR^BR^C$, —$C(O)R^D$, —C(O)OH, —$C(O)OR^D$, and —$S(O)_2R^D$;

$R^A$ is, at each occurrence, independently hydrogen, $C_1$-$C_6$ alkyl, halo-$C_1$-$C_6$ alkyl, —$C(O)NR^BR^C$, —$C(O)R^D$, or —$C(O)OR^D$;

each of $R^B$ and $R^C$ is independently hydrogen or $C_1$-$C_6$ alkyl; or $R^B$ and $R^C$ together with the atom to which they are attached form a 3-7-membered heterocyclyl optionally substituted with 1-3 $R^Z$;

each $R^D$ is independently $C_1$-$C_6$ alkyl or halo-$C_1$-$C_6$ alkyl;

each $R^E$ is independently hydrogen, $C_1$-$C_6$ alkyl, or halo-$C_1$-$C_6$ alkyl;

each $R^F$ is independently hydrogen, $C_1$-$C_6$ alkyl, or halo; and m is 1 when $R^F$ is hydrogen or $C_1$-$C_6$ alkyl, 3 when $R^F$ is $C_1$-$C_6$ alkyl, or 5 when $R^F$ is halo.

2. The compound of claim 1, wherein D is

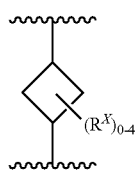

3. The compound of claim 1, wherein each $R^X$ is independently selected from the group consisting of oxo, —OH, —C(O)OH, —C(O)OR$^D$, halo, and hydroxy-C$_1$-C$_6$ alkyl.

4. The compound of claim 1, wherein L$^1$ is selected from a bond, —CH$_2$O—*, —CH$_2$CH$_2$O—*, —CH$_2$OCH$_2$—*, —N(CH$_3$)—*, —NH—*, or —O—*, wherein "—*" indicates the attachment point to A.

5. The compound of claim 1, wherein R$^1$ is hydrogen, —CH$_3$, or —CH$_2$CH$_2$OH.

6. The compound of claim 1, wherein each of A and Z is independently phenyl, pyridyl, pyrimidinyl, pyrazinyl, oxazolyl, isoxazolyl, indolyl, imidazolyl, pyrrolyl, triazolyl, or pyrazolyl, each of which is optionally substituted with 1-5 R$^Y$ groups.

7. The compound of claim 1, wherein A is selected from the group consisting of:

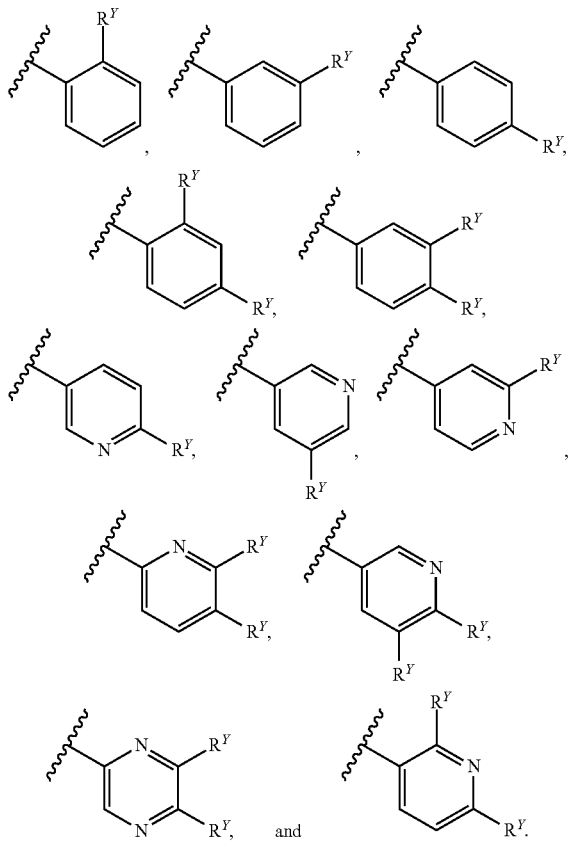

8. The compound of claim 1, wherein Z is selected from the group consisting of:

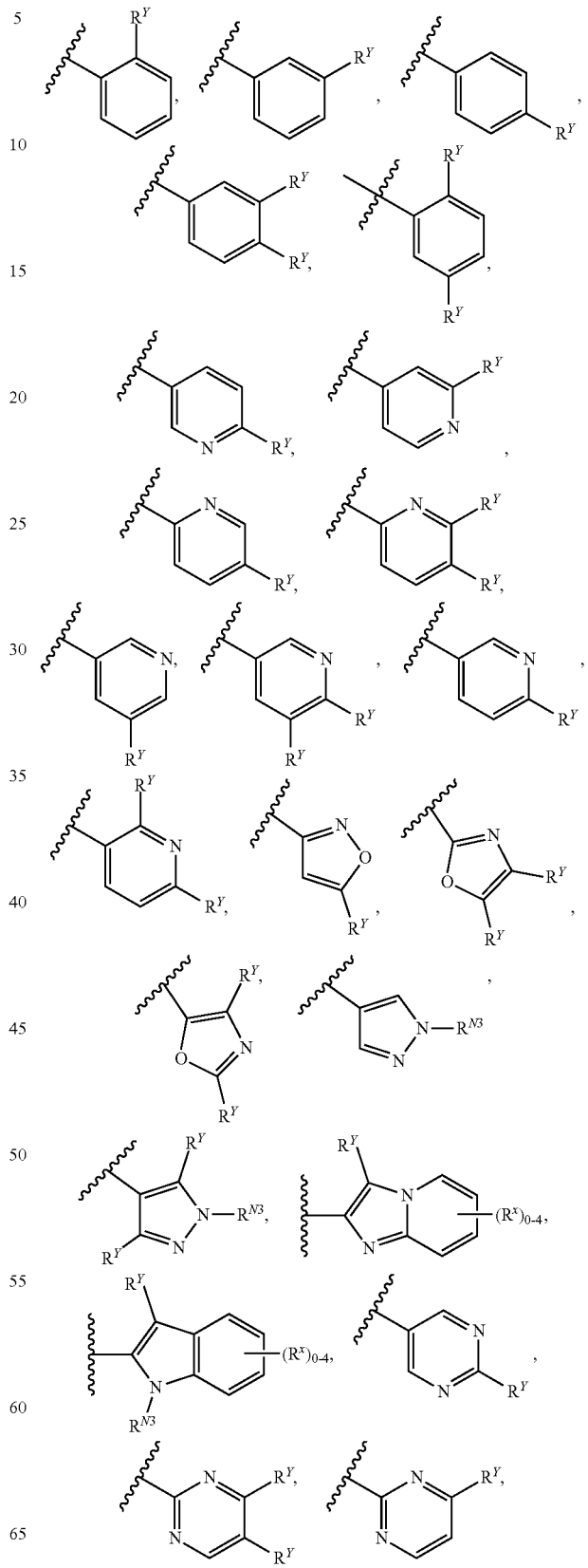

-continued

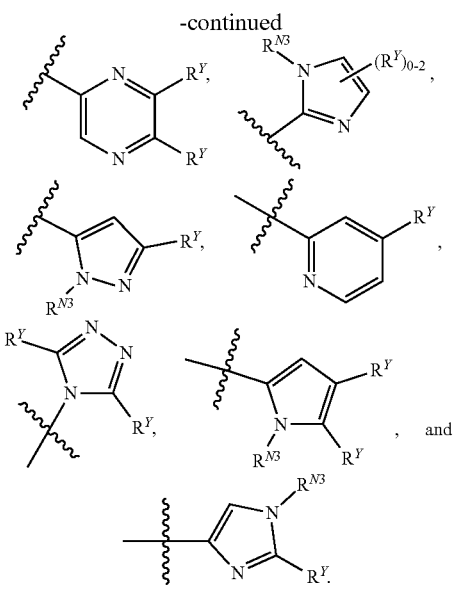

wherein $R^{N3}$ is hydrogen or —CH$_3$.

9. The compound of claim 1, wherein each $R^Y$ is independently selected from the group consisting of hydrogen, chloro, fluoro, —CHF$_2$, —CF$_3$, —CH$_3$, —CH$_2$CH$_3$, —CH(CH$_3$)$_2$, —OCH$_3$, —OCHF$_2$, —OCF$_3$, —OCH$_2$CF$_3$, —OCH(CH$_3$)$_2$, —CN, —C(O)NH$_2$, —CH$_2$OH, and

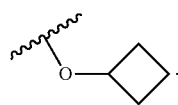

10. The compound of claim 1, wherein $L^2$ is selected from a bond, —CH$_2$—*, —CH$_2$CH$_2$—*, or —CH$_2$CH$_2$O—* wherein "—*" indicates the attachment point to Z.

11. The compound of claim 1, wherein $R^2$ is hydrogen or —CH$_3$.

12. The compound of claim 1, wherein $L^2$ and $R^2$, together with the nitrogen to which they are attached, form a 4-7 membered monocyclic or 7-9 membered spirocyclic heterocyclyl, each of which is optionally substituted with 1-5 $R^W$.

13. The compound of claim 1, wherein the compound is represented by Formula (II):

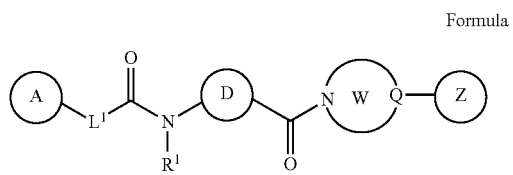

Formula (II)

wherein:
W is a 4-7 membered monocyclic or 7-9 membered spirocyclic heterocyclyl, wherein the 4-7 membered monocyclic or 7-9 membered spirocyclic heterocyclyl is optionally substituted with 1-4 $R^W$;
Q is nitrogen or C($R^Q$); and
$R^Q$ is selected from the group consisting of hydrogen, hydroxyl, and C$_1$-C$_6$ alkyl.

14. The compound of claim 13, wherein Q is nitrogen, and W is a piperazine, piperazinone, or 2,6-diazaspiro[3.3]heptane moiety, each of which is optionally substituted with 1-4 $R^W$ groups, and each $R^W$ is independently selected from the group consisting of C$_1$-C$_6$ alkyl, halo-C$_1$-C$_6$ alkyl, halo, oxo, cyano, and —OR$^A$.

15. The compound of claim 13, wherein W is selected from the group consisting of:

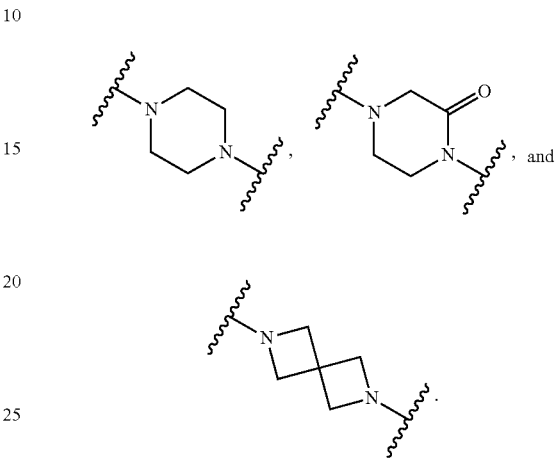

16. The compound of claim 13, wherein Q is CH, and W is an azetidine, pyrrolidine, piperidine, or 2-azaspiro[3.3]heptane moiety, each of which is optionally substituted with 1-4 $R^W$ groups, and each $R^W$ is independently C$_1$-C$_6$ alkyl, halo-C$_1$-C$_6$ alkyl, halo, oxo, cyano, or —OR$^A$.

17. The compound of claim 13, wherein W is selected from the group consisting of:

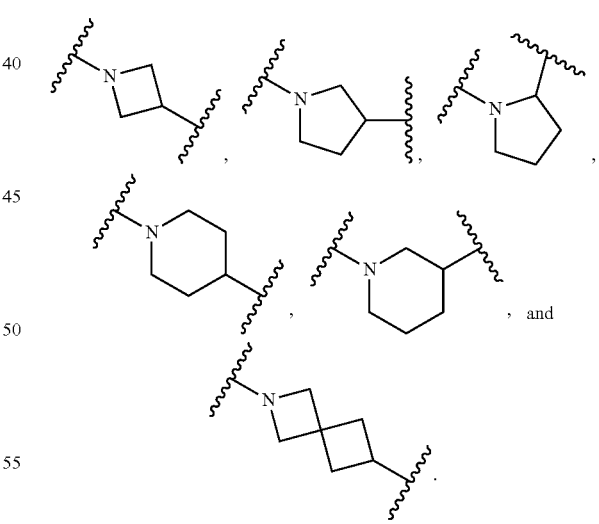

18. The compound claim 1, wherein one $R^Y$, $R^2$, and $L^2$, together with the nitrogen to which $R^2$ and $L^2$ are attached, form a 4-9 membered monocyclic heterocycle, wherein Z is fused to the formed 4-9 membered monocyclic heterocycle, wherein the available carbon atoms of Z are optionally substituted with 1-4 $R^Y$; and wherein if Z contains a substitutable nitrogen moiety, the substitutable nitrogen may be optionally substituted with $R^{N3}$.

19. The compound of claim 1, wherein the compound of Formula (I) is a compound of Formula (I-a):

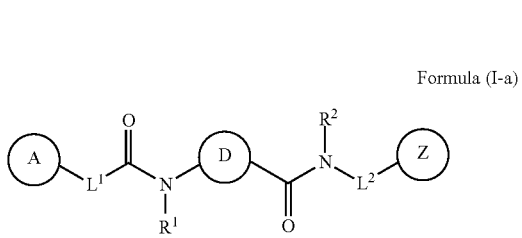

Formula (I-a)

or a pharmaceutically acceptable salt thereof, wherein:

D is cyclobutyl optionally substituted with 1-4 $R^X$ groups;

$L^1$ is selected from the group consisting of a bond, —CH₂O—*, —CH₂OCH₂—*, —NCH₃—, —NH—, and —O—, wherein "—*" indicates the attachment point to A;

$R^1$ is selected from the group consisting of hydrogen and —CH₃;

$L^2$ is selected from the group consisting of a bond and —CH₂—*, wherein "—*" indicates the attachment point to Z;

$R^2$ is selected from the group consisting of hydrogen and —CH₃; or $L^2$ and $R^2$, together with the nitrogen to which they are attached, form an azetidine, pyrrolidine, piperidine, 2-azaspiro[3.3]heptane, piperazine, piperazinone, or 2,6-diazaspiro[3.3]heptane moiety, each of which is optionally substituted with 1-4 $R^W$ groups; or one $R^Y$, $R^2$, and $L^2$, together with the nitrogen to which $R^2$ and $L^2$ are attached, form a 4-9 membered monocyclic heterocycle, wherein Z is fused to the formed 4-9 membered monocyclic heterocycle, wherein the available carbon atoms of Z are optionally substituted with 1-4 $R^Y$; and wherein if Z contains a substitutable nitrogen moiety, the substitutable nitrogen may be optionally substituted with $R^{N3}$;

A is phenyl or pyridyl, each of which is optionally substituted with 1-5 $R^Y$ groups;

Z is phenyl, pyridyl, oxazolyl, isoxazolyl, imidazolyl, pyrimidinyl, or pyrazolyl, each of which is optionally substituted on one or more available carbons with 1-5 $R^Y$ groups; and wherein pyrazolyl may be optionally substituted on an available nitrogen with hydrogen or —CH₃;

each $R^W$ is independently fluoro, chloro, oxo, —OH, —OCH₃, —CF₃, —CH₃, —CH₂CH₃, or —CH(CH₃)₂;

each $R^X$ is independently fluoro, oxo, —OH, O—CH₃, —C(O)OH, or —C(O)OCH₃;

each $R^Y$ is independently chloro, fluoro, —CHF₂, —CF₃, —CH₃, —CH₂CH₃, —CH(CH₃)₂, —OCH₃, —OCHF₂, —OCF₃, —OCH₂CF₃, —OCH(CH₃)₂, or —CN; or 2 $R^Y$ groups on adjacent atoms, together with the atoms to which they are attached form a furanyl, pyrrolyl, pyridyl, phenyl, or dioxolanyl ring, each of which is optionally substituted with 1-2 $R^X$.

20. A compound selected from the group consisting of:

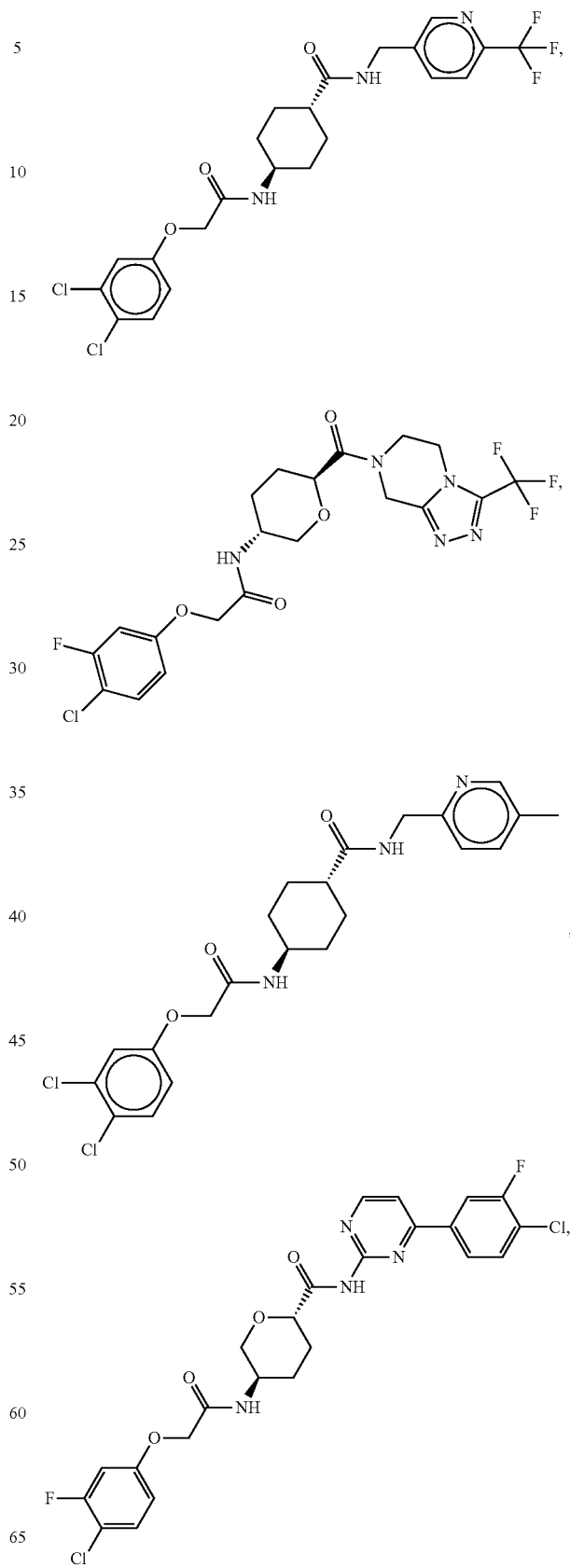

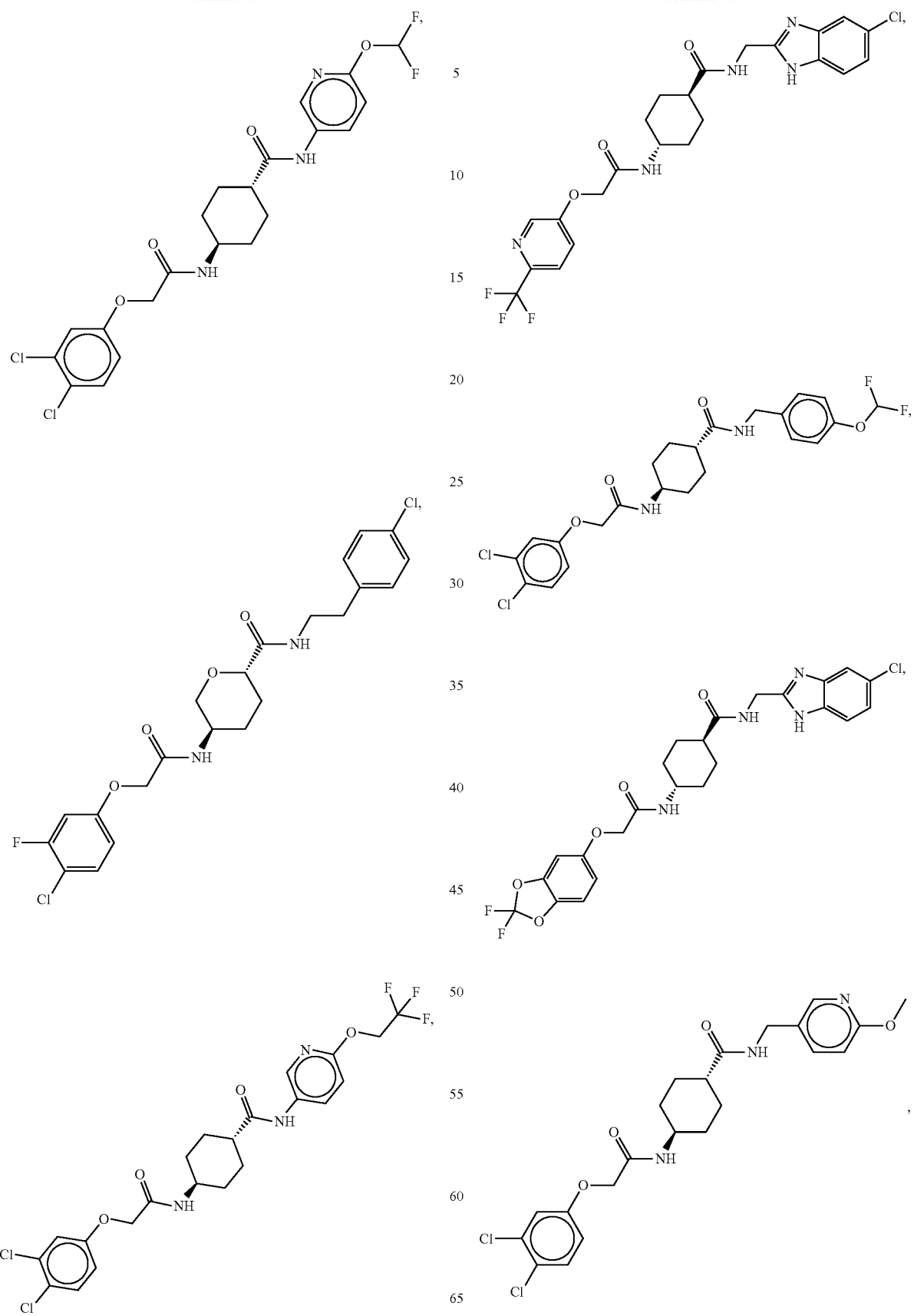

221
-continued
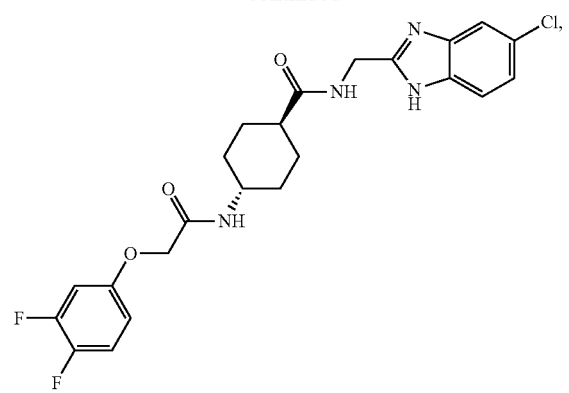
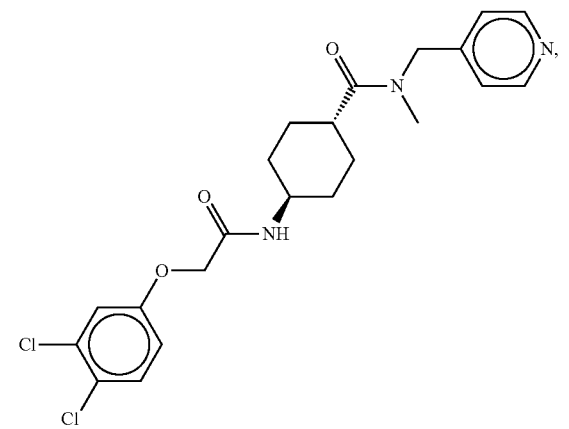
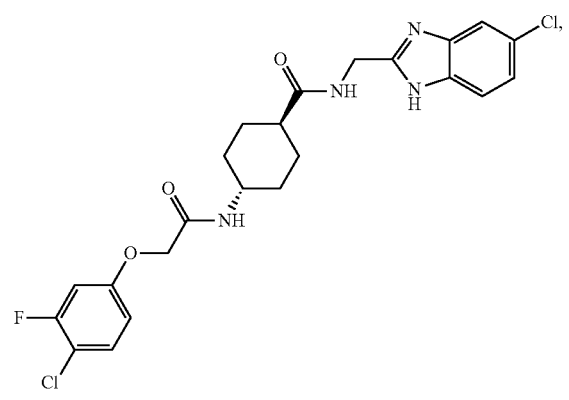
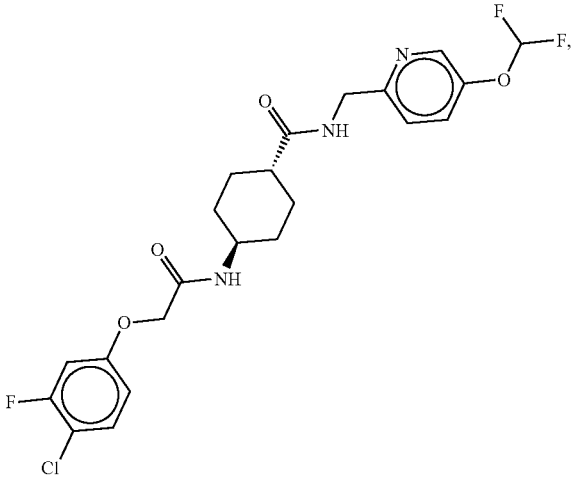
222
-continued
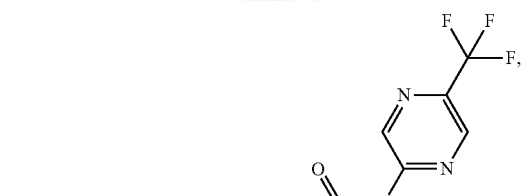
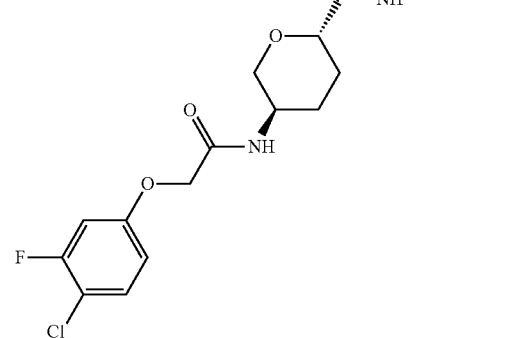
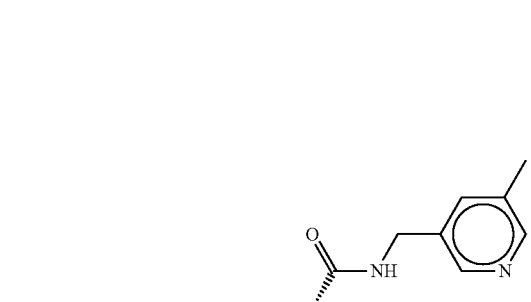
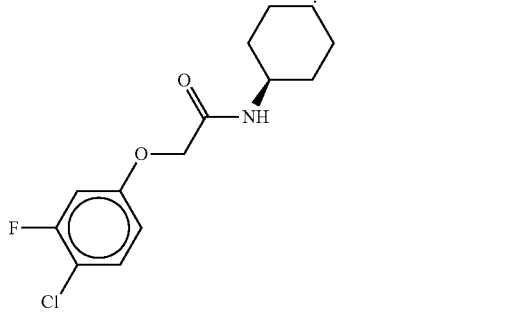
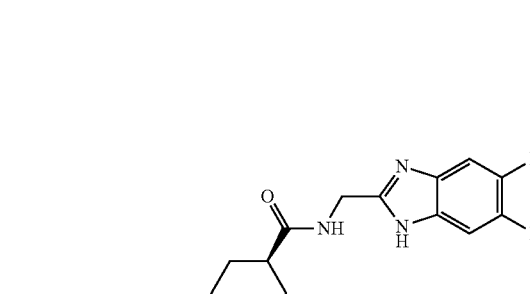
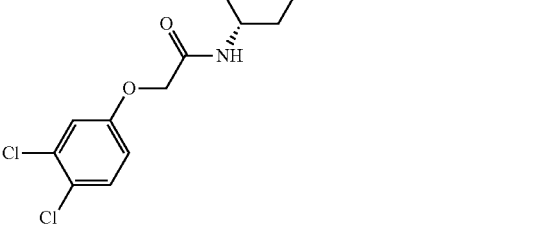

223
-continued
224
-continued
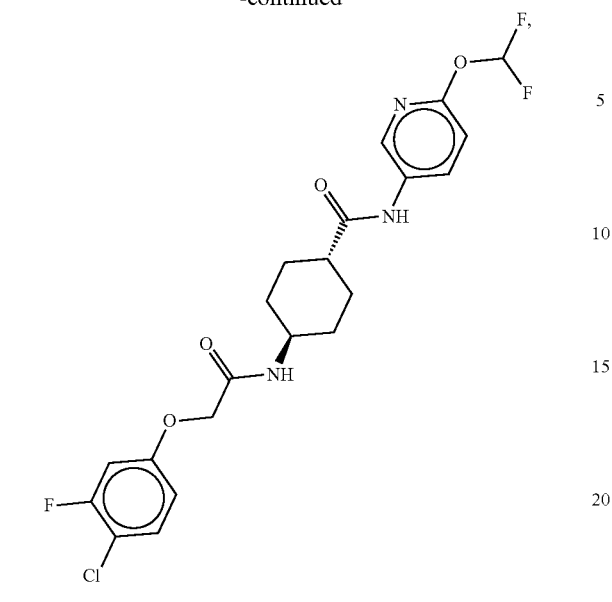
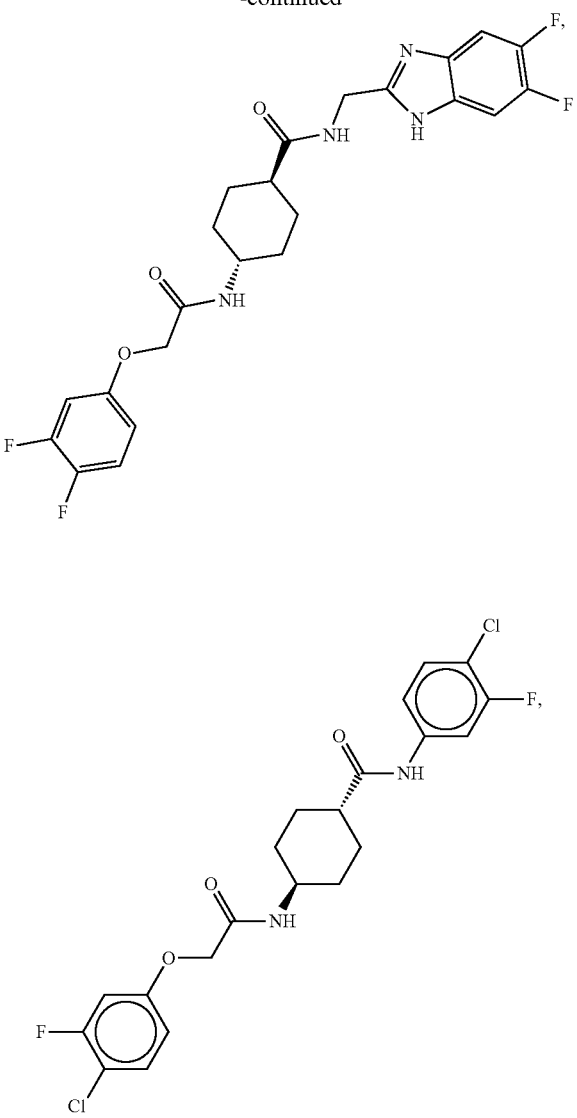
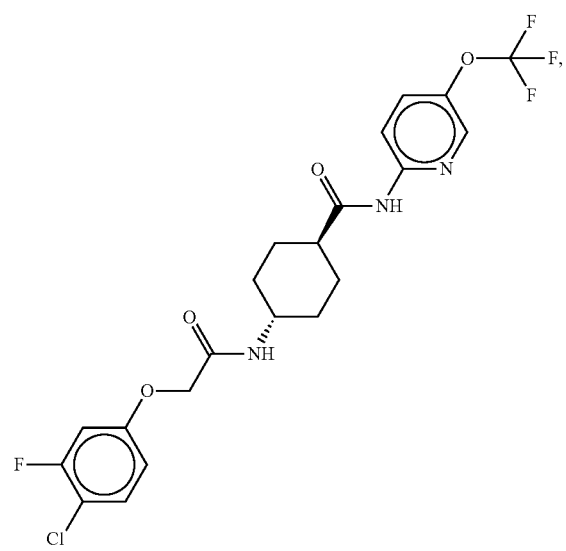

225
-continued
226
-continued
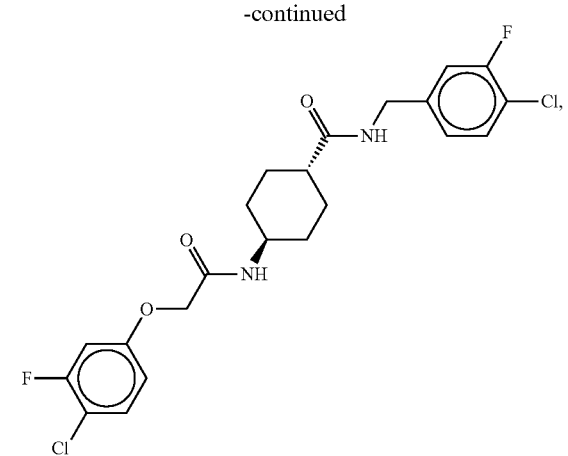
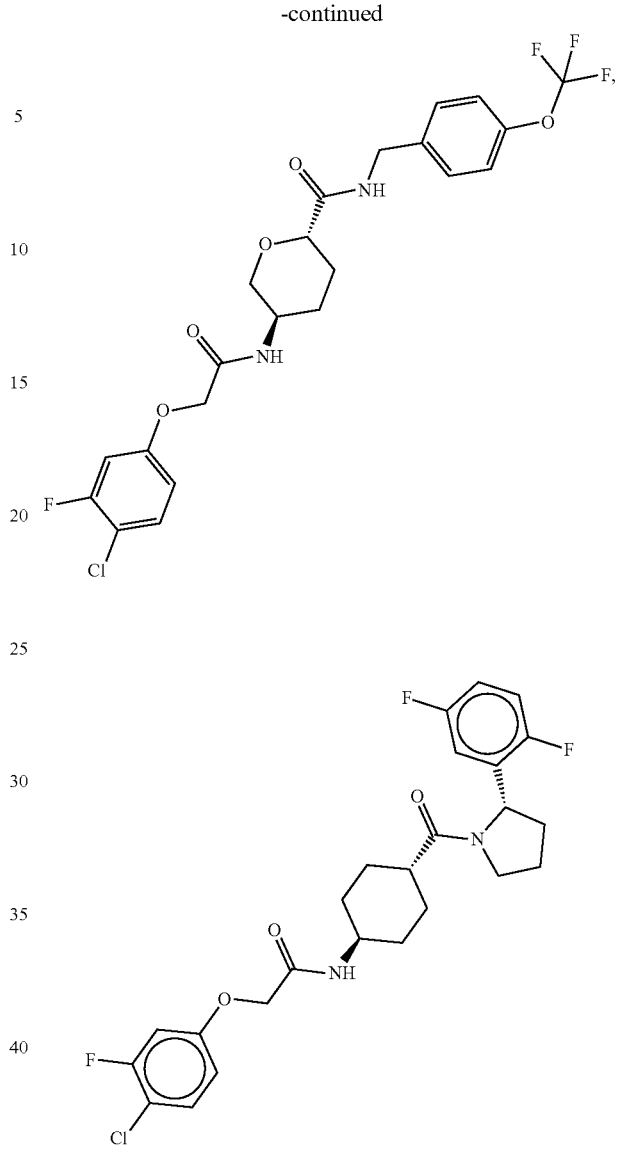
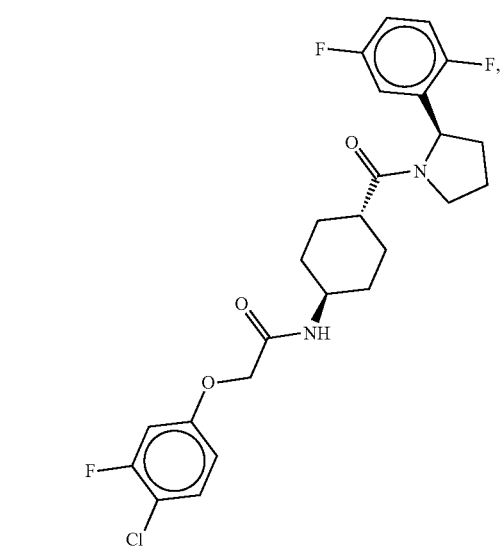
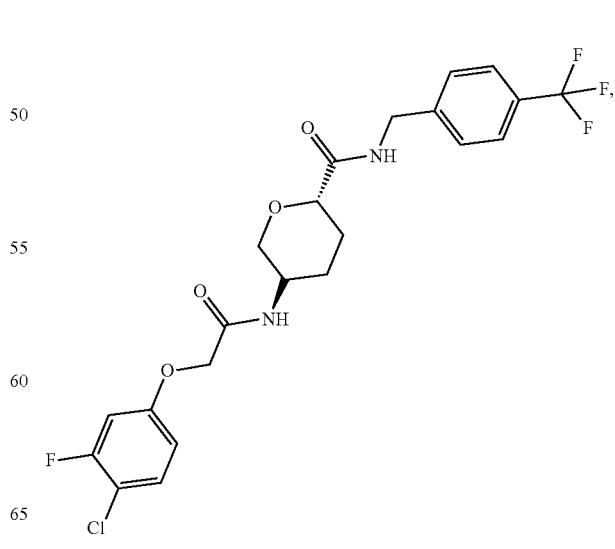

227
-continued
228
-continued
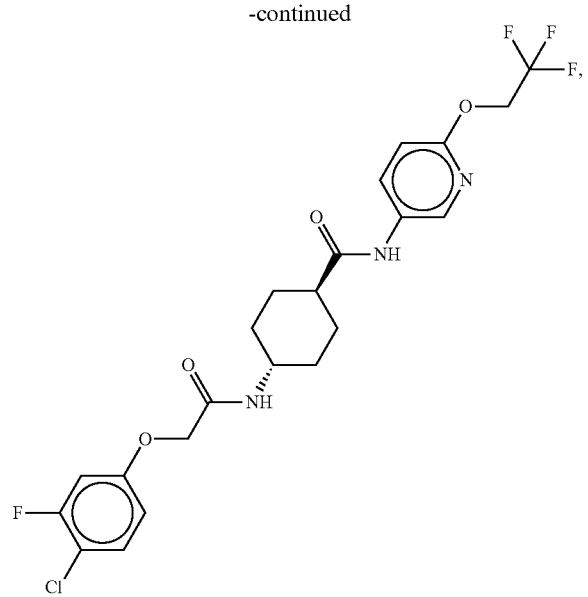
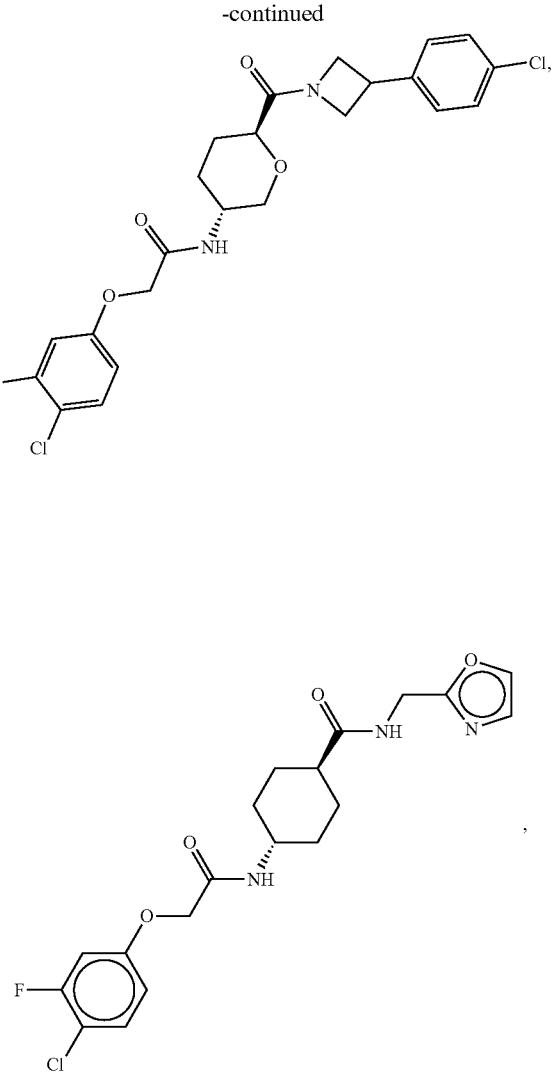

229
-continued
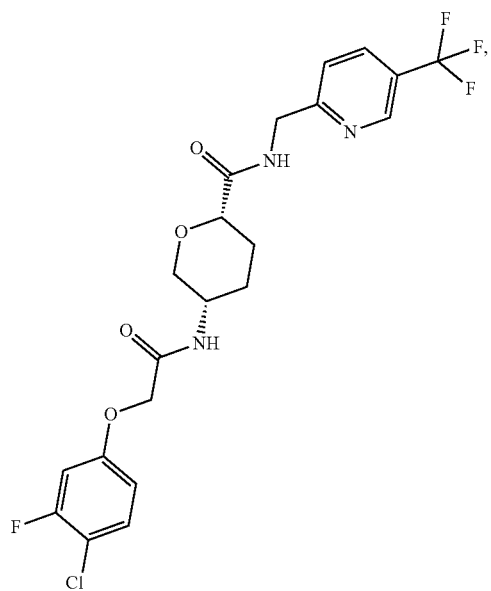
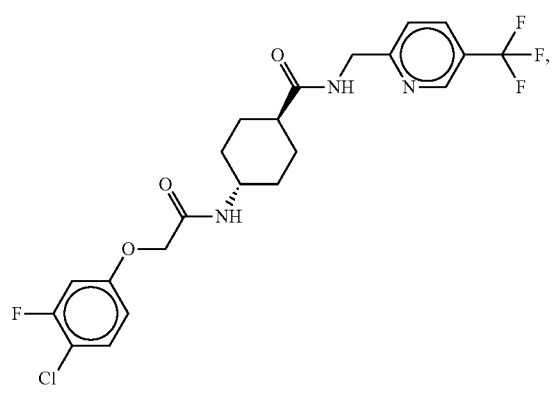
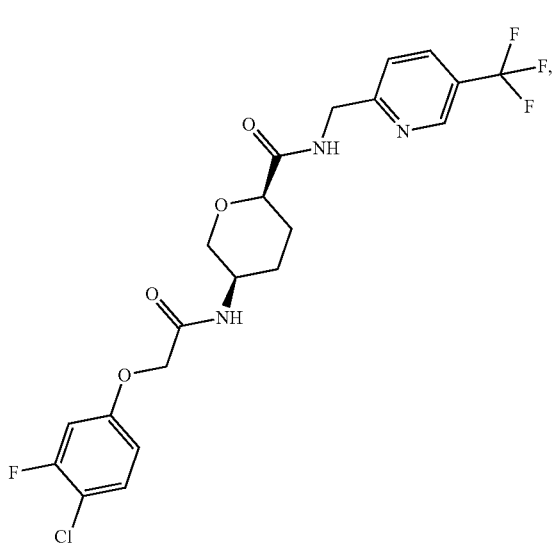
230
-continued
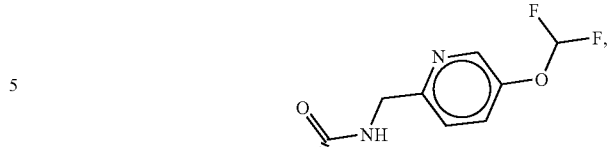

231
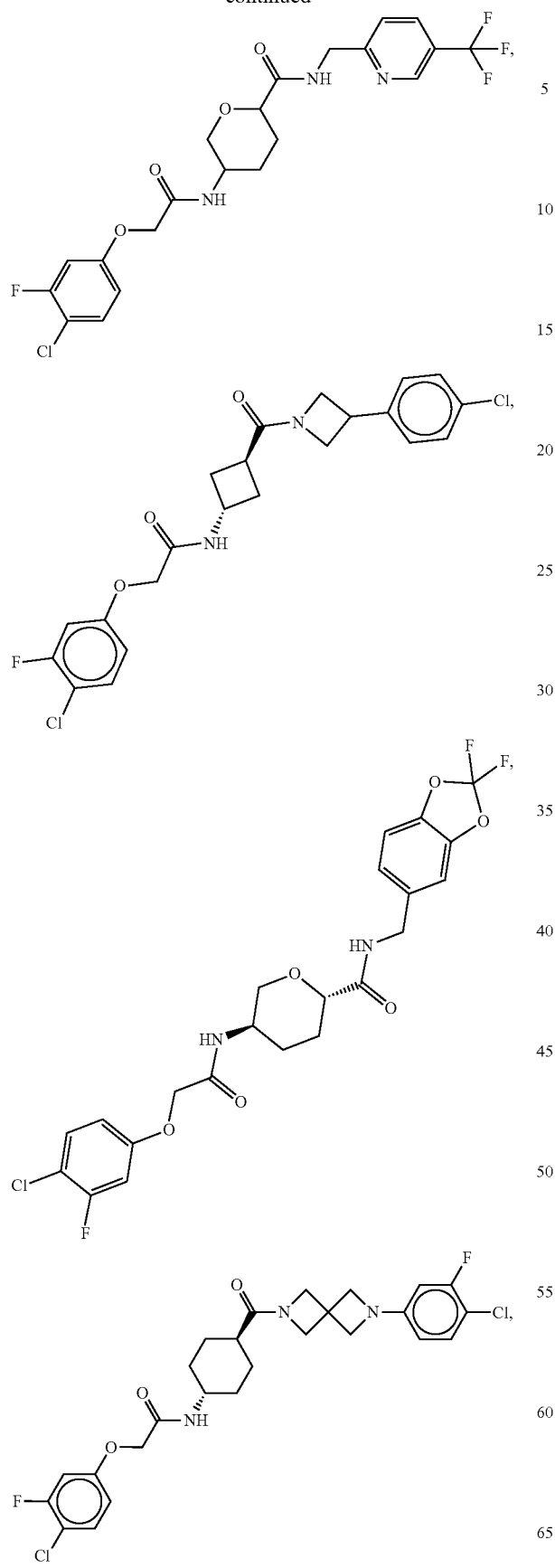
232
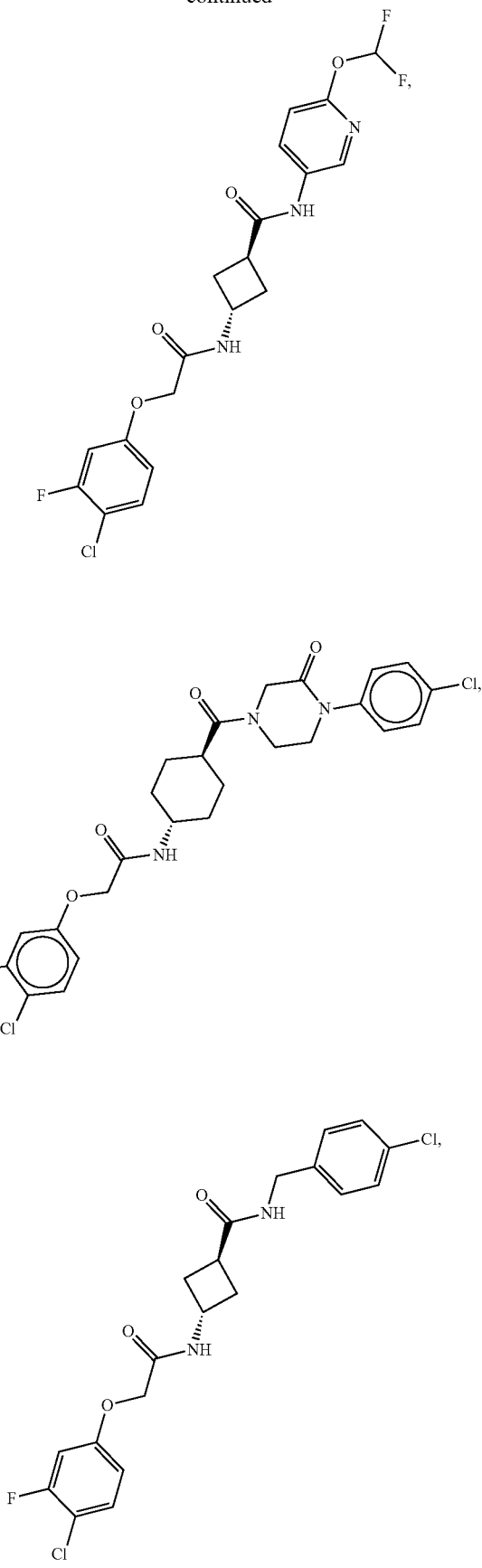

233
-continued
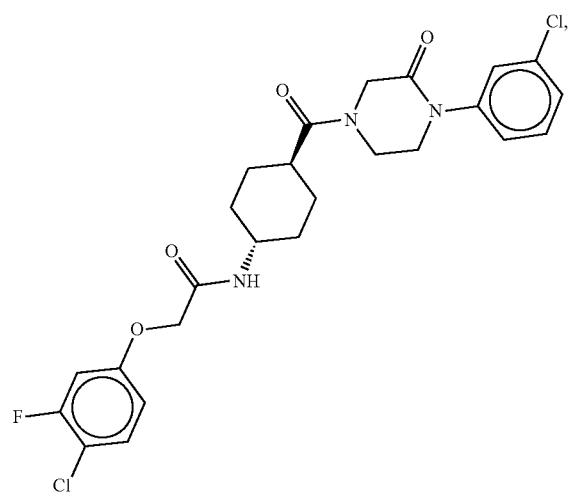
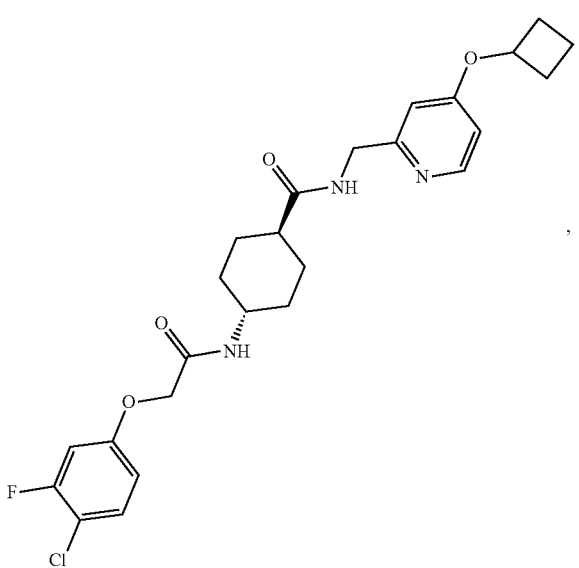
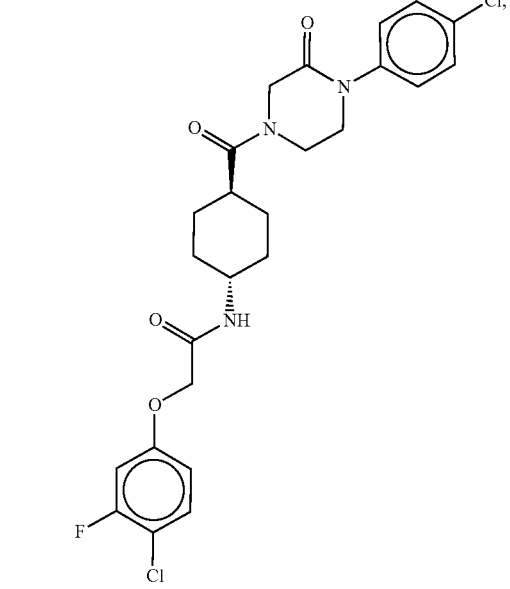
234
-continued
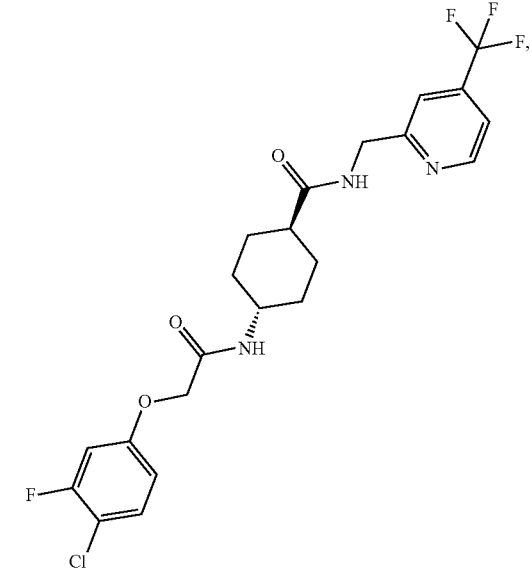
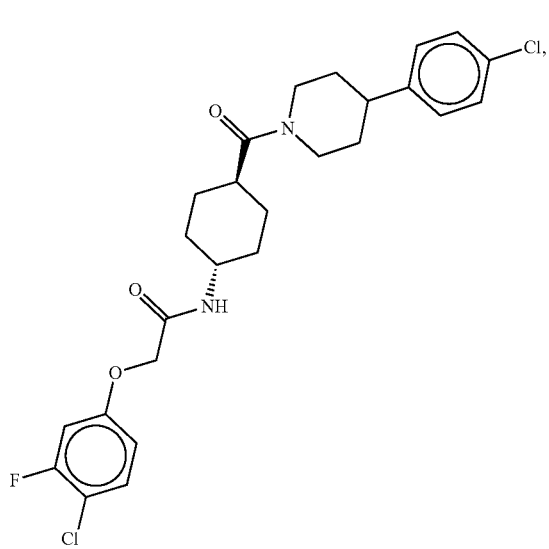
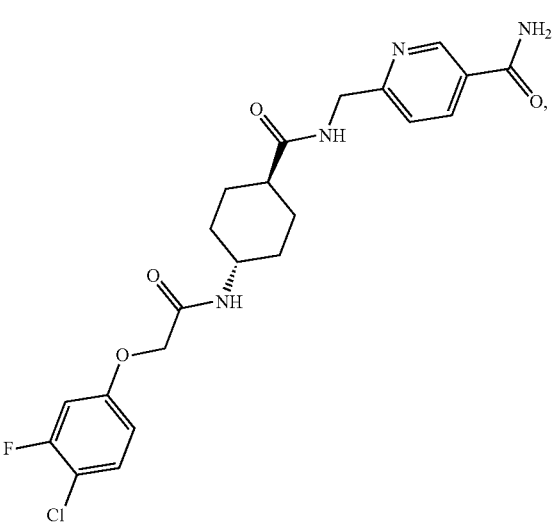

235
-continued
236
-continued
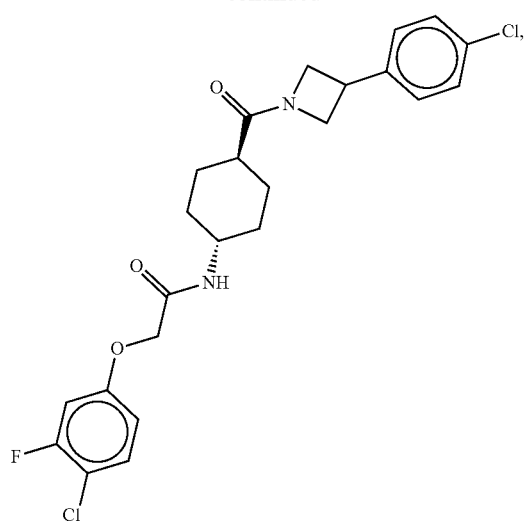
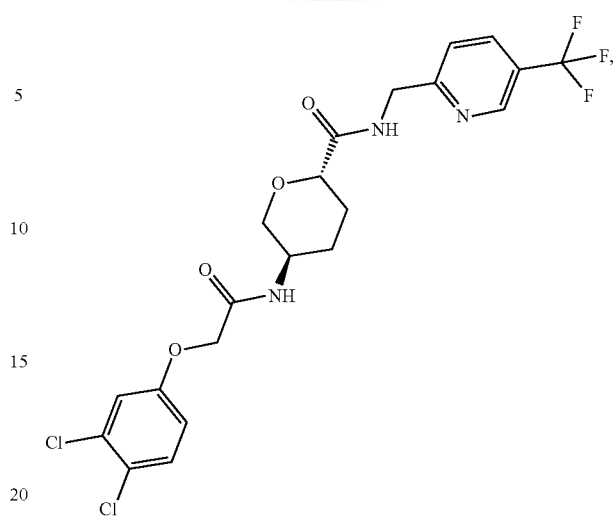
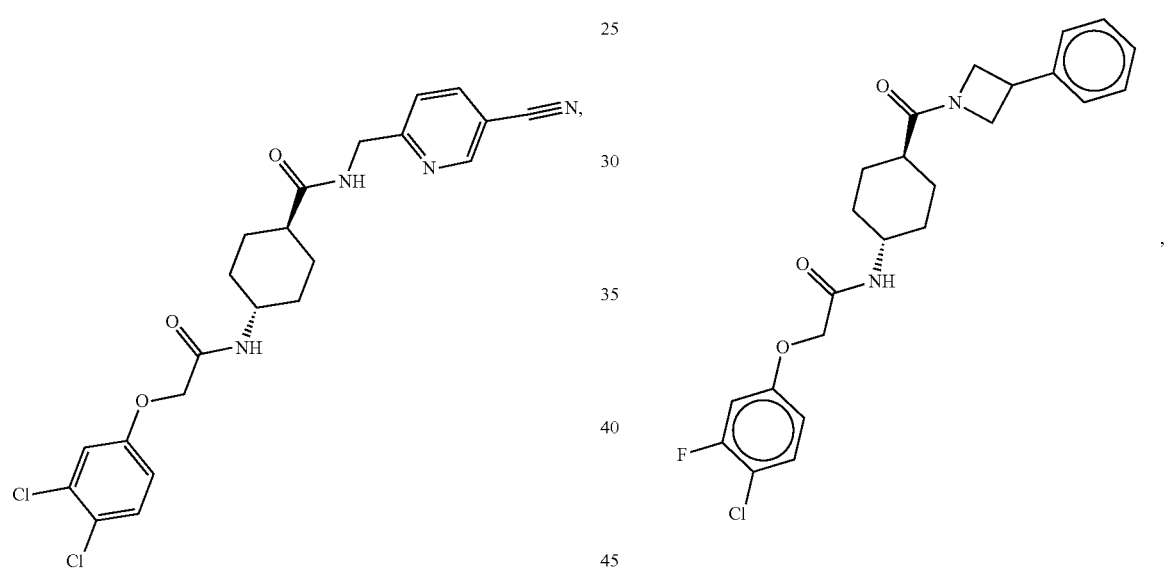
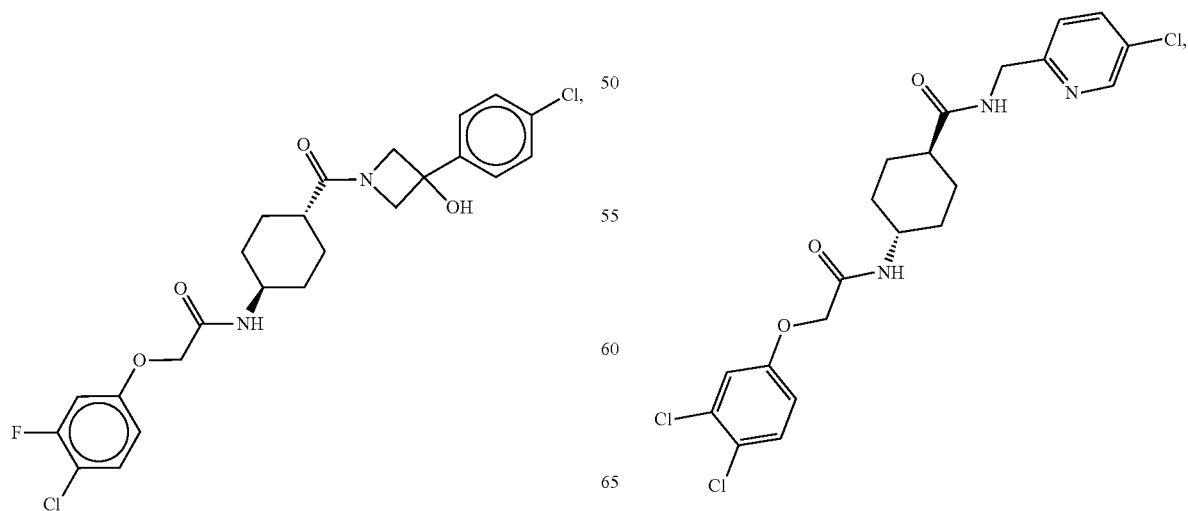

237
-continued
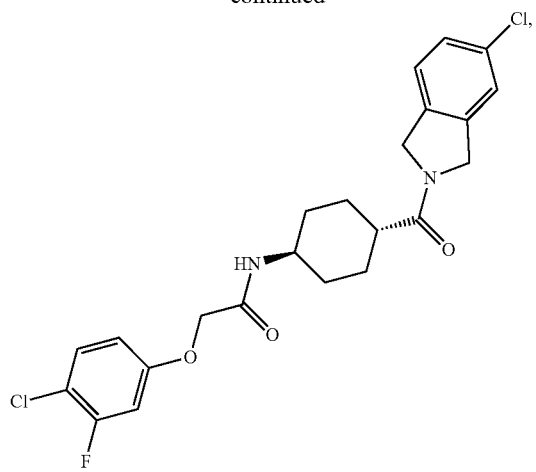
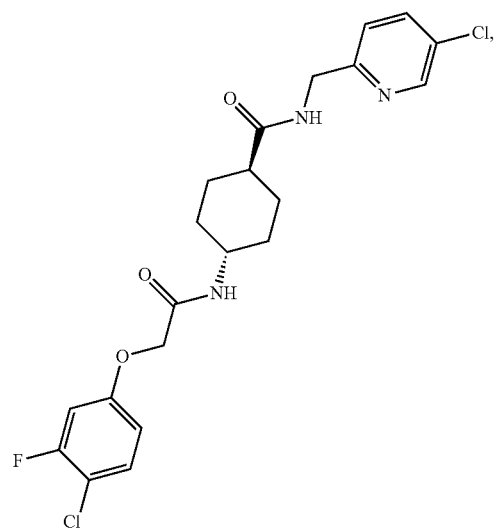
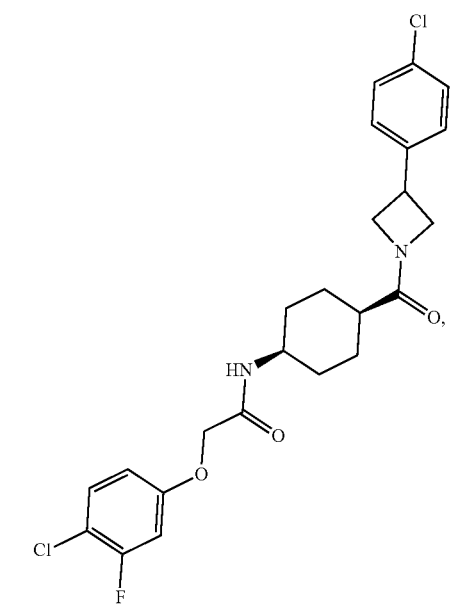
238
-continued
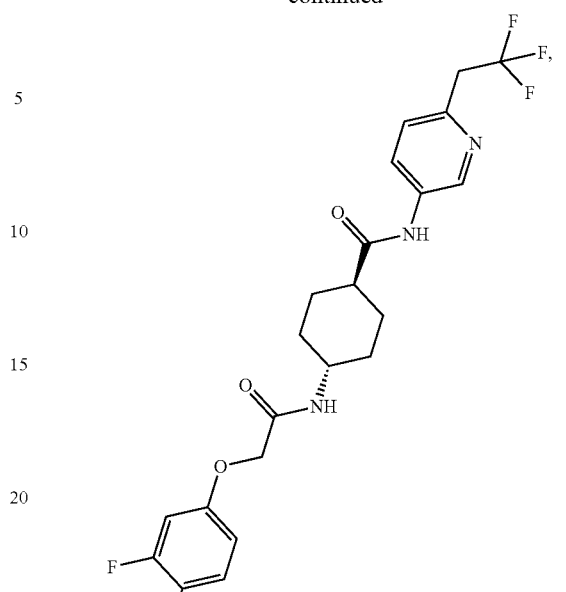
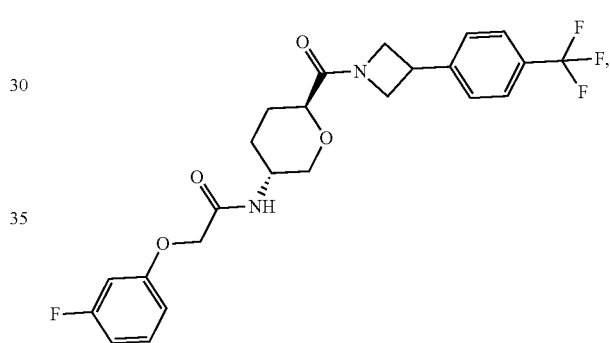

239
-continued
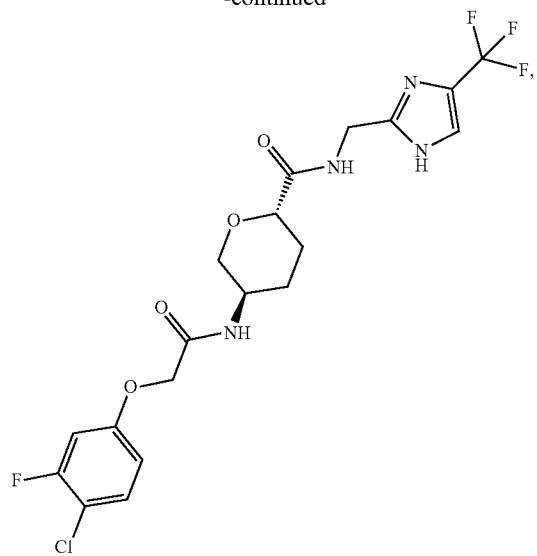
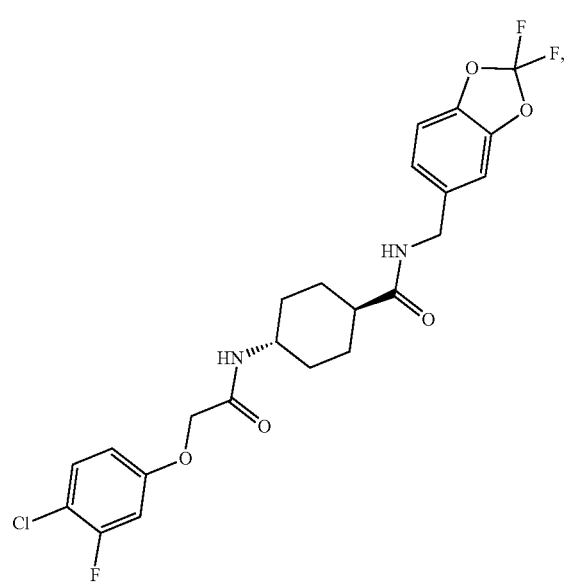
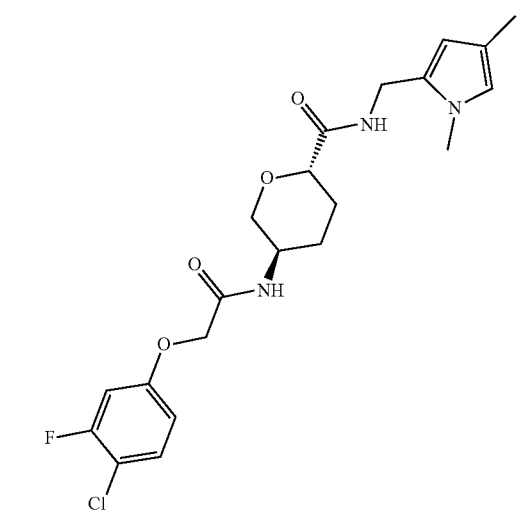
240
-continued
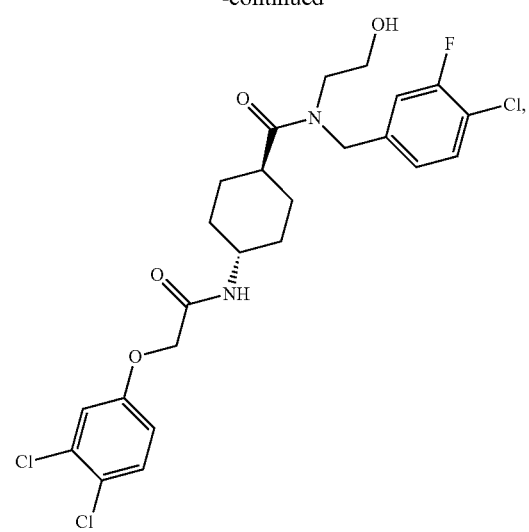

241
-continued
242
-continued
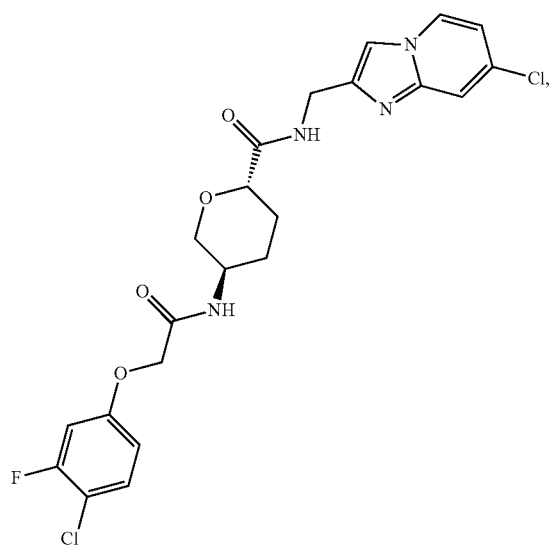
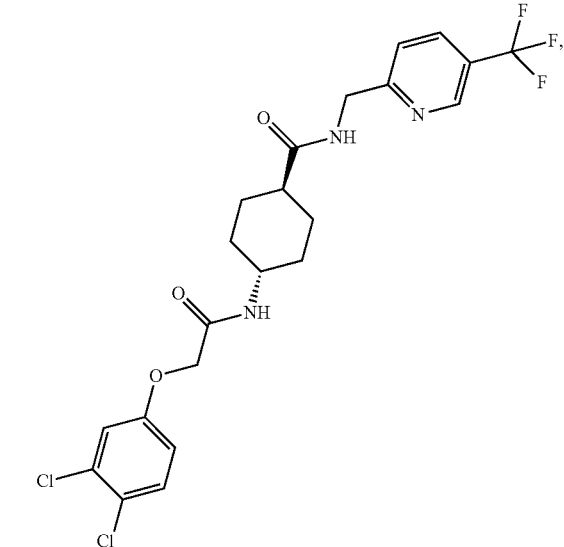
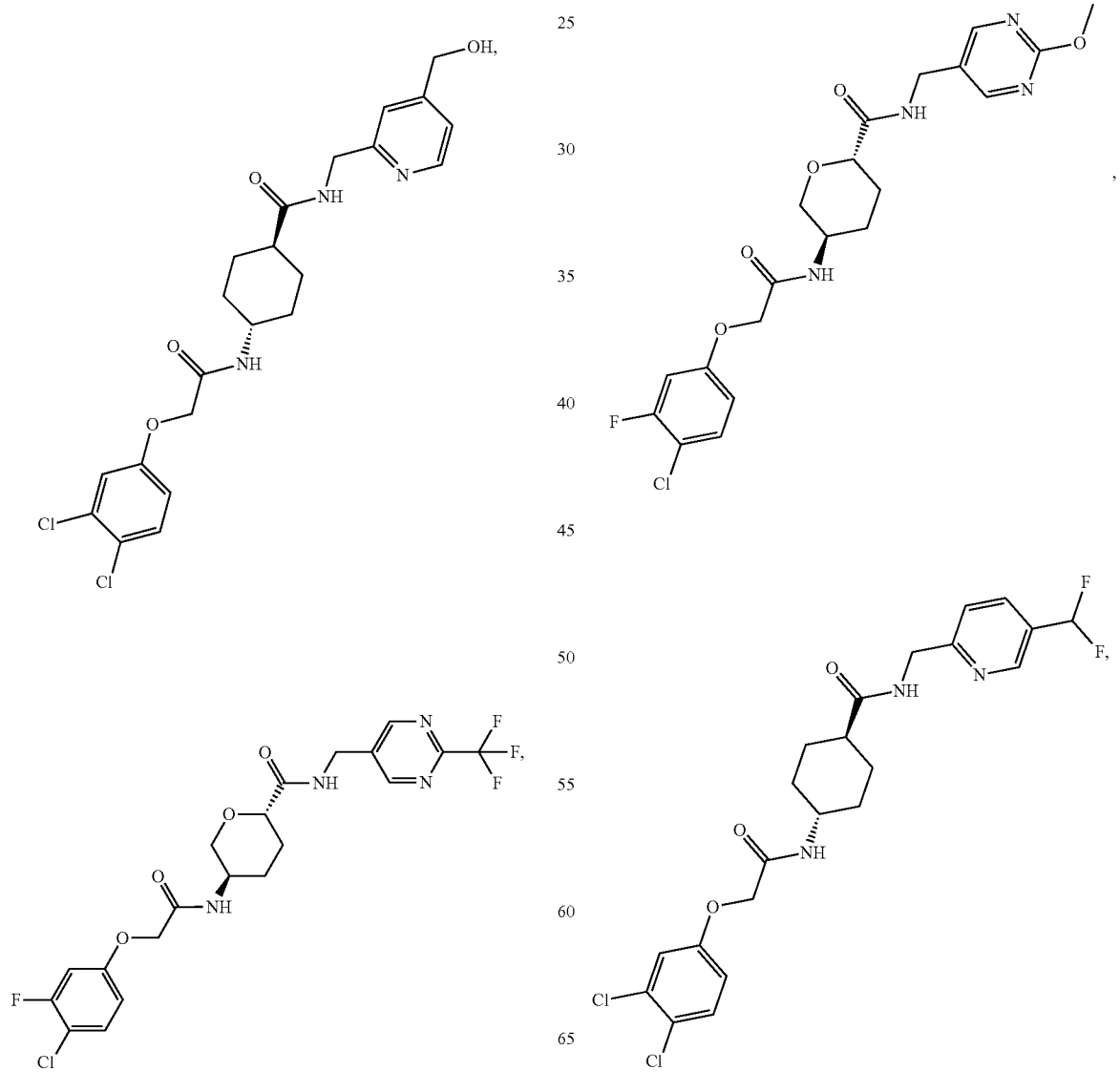

243
-continued
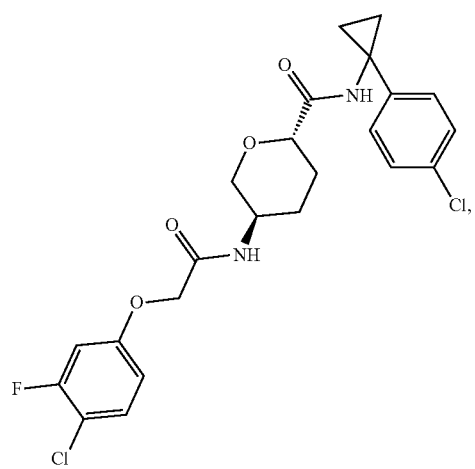
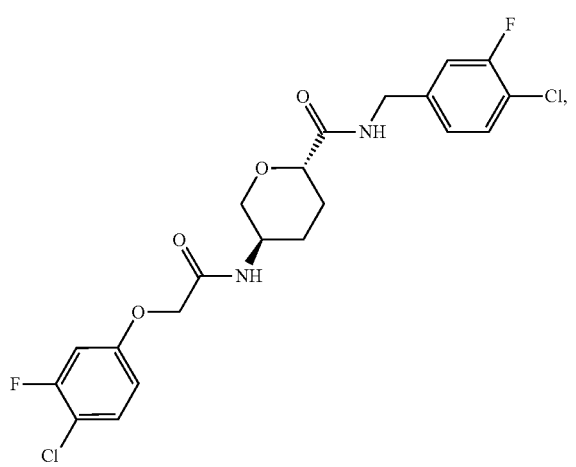
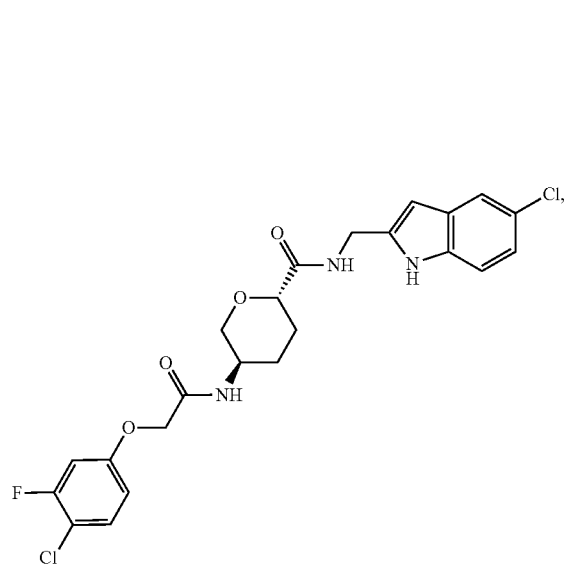
244
-continued
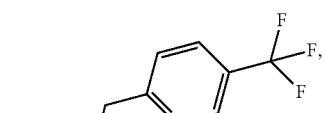
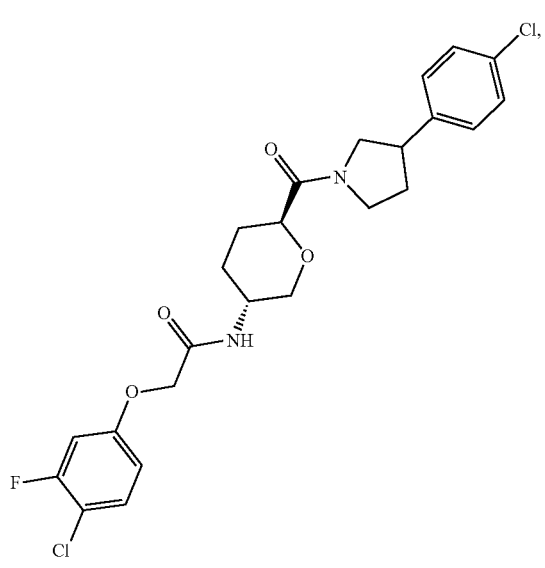

-continued
and
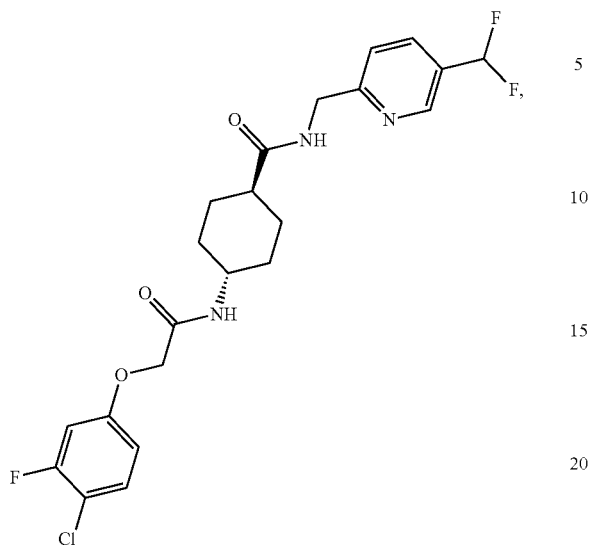
or a pharmaceutically acceptable salt thereof.
* * * * *